US011516989B2

(12) United States Patent
Riley

(10) Patent No.: US 11,516,989 B2
(45) Date of Patent: Dec. 6, 2022

(54) ENDOPHYTE COMPOSITIONS AND METHODS FOR IMPROVEMENT OF PLANT TRAITS

(71) Applicant: Indigo Ag, Inc., Boston, MA (US)

(72) Inventor: Raymond Riley, Woodbury, MN (US)

(73) Assignee: Indigo Ag, Inc., Boston, MA (US)

( * ) Notice: Subject to any disclaimer, the term of this patent is extended or adjusted under 35 U.S.C. 154(b) by 0 days.

(21) Appl. No.: 16/837,881

(22) Filed: Apr. 1, 2020

(65) Prior Publication Data

US 2021/0139928 A1 May 13, 2021

Related U.S. Application Data

(62) Division of application No. 15/829,865, filed on Dec. 1, 2017, now Pat. No. 10,640,783.

(60) Provisional application No. 62/556,288, filed on Sep. 8, 2017, provisional application No. 62/467,755, filed on Mar. 6, 2017, provisional application No. 62/467,740, filed on Mar. 6, 2017, provisional application No. 62/467,742, filed on Mar. 6, 2017, provisional application No. 62/466,256, filed on Mar. 2, 2017, provisional application No. 62/465,834, filed on Mar. 2, 2017, provisional application No. 62/466,253, filed on Mar. 2, 2017, provisional application No. 62/465,798, filed on Mar. 1, 2017, provisional application No. 62/465,819, filed on Mar. 1, 2017, provisional application No. 62/465,797, filed on Mar. 1, 2017.

(51) Int. Cl.

| | |
|---|---|
| ***C12N 15/82*** | (2006.01) |
| ***A01H 17/00*** | (2006.01) |
| ***C05F 11/08*** | (2006.01) |
| ***A01N 63/30*** | (2020.01) |

(52) U.S. Cl.

CPC ............ *A01H 17/00* (2013.01); *A01N 63/30* (2020.01); *C05F 11/08* (2013.01); *C12N 15/8202* (2013.01); *C12N 15/8262* (2013.01)

(58) Field of Classification Search

None

See application file for complete search history.

(56) References Cited

U.S. PATENT DOCUMENTS

| | | | |
|---|---|---|---|
| 2,200,532 | A | 5/1940 | Sherman |
| 4,940,834 | A | 7/1990 | Hurley et al. |
| 5,041,290 | A | 8/1991 | Gindrat et al. |
| 5,113,619 | A | 5/1992 | Leps et al. |
| 5,229,291 | A | 7/1993 | Nielsen et al. |
| 5,292,507 | A | 3/1994 | Charley |
| 5,415,672 | A | 5/1995 | Fahey et al. |
| 5,730,973 | A | 3/1998 | Morales et al. |
| 5,919,447 | A | 7/1999 | Marrone et al. |
| 5,994,117 | A | 11/1999 | Bacon et al. |
| 6,072,107 | A | 6/2000 | Latch et al. |
| 6,077,505 | A | 6/2000 | Parke et al. |
| 6,337,431 | B1 | 1/2002 | Tricoli et al. |
| 6,495,133 | B1 | 12/2002 | Xue |
| 6,602,500 | B1 | 8/2003 | Kharbanda et al. |
| 6,681,186 | B1 | 1/2004 | Denisov et al. |
| 6,689,880 | B2 | 2/2004 | Chen et al. |
| 6,823,623 | B2 | 11/2004 | Minato et al. |
| 7,037,879 | B2 | 5/2006 | Imada et al. |
| 7,084,331 | B2 | 8/2006 | Isawa et al. |
| 7,335,816 | B2 | 2/2008 | Kraus et al. |
| 7,341,868 | B2 | 3/2008 | Chopade et al. |
| 7,485,451 | B2 | 2/2009 | VanderGheynst et al. |
| 7,555,990 | B2 | 7/2009 | Beaujot |
| 7,632,985 | B2 | 12/2009 | Malven et al. |
| 7,763,420 | B2 | 7/2010 | Stritzker et al. |
| 7,906,313 | B2 | 3/2011 | Henson et al. |
| 7,977,550 | B2 | 7/2011 | West et al. |
| 8,143,045 | B2 | 3/2012 | Miansnikov et al. |
| 8,455,198 | B2 | 6/2013 | Gao et al. |
| 8,455,395 | B2 | 6/2013 | Miller et al. |
| 8,465,963 | B2 | 6/2013 | Rolston et al. |
| 8,728,459 | B2 | 5/2014 | Isawa et al. |
| 8,975,489 | B2 | 3/2015 | Craven |
| 9,049,814 | B2 | 6/2015 | Marx et al. |
| 9,113,636 | B2 | 8/2015 | von Maltzahn et al. |
| 9,277,751 | B2 | 3/2016 | Sword |
| 9,288,995 | B2 | 3/2016 | von Maltzahn et al. |
| 9,295,263 | B2 | 3/2016 | von Maltzahn et al. |
| 9,364,005 | B2 | 6/2016 | Mitter et al. |
| 9,408,394 | B2 | 8/2016 | von Maltzahn et al. |
| 9,532,572 | B2 | 1/2017 | von Maltzahn et al. |

(Continued)

FOREIGN PATENT DOCUMENTS

| | | |
|---|---|---|
| CA | 1041788 | 11/1978 |
| CA | 1229497 | 11/1987 |

(Continued)

OTHER PUBLICATIONS

Wiebold et al. (Agriculture Experiment Station, College of Agriculture, Food & Natural Resources, University of Missouri, Special Report 589, pp. 1-124).*

PCT International Search Report and Written Opinion PCT/AU2018/050387, dated Apr. 27, 2018.

PCT International Search Report and Written Opinion for PCT/US2018/051467, dated Feb. 4, 2019, 22 pages.

United States Patent Office, Non-Final Office Action, U.S. Appl. No. 14/766,065, dated Oct. 27, 2017, 11 Pages.

United States Patent Office, Non-Final Office Action, U.S. Appl. No. 14/964,429, dated Aug. 9, 2016, 6 Pages.

(Continued)

*Primary Examiner* — Vinod Kumar

(74) *Attorney, Agent, or Firm* — Goodwin Procter LLP

(57) ABSTRACT

This invention relates to methods and materials for modulating the characteristics of a plant, said plant having been heterologously disposed to an endophyte or a plurality of endophytes, or derived from a plant reproductive element heterologously disposed to an endophyte or a plurality of endophytes.

10 Claims, 5 Drawing Sheets

Specification includes a Sequence Listing.

(56) References Cited

U.S. PATENT DOCUMENTS

| | | | |
|---|---|---|---|
| 9,532,573 | B2 | 1/2017 | von Maltzahn et al. |
| 9,545,111 | B2 | 1/2017 | Sword |
| 9,622,485 | B2 | 4/2017 | von Maltzahn et al. |
| 9,652,840 | B1 | 5/2017 | Shriver et al. |
| 9,687,001 | B2 | 6/2017 | Vujanovic et al. |
| 9,756,865 | B2 | 9/2017 | Sword |
| 10,058,101 | B2 | 8/2018 | von Maltzahn et al. |
| 10,076,120 | B2 | 9/2018 | von Maltzahn et al. |
| 10,104,862 | B2 | 10/2018 | Vujanovic et al. |
| 10,136,646 | B2 | 11/2018 | Von Maltzahn et al. |
| 10,212,912 | B2 | 2/2019 | Vujanovic et al. |
| 10,306,890 | B2 | 6/2019 | Mitter et al. |
| 10,362,787 | B2 | 7/2019 | Witter et al. |
| 10,499,652 | B2 | 12/2019 | von Maltzahn et al. |
| 10,499,653 | B2 | 12/2019 | von Maltzahn et al. |
| 10,499,654 | B2 | 12/2019 | von Maltzahn et al. |
| 10,667,523 | B2 | 6/2020 | Ambrose et al. |
| 11,151,379 | B2 | 10/2021 | Freitag et al. |
| 2002/0142917 | A1 | 10/2002 | Triplett et al. |
| 2005/0070435 | A1 | 3/2005 | Chopade et al. |
| 2005/0072047 | A1 | 4/2005 | Conkling et al. |
| 2006/0046246 | A1 | 3/2006 | Zeng et al. |
| 2006/0178269 | A1 | 8/2006 | Medina-Vega |
| 2006/0185207 | A1 | 8/2006 | Mitcheltree |
| 2007/0028318 | A1 | 2/2007 | Livore et al. |
| 2007/0055456 | A1 | 3/2007 | Raftery et al. |
| 2007/0142226 | A1 | 6/2007 | Franco |
| 2007/0292953 | A1 | 12/2007 | Mankin et al. |
| 2008/0229441 | A1 | 9/2008 | Young et al. |
| 2008/0289060 | A1 | 11/2008 | De Beuckeleer et al. |
| 2009/0155214 | A1 | 6/2009 | Isawa et al. |
| 2009/0300781 | A1 | 12/2009 | Bancroft et al. |
| 2010/0064392 | A1 | 3/2010 | Yang et al. |
| 2010/0095396 | A1 | 4/2010 | Voeste et al. |
| 2010/0205690 | A1 | 8/2010 | Biasing et al. |
| 2010/0227357 | A1 | 9/2010 | Redman et al. |
| 2011/0182862 | A1 | 7/2011 | Green et al. |
| 2011/0195406 | A1 | 8/2011 | Sorenson et al. |
| 2012/0108431 | A1 | 5/2012 | Williams et al. |
| 2012/0131696 | A1 | 5/2012 | Aayal et al. |
| 2012/0144533 | A1 | 6/2012 | Craven |
| 2012/0149571 | A1 | 6/2012 | Kloepper et al. |
| 2012/0178624 | A1 | 7/2012 | Kaminskyj et al. |
| 2012/0324599 | A1 | 12/2012 | Kerns et al. |
| 2013/0031673 | A1 | 1/2013 | Grandlic et al. |
| 2013/0071425 | A1 | 3/2013 | Vidal et al. |
| 2013/0079225 | A1 | 3/2013 | Smith et al. |
| 2013/0150240 | A1 | 6/2013 | Newman et al. |
| 2013/0233501 | A1 | 9/2013 | Van Zyl et al. |
| 2014/0020136 | A1 | 1/2014 | Van Der Wolf et al. |
| 2014/0109249 | A1 | 4/2014 | Turner et al. |
| 2014/0115731 | A1 | 4/2014 | Turner et al. |
| 2014/0134629 | A1 | 5/2014 | Turner et al. |
| 2014/0147425 | A1 | 5/2014 | Henn et al. |
| 2014/0342905 | A1 | 11/2014 | Bullis et al. |
| 2015/0020239 | A1 | 1/2015 | von Maltzahn et al. |
| 2015/0033420 | A1 | 1/2015 | Rodriguez et al. |
| 2015/0126365 | A1 | 5/2015 | Sword |
| 2015/0230478 | A1 | 8/2015 | Vujanovic et al. |
| 2015/0242970 | A1 | 8/2015 | Avey et al. |
| 2015/0320050 | A1 | 11/2015 | von Maltzahn et al. |
| 2015/0335029 | A1 | 11/2015 | Mitter et al. |
| 2015/0366217 | A1 | 12/2015 | Vujanovic et al. |
| 2015/0368607 | A1 | 12/2015 | Arnold et al. |
| 2015/0370935 | A1 | 12/2015 | Starr |
| 2015/0373993 | A1 | 12/2015 | von Maltzahn et al. |
| 2016/0021891 | A1 | 1/2016 | von Maltzahn et al. |
| 2016/0150796 | A1 | 6/2016 | von Maltzahn et al. |
| 2016/0174570 | A1 | 6/2016 | Vujanovic et al. |
| 2016/0192662 | A1 | 7/2016 | Sword |
| 2016/0205947 | A1 | 7/2016 | Sword |
| 2016/0235074 | A1 | 8/2016 | von Maltzahn et al. |
| 2016/0255844 | A1 | 9/2016 | Mitter et al. |
| 2016/0260021 | A1 | 9/2016 | Marek |
| 2016/0286821 | A1 | 10/2016 | Sword |
| 2016/0290918 | A1 | 10/2016 | Xu et al. |
| 2016/0316760 | A1 | 11/2016 | Ambrose et al. |
| 2016/0316763 | A1 | 11/2016 | Sword |
| 2016/0330976 | A1 | 11/2016 | Mitter et al. |
| 2016/0338360 | A1 | 11/2016 | Mitter et al. |
| 2016/0366892 | A1 | 12/2016 | Ambrose et al. |
| 2017/0020138 | A1 | 1/2017 | von Maltzahn et al. |
| 2017/0064361 | A1 | 3/2017 | Pinca, IV et al. |
| 2017/0161560 | A1 | 6/2017 | Itzhaky et al. |
| 2017/0164619 | A1 | 6/2017 | von Maltzahn et al. |
| 2017/0164620 | A1 | 6/2017 | von Maltzahn et al. |
| 2017/0215358 | A1 | 8/2017 | Franco et al. |
| 2017/0223967 | A1 | 8/2017 | Mitter et al. |
| 2018/0020677 | A1 | 1/2018 | Ambrose et al. |
| 2018/0092365 | A1 | 4/2018 | Sword |
| 2018/0153174 | A1 | 6/2018 | Riley et al. |
| 2018/0177196 | A1* | 6/2018 | Sword .................... C05F 11/08 |
| 2018/0189564 | A1 | 7/2018 | Freitag et al. |
| 2018/0213800 | A1 | 8/2018 | Djonovic et al. |
| 2018/0249716 | A1 | 9/2018 | Riley |
| 2018/0251776 | A1 | 9/2018 | Riley |
| 2019/0130999 | A1 | 5/2019 | Oppenheim et al. |
| 2021/0372997 | A1 | 12/2021 | Von Maltzahn et al. |

FOREIGN PATENT DOCUMENTS

| | | | |
|---|---|---|---|
| CA | 2562175 | | 1/2013 |
| CA | 2916678 | A1 | 12/2014 |
| CA | 2960032 | A1 | 3/2015 |
| CA | 2935218 | A1 | 7/2015 |
| CA | 2953466 | A1 | 12/2015 |
| CA | 2953697 | A1 | 12/2015 |
| CN | 1604732 | | 4/2005 |
| CN | 1948459 | A | 4/2007 |
| CN | 101311262 | A | 11/2008 |
| CN | 101423810 | A | 5/2009 |
| CN | 101570738 | | 11/2009 |
| CN | 101693881 | A | 4/2010 |
| CN | 102123596 | A | 7/2011 |
| CN | 102168022 | A | 8/2011 |
| CN | 102352327 | A | 2/2012 |
| CN | 102010835 | B | 4/2012 |
| CN | 102533601 | B | 10/2013 |
| CN | 103642725 | A | 3/2014 |
| CN | 103865837 | | 6/2014 |
| CN | 104250616 | A | 12/2014 |
| CN | 104560742 | A | 1/2015 |
| CN | 104388356 | A | 3/2015 |
| CN | 105886428 | | 8/2016 |
| CN | 106434493 | | 2/2017 |
| EP | 0192342 | | 8/1986 |
| EP | 0223662 | | 5/1987 |
| EP | 0378000 | | 7/1990 |
| EP | 0494802 | | 7/1992 |
| EP | 0818135 | | 1/1998 |
| EP | 1621632 | | 2/2006 |
| EP | 1935245 | | 6/2008 |
| EP | 2676536 | | 12/2013 |
| EP | 3041338 | | 7/2016 |
| EP | 3659414 | | 6/2020 |
| JP | 2003300804 | A | 10/2003 |
| JP | 2009/072168 | | 4/2009 |
| KR | 20050039979 | | 5/2005 |
| KR | 20100114806 | A | 10/2010 |
| KR | 101066283 | | 9/2011 |
| KR | 101091151 | | 12/2011 |
| KR | 20130023491 | | 3/2013 |
| RU | 2043028 | | 10/1995 |
| WO | WO 1988/009114 | | 1/1988 |
| WO | WO 1994/016076 | | 7/1994 |
| WO | 98/35017 | | 8/1998 |
| WO | 99/59412 | | 11/1999 |
| WO | WO 2000/029607 | | 5/2000 |
| WO | WO 2001/083697 | | 11/2001 |
| WO | WO 2001/083818 | | 11/2001 |
| WO | WO 2002/065836 | | 8/2002 |
| WO | WO 2004/046357 | | 6/2004 |
| WO | WO 2005/003328 | | 1/2005 |
| WO | WO 2007/021200 | | 2/2007 |

(56) References Cited

FOREIGN PATENT DOCUMENTS

| | | |
|---|---|---|
| WO | WO 2007/107000 | 9/2007 |
| WO | WO 2008/103422 | 8/2008 |
| WO | WO 2009/012480 A2 | 1/2009 |
| WO | WO 2009/078710 A1 | 6/2009 |
| WO | WO 2009/126473 A1 | 10/2009 |
| WO | WO 2010/109436 | 9/2010 |
| WO | WO 2010/115156 | 10/2010 |
| WO | 2011/011627 A1 | 1/2011 |
| WO | WO 2011/001127 | 1/2011 |
| WO | WO 2011/082455 | 7/2011 |
| WO | WO 2011/112781 | 9/2011 |
| WO | WO 2011/117351 | 9/2011 |
| WO | 2012/016140 | 2/2012 |
| WO | WO 2012/034996 | 3/2012 |
| WO | WO 2013/016361 | 1/2013 |
| WO | WO 2013/029112 | 3/2013 |
| WO | WO 2013/090628 | 6/2013 |
| WO | WO 2013/122473 | 8/2013 |
| WO | WO 2013/177615 | 12/2013 |
| WO | WO 2013/190082 | 12/2013 |
| WO | WO 2014/046553 | 3/2014 |
| WO | WO 2014/082950 | 6/2014 |
| WO | WO 2014/121366 | 8/2014 |
| WO | WO 2014/206953 | 12/2014 |
| WO | WO 2014/210372 | 12/2014 |
| WO | WO 2015/035099 | 3/2015 |
| WO | WO 2015/069938 | 5/2015 |
| WO | WO 2015/100431 | 7/2015 |
| WO | WO 2015/100432 | 7/2015 |
| WO | 2015/114552 | 8/2015 |
| WO | WO 2015/192172 | 12/2015 |
| WO | WO 2015/200852 | 12/2015 |
| WO | WO 2015/200902 | 12/2015 |
| WO | WO 2016/090212 | 6/2016 |
| WO | WO 2016/109758 | 7/2016 |
| WO | WO 2016/179046 | 11/2016 |
| WO | WO 2016/179047 | 11/2016 |
| WO | WO 2016/200987 | 12/2016 |
| WO | 2018094027 | 5/2018 |
| WO | WO 2018/102733 | 6/2018 |
| WO | WO 2018/160244 | 9/2018 |
| WO | WO 2018/160245 | 9/2018 |
| WO | 2019/046909 | 3/2019 |
| WO | WO 2016/057991 | 3/2019 |
| WO | 2019084380 | 5/2019 |
| WO | 2019113468 | 6/2019 |

OTHER PUBLICATIONS

United States Patent Office, Final Office Action, U.S. Appl. No. 14/964,429, dated May 31, 2017, 9 Pages.

United States Patent Office, Non-Final Office Action, U.S. Appl. No. 15/212,038, dated Sep. 21, 2016, 10 Pages.

United States Patent Office, Non-Final Office Action, U.S. Appl. No. 15/063,350, dated Nov. 10, 2016, 18 Pages.

United States Patent Office, Final Office Action, U.S. Appl. No. 14/614,193, dated Dec. 22, 2016, 13 Pages.

United States Patent Office, Final Office Action, U.S. Appl. No. 14/614,193, dated Jul. 18, 2017, 14 Pages.

United States Patent Office, Final Office Action, U.S. Appl. No. 14/614,193, dated May 3, 2018, 10 Pages.

United States Patent Office, Non-Final Office Action, U.S. Appl. No. 15/107,973, dated Apr. 10, 2017, 39 Pages.

United States Patent Office, Final Office Action, U.S. Appl. No. 15/107,973, dated Jan. 26, 2018, 20 Pages.

United States Patent Office, Final Office Action, U.S. Appl. No. 14/410,537, dated May 5, 2017, 9 Pages.

United States Patent Office, Non-Final Office Action, U.S. Appl. No. 15/034,862, dated May 19, 2017, 8 Pages.

United States Patent Office, Final Office Action, U.S. Appl. No. 15/034,862, dated Jan. 12, 2018, 14 Pages.

United States Patent Office, Non-Final Office Action, U.S. Appl. No. 15/436,592, dated Aug. 30, 2017, 17 Pages.

United States Patent Office, Non-Final Office Action, U.S. Appl. No. 15/436,609, dated Aug. 30, 2017, 21 Pages.

United States Patent Office, Non-Final Office Action, U.S. Appl. No. 14/916,514, dated Sep. 20, 2017, 31 Pages.

United States Patent Office, Non-Final Office Action, U.S. Appl. No. 15/143,398, dated Sep. 22, 2017, 17 Pages.

United States Patent Office, Non-Final Office Action, U.S. Appl. No. 15/143,394, dated Sep. 25, 2017, 15 Pages.

United States Patent Office, Non-Final Office Action, U.S. Appl. No. 15/107,965, dated Jun. 21, 2018, 27 Pages.

Abello, J., et al., "Agrobacterium-mediated transformation of the endophytic fungus *Acremonium implicatum* associated with *Brachiaria* grasses", Mycological Research, pp. 407-413, vol. 112, Pt 3.

Al-Askar AA, "Microbiological studies on the in vitro inhibitory effect of Streptomyces collinus albescens against some phytopathogenic fungi", African Journal of Microbiology Research, 2012, 6: 3277-3283 & GenBank Accession No. AB184101, May 20, 2008.

Ardakani, M.R. et al., "Absorption of N, P, K through triple inoculation of wheat (*Triticum aestivum* L.) by Azospirillum brasilense, *Streptomyces* sp., Glomus intraradices and manure application," Physiol Mol Biol Plants, 2011, vol. 17, No. 2, pp. 181-192.

Bandara, W.M.M.S., et al., "Interactions among endophytic bacteria and fungi: effects and potentials", Journal of Biosciences, Dec. 2006, vol. 31, No. 5, pp. 645-650.

Barnett, S., et al., "Selection of microbes for control of Rhizoctonia root rot on wheat using a high throughput pathosystem", Biological Control, Jul. 6, 2017, 113: 45-57.

Bashan, Yoav Ed, et al., "Inoculants of plant growth-promoting bacteria for use in agriculture," Biotechnology Advances, Elsevier Publishing, Barking, GB, vol. 16, No. 4, Jul. 1, 1998, pp. 729-770, XP004123985.

Bashan, Yoav E., et al., "Alginate Beads as Synthetic Inoculant Carriers for Slow Release of Bacteria that Affect Plant Growth," Applied and Environmental Microbiology, pp. 1089-1098, May 1986.

Bragantia, et al: "Identificaqao E Avaliaqao De Rizobacterias Isoladas De Raizes De Milho," Jan. 1, 2010, pp. 905-911, Retrieved from the Internet: URL:http://www.scielo.br/pdf/brag/v69n4/v69n4a17.pdf (With English Abstract).

Chenhua Li , et al., "Change in deep soil microbial communities due to long-term fertilization," Soil Biology and Biochemistry, vol. 75, Mar. 5, 2014, pp. 264-272, XP055530941.

Cheow, W.S., et al., "Biofilm-like Lactobacillus rhamnosus Probiotices Encapsulated in Algiinate and Carrageenan Microcapsules Exhibiting Enhanced Thermotolerance and Freeze-drying Resistance," Biomacromolecules 2013, vol. 14(9):3214-3222.

De Medeiros, L., et al., "Evaluation of Herbicidal Potential of Depsides from Cladosporium uredinicola an Endophytic Fungus found in Guava Fruit," J. Braz. Chern. Soc., 2012, vol. 23, No. 8, p. 1551-1557.

De Santi, M. et al., "A combined morphologic and molecular approach for characterizing fungal microflora from a traditional Italian cheese (Fossa cheese)," Inter. Dairy J., 2010, vol. 10, No. 7, pp. 465-471.

Fatima Z et al., "Antifungal activity of plant growth-promoting rhizobacteria isolates against Rhizoctonia solani in wheat", African Journal of Biotechnology, 2009, 8: 219-225.

GenBank Accession No. KY643705, Feb. 27, 2017.

GenBank Accession No. KF951483, Jan. 5, 2014.

GenBank Accession No. KJ152029, May 6, 2015.

GenBank Accession No. KJ162248, Apr. 8, 2014.

NCBI, GenBank Accession No. XP_002568042, Aug. 14, 2009, 4 Pages, Berg, V.D., et al., "Genome sequencing and analysis of the filamentous fungus," Nat. Biotechnol. 26 (10), 1161-1168 (2008).

Goudjal, Y., et al., "Biocontrol of Rhizoctonia solanidamping-off and promotion of tomato plant growth by endophytic actinomycetes isolated from native plants of Algerian Sahara", Microbiological Research, 2014, vol. 169, No. 1, pp. 59-65.

Guo, X., et al., "Red Soils Harbor Diverse Culturable Actinomycetes That Are Promising Sources of Novel Secondary Metabolites", Applied and Environmental Microbiology, Feb. 27, 2015, vol. 81, No. 9, pp. 3086-3103.

(56) References Cited

OTHER PUBLICATIONS

Hain, T., et al., "Chitinolytic transgenes from Streptomyces albidoflavus as phytochemicals defences against herbivorous insects, use in transgenic plants and effect in plant development", International Journal of Systematic Bacteriology, Jan. 1997, vol. 47, No. 1, pp. 202-206.
Hanshew, A., et al., "Characterization of Actinobacteria Associated with Three Ant-Plant Mutualisms", Microbial Ecology, Aug. 6, 2017, vol. 69, No. 1, pp. 192-203.
Hjort, K., et al., "Chitinase genes revealed and compared in bacterial isolates, DNA extracts and a metagenomic library from a phytopathogen-suppressive soil", FEMS Microbiology Ecology, Feb. 2010, vol. 71, No. 2, pp. 197-207.
Iverson, C., et al., "The taxonomy of Enterobacter sakazakii: proposal of a new genus *Cronobacter* gen. nov. and descriptions of *Cronobacter sakazakii* comb. nov. *Cronobacter sakazakii* subsp. *sakazakii,* comb, nov., *Cronobacter sakazakii* subsp. *malonaticus* subsp. nov., *Cronobacter turicensis* sp. nov., *Cronobacter muytjensii* sp. nov., *Cronobacter dublinensis* sp. nov. and *Cronobacter* genomospecies I", BMC Evolutionary Biology 2007, Apr. 17, 2017, 11 pages.
Joe, M.M. et al., "Development of alginate-based aggregate inoculants of *Methylobacterium* sp. and Azospirillum brasilense tested under in vitro conditions to promote plant growth," Journal of Applied Microbiology 2013, 116(2):408-423, XP055225426, Nov. 22, 2013.
Li, M., et al., "ATP Modulates the Growth of Specific Microbial Strains", Current Microbiology, May 30, 2010, vol. 62, No. 1, pp. 84-89.
Manoharan, M. J. et. Al., "Survival of flocculated cells in alginate and its inoculatin effect on growth and yield of maize under water deficit conditions," EP J of Siil Biology, Gauthier-Villars, Montrouge, FR, vol. 50, Mar. 7, 2012, pp. 198-206, XP028421147.
Murali, Gopal, et al., "Microbiome Selection Could Spur Next-Generation Plant Breeding Strategies," Frontiers in Microbiology, vol. 7, Dec. 7, 2016, XP055531064.
Ogbo, F., et al., "Some Characteristics of a Plant Growth Promoting iEnterobacter/isp. Isolated from the Roots of Maize", Advances in Microbiology, Jan. 1, 2012, vol. 02, No. 03, pp. 368-374.
Orakçi GE et al, "Selection of antagonistic actinomycete isolates as biocontrol agents against root-rot fungi", Fresenius Environmental Bulletin, 2010, 19: 417-424 & GenBank Accession No. GQ475299, Oct. 5, 2009.
Partida-Martinez, L.P., et al., "Endosymbiont-Dependent Host Reproduction Maintains Bacterial-Fungal Mutualism", Current Biology, May 1, 2007, vol. 17, No. 9, pp. 773-777.
"Sequence Alignment of JQ047949 with Instant SEQ ID No. 2," Search conducted on Jan. 2, 2019. 2 pages.
Sharma et al., "Detection and identification of bacteria intimately associated with fungi of the order Sebacinales", Cellular Microbiology, Aug. 5, 2008, pp. 2235-2246, vol. 10, No. 11.
Wang, L. et al. Application of Bioorganic Fertilizer Significantly Increased Apple Yields and Shaped Bacterial Community Structure in Orchard Soil.
Whelehan, et al., "Microencapsulation using vibrating technology," Journal of Microencapsulation 2011, vol. 28(8), pp. 669-688.
Yashiro et al., "Effect of Streptomycin Treatment on Bacterial Community Structure in the Apple Phyllosphere," PLOS ONE, May 21, 2012, vol. 7, No. 5, 10 pages.
Zhao, Jun, et al., "Effects of organic-inorganic compound fertilizer with reduced chemical fertilizer application on crop yields, soil biological activity and bacterial community structure in a rice-wheat cropping system," Applied Soil Ecology, vol. 99, Nov. 28, 2015, pp. 1-12, XP055530937.
Hamayun, M., et al., "Gibberellin production and plant growth promotion from pure cultures of *Cladosporium* sp. MH-6 isolated from cucumber (*Cucumis sativus* L.)", Mycologia, 102 (5), 2010, pp. 989-995.
Shupeng, T., et al. "Advances in Study of Interactions between Mycorrhizal Fungi and Bacteria", Journal of Qingdao Agricultural University (Natural Science Edition), vol. 30, Issue 4, pp. 240-246, Dec. 31, 2013.
Kim, S., et al., "Physiological and proteomic analyses of Korean F1 maize (*Zea mays* L.) hybrids under water-deficit stress during flowering", Appl. Biol. Chern. (2019) 62:32.
Halligan, B., et al., "Cloning of the murine cDNA encoding VDJP, a protein homologous to the large subunit of replication factor C and bacterial DNA ligases", GENE (1995) 217-222.
Arend, J., et al., "Hydroquinone: O-glucosytransferase from cultivated Rauvolfia cells: enrichment and partial amino acid sequences", Phytochemistry (2000) 53:187-193.
Enchev, R., et al., "Protein neddylation: beyond cullin-RING ligases", (Nature Reviews: Molecular Cell Biology (2015) 16:30-44.
Bais, H., et al., "The Role of Root Exudates in Rhizophere Interactions with Plants and Other Organisms", Annual Review. Plant Biol. (2006) 57:233-266.
Goepfert, S., et al., "Molecular Identification and Characterization of the *Arabidopsis* D3,5, D2,4-Dienoyl-Coenzyme A Isomerase, a Peroxisomal Enzyme Participating in the b-Oxidation Cycle of Unsaturated Fatty Acids1", Plant Physiology (2005) 138:1947-1956.
Thomas, P., et al: "Endophytic Bacteria Associated with Growing Shoot Tips of Banana (*Musa* sp.) cv. Grand Naine and the Affinity of Endophytes to the Host", Microbial Ecology, Springer-Verlag, NE, vol. 58, No. 4, Jul. 25, 2009 (Jul. 25, 2009), pp. 952-964, XP019757395, ISSN: 1432-184X, DOI: 10.1007 /S00248-009-9559-Z.
Database Geneseq [Online] Sep. 30, 2010 (Sep. 30, 2010), "Cellulomonas fermentans 16s rRNA gene SEQ ID:39", retrieved from EBI accession No. GSN:AWL84299 Database accession No. AWL84299; & JP 2009 072168 A (Univ of Occupational & Environ) Apr. 9, 2009 (Apr. 9, 2009).
European Patent Office, Partial European Search Report, European Patent Application No. 20171870.7, dated Nov. 20, 2020, 18 Pages.
European Patent Office, European Search Report, European Patent Application No. 20171870.7, dated Mar. 1, 2021, 15 Pages.
GenBank Accession NR_041978, dated Aug. 8, 2011. (Year: 2011).
GenBank Accession AF394537, dated Jul. 2, 2002. (Year: 2002).
Andreolli, M., et al., "Endophytic Burkholderia fungorum DBT1 can improve phytoremediation efficiency of polycyclic aromatic hyrocarbons", Chemosphere, Pergamon Press, Oxford, GB, vol. 92, No. 6, May 21, 2013, pp. 688-694.
Extended European Search Report for EP 20202875.9, received on Apr. 19, 2021, 16 pages.
Douglas, G., et al., "PICRUSt2 for prediction of metagenome functions", Nature Biotechnology, vol. 38, No. 6, Jun. 1, 2020, pp. 685-688.
Antony-Badu, S., et al., "Multiple *Streptomyces* species with distinct secondary metabolomes have identical 16S rRNA gene sequences." Scientific Reports 7.1, Sep. 2017, No. 7, 11089, pp. 1-8.
Artursson, V., et al., "Interactions between arbuscular mycorrhizal fungi and bacteria and their potential for stimulating plant growth", Environmental Microbiology, vol. 8, No. 1, Jan. 1, 2006, pp. 1-10.
Azcon, R., et al., "Selective interactions between different species of mycorrhizal fungi and Rhizobium meliloti strains, and their effects on growth, N2-fixation (15N) and nutrition of Medicago sativa L," New PhytoL., 1991, vol. 117, pp. 399-404.
Bing, LA, et al., "Suppression of *Ostrinia nubilalis* (Hübner) (Lepidoptera: Pyralidae) by endophytic *Beauveria bassiana* (Balsamo) Vuillemin", Environmental Entomol, Entomological Society of America, College Park, MD, US, vol. 20, Jan. 1, 1991, pp. 1207-1211.
Compant, S., et al., "Endophytic colonization of Vitis vinfera L. by Burkholderia phytofirmans strain PsJN: from the rhizosphere to inflorescence tissues," FEMS Microbiol Ecol, 2008, pp. 84-93, vol. 63.
NCBI GenBank: Accession No. JX880250.1, "Enterobacteriaceae bacterium Clerol 16S ribosomal RNA gene, partial sequence," NIH, Jun. 24, 2015, 2 Pages, can be retreived at <URL:https://www.ncbi.nlm.nih.gov/nucleotide/JX880250.1?report=genbank&log$=nuclalign&blast_rank=80&RID=KWUPBV08015>.
NCBI, GenBank Accession No. KX641980.1, Jul. 29, 2017, Scott, M., et al., "*Dothideomycetes* sp. isolate FT14-6 internal transcribed spacer 1, partial sequence; 5.8S ribosomal RNA gene and internal transcribed spacer 2, complete sequence; and large subunit ribo-

(56) References Cited

OTHER PUBLICATIONS somal RNA gene, partial sequence," 2 Pages, Can be retrieved at <URL:https://www.ncbi.nlm.nih.gov/nuccore/KX641980>.
Database EMBL [Online] Oct. 1, 2001, 2 Pages, "Setosphaeria monoceras 28S ribosomal RNA gene, partial sequence," XP002777918, retrieved from EBI accession No. EM_STD:AY016368 Database accession No. AY016368 sequence.
Fox, G., et al., "How close is close: 16S rRNA sequence identity may not be sufficient to guarantee species identity." International Journal of Systematic and Evolutionary Microbiology 42.1, 1992, pp. 166-170.
Hubbard, M., et al., 2011. "Agricultural Potential of Fungal Endophytes of Grasses, Cereals and Wheat," In: Wheat: Genetics, Crops and Food Production. Nova Science Publishers Hauppauge, NY, USA. pp. 333-345.
Impullitti, A.E., et al., "Fungal endophyte diversity in soybean", Journal of Applied Microbiolog, vol. 114, No. 5, May 1, 2013, pp. 1500-1506.
Kanbar, A., et al., "Relationship between Root and Yield Morphological Characters in Rainfed Low Land Rice (*Oryza sativa* L.)," Cereal Research Communications, 2009, vol. 37, No. 2, pp. 261-268.
Nassar, A., et al., "Promotion of plant growth by an auxin-producing isolate of the yeast *Williopsis saturnus* endophytic in maize (*Zea mays* L.) roots", Biology and Fertility of Soils; Cooperating Journal of International Society of Soil Science, Springer, Berlin, DE, vol. 42, No. 2, Nov. 1, 2005, pp. 97-108.
O'Hanlon, K., et al., "Exploring the potential of symbiotic fungal endophytes in cereal disease suppression", Biological Control, vol. 63, No. 2, Sep. 5, 2012, pp. 69-78.
Sarkar, S., et al., "New report of additional enterobacterial species causing wilt in West Bengal, India," Canadian Journal of Microbiology, 2015, vol. 61, No. 7, pp. 477-486.
Vujanovic, V., et al.: "Fungal communities associated with durum wheat production system: A characterization by growth stage, plant organ and preceding crop", Crop Protection, Elsevier Science, GB, vol. 37, Feb. 19, 2012, pp. 26-34.
Zhang, Y., et al., BcGsl, a glycoprotein from Botrytis cinerea, elicits defence response and improves disease resistance in host plants. Biochemical and biophysical research communications, Biochemical and Biophysical Research Communications, 2015, vol. 457, No. 4, pp. 627-634.
Zhang, W., et al., Host range of Exserohilum monoceras, a potential bioherbicide for the control of *Echinochloa* species, Canadian Journal of Botany/ Journal Canadien De Botan, National Research Council, Ottawa, CA, vol. 75, Jan. 1, 1997, pp. 685-692.
NCBI GenBank: Accession No. XP55670271, "*Enterobacter* sp. MLB05 16S ribosomal RNA gene, partial sequence—Nucleotide", Jun. 9, 2012, 1 Page, can be retreived at URL:https://www.ncbi.nlm.nih.gov/nuccore/JQ765415.1/.
NCBI GenBank: Accession No. XP55670274, "*Enterobacter* sp. CR 6-3 16S ribosomal RNA gene, partial sequence—Nucleotide", Mar. 27, 2013, 1 Page, can be retreived at URL:https://www.ncbi.nlm.nih.gov/nuccore/KC355340.
NCBI GenBank: Accession No. XP55670279, "Uncultured bacterium clone bb2s4 16S ribosomal RNA gene, partial seque—Nucleotide", May 6, 2005, 1 Page, can be retreived at URL:https://www.ncbi.nlm.nih.gov/nuccore/DQ068880.
Bently, S.D., et al., "Complete genome sequence of the model actinomycete Streptomyces coelicolor A3(2)," Nature. May 9, 2002;417(6885):141-7. (Year: 2002).
Gabor, J., et al., "Mycorrhizal fungi effects on nutrient composition and yield of soybean seeds," Journal of Plant Nutrition, 20:4-5, 581-591, 1997.
Gopalakrishnan, S. et al., "Plant growth-promoting activities of *Streptomyces* spp. In sorghum and rice", SpringerPlus, 2/1/574, pp. 1-8, http://www.springerplus.eom/content/2/1/574, 2013.
Groppe, K., et al., "Interaction between the endophytic fungus *Epichloe bromicola* and the grass *Bromus erectus:* effects of endophyte infection, fungal concentration and environment on grass growth and flowering," Mol Ecol., 8:1827-1835, 1999.
Hubbard, M., "Fungal Endophytes that Confer Heat and Drought Tolerance to Wheat," Doctoral dissertation, University of Saskatchewan, 2012.
Ikeda, H., et al., "Complete genome sequence and comparative analysis of the industrial microorganism *Streptomyces avermitilis,*" Nat Biotechnol. May 2003;21 (5) :526-31. Epub Apr. 14, 2003. (Year: 2003).
Langille, M., et al., "Predictive functional profiling of microbial communities, using 16S rRNA marker gene sequences", Nature Biotechnology, vol. 31, No. 9, Sep. 2013, 11 pages.
Lee, J., et al., "*Streptomyces koyangensis* sp. nov., a novel actinomycete that produces 4-phenyl-3-butenoic acid," Int J Syst Evol Microbial. Jan. 2005;55(Pt 1):257-62. (Year: 2005).
Pacovsky, R., "Carbohydrate, protein and amino acid status of Glycine-Glomus-Bradyrhizobium symbioses," Physiologia Pantarium; 75:346-354, 1989).
Wiebold, M., et al., "Agriculture Experiment Station, College of Agriculture, Food & Natural Resources, University of Missouri, Special Report 589, pp. 1-124)."
PCT International Search Report and Written Opinion for PCT/AU2018/050387, dated Jul. 12, 2018, 8 pages.
PCT International Search Report and Written Opinionfor PCT/US2018/051467, dated Mar. 25, 2019 26 pages.
Invitation to Pay Additional Fees, PCT Application No. PCT/CA2013/000091, Mar. 27, 2013, 2 Pages.
International Search Report and Written Opinion for PCT/EP2013/062976, dated Dec. 22, 2014, 9 Pages.
International Search Report and Written Opinion, Application No. PCT/US2014/054160, dated Dec. 9, 2014, 21 Pages.
Invitation to Pay Additional Fees, PCT Application No. PCT/US2014/064411, dated Feb. 5, 2015, 2 Pages.
International Search Report and Written Opinion, International Application No. PCT/US2014/064411, dated Mar. 27, 2015, 15 Pages.
International Search Report and Written Opinion, International Application No. PCT/US2014/072399, dated Jun. 26, 2015, 22 Pages.
Invitation to Pay Additional Fees, PCT Application No. PCT/US2014/072400, dated Apr. 16, 2015, 6 Pages.
International Search Report and Written Opinion, Application No. PCT/US2014/072400, dated Jul. 8, 2015, 38 Pages.
Invitation to Pay Additional Fees, PCT Application No. PCT/US2015/038110, dated Sep. 22, 2015, 8 Pages.
Result 11 from a search in the GenEmbl database, GenEmbl Record No. EU 977189, Smith et al., "Bioactive endophytes warrant intensified exploration and conservation," PLoS ONE 3(8):E3052, 2008.
Result 3 from a search in the GenEmbl database, GenEmbl Record No. KF011597, Paenibacillus strain No. HA13, Park et al., "Isolation and characterization of humic substances-degrading bacteria from the subarctic Alaska grasslands," J Basic Microbiol, 2013.
Chaves, J., et al., "Identification and Phylogeny of Streptomyces Based on Gene Sequences", Research Journal of Microbiology, vol. 13, No. 1, Dec. 15, 2017, pp. 13-20, XP055675917.
Girard, G., et al., "A novel taxonomic marker that discriminates between morphologically complex actinomycetes", Open Biology, vol. 3, No. 10, Oct. 2013, p. 130073,XP055675916.
Guo, Y., et al. "A multi locus phylogeny of the Streptomyces griseus 16S rRNA gene clade: use of multilocus sequence analysis for streptomycete systematics", International Journal of Systematic and Evolutionary Microbiology, vol. 58, No. 1, 2008, pp. 149-159, XP055675936.
PCT International Search Report and Written Opinion for PCT/US2017/064292, dated May 11, 2018, 20 Pages.
Invitation to Pay Additional Fees, PCT Application No. PCT/US2015/038187, dated Oct. 14, 2015, 5 Pages.
PCT International Search Report and Wlitten Opinion, PCT Application No. PCT/US2015/068206, dated Jun. 27, 2016, 20 Pages.
PCT International Search Report and Wrrtten Opinion, PCT Application No. PCT/US2016/030292, dated Aug. 12, 2016, 20 Pages.

(56) References Cited

OTHER PUBLICATIONS

PCT International Search Report and Wrrtten Opinion, PCT Application No. PCT/US2016/030293, dated Aug. 11, 2016, 23 Pages.
PCT International Search Report and Wlitten Opinion, PCT Application No. PCT/US2016/036504, dated Nov. 4, 2016, 18 Pages.
Soe, K.M, et al, "Evaluation of effective Myanmar Bradyrhizobium strains isolated from Myanmar soybean and effects of coinoculation with Streptomyces griseoglavus P4 for nitrogen fixation", Soil science and plant nutrition 59.3 (2013): 361-370 (Year: 2013).
Ngom, A et al., "A novel symbiotic nitrogen-fixing member of the Ochrobactrum clade isolated from root nodues of Acacia mangium". J. Gen. Appl. Microbiol. (2004) 50: 17-27.
Trujillo, M.E et al., "Nodulation of Lupinus albus by strins of *Ochrobactrum lupini* sp. nov." Appl. Environ Microbiol Mar. 2005; 71(3): 1318-1327.
Bal, H.B et al., "Isolation of ACC deaminase producting PGPR from rice rhizosphere and evaluating their plant growth promoting activity under salt stress" Plant Soil (2013) 366: 93-105 doi: 10/1007/s11104-012-1402-5.
Chakraborty et al., "Evaluation of Ochrobactrum anthropi TRS-2 and its talcbased formulation for enhancement of growth of tea plants and management of brown root rot disease." Journal of Applied Microbiology, 2009, 107(2):625-634 DOI:10.1111/j.1365-2672.2009.04242.x <https://doi.org/10.1111/j.1365-2672.2009.04242.x.
Sulistiyani, et al., "Population and Diversity of Endophytic Bacteria Associated with Medicinal Plan Curumma zedoaria", Microbiology Indonesia 8.2 (2014):4.
Bevivino, A., et al., "Characerization of free-living maize rhizosphere populatin of Burkholderia cepacia: effect of seed treatment on disease suppresssion and growth promotion of maize", FEMS Microbiology Ecology 27 (1998) 225-237.
Ciccillo, F., et al., Effects of two different application methods of Burkholderia ambifaria MCI 7 on plant growth and rhizospheric bacterial diversity.
Estrada, P., et al., "A N2-fixing endophytic *Burkholderia* sp. associated with maize plants culitvated in Mexico", Canadian Journal of Microbiology (2002), vol. 48(4), pp. 528-536.
Sharma, V.K., et al., "Enhancement of verticillium wilt resistance in tomato transplants by in vitro co-culture of seedlings with a plant growth promoting rhizobacterium (*Pseudomonas* sp. strain PsJN)", Canadian Journal of Microbiology (1998), vol. 44(6), pp. 285-294.
Grady, E., et al., "Current knowledge and perspectives of Paenibacillus: a review" Microb Cell Fact (2016) 15:203.
Li, J., et al., "Antitumour and antimicrobial activities of endophytic stretomycetes from pharmaceutical plants in rainforest", Lett Appl Microbiol. Dec. 2008; 47(6): 574-80. (Year: 2008).
PCT Invitation to Pay Additional Fees, PCT Application No. PCT/CA2013/000091, dated Mar. 27, 2013, 2 Pages.
PCT International Search Report and Written Opinion for PCT/CA2013/000091, dated Sep. 20, 2013, 17 Pages.
PCT International Search Report and Written Opinion for PCT/EP2013/062976, dated Dec. 22, 2014, 9 Pages.
PCT International Search Report, Application No. PCT/US2014/044427, dated Dec. 3, 2014, 9 Pages.
PCT International Search Report and Written Opinion, Application No. PCT/US2014/054160, dated Dec. 9, 2014, 21 Pages.
PCT Invitation to Pay Additional Fees, PCT Application No. PCT/US2014/064411, dated Feb. 5, 2015, 2 Pages.
PCT International Search Report and Written Opinion, International Application No. PCT/US2014/064411, dated Mar. 27, 2015, 15 Pages.
PCT Invitation to Pay Additional Fees, PCT Application No. PCT/US2014/072399, dated Apr. 14, 2015, 2 Pages.
PCT International Search Report and Written Opinion, International Application No. PCT/US2014/072399, dated Jun. 26, 2015, 22 Pages.
PCT Invitation to Pay Additional Fees, PCT Application No. PCT/US2014/072400, dated Apr. 16, 2015, 6 Pages.
PCT International Search Report and Written Opinion, Application No. PCT/US2014/072400, dated Jul. 8, 2015, 38 Pages.
PCT International Search Report and Written Opinion, Application No. PCT/AU2014/000360, dated Aug. 5, 2015, 12 Pages.
PCT Invitation to Pay Additional Fees, PCT Application No. PCT/US2015/038110, dated Sep. 22, 2015, 8 Pages.
PCT Invitation to Pay Additional Fees, PCT Application No. PCT/US2015/038187, dated Oct. 14, 2015, 5 Pages.
PCT International Search Report and Written Opinion, PCT Application No. PCT/US2015/038110, dated Dec. 11, 2015, 36 Pages.
PCT International Search Report and Written Opinion, PCT Application No. PCT/US2015/038187, dated Jan. 22, 2016, 36 Pages.
PCT Invitation to Pay Additional Fees, PCT Application No. PCT/US2015/068206, dated Apr. 12, 2016, 5 Pages.
PCT International Search Report and Written Opinion, PCT Application No. PCT/US2015/068206, dated Jun. 27, 2016, 20 Pages.
PCT International Search Report and Written Opinion, PCT Application No. PCT/US2016/030292, dated Aug. 12, 2016, 20 Pages.
PCT International Preliminary Report on Patentability, PCT Application No. PCT/US2016/030292, dated Aug. 2, 2017, 23 Pages.
PCT International Search Report and Written Opinion, PCT Application No. PCT/US2016/030293, dated Aug. 11, 2016, 23 Pages.
PCT International Search Report and Written Opinion, PCT Application No. PCT/US2016/036504, dated Nov. 4, 2016, 18 Pages.
PCT International Search Report and Written Opinion, PCT Application No. PCT/US2016/039191, dated Nov. 29, 2016, 20 Pages.
PCT International Search Report and Written Opinion, PCT Application No. PCT/US2016/068144, dated May 18, 2017, 30 Pages.
PCT Invitation to Pay Additional Fees, PCT Application No. PCT/US2017/064351, dated Feb. 9, 2018, 18 Pages.
PCT International Search Report and Written Opinion, PCT Application No. PCT/US2017/064351, dated Apr. 9, 2018, 25 Pages.
PCT Invitation to Pay Additional Fees, PCT Application No. PCT/US2017/064361, dated Mar. 7, 2018, 18 Pages.
PCT International Search Report and Written Opinion for PCT/US2017/064361, dated May 11, 2018, 22 Pages.
PCT Invitation to Pay Additional Fees, PCT Application No. PCT/US2017/064292, dated Mar. 5, 2018, 15 Pages.
PCT International Search Report and Written Opinion, PCT Application No. PCT/US2017/064292, dated May 11, 2018, 20 Pages.
PCT International Search Report and Written Opinion, PCT Application No. PCT/USS2017/068255, dated Mar. 19, 2018, 14 Pages.
Canadian Patent Office, Office Action, Canadian Patent Application No. CA 2,953,466, dated Dec. 11, 2017, 7 Pages.
Canadian Patent Office, Office Action, Canadian Patent Application No. 2,916,678, dated Feb. 8, 2017, 8 Pages.
Canadian Patent Office, Office Action, Canadian Patent Application No. 2,935,218, dated Jun. 13, 2017, 5 Pages.
Canadian Patent Office, Office Action, Canadian Patent Application No. 2,935,218, dated May 8, 2018, 5 Pages.
Canadian Patent Office, Office Action, Canadian Patent Application No. CA 2,953,697, dated Oct. 12, 2017, 6 Pages.
Canadian Patent Office, Office Action, Canadian Patent Application No. CA 2,952,057, dated Oct. 12, 2017, 4 Pages.
Canadian Patent Office, Office Action, Canadian Patent Application No. CA 2,929,487, dated Dec. 7, 2017, 4 Pages.
Chinese Patent Office, Office Action, Chinese Patent Application No. 201480072142.7, dated Apr. 25, 2017, 14 Pages (with English translation).
Chinese Patent Office, 2nd Office Action for Chinese Patent Application No. CN 201480072142.7, dated Oct. 30, 2017, 13 Pages, (with English translation).
European Patent Office, Supplementary Partial European Search Report, European Patent Application No. 13874703.5, dated Jun. 21, 2016, 3 Pages.
European Patent Office, Supplementary European Search Report, European Patent Application No. 13874703.5, dated Oct. 21, 2016, 16 Pages.
European Patent Office, Communication Pursuant to Article 94(3) EPC for European Patent Application No. 13874703.5, dated Jan. 5, 2018, 4 Pages.

(56) References Cited

OTHER PUBLICATIONS

European Patent Office, Supplementary European Search Report, European Patent Application No. 14860187.5, dated May 24, 2017, 9 Pages.
European Patent Office, Supplementary European Search Report, European Patent Application No. 14874589.6, dated Jul. 11, 2017, 9 Pages.
European Patent Office, Communication Pursuant to Article 94(3) EPC for European Patent Application No. EP 14748326.7, dated Feb. 15, 2018, 7 Pages.
European Patent Office, Examination Report, European Patent Application No. 14748326.7, dated Jul. 19, 2017, 4 Pages.
European Patent Office, Examination Report for European Patent Application No. EP 14777213.1, dated Oct. 20, 2017, 12 Pages.
European Patent Office, Supplementary European Search Report, European Patent Application No. EP 15809264.3, dated Dec. 4, 2017, 16 Pages.
European Patent Office, Communication Pursuant to Article 94(3) EPC for European Patent Application No. 15810847.2, dated Nov. 17, 2017, 17 Pages.
European Patent Office, Supplementary European Search Report for European Patent Application No. 15810847.2, dated Feb. 28, 2018, 19 Pages.
European Patent Office, Supplementary European Search Report, European Patent Application No. EP 15812324.0, dated Nov. 2, 2017, 19 Pages.
European Patent Office, Extended European Search Report, European Patent Application No. EP 15812324.0, dated Feb. 21, 2018, 23 Pages.
European Patent Office, Extended European Search Report, European Patent Application No. EP 15809264.3, dated Mar. 12, 2018, 14 Pages.
European Patent Office, Extended European Search Report, European Patent Application No. EP 15876324.3, dated Jun. 12, 2018, 9 Pages.
Intellectual Property Australia, Examination Report for Australian Patent Application No. 2016202480, dated Apr. 28, 2016, 2 Pages.
Intellectual Property Australia, Examination Report for Australian Patent Application No. 2014346664, dated Nov. 24, 2016, 3 Pages.
Intellectual Property Australia, Examination Report for Australian Patent Application No. 2014315191, dated Jul. 15, 2017, 6 Pages.
Intellectual Property Australia, Examination Report for Australian Patent Application No. 2015279600, dated Jul. 21, 2017, 7 Pages.
Intellectual Property Australia, Examination Report for Australian Patent Application No. 2015278238, dated Jul. 24, 2017, 3 Pages.
Intellectual Property Australia, Examination Report No. 1 for Australian Patent Application No. AU 2017254880, dated Nov. 15, 2017, 2 Pages.
Intellectual Property Australia, Examination Report No. 1 for Australian Patent Application No. AU 2017201009, dated Apr. 4, 2018, 3 Pages.
Intellectual Property Australia, Examination Report No. 1 for Australian Patent Application No. AU 2017210482, dated May 15, 2018, 4 Pages.
New Zealand Intellectual Property Office, First Examination Report, New Zealand Patent Application No. 715728, dated May 10, 2016, 4 Pages.
New Zealand Intellectual Property Office, First Examination Report, New Zealand Patent Application No. 715728, dated Dec. 5, 2016, 3 Pages.
New Zealand Intellectual Property Office, First Examination Report, New Zealand Patent Application No. 727449, dated Jun. 8, 2017, 7 Pages.
New Zealand Intellectual Property Office, First Examination Report, New Zealand Patent Application No. 726116, dated Jun. 29, 2017, 2 Pages.
New Zealand Intellectual Property Office, First Examination Report, New Zealand Patent Application No. 726116, dated Sep. 26, 2017, 5 Pages.
New Zealand Intellectual Property Office, Further Examination Report, New Zealand Patent Application No. 726116, dated Feb. 27, 2018, 6 Pages.
New Zealand Intellectual Property Office, First Examination Report, New Zealand Patent Application No. 728495, dated Jul. 12, 2017, 5 Pages.
New Zealand Intellectual Property Office, First Examination Report for New Zealand Patent Application No. NZ 728483, dated Dec. 8, 2017, 2 Pages.
Russian Patent Office, Office Action for Russian Patent Application No. RU 2017127214, dated Nov. 22, 2017, 4 Pages, (with English translation).
Russian Patent Office, Office Action for Russian Patent Application No. RU 2015137613, dated Jun. 7, 2017, 14 Pages (with English translation).
Russian Patent Office, Office Action for Russian Patent Application No. RU 2017141758, dated Apr. 17, 2018, 4 Pages (with Concise Explanation of Relevance).
Russian Patent Office, Office Action for Russian Patent Application No. RU 2017141632, dated Apr. 17, 2018, 4 Pages (with Concise Explanation of Relevance).
Ukraine Patent Office, Office Action for Ukrainian Patent Application No. a201508515, dated May 19, 2017, 14 Pages (with English translation).
Ukraine Patent Office, Office Action for Ukrainian Patent Application No. a201508515, dated Feb. 20, 2018, 9 Pages (with English translation).
Office Action for Israel Patent Application No. IL 255682, dated Mar. 15, 2018, 2 Pages (Translation).
Office Action for Israel Patent Application No. IL 255684, dated Mar. 19, 2018, 2 Pages (Translation).
Office Action for Israel Patent Application No. IL 255685, dated Mar. 20, 2018, 2 Pages (Translation).
Office Action for Israel Patent Application No. IL 255688, dated Mar. 22, 2018, 2 Pages (Translation).
Office Action for Israel Patent Application No. IL 245385, dated Apr. 23, 2018, 3 Pages (With Concise Explanation of Relevance).
Abarenkov, K., et al., "PlutoF-A Web Based Workbench for Ecological and Taxonomic Research, with an Online Implementation for Fungal ITS Sequences," Evol Bioinform Online, 2010, pp. 189-196, vol. 6.
Abarenkov, K., et al., "The UNITE Database for Molecular Identification of Fungi—Recent Updates and Future Perspectives," New Phytol., 2010, pp. 281-285, vol. 186.
Abdellatif, L., et al., "Endophytic hyphal compartmentalization is required for successful symbiotic Ascomycota association with root cells," Mycological Research, 2009, pp. 782-791, vol. 113.
Abdellatif, L., et al., "Characterization of virulence and PCR-DGGE profiles of Fusarium avenaceum from western Canadian Prairie Ecozone of Saskatchewan," Canadian Journal of Plant Pathology, 2010, pp. 468-480.
Abdou, R., et al., "Botryorhodines A-D, antifungal and cytotoxic depsidones from Botryosphaeria rhodina, an endophyte of the medicinal plant *Bidens pilosa*," Phytochemistry, 2010, vol. 71, pp. 110-116.
Abou-Shanab, R. A., et al: "Characterization of Ni-resistant bacteria in the rhizosphere of the hyperaccumulator Alyssum murale by 16S rRNA gene sequence analysis", World Journal of Microbiology and Biotechnology, vol. 26, No. 1, Aug. 15, 2009, pp. 101-108.
Adhikari, M., et al., "A New Record of Pseudeurotium bakeri from Crop Field Soil in Korea," The Korean Journal of Mycology, 2016, pp. 145-149, vol. 44.
Ahmad, F., et al., "Screening of Free-Living Rhizospheric Bacteria for Their Multiple Plant Growth Promoting Activities," Microbiol Res., 2008, pp. 173-181, vol. 163.
Alvarez-Perez, S., et al., "Zooming-in on floral nectar: a first exploration of nectar-associated bacteria in wild plant communities," FEMS Microbiol. Ecol., 2012, vol. 80, No. 3, pp. 591-602.
Amann, R., et al., "The Identification of Microorganisms by Fluorescence in Situ Hybridisation," Curr Opin Biotechnol., 2001, pp. 231-236, vol. 12.
Amatuzzi, R.F., et al., "Univers1dade Federal Do Parana," Jan. 1, 2014, 52 Pages. (With English Abstract).

(56) References Cited

OTHER PUBLICATIONS

Amatuzzi, R.F., et al., "Potential of endophytic fungi as biocontrol agents of *Duponchelia fovealis* (Zeller) (Lepidoptera:Crambidae," Brazilian Journal of Biology, Nov. 9, 2017, 7 Pages.
Apel, K., et al., "Reactive Oxygen Species: Metabolism, Oxidative Stress, and Signal Transduction," Annu Rev Plant Biol., 2004, pp. 373-399, vol. 55.
Arendt, K. R., et al., "Isolation of endohyphal bacteria from foliar Ascomycota and in vitro establishment of their symbiotic associations," Appl. Environ. Microbiol., 2016, pp. 2943-2949, vol. 82, No. 10.
Ashrafuzzaman, M., et al., "Efficiency of plant growth-promoting rhizobacteria (PGPR) for the enhancement of rice growth," African Journal of Biotechnology, 2009, pp. 1247-1252, vol. 8, No. 7.
Aveskamp, M., et al., "DNA phylogeny reveals polyphyly of Phoma section Peyronellaea and multiple taxonomic novelties," Mycologia, 2009, vol. 101, No. 3, pp. 363-382.
Bacon, C. W., et al., "Isolation, In Planta Detection, and Uses of Endophytic Bacteria for Plant Protection," Manual of Environmental Microbiology, 2007, pp. 638-647.
Baker, K. F., et al., "Dynamics of Seed Transmission of Plant Pathogens," Annu Rev Phytopathol., 1966, pp. 311-334,vol. 4.
Baltruschat, H., et al., "Salt tolerance of barley induced by the root endophyte Piriformospora indica is associated with a strong increase in antioxidants," New Phytologist., 2008, pp. 501-510, vol. 180.
Bensch, K., et al., "Species and ecological diversity within the Cladosporium cladosporioides complex (Davidiellaceae, Capnodiales)," Studies in Mycology, 2010, pp. 1-94, vol. 67.
Bethlenfalvay, G., et al., "Mycorrhizal fungi effects on nutrient composition and yield of soybean seeds", Journal of Plant Nutrition, vol. 20, No. 4-5, Apr. 1, 1997, pp. 581-591.
Block, C. C., et al., "Seed Transmission of Pantoea stewartii in Field and Sweet Corn," Plant Disease, 1998, pp. 775-780, vol. 82.
Brinkmeyer, R., et al., "Uncultured Bacterium Clone ARKMP-100 16S Ribosomal RNA Gene, Partial Sequence," NCBI GenBank Accession No. AF468334, Submitted Jan. 14, 2002.
Brodie, E.L., et al., "Uncultured Bacterium Clone BANW722 16S Ribosomal RNA Gene, Partial Sequence," NCBI GenBank Accession No. DQ264636, Submitted Oct. 25, 2005.
Bulgarelli, D., et al., "Structure and Functions of the Bacterial Microbiota of Plants," Annu Rev Plant Biol., 2013, pp. 807-838, vol. 64.
Buttner, D., et al., "Regulation and secretion of Xanthomonas virulence factors," FEMS Microbiology Reviews, 2010, pp. 107-133, vol. 34, No. 2.
Caporaso, J.G., et al., "Ultra-High-Throughput Microbial Community Analysis on the Illumina HiSeq and MiSeq Platforms," ISME J., 2012, pp. 1621-1624, vol. 6.
Castillo, D., et al., "Fungal Entomopathogenic Endophytes: Negative Effects on Cotton Aphid Reproduction in Greenhouse and Field Conditions," PowerPoint Presentation dated Mar. 23, 2013.
Castillo, D., et al., "Fungal Endophytes: Plant Protective Agents Against Herbivores," Power Point Presentation dated Aug. 4, 2013.
Cavalier-Smith, T., "A Revised Six-Kingdom System of Life," Biol Rev Camb Philos Soc., 1998, pp. 203-266, vol. 73.
Cha, C., et al., "Production of Acyl-Homoserine Lactone Quorum-Sensing Signals by Gram-Negative Plant Associated Bacteria," Mol Plant Microbe Interact., 1998, pp. 1119-1129, vol. 11, No. 11.
Chagas, F., et al., "A Mixed Culture of Endophytic Fungi Increases Production of Antifungal Polyketides," J. Chem Ecol., Oct. 2013, pp. 1335-1342, vol. 39.
Chernin, L. S., et al., "Chitinolytic Activity in Chromo bacterium violaceum: Substrate Analysis and Regulation by Quorum Sensing," J Bacteriol., 1998, pp. 4435-4441, vol. 180, No. 17.
Clark, E. M., et al., "Improved Histochemical Techniques for the Detection of Acremonium coenophilum in Tall Fescue and Methods of in vitro Culture of the Fungus," J. Microbiol Methods, 1983, pp. 149-155, vol. 1.
Clarridge, J., "Impact of 16S rRNA Gene Sequence Analysis for Identification of Bacteria on Clinical Microbiology and Infectious Diseases," Clinical Microbiology Reviews, Oct. 2004, pp. 840-862, vol. 17, No. 4.
Clay, K., "Effects of fungal endophytes on the seed and seedling biology of Lolium perenne and Festuca arundinacea," Oecologia, 1987, pp. 358-362, vol. 73.
Clough, S. J., et al., "Floral Dip: A Simplified Method for Agrobacterium-mediated Transformation of *Arabidopsis thaliana,*" Plant J., 1998, pp. 735-743, vol. 16, No. 6.
Compant, S., et al., "Endophytes of Grapevines Flowers, Berries, and Seeds: Identification of Cultivable Bacteria, Comparison with Other Plant Parts, and Visualization of Niches of Colonization," Microbial Ecology, 2011, pp. 188-197, vol. 62.
Coombs, J. T., et al., "Isolation and Identification of Actinobacteria from Surface-Sterilized Wheat Roots," Applied and Environmental Microbiology, 2003, pp. 5603-5608, vol. 69, No. 9.
Conn, V. M., "Effect of Microbial Inoculants on the Indigenous Actinobacterial Endophyte Population in the Roots of Wheats as Determined by Terminal Restriction Fragment Length Polymorphism," Applied and Environmental Microbiology, 2004, pp. 6407-6413, vol. 70, No. 11.
Cottyn, B., et al., "Phenotypic and genetic diversity of rice seed-associated bacteria and their role in pathogenicity and biological control," Journal of Applied Microbiology, 2009, pp. 885-897, vol. 107.
Cox, C. D., "Deferration of Laboratory Media and Assays for Ferric and Ferrous Ions," Methods Enzymol., 1994, pp. 315-329, vol. 235.
Craine, J. M., et al., "Global Diversity of Drought Tolerance and Grassland Climate-Change Resilience," Nature Climate Change, 2013, pp. 63-67, vol. 3.
Dalal, J.M., et al., "Utilization of Endophytic Microbes for Induction of Systemic Resistance (ISR) in Soybean (*Glycine max* (L) Merril) Against Challenge Inoculation with R. solani," Journal of Applied Science and Research, 2014, pp. 70-84, vol. 2, No. 5.
Danhorn, T., et al., "Biofilm Formation by Plant-Associated Bacteria," Annu Rev Microbiol., 2007, pp. 401-422, vol. 61.
Daniels, R., et al., "Quorum Signal Molecules as Biosurfactants Affecting Swarming in Rhizobium etli," PNAS, 2006, pp. 14965-14970, vol. 103, No. 40.
Darsonval, A., et al., "Adhesion and Fitness in the Bean Phyllosphere and Transmission to Seed of *Xanthomonas fuscans* subsp. *fuscans,*" Molecular Plant-Microbe Interactions, 2009, pp. 747-757, vol. 22, No. 6.
Darsonval, A., et al., "The Type III Secretion System of *Xanthomonas fuscans* subsp. *fuscans* is involved in the Phyllosphere Colonization Process and in Transmission to Seeds of Susceptible Beans," Applied and Envioronmental Mirobiology, 2008, pp. 2669-2678, vol. 74, No. 9.
Dbget, "Orthology: K14454," 2005, 2 pages, can be retrieved at <URL:http://www.genome.jp/dbget-bin/www_bget?ko:K14454>.
De Freitas, J. R., et al., "Phosphate-Solubilizing Rhizobacteria Enhance the Growth and Yield but not Phosphorus Uptake of Canola (*Brassica napus* L.)," Biol Fertil Soils, 1997, pp. 358-364, vol. 24.
De Lima Favaro, L. C., et al., "Epicoccum nigrum P16, a Sugarcane Endophyte, Produces Antifungal Compounds and Induces Root Growth," PLoS One, 2012, pp. 1-10, vol. 7, No. 6.
De Melo Pereira, G. V., et al. "A Multiphasic Approach for the Identification of Endophytic Bacterial in Strawberry Fruit and their Potential for Plant Growth Promotion," Microbial Ecology, 2012, pp. 405-417, vol. 63, No. 2.
De Souza, J. J., et al., "Terpenoids from Endophytic Fungi," Molecules, 2011, pp. 10604-10618, vol. 16, No. 12.
Dennis, C., et al., "Antagonistic Properties of Species Groups of Trichoderma," Trans Brit Mycol Soc, 1971, pp. 25-39, vol. 57, No. 1.
Desiro, A., et al., "Detection of a novel intracellular microbiome hosted in arbuscular mycorrhizal fungi," ISME Journal, 2014, pp. 257-270, vol. 8.
Djordjevic, D., et al., "Microtiter Plate Assay for Assessment of Listeria monocytogenes Biofilm Formation," Annl Environ Microbiol., 2002, pp. 2950-2958, vol. 68, No. 6.

(56) References Cited

OTHER PUBLICATIONS

Don, R. H., et al., "Properties of Six Pesticide Degradation Plasmids Isolated From Alcaligenes Paradoxus and Alcaligenes eutrophus," J Bacteriol., 1981, pp. 681-686, vol. 145, No. 2.
Dunbar, J, et al., "Uncultured Bacterium Clone NT42a2_20488 16S Ribosomal RNA Gene, Partial Sequence," NCBI GenBankAccession No. JQ378705. Submitted Nov. 8, 2012, 1 Page.
Eberhard, A., et al., "Structural Identification of Autoinducer of Photobacterium fischeri Luciferase," Biochem., 1981, pp. 2444-2449, vol. 20.
Edgar, R. C., "Search and Clustering Orders of Magnitude Faster than BLAST," Bioinformatics, 2010, pp. 2460-2461, vol. 26, No. 19.
Edgar, R. C., "UPARSE: Highly Accurate OTU Sequences From Microbial Amplicon Reads," Nat Methods, 2013, pp. 996-998, vol. 10, No. 10.
Ek-Ramos, M. J., "Ecology, Distribution and Benefits of Fungal Endophytes Isolated from Cultivated Cotton (*Gossypium hirsutum*) in Texas," Power Point Presentation dated Nov. 7, 2012, 27 Pages.
Ek-Ramos, M. J., et al., "Spatial and Temporal Variation in Fungal Endophyte Communities Isolated from Cultivated Cotton (*Gossypium hirsutum*)," PLoS ONE, 2013, vol. 8, No. 6, 13 Pages, e66049.
Ek-Ramos, M. J., et al., "Spatial and Temporal Variation in Fungal Endophyte Communities Isolated from Cultivated Cotton (*Gossypium hirsutum*)," Power Point Presentation dated Jan. 7, 2013, 18 Pages.
El-Shanshoury, A. R., "Growth Promotion of Wheat Seedlings by Streptomyces atroolivaceus," Journal of Agronomy and CropScience, 1989, pp. 109-114, vol. 163.
Emerson, D., et al., Identifying and Characterizing Bacteria in an Era of Genomics and Proteomics, BioScience, 2008, pp. 925-936, vol. 58, No. 10.
Endre, G., et al., "A Receptor Kinase Gene Regulating Symbiotic Nodule Development," Nature, 2002, pp. 962-966, vol. 417.
Faria, D. C., et al., "Endophytic Bacteria Isolated from Orchid and Their Potential to Promote Plant Growth," World J Microbiol Biotechnol., 2013, pp. 217-221, vol. 29.
Ferrando, L., et al., "Molecular and Culture-Dependent Analyses Revealed Similarities in the Endophytic Bacterial Community Composition of Leaves from Three Rice (*Oryza sativa*) Varieties," FEMS Microbiol Ecol., 2012, pp. 696-708, vol. 80.
Fiehn, O., et al., "Metabolite Profiling for Plant Functional Genomics," Nature Biotechnol., 2000, pp. 1157-1161, vol. 8.
Fierer, N., et al., "Cross-Biome Metagenomic Analyses of Soil Microbial Communities and Their Functional Attributes," Proc Natl Acad Sci USA, 2012, pp. 21390-21395, vol. 109, No. 52.
Fincher, G. B., "Molecular and Cellular Biology Associated with Endosperm Mobilization in Germinating Cereal Grains," Annu Rev Plant Phvsiol Plant Mol Biol., 1989, pp. 305-346, vol. 40.
Fisher, P. J., et al., "Fungal saprobes and pathogens as endophytes of rice (*Oryza sativa* L.)," New Phytol., 1992, pp. 137-143, vol. 120.
Fisher, P. R., et al., "Isolation and Characterization of the Pesticide-Degrading Plasmid pJP1 from Alcaligenes paradoxus," J Bacteriol., 1978, pp. 798-804, vol. 135, No. 3.
Franco, C., et al., "Actinobacterial Endophytes for Improved Crop Performance," Australasian Plant Pathology, 2007, pp. 524-531, vol. 36.
Fulthorpe, R. R., et al., "Distantly Sampled Soils Carry Few Species in Common," ISME J., 2008, pp. 901-910, vol. 2.
Gantner, S., et al., "Novel Primers for 16S rRNA-based Archaeal Community Analyses in Environmental Samples," J Microbiol Methods, 2011, pp. 12-18, vol. 84.
Gao, Z., et al., "Quantitation of Major Human Cutaneous Bacterial and Fungal Populations," J Clin Microbiol., 2010, pp. 3575-3581, vol. 48, No. 10.
Garazzino, S., et al., "Osteomyelitis Caused by Enterobacter cancerogenus Infection following a Traumatic Injury: Case Report and Review of the Literature," J Clin Microbiol., Mar. 2005, vol. 43, No. 3, pp. 1459-1461.
Gasser, I., et al., "Ecology and Characterization of Polyhydroxyalkanoate-Producing Microorganisms on and in Plants," FEMS Microbiol Ecol., 2010, pp. 142-150, vol. 70.
Gavrish, E, et al., "*Lentzea* sp. MS6 16S Ribosomal RNA Gene, Partial Sequence," NCBI GenBank Accession No. EF599958. Submitted May 9, 2007, 1 Page.
Gebhardt, J., et al., "Characterization of a single soybean cDNA encoding cytosolic and glyoxysomal isozymes of aspartate aminostransferase," Plant Molecular Biology, 1998, pp. 99-108, vol. 37.
GenBank: AF034210.1 "Glycine max aspartate aminotransferase glyoxysomal isozyme AAT1 precursor and aspartate aminotransferase cytosolic isozyme AAT2 (AAT) mRNA, complete cds," NCBI, May 26, 1998, 2 Pages, can be retrieved at <URL:https://www.ncbi.nlm.nih.gov/nuccore/AF034210>.
GenBank: JN210900.1, "*Enterobacter* sp. WS05 16S ribosomal RNA gene, partial sequence," NCBI, Sep. 24, 2012, 1 Page, can be retrieved at <URL:https://www.ncbi.nlm.nih.gov/nuccore/jn210900>.
GenBank: NP_001237541.1, "aspartate aminotransferase glyoxysomal isozyme AAT1 precursor [Glycine max]," NCBI, Oct. 29, 2016, 2 Pages, can be retrieved at <URL:https://www.ncbi.nlm.nih.gov/protein/NP_001237541.1>.
NCBI GenBank: CP000653.1 "*Enterobacter* sp. 638, complete genome" Jan. 28, 2014, 5 Pages, Can be retrieved at <URL:https://www.ncbi.nlm.nih.gov/nuccore/CP000653.1>.
NCBI GenBank: CP000653.1 "*Enterobacter* sp. 638, complete genome" ASM1632v1, Apr. 18, 2007, 2 Pages, Can be retrieved at <URL:https://www.ncbi.nlm.nih.gov/assembly/GCA_000016325.1>.
NCBI GenBank: EU340965.1 "*Enterobacter* sp. 638 16S ribosomal RNA gene, partial sequence" Jan. 30, 2009, 1 Page, Can be retrieved at <URL:https://www.ncbi.nlm.nih.gov/nuccore/EU340965.1>.
NCBI GenBank: EBI accession No. EM STD:JQ759988, "*Dothideomycetes* sp. genotype 226 isolate FL0175 internal transcribed spacer 1, partial sequence; 5.85 ribosomal RNA gene and internal transcribed spacer 2, complete sequence; and 285 ribosomal RNA gene, partial sequence," May 17, 2012, 2 Pages.
NCBI GenBank: EBI accession No. EM STD:GU055658, "Uncultured Periconia clone NG R 806 18S ribosomal RNA gene, partial sequence; internal transcribed spacer 1, 5.8S ribosomal RNA gene, and internal transcribed spacer 2, complete sequence; and 28S ribosomal RNA gene, partial sequence," Oct. 27, 2009, 2 Pages.
GenEmbl Database, GenEmbl Record No. KF673660, Sandberg, et al., "Fungal endophytes of aquatic macrophytes: diverse host-generalists characterized by tissue preferences and geographic structure," 2013, 35 Pages.
GenEmbl Database, GenEmbl Record No. KP991588, Huang, et al., "Pervasive effects of Wildfire on foliar endophyte communities in montane forest trees," Mar. 2015, 35 Pages.
GenEmbl Database, GenEmbl Record No. JN872548, 38 Pages, Alvarez-Perez, S., et al., "Zooming-in on floral nectar: a first exploration of nectar-associated bacteria in wild plant communities," FEMS Microbiol. Ecol., 2012, vol. 80, No. 3, pp. 591-602.
GenEmbl database, GenEmbl Record No. EU 977189, Jan. 21, 2009, 4 pages, Smith, S.A., et al., "Bioactive endophytes warrant intensified exploration and conservation," PloS ONE 3(8):E3052, 2008.
GenEmbl database, GenEmbl Record No. KF011597, Paenibacillus strain No. HA 13, Aug. 26, 2013, 5 Pages, Park, H.J., et al., "Isolation and characterization of humic substances-degrading bacteria from the subarctic Alaska grasslands," J Basic Microbiol, 2013.
Database Geneseq Database accession No. BAP97938 "Pantoea dispersa strain KACC91642P 16S rDNA sequence, SEQ ID 1" Aug. 15, 2013, 1 Page.
Gilmour, S. J., et al., "Overexpression of the *Arabidopsis* CBF3 Transcriptional Activator Mimics Multiple Biochemical Changes Associated with Cold Acclimation," Plant Physiol., 2000, pp. 1854-1865, vol. 124.
Giraldo, A., et al., "Phylogeny of Sarocladium (Hypocreales)," Persoonia, 2015, pp. 10-24, vol. 34.

(56) References Cited

OTHER PUBLICATIONS

Gitaitis, R., et al., "The Epidemiology and Management of Seedborne Bacterial Diseases," Annu Rev Phytopathol., 2007, pp. 371-397, vol. 45.

Grondona, I., et al., "TUSAL®, a commercial biocontrol formulation based on Trichoderma," Bulletin OILB/SROP, 2004, pp. 285-288, vol. 27, No. 8.

Gu, O., et al., "*Glycomyces sambucus* sp. nov., an endophytic actinomycete islolated from the stem of Sambucus adnata Wall," International Journal of Systematic and Evolutionary Microbiology, 2007, pp. 1995-1998, vol. 57.

Haake, V., et al., "Transcription Factor CBF4 is a Regulator of Drought Adaptation in *Arabidopsis,*" Plant Physiol., 2002, pp. 639-648, vol. 130.

Haas, D., et al., "R Factor Variants with Enhanced Sex Factor Activity in Pseudomonas aeruginosa," Mol Gen Genet., 1976, pp. 243-251, vol. 144.

Hahm, M-S., et al., "Biological Control and Plant Growth Promoting Capacity of Rhizobacteria and Pepper Under Greenhouse and Field Conditions," The Journal of Microbiology, The Microbiological Society of Korea, Heidelberg, Jun. 30, 2012, pp. 380-385, vol. 50, No. 3.

Hallman, J., et al., "Bacterial Endophytes in Agricultural Crops," Canadian J Microbiol., 1997, pp. 895-914, vol. 43.

Hamayun, M., et al., "Cladosporium sphaerospermum as a new plant growth-promoting endophyte from the roots of Glycine max (L.) Merr," World Journal of Microbiology and Biotechnology, Kluwer Academic Publishers, Feb. 15, 2009, pp. 627-632, vol. 25, No. 4.

Hanson, L.E., "Reduction of Verticillium Wilt Symptoms in Cotton Following Seed Treatment with Trichoderma virens," The Journal of Cotton Science, 2000, pp. 224-231, vol. 4, No. 4.

Hanson, L.E., "Reduction of Verticillium Wilt Symptoms in Cotton Following Seed Treatment with Trichoderma virens," Proceedings Beltwide Cotton Conferences, 2000, vol. 1. (Abstract), 1 Page.

Hardegree, S. P. et al., "Effect of Polyethylene Glycol Exclusion on the Water Potential of Solution-Saturated Filter Paper," Plant Physiol., 1990, pp. 462-466, vol. 92.

Hardoim, P. R., et al., "Assessment of Rice Root Endophytes and Their Potential for Plant Growth Promotion," In: Hardoim, P.R., Bacterial Endophytes of Rice—Their Diversity, Characteristics and Perspectives, Groningen, 2011, pp. 77-100.

Hardoim, P. R., et al., "Dynamics of Seed-Borne Rice Endophytes on Early Plant Growth Stages," PLoS ONE, 2012, vol. 7, No. 2, 13 Pages.

Harman, G.E., et al., "Symposium: biocontrol and biotechnological methods for controlling cotton pests," Proceedings of the Beltwide Cotton Production Research Conf., 1989, Memphis, Tennessee, USA, pp. 15-20. (Abstract).

Hepler, P. K., et al., "Polarized Cell Growth in Higher Plants," Annu Rev Cell Dev Biol., 2001, pp. 159-187, vol. 17.

Hiatt, E. E., et al., "Tall Fescue Endophyte Detection: Commerical Immunoblot Test Kit Compared with Microscopic Analysis," Crop Science, 1999, pp. 796-799, vol. 39.

Hibbett, D. S., et al., "A Higher-Level Phylogenetic Classification of the Fungi," Mycol Res., 2007, pp. 509-547, vol. 111.

Hill, N. S., et al., "Endophyte Survival during Seed Storage: Endophyte-Host Interactions and Heritability," Crop Sci., 2009, pp. 1425-1430, vol. 49.

Hill N. S., et al., "Endophyte Survival during Seed Storage: Endophyte-Host Interactions and Heritability," PowerPoint, Dept. Crop Soil Sciences, University of Georgia, Nov. 16, 2012, 3 Pages.

Hinton, D. M., et al., "Enterobacter cloacae is an endophytic symbiont of corn," Mycopathologia, 1995, pp. 117-125, vol. 129.

Hoffman, M., et al., "Diverse Bacteria Inhabit Living Hyphae of Phylogenetically Diverse Fungal Endophytes," Applied and Environmental Microbiology, Jun. 2010, pp. 4063-4075, vol. 76, No. 12.

Hoffman, M., et al., "Endohyphal Bacterium Enhances Production of Indole-3-Acetic Acid by a Foliar Fungal Endophyte," PLOS One, Sep. 24, 2013, pp. 1-8, vol. 8, Issue 9, e73132.

Howell, C.R., et al., "Induction of Terpenoid Synthesis in Cotton Roots and Control of Rhizoctonia solani by Seed Treatment with Trichoderma virens," Phytopathology, 2000, pp. 248-252, vol. 90, No. 3.

Hubbard, M., et al., "Fungal Endophytes Improve Wheat Seed Germination Under Heat and Drought Stress," Botany, 2012, pp. 137-149, vol. 90.

Humann, J., et al., "Complete genome of the onion pathogen *Enterobacter cloacae* EcWSUI," Standard in Genomic Sciences, Dec. 31, 2011, vol. 5, No. 3, pp. 279-286.

Hung, P.Q., et al., "Isolation and Characterization of Endophytic Bacteria in Soybean (*Glycine* Sp.)," Omonrice, 2004, pp. 92-101, vol. 12.

Idris, A., et al., "Efficacy of Rhizobacteria for Growth Promotion in Sorghum Under Greenhouse Conditions and Selected Modes of Action Studies," J Agr Sci., 2009, pp. 17-30, vol. 147.

Ikeda, S., et al., "The Genotype of The Calcium/Calmodulin-Dependent Protein Kinase Gene (CCaMK) Determines Bacterial Community Diversity in Rice Roots Under Paddy And Upland Field Conditions," Applied and Environmental Microbiology, 2011, pp. 4399-4405, vol. 77, No. 13.

Imoto, K., et al., "Comprehensive Approach to Genes Involved in Cell Wall Modifications in *Arabidopsis thaliana,*" Plant Mol Biol., 2005, pp. 177-192, vol. 58.

Jalgaonwala, R., et al., "A Review on Microbial Endophytes from Plants: A Treasure Search for Biologically Active Metabolites," Global Journal of Research on Medicinal Plants & Indigenous Medicine, 2014, pp. 263-277, vol. 3, No. 6.

Janda, J. M., et al., "16S rRNA Gene Sequencing for Bacterial Identification in the Diagnostic Laboratory: Pluses, Perils, and Pitfalls," Journal of Clinical Microbiology, 2007, pp. 2761-2764, vol. 45, No. 9.

Johnston-Monje, D., et al., "Conservation and Diversity of Seed Associated Endophytes in *Zea* Across Boundaries of Evolution, Ethnography and Ecology," PLOS ONE, vol. 6, No. 6, Jun. 3, 2011, p. e20396, 22 Pages.

Johnston-Monje, D., et al., "Plant and Endophyte Relationships: Nutrient Management," Comprehensive Biotechnol., 2011, pp. 713-727, vol. 4.

Johnston-Monje, D., "Microbial Ecology of Endophytic Bacteria in *Zea* Species as Influenced by Plant Genotype, Seed Origin, and Soil Environment," Thesis, University of Guelph, 2011, 230 Pages.

Jones, K.L., "Fresh Isolates of Actinomycetes in which the Presence of Sporogenous Aerial Mycelia is a Fluctuating Characteristic," J Bacteriol., 1949, pp. 141-145, vol. 57, No. 2.

Jung, C., et al., "The Effects of Endohyphal Bacteria on Anti-Cancer and Anti-Malaria Metabolites of Endophytic Fungi," Honors Thesis, University of Arizona, May 2012, 15 Pages.

Kaga, H., et al., "Rice Seeds as Sources of Endophytic Bacteria," Microbes Environ., 2009, pp. 154-162, vol. 24, No. 2.

Kalns, L., et al., "The Effects of Cotton Fungal Endophytes in the Field on Arthropod Community Structure," Power Point Presentation dated Jan. 7, 2013.

Kang, B. H., et al., "Members of the *Arabidopsis* Dynamin-Like Gene Family, ADL1, are Essential for Plant Cytokinesis and Polarized Cell Growth," Plant Cell, 2003, pp. 899-913, vol. 15.

Kasana, R. C., et al., "A Rapid and Easy Method for the Detection of Microbial Cellulases on Agar Plates Using Gram's Iodine," Curr Microbiol., 2008, pp. 503-507, vol. 57.

Khan, A.L., et al., "Salinity Stress Resistance Offered by Endophytic Fungal Interaction Between Penicillium minioluteum LHL09 and Glycine max. L," J. Microbiol. Biotechnol., 2011, pp. 893-902, vol. 21, No. 9.

Kim, M., et al., "Towards a taxonomic coherence between average nucleotide identity and 16S rRNA gene sequence similarity for species demarcation of prokaryotes", Int J Systematic Evolutionary Microbial., 2014, vol. 64, pp. 346-351.

Klaubauf, S., et al., "Molecular diversity of fungal conmunities in agricultural soils from Lower Austria," Fungal Diversity, Aug. 13, 2010, pp. 65-75, vol. 44, No. 1.

(56) References Cited

OTHER PUBLICATIONS

Knapp, D., et al., "Inter- and intraspecific functional diversity of fungal root endophytes of semiarid sandy grasslands," Acta Microbiologica et Immunologica Hungarica, Nov. 2017, pp. 1-101, vol. 64, Issue Supplement 1.
Kruger, M., et al., "DNA-Based Species Level Detection of Glomeromycota: One PCR Primer Set for All Arbuscular Mycorrhizal Fungi," New Phvtol., 2009, pp. 212-223, vol. 183.
Kuklinsky-Sobral, J., et al., "Isolation and Characterization of Endophytic Bacteria from Soybean (*Glycine max*) Grown in Soil Treated with Glyphosate Herbicide," Plant and Soil, 2005, pp. 91-99, vol. 273.
Kuklinsky-Sobral, J., et al., "Isolation and characterization of soybean-associated bacteria and their potential for plant growth promotion," Environmental Microbiology, 2004, pp. 1244-1251, vol. 6, No. 12.
Kumar, S., et al., "MEGA7: Molecular Evolutionary Genetics Analysis version 7.0 for bigger datasets," Molecular Biology and Evolution, Mar. 22, 2016, vol. 33, pp. 1870-1874.
Kumar, A., et al., "Bio-control potential of *Cladosporium* sp. (MCPL-461), against a noxious weed *Parthenium hysterophorus* L.," J. Environ Biol., Mar. 2009, pp. 307-312, vol. 30, Issue 2.
Kusari, S., et al. "Chemical ecology of endophytic fungi: origins of secondary metabolites," Cell Press, Chem & Biol., 2012, pp. 792-798, vol. 19.
Labeda, D.P., et al., "Phylogenetic study of the species within the family Streptomycetaceae," Antonie van Leeuwenhoek, 2012, vol. 101, pp. 73-104, Springer.
Lanver, D., et al., "Sho1 and Msb2-Related Proteins Regulate Appressorium Development in the Smut Fungus *Ustilago aydis,*" Plant Cell, 2010, pp. 2085-2101, vol. 22.
Laus, M. C., et al., "Role of Cellulose Fibrils and Exopolysaccharides of Rhizobium Teguminosarum in Attachment to and Infection of *Vicia sativa* Root Hairs," Mol Plant Microbe Interact., 2005, pp. 533-538, vol. 18, No. 6.
Le, X.H., et al., "Effects of endophytic Streptomyces on the lucerne (*Medicago sativa* L.) symbiosis at different levels of nitrogen," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 66-67.
Le, X.H., et al., "Isolation and characterisation of endophytic actinobacteria and their effect on the early growth and nodulation of lucerne (*Medicago sativa* L.)," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 134-136.
Lehman, S.G., "Treat Cotton Seed," Review of Applied Mycology, 1945, 24, 369, 16 Pages.
Lehman, S.G., "Treat Cotton Seed," Research and Farming III, Progr. Rept., 1945, 3, 5, 16 Pages.
Leonard, C. A., et al., "Random Mutagenesis of the Aspergillus oryzae Genome Results in Fungal Antibacterial Activity," Int J Microbiol., 2013, vol. 2013, Article ID 901697, 6 Pages.
Li, H. M., et al., "Expression of a Novel Chitinase by the Fungal Endophyte in Poa ampla," Mycologia, 2004, pp. 526-536, vol. 96, No. 3.
Li, H., et al., "Endophytes and their role in phytoremediation," Fungal Diversity, 2012, pp. 11-18, vol. 54.
Li, Q., "Agrobacterium tumefaciens Strain TA-AT-10 16S Ribosomal RNA Gene, Partial Sequence: GenBank: KF673157.1," Submitted Sep. 17, 2013.
Liu, M., et al., "A Novel Screening Method for Isolating Exopolysaccharide-Deficient Mutants," Appl Environ Microbiol., 1998, pp. 4600-4602, vol. 64, No. 11.
Liu, Y., et al., "Investigation on Diversity and Population Succession Dynamics of Endophytic Bacteria from Seeds of Maize (*Zea mays* L., Nongda108) at Different Growth Stages," Ann Microbiol., 2013, pp. 71-79, vol. 63.
Liu, D., et al., "Osmotin Overexpression in Potato Delays Development of Disease Symptoms," Proc Natl Acad Sci USA, 1994, pp. 1888-1892, vol. 91.
Liu, Y., et al., "Phylogenetic relationships among ascomycetes: evidence from an RNA polymerase II subunit," Mol. Biol. Evol. 1999. vol. 16, No. 12, pp. 1799-1808.
Liu, Y., et al., "Study on Diversity of Endophytic Bacterial Communities in Seeds of Hybrid Maize and their Parental Lines," Arch Microbiol., 2012, pp. 1001-1012, vol. 194.
Long, H. H., et al., "The Structure of the Culturable Root Bacterial Endophyte Community of Nicotiana attenuata is Organized by Soil Composition and Host Plant Ethylene Production and Perception," New Phytol., 2010, pp. 554-567, vol. 185.
Lopez-Lopez, A., et al., "Phaseolus vulgaris Seed-Borne Endophytic Community with Novel Bacterial Species such as *Rhizobium endophyticum* sp. nov.," Systematic Appl Microbiol., 2010, pp. 322-327, vol. 33.
Lorck, H., "Production of Hydrocyanic Acid by Bacteria," Physiol Plant, 1948, pp. 142-146, vol. 1.
Lugtenberg, B., et al., "Plant-Growth-Promoting Rhizobacteria," Ann. Rev. Microbiol., 2009, pp. 541-556, vol. 63.
Lundberg, D. S., et al., "Defining the Core *Arabidopsis thaliana* Root Microbiome," Nature, 2012, pp. 86-90, vol. 488, No. 7409.
Lundberg, D. S., et al., "Practical Innovations for High-Throughput Amplicon Sequencing," Nat Methods, 2013, pp. 999-1002, vol. 10, No. 10.
Ma, Y., et al., "Plant Growth Promoting Rhizobacteria and Endophytes Accelerate Phytoremediation of Metalliferous Soils," Biotechnology Advances, 2011, pp. 248-258, vol. 29.
Madi, L. et al., "Aggregation in Azospirillum brasilense Cd: Conditions and Factors Involved in Cell-to-Cell Adhesion," Plant Soil, 1989, pp. 89-98, vol. 115.
Mandyam, K., et al., "Mutualism-parasitism paradigm synthesized from results of root-endophyte models", Frontiers in Microbiology, Jan. 12, 2015, pp. 1-14, vol. 5.
Mannisto, M.K., et al., "Characterization of Psychrotolerant Heterotrophic Bacteria From Finnish Lapland," Svst Appl Microbiol., 2006, pp. 229-243, vol. 29.
Mano, H., et al., "Culturable Surface and Endophytic Bacterial Flora of the Maturing Seeds of Rice Plants (*Oryza sativa*) Cultivated in a Paddy Field," Microbes Environ., 2006, vol. 21, No. 2.
Manter, D. K., et al., "Use of the ITS Primers, ITSIF and ITS4, to Characterize Fungal Abundance and Diversity in Mixed-Template Samples by qPCR and Length Heterogeneity Analysis," J Microbiol Methods, 2007, pp. 7-14, vol. 71.
Mao, W., et al., "Seed Treatment with a Fungal or a Bacterial Antagonist for Reducing Corn Damping-off Caused by Species of Pythium and Fusarium," Plant Disease, 1997, pp. 450-454, vol. 81, No. 5.
Marasco, R., et al., "A Drought Resistance-Promoting Microbiome is Selected by Root System Under Desert Farming," PLoS ONE, 2012, vol. 7, No. 10, 14 Pages.
Marquez, L. M., et al., "A Virus in a Fungus in a Plant: Three-Way Symbiosis Required for Thermal Tolerance," Science, 2007, pp. 513-515, vol. 315.
Mastretta, C., et al., "Endophytic Bacteria from Seeds of Nicotiana Tabacum Can Reduce Cadmium Phytotoxicity," Intl J Phytoremediation, 2009, pp. 251-267, vol. 11.
Mateos, P. F., et al., "Cell-Associated Pectinolytic and Cellulolytic Enzymes in Rhizobium leguminosarum biovar trifolii," Appl Environ Microbiol., 1992, pp. 816-1822, vol. 58, No. 6.
McDonald, D., et al., "An Improved Greengenes Taxonomy with Explicit Ranks for Ecological and Evolutionary Analyses of Bacteria and Archaea," ISME J., 2012, pp. 610-618, vol. 6.
McGuire, K.L., et al., "Digging the New York City Skyline: Soil Fungal Communities in Green Roofs and City Parks," PloS One, 2013, vol. 8, No. 3, 13 Pages.
Medina, P., et al., "Rapid Identification of Gelatin and Casein Hydrolysis Using TCA," J Microbiol Methods, 2007, pp. 391-393, vol. 69.
Mehnaz, S., et al., "Growth Promoting Effects of Corn (*Zea mays*) Bacterial Isolates Under Greenhouse and Field Conditions," Soil Biology and Biochemistry, 2010, pp. 1848-1856, vol. 42.
Mehnaz, S., et al., "Isolation and 16S rRNA sequence analysis of the beneficial bacteria from the rhizosphere of rice," Canada Journal of Microbiology, 2001, pp. 110-117, vol. 47, No. 2.

(56) References Cited

OTHER PUBLICATIONS

Mei, C., et al., "The Use of Beneficial Microbial Endophytes for Plant Biomass and Stress Tolerance Improvement," Recent Patents on Biotechnology, 2010, pp. 81-95, vol. 4.
Michel, B. E., et al., "The Osmotic Potential of Polyethylene Glycol 6000," Plant Physiol., 1973, pp. 914-916, vol. 51.
Misk, A., et al., "Biocontrol ofchickpea root rot using endophytic actinobacteria", Biocontrol, vol. 56, No. 5, Mar. 12, 2011, pp. 811-822, XP036215297.
Miyoshi-Akiyama, T., et al., "Multilocus Sequence Typing (MLST) for Characterization of Enterobacter cloacae," PLoS ONE, 2013, vol. 8, No. 6, 10 Pages, e66358.
Moe, L. A., "Amino Acids in the Rhizosphere: From Plants to Microbes," American Journal of Botany, 2013, pp. 1692-1705, vol. 100, No. 9.
Mohiddin, F. A., et al., "Tolerance of Fungal and Bacterial Biocontrol Agents to Six Pesticides Commonly Used in the Control of Soil Borne Plant Pathogens," African Journal of Agricultural Research, 2013, pp. 5331-5334, vol. 8, No. 43.
Mousa, W. K., et al., "The Diversity of Anti-Microbial Secondary Metabolites Produced by Fungal Endophytes: An Interdisciplinary Perspective," Front Microbiol., 2013, vol. 4, No. 65, 18 Pages.
Mundt, J.O., et al., "Bacteria Within Ovules and Seeds," Appl Environ Microbiol., 1976, pp. 694-698, vol. 32, No. 5.
Naik, B. S., et al., "Study on the diversity of endophytic communities from rice (*Oryza sativa* L.) and their antagonistic activities in vitro," Microbiological Research, 2009, pp. 290-296, vol. 164.
Naveed, M., "Maize Endophytes—Diversity, Functionality and Application Potential," University of Natural Resources and Life Sciences, 2013, pp. 1-266 and 81-87; Tables 1-3; Figure 2.
Nejad, P. et al., "Endophytic Bacteria Induce Growth Promotion and Wilt Disease Suppression in Oilseed Rape and Tomato," Biological Control, 2000, pp. 208-215, vol. 18.
Neslon, E.B., "Microbial Dynamics and Interactions in the Spermosphere," Ann. Rev. Phytopathol., 2004, pp. 271-309, vol. 42.
Nikolcheva, L.G., et al., "Taxon-Specific Fungal Primers Reveal Unexpectedly High Diversity During Leaf Decomposition in a Stream," Mycological Progress, 2004, pp. 41-49, vol. 3, No. 1.
Nimnoi, P., et al., "Co-Inoculation of Soybean (*Glycin max*) with Actinomycetes and Bradyrhizobium Japonicum Enhances Plant Growth, Nitrogenase Activity and Plant Nutrition," Journal of Plant Nutrition, 2014, pp. 432-446, vol. 37.
Nishijima, K.A., et al., "Demonstrating Pathogenicity of Enterobacter cloacae on Macadamia and Identifying Associated Volatiles of Gray Kernel of Macadamia in Hawaii," Plant Disease, Oct. 2007, vol. 91, No. 10, pp. 1221-1228.
Normander, B., et al., "Bacterial Origin and Community Composition in the Barley Phytosphere as a Function of Habitat and Presowing Conditions," Appl Environ Microbiol., Oct. 2000, pp. 4372-4377, vol. 66, No. 10.
Okunishi, S., et al., "Bacterial Flora of Endophytes in the Maturing Seeds of Cultivated Rice (*Oryza sativa*)," Microbes and Environment, 2005, pp. 168-177, vol. 20, No. 3.
Op De Beeck, M., et al., "Comparison and Validation of Some ITS Primer Pairs Useful for Fungal Metabarcoding Studies," PLOS ONE, Jun. 2014, vol. 9, Issue 6, e97629, pp. 1-11.
Orole, O. O., et al., "Bacterial and fungal endophytes associated with grains and roots of maize," Journal of Ecology and the Natural Enviornment, 2011, pp. 298-303, vol. 3, No. 9.
Partida-Martinez, L.P., et al., "The Microbe-Free Plant: Fact or Artifact?" Front Plant Sci., 2011, vol. 2, No. 100, 16 Pages.
Pearson, W.R., et al., "Rapid and Sensitive Sequence Comparison With FASTP and FASTA," Methods Enzymol., 2011, pp. 63-98, vol. 183.
Pedraza, R. O., et al., "Azospirillum inoculation and nitrogen fertilization effect on grain yield and on the diversity of endophytic bacteria in the phyllosphere of rice rainfed crop," European Journal of Soil Biology, 2009, pp. 36-43, vol. 45.
Perez-Fernandez, M. A., et al., "Simulation of Germination of Pioneer Species Along an Experimental Drought Gradient," J Environ Biol., 2006, pp. 669-685, vol. 27, No. 4.
Perez-Miranda, S., et al., "O-CAS, A Fast and Universal Method for Siderophore Detection," J Microbiol Methods, 2007, pp. 127-131, vol. 70.
Petti, C. A., "Detection and Identification of Microorganisms by Gene Amplification and Sequencing," Clinical Infectious Diseases, 2007, pp. 1108-1114, vol. 44.
Phalip, V., et al., "A Method for Screening Diacetyl and Acetoin-Producing Bacteria on Agar Plates," J Basic Microbiol., 1994, pp. 277-280, vol. 34.
Philippot, L., et al., "Going Back to the Roots: The Microbial Ecology of the Rhizosphere," Nat Rev Microbiol., Nov. 2013, pp. 789-799, vol. 11.
Philrice Batac, Philippine Rice R&D Highlights, 2012, Area-Based R&D Projects, 52 Pages, [online][Retrieved Aug. 11, 2016] Retrieved from the Internet <URL:http://www.philrice.gov.ph/2012-rd-highlights/>.
Pillay, V. K., et al., "Inoculum Density, Temperature, and Genotype Effects on in vitro Growth Promotion and Epiphytic and Endophytic Colonization of Tomato (*Lycopersicon esculentum* L.) Seedlings Inoculated with a Pseudomonad Bacterium," Can J Microbiol., 1997, pp. 354-361, vol. 43.
Powell, W. A., et al., "Evidence of Endophytic Beauveria Bassiana in Seed-Treated Tomato Plants Acting as a Systemic Entomopathogen to Larval *Helicoverpa zea* (Lepidoptera: Noctuidae)," J. Entomol. Sci., 2009, pp. 391-396, vol. 44, No. 4.
Quadt-Hallmann, A., et al., "Bacterial Endophytes in Cotton: Mechanisms of Entering the Plant," Can J Microbiol., 1997, pp. 577-582, vol. 43.
R Core Team, "R: A Language and Environment for Statistical Computing," R Foundation for Statistical Computing, Vienna, Austria, May 2013, ISBN: 3-900051-07-0. Available online at http://www.R- 25 project.org/, 3604 Pages.
Rae, R., et al., "A subset of naturally isolated Bacillus strains show extreme virulence to the free-living nematodes Caenorhabditis elegans and Pristionchus pacificus", Environmental Microbiology, 2010, pp. 3007-3021, vol. 12, No. 11.
Rasmussen, S., et al., "Grass-endophyte interactions: a note on the role of monosaccharide transport in the Neotyphodium lolii-Lolium perenne symbiosis," New Phytologist, 2012, pp. 7-12, vol. 196.
Ravel, C., et al., "Beneficial effects of Neotyphodium lolii on the growth and the water status in perennial ryegrass cultivated under nitrogen deficiency or drought stress," Agronomie, 1997, pp. 173-181, vol. 17.
Redman, R. S., et al., "Thermotolerance Generated by Plant/Fungal Symbiosis," Science, Nov. 2002, vol. 298, 1 Page (with 4 pages of supplemental material).
Reiter, B., et al., "Response of Endophytic Bacterial Communities in Potato Plants to Infection with *Erwinia carotovora* subsp. *atroseptica*," Appl Environ Microbiol., 2001, pp. 2261-2268, vol. 68, No. 5.
Ren, Y., et al., "Complete Genome Sequence of *Enterobacter cloacae* subsp. *cloacae* Type Strain ATCC 13047," J. Bacteriol. May 2010, vol. 192, No. 9, pp. 2463-2464.
Riess, K., et al., "High genetic diversity at the regional scale and possible speciation in Sebacina epigaea and S. incrustans," BMC Evolutionary Biology, 2013, vol. 13, No. 102, 17 Pages.
Riken, GI No. GMFL01-01-D03, 2 Pages, [online] [Retrieved on Dec. 18, 2017] Retrieved from the internet <URL:http://spectra.psc.riken.jp/menta.cgi/rsoy/datail?id=GMFL01-01-D03>.
Rodriguez, H., et al., "Expression of a Mineral Phosphate Solubilizing Gene From Erwinia herbicola in Two Rhizobacterial Strains," J Biotechnol., 2001, pp. 155-161, vol. 84.
Rodriguez, R.J., et al., "Stress Tolerance in Plants via Habitat-Adapted Symbiosis," ISME J., 2008, pp. 404-416, vol. 2.
Rodriguez-Navarro, D., et al., "Soybean Interactions with Soil Microbes, Agronomical and Molecular Aspects," Agronomy for Sustainable Development, 2011, pp. 173-190, vol. 31, No. 1.
Roessner, U., et al., "Metabolic Profiling Allows Comprehensive Phenotyping of Genetically or Environmentally Modified Plant Systems," Plant Cell, 2001 ,pp. 11-29, vol. 13.

(56) References Cited

OTHER PUBLICATIONS

Rosado, A. S., et al., "Phenotypic and Genetic Diversity of Paenibacillus azotofixans Strains Isolated from the Rhizoplane or Rhizosphere Soil of Different Grasses," J App Microbiol., 1998, pp. 216-226, vol. 84.
Rosenblueth, A., et al., "Seed Bacterial Endophytes: Common Genera, Seed-to-Seed Variability and Their Possible Role in Plants," Acta Hort., 2012, pp. 39-48, vol. 938.
Rosenblueth, M., et al., "Bacterial Endophytes and Their Interactions With Host," Molecular Plant-Microbe Interactions, 2006, pp. 827-837, vol. 19, No. 8.
Ross, P.L., et al., "Multiplexed Protein Quantitation in *Saccharomyces cerevisiae* Using Amine-Reactive Isobaric Tagging Reagents," Mol Cell Proteomics, 2004, pp. 1154-1169, vol. 3, No. 12.
Saleem, M., et al., "Perspective of Plant Growth Promoting Rhizobacteria (PGPR) Containing ACC Deaminase in Stress Agriculture," J Ind Microbiol Biotechnol., Oct. 2007, pp. 635-648, vol. 34.
Samac, D.A., et al., "Recent Advances in Legume-Microbe Interactions: Recognition, Defense Response, and Symbiosis from a Genomic Perspective," Plant Physiol., 2007, pp. 582-587, vol. 144.
Samways, M.J., et al., "Assessment of the Fungus *Cladosporium oxyspoum* (Berk. and Curt.) as a Potential BioControl Agent Against Certain Homoptera," Elsevier Science Publioshers B.V., Jan. 1, 1986, pp. 231-239.
Sardi, P., et al., "Isolation of Endophytic Streptomyces Strains from Surface Sterilized Roots," Applied and Environmental Microbiology, 1992, pp. 2691-2693, vol. 58, No. 8.
Sarwar, M., et al., "Tryptophan Dependent Biosynthesis of Auxins in Soil," Plant Soil, 1992, pp. 207-215, vol. 147.
Saunders, M., et al., "Host-Synthesized Secondary Compounds Influence the In Vitro Interactions between Fungal Endophytes of Maize", Applied and Environmental Microbiology, Nov. 9, 2007, pp. 136-142, vol. 74 , No. 1.
Schmieder, R., et al., "Quality Control and Preprocessing of Metagenomic Datasets," Bioinformatics, 2011, pp. 863-864, vol. 27, No. 6.
Schneider, C., et al., "Endophytes for plant protection: the state of the art Proceedings," DPG Spectrum Phytomedizin, Proceedings of the 5th International Symposium on Plant Protection and Plant Health in Europe, May 26-29, 2013, 347 Pages.
Schoch, C. L., et al., "Nuclear Ribosomal Internal Transcribed Spacer (ITS) Region as a Universal DNA Barcode Marker for Fungi," Proc Natl Acad Sci USA, 2012, pp. 6241-6246, vol. 109, No. 16.
Schwyn, B et al., "Universal Chemical Assay for the Detection and Determination of Siderophores," Analytical Biochemistry, 1987, pp. 47-56, vol. 160.
Senthilkumar, M., et al., "Biocontrol Potential of Soybean Bacterial Endophytes Against Charcoal Rot Fungus, *Rhizoctonia batatiola,*" Current Microbiology, 2009, vol. 58, pp. 288-293.
Sessitsch, A., et al., "*Burkholderia phytofirmans* sp. Nov., a novel plant-associated bacterium with plant-beneficial properties," International Journal of Systematic and Evoluntary Microbiology, 2005, pp. 1187-1192, vol. 55.
Shapiro-Ilan, D.I., et al., "The Potential for Enhanced Fungicide Resistance in Beauveria Bassiana Through Strain Discovery and Artificial Selection," Journal of Invertebrate Pathology, 2002, pp. 86-93, vol. 81.
Shankar, M., et al.,"Root colonization of a rice growth promoting strain of Enterobacter cloacae," Journal of Basic Microbiology, 2011, pp. 523-530, vol. 51.
Shiraishi, A., et al., "Nodulation in black locust by the ammaproteobacteria *Pseudomonas* sp. and the Betaproteobacteria *Burkholderia* sp", Systematic and Applied Microbiology, Aug. 2010, pp. 269-274, vol. 33, No. 5.
Simola, L., et al., "The Effect of Some Protein and Non-Protein Amino Acids on the Growth of Cladosporium herbarum and Trichotheeium roseum," Effect of Amino Acids on Fungi, Physiologia Plantarum, 1979, pp. 381-387, vol. 46.
Singh, A. K., et al., "Uncultured *Actinomyces* sp. Clone EMLACT 80 IV (New) 16S Ribosomal RNA Gene, Partial Sequence," NCBI GenBank Accession No. JQ285908. Submitted Dec. 13, 2011.
Soares, M. M. C. N., et al., "Screening of Bacterial Strains for Pectinolytic Activity Characterization of the Polygalacturonase Produced by *Bacillus* SP," Revista de Microbiolgia, 1999, pp. 299-303, vol. 30.
Soe, K.M., et al., "Effects of endophytic actinomycetes and Bradyrhizobium japonicum strains on growth, nodulation, nitrogen fixation and seed weight of different soybean varieties," Soil Science and Plant Nutrition, 2012, pp. 319-325, vol. 58, No. 3.
Soe, K.M., et al., "Low-Density Co-Inoculation of Myanmar Bradyrhizobium yuanmingense MAS34 and Streptomyces griseoflavus P4 to Enhance Symbiosis and Seed Yield in Soybean Varieties," American Journal of Plant Sciences, 2013, pp. 1879-1892, vol. 4.
Sogonov, M.V., et al., "The hyphomycete *Teberdinia hygrophila* gen. nov., sp. nov. and related anamorphs of *Pseudeurotium* species," Mycologia, May 2005, pp. 695-709, vol. 97, No. 3.
Song, M., et al., "Effects of Neotyphodium Endophyte on Germination of Hordeum brevisubulatum under Temperature and Water Stress Conditions," Acta Agrestia Sinica, 2010, pp. 834-837, vol. 18, No. 6. (English Abstract).
Souleimanov, A., et al., "The Major Nod Factor of Bradyrhizobium japonicum Promotes Early Growth of Soybean and Corn," J. Exp. Bot., 2002, pp. 1929-1934, vol. 53, No. 376.
Spiekermann, P., et al., "A Sensitive, Viable-Colony Staining Method Using Nile Red for Direct Screening of Bacteria that Accumulate Polyhydroxyalkanoic Acids and Other Lipid Storage Compounds," Arch Microbiol., 1999, pp. 73-80, vol. 171.
Staudt, A. K., et al., "Variations in Exopolysaccharide Production by Rhizobium tropici," Arch Microbiol., 2012, pp. 197-206, vol. 194.
Stielow, J.B., et al., "One fungus, which genes? Development and assessment of universal primers for potential secondary fungal DNA barcodes," Persoonia: Molecular Phylogeny and Evolution of Fungi, 2015, vol. 35, pp. 242-263.
Strobel, G. A., "Endophytes as Sources of Bioactive Products," Microbes and Infection, 2003, pp. 535-544, vol. 5.
Sturz, A. V., et al., "Weeds as a Source of Plant Growth Promoting Rhizobacteria in Agricultural Soils," Can J Microbiol., 2001, pp. 1013-1024, vol. 47, No. 11.
Surette, M. A., et al. "Bacterial Endophytes in Processing Carrots (*Daucus carota* L. var. *sativus*): Their Localization, Population Density, Biodiversity and Their Effects on Plant Growth," Plant and Soil, 2003, pp. 381-390, vol. 253, No. 2.
Suto, M., et al., "Endophytes as Producers of Xylanase," J Biosci Bioeng., 2002, pp. 88-90, vol. 93, No. 1.
Sword, G., "Manipulating Fungal Endophytes to Protect Plants from Insects and Nematodes," Power Point Presentation dated Aug. 7, 2013.
Sword, G., et al., "Manipulating Fungal Endophytes for the Protection of Cotton in the Field," Power Point Presentation dated Jan. 7, 2013.
Sword, G., et al., "Field Trials of Potentially Beneficial Fungal Endophytes in Cotton," Power Point Presentation dated Jan. 7, 2013.
Sword, G., "Fungal Endophytes to Protect Cotton from Insects and Nematodes," Power Point Presentation dated Dec. 7, 2012, 20 Pages.
Sword, G., "Natural Enemies—The Forgotten Basis of IPM?," Power Point Presentation dated Sep. 6, 2013.
Taghavi, S., et al., "Genome Survey and Characterization of Endophytic Bacteria Exhibiting a Beneficial Effect on Growth and Development of Poplar Trees," Applied and Environmental Microbiology, 2009, pp. 748-757, vol. 75, No. 3.
Taghavi, S., et al., "Genome Sequence of the Plant Growth promoting Endophytic Bacterium *Enterobacter* sp. 638", PLoS Genet., May 2010, pp. 1-15, vol. 6, Issue 5, e1000943.
Tamura, K., et al., "Estimation of the No. of nucleotide substitutions in the control region of mitochondrial DNA in humans and chimpanzees," Molecular Biology and Evolution, 1993, vol. 10, No. 3, pp. 512-526.

(56) References Cited

OTHER PUBLICATIONS

Taylor, A. G., et al., "Concepts and Technologies of Selected Seed Treatments," Annu. Rev. Phytopathol., 1990, pp. 321-339, vol. 28.
Teather, R. M., et al., "Use of Congo Red-Polysaccharide Interactions in Enumeration and Characterization of Cellulolytic Bacteria from the Bovine Rumen," Appl Environ Microbiol., 1982, pp. 777-780, vol. 43, No. 4.
Thakur, A., et al., "Detrimental effects of endophytic fungus *Nigrospora* sp. on survival and development of Spodoptera litura," Biocontrol Science and Technology, Feb. 1, 2012, pp. 151-161, vol. 22, No. 2.
Thakur, A., et al., "Enhanced Resistance to Spodoptera litura in Endophyte Infected Cauliflower Plants," Environmental Entomology, Apr. 1, 2013, pp. 240-246, vol. 42, No. 2.
Thakur, A., et al., "Suppression of Cellular Immune Response in Spodoptera litura (Lepidoptera: Noctuidae) Larvae by Endophytic Fungi *Nigrospora oryzae* and *Cladosporium uredinicola*,", Annals of the Entomological Society of America, May 1, 2014, pp. 674-679, vol. 107, No. 3.
Theis, K. R., et al., "Uncultured Bacterium Clone GM2GI8201A64RC 16S Ribosomal RNA Gene, Partial Sequence," NCBI GenBank Accession No. JX051943, Submitted May 14, 2012.
Thomas, L., et al., "Development of Resistance to Chlorhexidine Diacetate in Pseudomonas aeruginosa and the Effect of a "Residual" Concentration," J Hosp Infect., 2000, pp. 297-303, vol. 46.
Thomashow, M. F., "So What's New in the Field of Plant Cold Acclimation? Lots!," Plant Physiol., 2001, pp. 89-93, vol. 125.
Tokala, R. T., et al., "Novel Plant-Microbe Rhizosphere Interaction Involving Streptomyces Lydicus WYEC108 and the Pea Plant (*Pisum sativum*)," Applied and Environmental Microbiology, May 2002, pp. 2161-2171, vol. 68, No. 5.
Trichoderma definition, 2016, 6 Pages, [online] [Retrieved on Sep. 16, 2016,] Retrieved from the Internet <URL:https://en.wikipedia.org/wiki/Trichoderma>.
Trotel-Aziz, P., et al., "Characterization of New Bacterial Biocontrol Agents *Acinetobacter, Bacillus, Pantoea* and *Pseudomonas* spp. Mediating Grapevine Resistance Against Botrytis cinerea," Environmental and Experimental Botany, 2008, pp. 21-32, vol. 64.
Truyens, S., et al., "Changes in the Population of Seed Bacteria of Transgenerationally Cd-Exposed *Arabidopsis thaliana*," Plant Biol., 2013, pp. 971-981, vol. 15.
U'Ren, J.M., et al., "Host and geographic structure of endophytic and endolichenic fungi at the continental scale," American Journal of Botany, May 1, 2012, pp. 898-914, vol. 99, No. 5.
Usadel, B., et al., "The Plant Transcriptome-From Integrating Observations to Models," Front Plant Sci., 2013, pp. 1-3, vol. 4., Article 48, 3 Pages.
Vacheron, J., et al., "Plant Growth-Promoting Rhizobacteria and Root System Functioning," Frontiers Plant Sci., 2013, vol. 4, Article 356, 19 Pages.
Valencia, C. U., et al., "Endophytic Establishment as an Unintended Consequence of Biocontrol with Fungal Entomopathogens," Power Point Presentation dated Jan. 7, 2013, 10 Pages.
Valencia, E., et al., "Mini-review: Brazilian fungi diversity for biomass degradation," Fungal Genetics and Biology, 2013, pp. 9-18, vol. 60.
Van Der Lelie, D., et al., "Poplar and its Bacterial Endophytes: Coexistence and Harmony," Critical Rev Plant Sci., 2009, pp. 346-358, vol. 28.
Verkley, G., et al., "Paraconiothyrium, a new genus to accommodate the mycoparasite *Coniothyrium minitans,* anamorphs of Paraphaeosphaeria, and four new species," Studies in Mycology, 2004, pp. 323-335, vol. 50.
Vining, K., et al., "Methylome Reorganization During in vitro Dedifferentiation and Regeneration of Populus trichocarpa," BMC Plant Biol., 2013, vol. 13, No. 92, 15 Pages.
Viruel, E., et al., "Pseudomonas thiveralensis Strain IEHa 16S Ribosomal RNA Fene, Partial Sequence," NCBI GenBank Accession No. GQ169380.1, Submitted May 15, 2009.
Visagie, C.M., et al., "Identification and nomenclature of the genus *Penicillium,*" Studies in Mycology, Jun. 2014, pp. 343-371, vol. 78.
Vujanovic, V., et al., "Viability Testing of Orchid Seed and the Promotion of Colouration and Germination," Annals of Botany, Mar. 17, 2000, pp. 79-86, vol. 86.
Vujanovic, V., et al., "Endophytic hyphal compartmentalization is required for successful mycobiont-wheat interaction as revealed by confocal laser microscopy," The proceedings of the Soils and Crops conference in Saskatoon (2008) published 2009, 7 Pages.
Vujanovic, V., et al., "A comparative study of endophytic mycobiota in leaves of Acer saccharum in eastern North America," Mycological Progress, May 2002, pp. 147-154, vol. 1, Issue 2.
Vujanovic, V., et al., "Orchid seed viability testing by fungal bioassays and molecular phylogeny," Floriculture, ornamental and plant biotechnology, 2006, vol. 63, pp. 563-569.
Vujanovic, V., et al., "Mycovitality—a new concept of plant biotechnology," Canadian Journal Plant Pathol, 2007, vol. 29, p. 451.
Vujanovic, V., et al., "19th International Conference on Arabidopsis. Research Proceedings—ICAR13," Jul. 23-27, 2008, 264 Pages, Montreal, QC, Canada.
Vujanovic, V., et al., "Mycovitality and mycoheterotrophy: where lies dormancy in terrestrial orchid and plants with minute seeds?" Symbiosis, 2007, vol. 44, pp. 93-99.
Vujanovic, V., et al., "Seed endosymbiosis: a vital relationship in providing prenatal care to plants," Can. J. Plant Sci., NRC Research Press, Feb. 6, 2017, pp. 972-981, vol. 97.
Waller, F., et al., "The Endophytic Fungus *Piriformospora indica* Reprograms Barley to Salt-Stress Tolerance, Disease Resistance, and Higher Yield," PNAS, 2005, pp. 13386-13391, vol. 102, No. 38.
Wang, B., et al., "Fungal endophytes of native *Gossypium* species in Australia," Mycological Research, 2007, pp. 347-354, vol. 111, No. 3.
Wang, K., et al., "Monitoring in Planta Bacterial Infection at Both Cellular and Whole-Plant Levels Using the Green Fluorescent Protein Variant GFPuv," New Phytol., 2007, pp. 212-223, vol. 174.
Wang, Q., et al., "Naive Bayesian Classifier for Rapid Assignment of rRNA Sequences into the New Bacterial Taxonomy," Appl. Environ. Microbiol., 2007, pp. 5261-5267, vol. 73, No. 16.
Waqas, M., et al., "Endophytic Fungi Produce Gibberellins and Indoleacetic Acid and Promotes Host-Plant Growth during Stress," Molecules, 2012, pp. 10754-10773, vol. 17.
Weaver, P.F., et al., "Characterization of Rhodopseudomonas capsulata," Arch Microbiol., 1975, pp. 207-216, vol. 105.
Weindling, R., "Relation of dosage to control of cotton seedling diseases by seed treatment," Plant Disease Reporter, 1943, 27, pp. 68-70.
Welty, R.E., et al., "Influence of Moisture Content, Temperature, and Length of Storage on Seed Germination and Survival of Endophytic Fungi in Seeds of Tall Fescue and Perennial Ryegrass," Phytopathyol., 1987, pp. 893-900, vol. 77, No. 6.
White, J. F., et al., "A Proposed Mechanism for Nitrogen Acquisition by Grass Seedlings Through Oxidation of Symbiotic Bacteria," Symbiosis, 2012, pp. 161-171, vol. 57.
Wiegand, I., et al., "Agar and Broth Dilution Methods to Determine the Minimal Inhibitory Concentration (MIC) of Antimicrobial Substances," Nature Protocols, 2008, pp. 163-175, vol. 3, No. 2.
Xu, M., et al., "Bacterial Community Compositions of Tomato (*Lycopersicum esculentum* Mill.) Seeds and Plant Growth Promoting Activity of ACC Deaminase Producing Bacillus subtilis (HYT-12-1) on Tomato Seedlings," World J Microbiol Biotechnol., 2014, pp. 835-845, vol. 30.
Xu, Y., et al., "Biosynthesis of the Cyclooligomer Despipeptide bassianolide, an Insecticidal Virulence Factor of Beauveria bassiana," Fungal Genetics and Biology, 2009, pp. 353-364, vol. 46.
Xue, Q.Y., et al., "Evaluation of the Strains of Acinetobacter and Enterobacter as potential Biocontrol Agents Against Ralstonia Wilt of Tomato," Biological Control, 2009, vol. 48, pp. 252-258.
Yandigeri, M. S., et al., "Drought-tolerant endophytic actinobacteria promote growth of wheat (*Triticum aestivum*) under water stress conditions," Plant Growth Regulation, 2012, pp. 411-420, vol. 68.
Yennamalli, R., et al., "Endoglucanases: insights into thermostability for biofuel applications", Biotech Biofuels, 2013, vol. 6, Issue 136, pp. 1-9.

(56) References Cited

OTHER PUBLICATIONS

Yezerski, A., et al., "The Effects of the Presence of Stored Product Pests on the Microfauna of a Flour Community," Journal of Applied Microbiology, 2005, pp. 507-515, vol. 98.
You, Y., et al., "Analysis of Genomic Diversity of Endophytic Fungal Strains Isolated from the Roots of Suaeda japonica and S. maritima for the Restoration of Ecosystems in Buan Salt Marsh," Korean Journal of Microbiology and Biotechnology, 2012, pp. 287-295, vol. 40, No. 4. (with English Abstract).
Youssef, Y.A., et al., "Production of Plant Growth Substances by Rhizosphere Myoflora of Broad Bean and Cotton," Biologia Plantarum, 1975, pp. 175-181, vol. 17, No. 3.
Zhao, J.H., et al., "Bioactive secondary metabolites from *Nigrospora* sp. LLGLM003, an endophytic fungus of the medicinal plant *Moringa oleifera* Lam." World Journal of Microbiology and Biotechnology, Kluwer Academic Publishers, Feb. 12, 2012, pp. 2107-2112, vol. 28, No. 5.
Zhang, J., et al: "Isolation and Characterization of Plant Growth-Promoting Rhizobacteria from Wheat Roots by Wheat Germ Agglutinin Labeled with Fluorescein Isothiocyanate", The Journal of Microbiology, Apr. 27, 2012, vol. 50, No. 2, pp. 191-198, GenBank Accession No. JN210900.
Zhou, W., et al., "Effects of the Fungal Endophyte *Paecilomyces* sp. in Cotton on the Roo-Knot Nematode Meloidogyne incognita," poster dated Jan. 7, 2013.
Zhu et al., *Helminthosporium velutinum* and *H. aquaticum* sp. nov. from aquatic habitats in Yunnan Province, China. Phytotaxa, 2016, vol. 253, No. 3, pp. 179-190.
Zimmerman, N.B., et al., "Fungal Endophyte Communities Reflect Environmental Structuring Across a Hawaiian Landscape," Proc Natl Acad Sci USA, 2012, pp. 13022-13027, vol. 109, No. 32.
Zuccaro, A., et al., "Endophytic Life Strategies Decoded by Genome and Transcriptome Analyses of the Mutualistic Root Symbiont Piriformospora indica," PLOS Pathogens, 2011, vol. 7, No. 10, e1002290.
Zuniga, A., et al., "Quorum Sensing and Indole-3-Acetic Acid Degradation Play a Role in Colonization and Plant Growth Promotion of *Arabidopsis thaliana* by Burkholderia phytofirmans PsJN," Mol Plant Microbe Interact., 2013, pp. 546-553, vol. 26, No. 5.
Communication pursuant to Article 94(3) EPC for European Patent Application No. EP 14777213.1, Jun. 18, 2018, 4 Pages.
First Examination Report for New Zealand Patent Application No. NZ 734085, Jun. 27, 2018, 6 Pages.
Govindarajan, M. et al., "Effects of the Inoculation of Burkholderia vietnamensis and Related Endophytic Diaztrophic Bacteria on Grain Yield of Rice", Mircobial Ecology, Apr. 4, 2007, 17 pages.
Lind, A., et al., "Drivers of genetic diversity in secondary metabolic gene clusters within a fungal species", PLOS Biology, Nov. 17, 2017, 26 pages.
Sha, T. et al., "Genetic diversity of the endemic gourmet mushroom *Thelephora ganbajun* from southwestern China", Microbiology (2008), 154, 3460-3468.
Sugita, T. et al., "Intraspecies Diversity of Cryptococcus laurentii as Revealed by Sequences of Internal Transcribed Spacer Regions and 28S rRNA Gene and Taxonomic Position of C. Taurentii Clinical Isolates", Journal of Clinical Microbiology, Apr. 2000, p. 1468-1471.
Kemp, N., et al., "Sarocladium zeae is a systemic endophyte of wheat and an effective biocontrol agent against Fusarium head blight", Biological Control, vol. 149, Publication No. 104329, 10 pages (2020).
Wicklow, D., et al., "A protective endophyte of maize: Acremonium zeae antibiotics inhibitory to Aspergillus flavus and Fasarium verticillioides", Mycol. Res. 109 (5):610-618 (May 2005).
Pan, J., et al., "Effects of host plant environment and Ustilago maydis infection on the fungal endophyte community of maize (*Zea mays*)", New Phytologist, vol. 178, pp. 147-156 (2008).
Wicklow, D., et al., "Occurrence of pyrrocidine and dihydroresorcylide production among Acremonium zeae populations from maize grown in different regions", Canadian Journal of Plant Pathology, vol. 30, pp. 425-433 (2008).
European Patent Office, Partial European Search Report, European Patent Application No. 18791606.9, dated Jul. 26, 2021, 16 Pages.
Abaid-Ullah, M., et al., "Plant Growth Promoting Rhizobacteria: An Alternate Way to Improve Yield and Quality of Wheat (*Triticum aestivum*)", International Journal of Agriculture and Biology, vol. 17, No. 1, Jan. 1, 2015, pp. 51-60.
Colla, G., et al., "Coating seeds with endophytic fungi enhances growth, nutrient uptake, yield and grain quality of winter wheat", International Journal of Plant Production, vol. 9, No. 2, Apr. 1, 2015, pp. 171-190.
Larran, S., et al., "Endophytes from wheat as biocontrol agents against tan spot disease", Biological Control, vol. 92, Sep. 11, 2015, pp. 17-23.
European Patent Office, Search Report, European Patent Application No. 17825317.5, dated Oct. 12, 2021, 9 Pages.
Yuan, J., et al., "Roots from distinct plant developmental stages are capable of rapidly selecting their own microbiome without the influence of environmental and soil edaphic factors", Soil Biology and Biochemistry 89 (2015): 206-209.
Bing, L., et al., Suppression of *Ostrinia nubilalis* (Hübner) (Lepidoptera: Pyralidae) by Endophytic *Beauveria bassiana* (Balsamo) Vuillemin, Environ. Entomol. 20(4): 1207-1211 (1991).
Frichot, E., et al., "Testing for Associations between loci and environmental gradients using latent factor mixed models", Mol. Biol. Evol. 30:7 1687-1699 (Year: 2013).
Bicego, M., et al., "Investigating Topic Models' Capabilities in Expression Microarray Data Classification", IEEE/transactions on computational biology and bioinformatics, 9:8 1831-1836 (Year: 2012).
Gerber, G., et al., "Inferring Dynamic Signatures of Microbes in Complex Host Ecosystems", PLOS Computational Biology 8:8 e1002624, 14 pages (Year: 2012).
Holmes, I., et al., "Dirichlet Multinomial Mixtures: Generative Models for Microbial Metagenomics", PLoSONE 7:2, e30126, 15 pages (Year: 2012).
Kim, Y., et al., "Deciphering the human microbiome using next-generation sequencing data and bioinformatics approaches", Methods 79-80, p. 52-59 (Year: 2015).
Anesi, A., et al., "Towards a scientific interpretation of the terrior concept: platicisity of the grape berry metabolome", BMP plant biology 15:191, 17 pages (Year: 2015).
Hill, S.T., The pursuit of hoppiness: propelling hop into the genomic era. Thesis, Oregon State University, 80 pages (Year: 2016).
Li, M., et al., "Persistent homology and the branching topologies of plants", American Journal of Botany, 104:3, 349-353 (Year: 2017).

* cited by examiner

Control MIC-68178

Control MIC-68178

Control MIC-68178/MIC-33414

ENDOPHYTE COMPOSITIONS AND METHODS FOR IMPROVEMENT OF PLANT TRAITS

CROSS REFERENCE TO RELATED APPLICATIONS

This application is a Divisional Application of U.S. application Ser. No. 15/829,865, filed Dec. 1, 2017, which claims priority to Provisional Application No. 62/556,288, filed Sep. 8, 2017; Provisional Application No. 62/467,740, filed Mar. 6, 2017; Provisional Application No. 62/467,742, filed Mar. 6, 2017; Provisional Application No. 62/467,755, filed Mar. 6, 2017; Provisional Application No. 62/466,253, filed Mar. 2, 2017; Provisional Application No. 62/465,834, filed Mar. 2, 2017; Provisional Application No. 62/466,256, filed Mar. 2, 2017; Provisional Application No. 62/465,797, filed Mar. 1, 2017; Provisional Application No. 62/465,819, filed Mar. 1, 2017; and Provisional Application No. 62/465,798, filed Mar. 1, 2017, the disclosures of which are incorporated by reference in their entirety.

SEQUENCE LISTING

The instant application contains a Sequence Listing with 71 sequences which has been submitted via EFS-Web and is hereby incorporated by reference in its entirety. Said ASCII copy, created on Apr. 1, 2020, is named IAI-101USD1_Sequence_Listing.txt, and is 54,909 bytes in size.

FIELD OF THE INVENTION

This invention relates to compositions and methods for improving the traits of plants, particularly plants important for human or animal consumption, for example rice (*Oryza sativa* and related varieties), soy (*Glycine max* and related varieties), wheat (*Triticum aestivum* and related varieties), and corn (*Zea mays* and related varieties). For example, this invention describes microbes that are capable of living within or heterologously disposed to a plant, and which can be used to impart improved traits to plants with which they are or have been heterologously disposed. The disclosed invention also describes methods of improving plant element characteristics by introducing microbes to parental plants. Further, this invention also provides methods of treating plant elements with microbes that are capable of living within a plant, particularly rice, soy, wheat, and corn, to impart improved yield, and other agronomic characteristics to that plant.

BACKGROUND

According the United Nations Food and Agricultural Organization, the world's population will exceed 9.6 billion people by the year 2050, which will require significant improvements in agricultural to meet growing food demands. There is a need for improved agricultural plants that will enable the nearly doubled food production demands with fewer resources and more environmentally sustainable inputs, for plants with improved responses to various abiotic stresses.

Today, crop performance is optimized primarily via technologies directed towards the interplay between crop genotype (e.g., plant breeding, genetically-modified (GM) crops) and its surrounding environment (e.g., fertilizer, synthetic herbicides, pesticides). While these paradigms have assisted in doubling global food production in the past fifty years, yield growth rates have stalled in many major crops, and shifts in the climate have been linked to production instability as well as changing pest and disease pressures, driving an urgent need for novel solutions to crop improvement. In addition to their long development and regulatory timelines, public fears of GM-crops and synthetic chemicals have challenged their use in many key crops and countries, resulting in a lack of acceptance for many GM traits and the exclusion of GM crops and many synthetic chemistries from some global markets. Thus, there is a significant need for innovative, effective, environmentally-sustainable, and publicly-acceptable approaches to improving the yield and other agronomically important characteristics of plants.

Provided herein are methods and compositions for improving agronomically important characteristics of plants by associating those plants with the disclosed endophytes.

SUMMARY OF INVENTION

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Exserohilum* and comprises at least one polynucleotide sequence at least 97% identical to a polynucleotide sequence selected from the group consisting of SEQ ID NOs: 60, 61, and 62, wherein the corn plant element is the variety Stine 9734 or a closely related variety thereof.

In one aspect, the invention provides a method of improving a trait of agronomic importance in a soybean plant, comprising heterologously disposing an endophyte to a soybean plant element in an amount effective to increase yield in the plant derived from the treated plant element relative to a plant derived from a reference plant element, wherein the endophyte is a member of the genus *Exserohilum* and comprises at least one polynucleotide sequence at least 97% identical to a polynucleotide sequence selected from the group consisting of SEQ ID NOs: 60, 61, and 62.

In one aspect, the invention provides a method of improving a trait of agronomic importance in a soybean plant, comprising heterologously disposing an endophyte to a soybean plant element in an amount effective to increase yield in the plant derived from the treated plant element relative to a plant derived from a reference plant element, wherein the endophyte is a member of the genus *Exserohilum* and comprises at least one polynucleotide sequence at least 97% identical to a polynucleotide sequence selected from the group consisting of SEQ ID NOs: 60, 61, and 62 and wherein the soybean plant is a variety selected from the group consisting of Pfister 38R25, Dairyland DSR1808R2Y, Stine 3920, and closely related varieties thereof.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Exserohilum* and comprises at least one polynucleotide sequence at least 97% identical to a polynucleotide sequence selected from the group consisting of SEQ ID NOs: 60, 61, and 62.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Exserohilum* and comprises at least one polynucleotide sequence at least 97% identical to a polynucleotide sequence selected from the group consisting of SEQ ID NOs: 60, 61, and 62, and wherein the wheat plant is a variety selected from the group consisting of SDSU Focus, SDSU Select, and closely related varieties thereof.

In one aspect, the invention provides a method of improving a trait of agronomic importance in a peanut plant, comprising heterologously disposing an endophyte to a peanut plant element in an amount effective to increase yield in the plant derived from the treated plant element relative to a plant derived from a reference plant element, wherein the endophyte is a member of the genus *Exserohilum* and comprises at least one polynucleotide sequence at least 97% identical to a polynucleotide sequence selected from the group consisting of SEQ ID NOs: 60, 61, and 62.

In one aspect, the invention provides a method of improving a trait of agronomic importance in a peanut plant, comprising heterologously disposing an endophyte to a peanut plant element in an amount effective to increase yield in the plant derived from the treated plant element relative to a plant derived from a reference plant element, wherein the endophyte is a member of the genus *Exserohilum* and comprises at least one polynucleotide sequence at least 97% identical to a polynucleotide sequence selected from the group consisting of SEQ ID NOs: 60, 61, and 62 and wherein the peanut plant is a variety selected from the group consisting of AT-9899, FloRun 107, Tamnut OL06, Georgia-06G, and closely related varieties thereof.

In one aspect, the invention provides a method of improving a trait of agronomic importance in a soybean plant, comprising heterologously disposing an endophyte to a soybean plant element in an amount effective to improve a trait of agronomic importance selected from the group consisting of root area, root length, and root dry weight in the plant derived from the treated plant element relative to a plant derived from a reference plant element, wherein the endophyte is a member of the genus *Epicoccum* and comprises at least one polynucleotide sequence at least 97% identical to a polynucleotide sequence selected from the group consisting of SEQ ID NOs: 63, 64, and 71.

In one aspect, the invention provides a method of improving a trait of agronomic importance in a soybean plant, comprising heterologously disposing an endophyte to a soybean plant element in an amount effective to improve a trait of agronomic importance selected from the group consisting of root area, root length, and root dry weight in the plant derived from the treated plant element relative to a plant derived from a reference plant element, wherein the endophyte is a member of the genus *Epicoccum* and comprises at least one polynucleotide sequence at least 97% identical to a polynucleotide sequence selected from the group consisting of SEQ ID NOs: 63, 64, and 71, and wherein the soybean is variety Stine 33E22 or a closely related variety thereof.

In one aspect, the invention provides a method of improving a trait of agronomic importance in a peanut plant, comprising heterologously disposing an endophyte to a peanut plant element in an amount effective to increase yield in the plant derived from the treated plant element relative to a plant derived from a reference plant element, wherein the endophyte is a member of the genus *Epicoccum* and comprises at least one polynucleotide sequence at least 97% identical to a polynucleotide sequence selected from the group consisting of SEQ ID NOs: 63, 64, and 71.

In one aspect, the invention provides a method of improving a trait of agronomic importance in a peanut plant, comprising heterologously disposing an endophyte to a peanut plant element in an amount effective to increase yield in the plant derived from the treated plant element relative to a plant derived from a reference plant element, wherein the endophyte is a member of the genus *Epicoccum* and comprises at least one polynucleotide sequence at least 97% identical to a polynucleotide sequence selected from the group consisting of SEQ ID NOs: 63, 64, and 71, and wherein the peanut plant is a variety selected from the group consisting of FloRun 107, Georgia-06G, and closely related varieties thereof.

In one aspect, the invention provides a method of improving a trait of agronomic importance in a rice plant, comprising heterologously disposing an endophyte to a rice plant element in an amount effective to increase root length in the plant derived from the treated plant element relative to a plant derived from a reference plant element, wherein the endophyte is a member of the genus *Epicoccum* and comprises at least one polynucleotide sequence at least 97% identical to a polynucleotide sequence selected from the group consisting of SEQ ID NOs: 63, 64, and 71.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Coniochaeta* and comprises at least one polynucleotide sequence at least 97% identical to a polynucleotide sequence selected from the group consisting of SEQ ID NOs: 38, 39, 40, and 41.

In one aspect, the invention provides a method of improving a trait of agronomic importance in a canola plant, comprising heterologously disposing an endophyte to a canola plant element in an amount effective to increase yield in the plant derived from the treated plant element relative to a plant derived from a reference plant element, wherein the endophyte is a member of the genus *Epicoccum* and comprises at least one polynucleotide sequence at least 97% identical to SEQ ID NO: 70, wherein the canola plant is the variety Brett Young 552 or a closely related variety thereof.

In one aspect, the invention provides a method of improving a trait of agronomic importance in a soybean plant, comprising heterologously disposing an endophyte to a soybean plant element in an amount effective to improve a trait of agronomic importance selected from the group consisting of root area, root length, and yield in the plant derived from the treated plant element relative to a plant derived from a reference plant element, wherein the endophyte is a member of the genus *Curvularia* and comprises at least one polynucleotide sequence at least 97% identical to a polynucleotide sequence selected from the group consisting of SEQ ID NOs: 65 and 66.

In one aspect, the invention provides a method of improving a trait of agronomic importance in a soybean plant, comprising heterologously disposing an endophyte to a soybean plant element in an amount effective to improve a trait of agronomic importance selected from the group consisting of root area, root length, and yield in the plant derived from the treated plant element relative to a plant derived from a reference plant element, wherein the endophyte is a member of the genus *Curvularia* and comprises at least one polynucleotide sequence at least 97% identical to a polynucleotide sequence selected from the group consisting of SEQ ID NOs: 65 and 66, and wherein the trait of agronomic importance is yield and the soybean plant is a variety selected from the group consisting of Pfister 38R25, Stine 3920, and closely related varieties thereof.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Curvularia* and comprises at least one polynucleotide sequence at least 97% identical to a polynucleotide sequence selected from the group consisting of SEQ ID NOs: 65 and 66.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Curvularia* and comprises at least one polynucleotide sequence at least 97% identical to a polynucleotide sequence selected from the group consisting of SEQ ID NOs: 65 and 66, wherein the wheat plant is a variety selected from the group consisting of SDSU Focus, SDSU Select, and closely related varieties thereof.

In one aspect, the invention provides a method of improving a trait of agronomic importance in a soybean plant, comprising heterologously disposing an endophyte to a soybean plant element in an amount effective to improve a trait of agronomic importance selected from the group consisting of root area, root length, dry shoot biomass, and yield in the plant derived from the treated plant element relative to a plant derived from a reference plant element, wherein the endophyte is a member of the genus *Curvularia* and comprises at least one polynucleotide sequence at least 97% identical to a polynucleotide sequence selected from the group consisting of SEQ ID NOs: 42, 43, 44, and 45.

In one aspect, the invention provides a method of improving a trait of agronomic importance in a soybean plant, comprising heterologously disposing an endophyte to a soybean plant element in an amount effective to improve a trait of agronomic importance selected from the group consisting of root area, root length, dry shoot biomass, and yield in the plant derived from the treated plant element relative to a plant derived from a reference plant element, wherein the endophyte is a member of the genus *Curvularia* and comprises at least one polynucleotide sequence at least 97% identical to a polynucleotide sequence selected from the group consisting of SEQ ID NOs: 42, 43, 44, and 45, wherein the trait of agronomic importance is yield and the soybean plant is a variety selected from the group consisting of Pfister 38R25, Stine 3920, and closely related varieties thereof.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Curvularia* and comprises at least one polynucleotide sequence at least 97% identical to a polynucleotide sequence selected from the group consisting of SEQ ID NOs: 42, 43, 44, and 45.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Curvularia* and comprises at least one polynucleotide sequence at least 97% identical to a polynucleotide sequence selected from the group consisting of SEQ ID NOs: 42, 43, 44, and 45, wherein the wheat plant is a variety selected from the group consisting of SDSU Focus, SDSU Select, and closely related varieties thereof.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Cladosporium* and comprises at least one polynucleotide sequence at least 97% identical to SEQ ID NO: 67, wherein the corn plant element is the variety Stine 9734 or a closely related variety.

In one aspect, the invention provides a method of improving a trait of agronomic importance in a soybean plant, comprising heterologously disposing an endophyte to a soybean plant element in an amount effective to improve a trait of agronomic importance selected from the group consisting of root area, root length, and yield in the plant derived from the treated plant element relative to a plant derived from a reference plant element, wherein the endophyte is a member of the genus *Cladosporium* and comprises at least one polynucleotide sequence at least 97% identical to SEQ ID NO: 67.

In one aspect, the invention provides a method of improving a trait of agronomic importance in a soybean plant, comprising heterologously disposing an endophyte to a soybean plant element in an amount effective to improve a trait of agronomic importance selected from the group consisting of root area, root length, and yield in the plant derived from the treated plant element relative to a plant derived from a reference plant element, wherein the endophyte is a member of the genus *Cladosporium* and comprises at least one polynucleotide sequence at least 97% identical to SEQ ID NO: 67, wherein the trait of agronomic importance is yield and the soybean plant is a variety selected from the group consisting of Pfister 38R25, Stine 3920, and closely related varieties thereof.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Cladosporium* and comprises at least one polynucleotide sequence at least 97% identical to SEQ ID NO: 67.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Cladosporium* and comprises at least one polynucleotide sequence at least 97% identical to SEQ ID NO: 67, wherein the wheat plant is a variety selected from the group consisting of SDSU Focus, SDSU Select, and closely related varieties thereof.

In one aspect, the invention provides a method of improving a trait of agronomic importance in a canola plant, comprising heterologously disposing an endophyte to a canola plant element in an amount effective to increase yield in the plant derived from the treated plant element relative to a plant derived from a reference plant element, wherein the endophyte is a member of the genus *Paecilomyces* and comprises at least one polynucleotide sequence at least 97% identical to SEQ ID NO: 69.

In one aspect, the invention provides a method of improving a trait of agronomic importance in a canola plant, comprising heterologously disposing an endophyte to a canola plant element in an amount effective to increase yield in the plant derived from the treated plant element relative to a plant derived from a reference plant element, wherein the endophyte is a member of the genus *Paecilomyces* and comprises at least one polynucleotide sequence at least 97% identical to SEQ ID NO: 69, wherein the canola plant is variety NCC1015 or a closely related variety thereof.

In one aspect, the invention provides a method of improving a trait of agronomic importance in a soybean plant, comprising heterologously disposing an endophyte to a soybean plant element in an amount effective to improve a trait of agronomic importance selected from the group consisting of root area, root length, and yield in the plant derived from the treated plant element relative to a plant derived from a reference plant element, wherein the endophyte is a member of the genus *Acremonium* and comprises at least one polynucleotide sequence at least 97% identical to a polynucleotide sequence selected from the group consisting of SEQ ID NOs: 46, 47, 48, 49, 50, and 51.

In one aspect, the invention provides a method of improving a trait of agronomic importance in a soybean plant, comprising heterologously disposing an endophyte to a soybean plant element in an amount effective to improve a trait of agronomic importance selected from the group consisting of root area, root length, and yield in the plant derived from the treated plant element relative to a plant derived from a reference plant element, wherein the endophyte is a member of the genus *Acremonium* and comprises at least one polynucleotide sequence at least 97% identical to a polynucleotide sequence selected from the group consisting of SEQ ID NOs: 46, 47, 48, 49, 50, and 51, wherein the trait of agronomic importance is yield and the soybean plant is variety Pfister 38R25 or a closely related variety thereof.

In one aspect, the invention provides a method of improving a trait of agronomic importance in a wheat plant, comprising heterologously disposing an endophyte to a wheat plant element in an amount effective to improve a trait of agronomic importance selected from the group consisting of decreasing grain moisture and increasing yield in the plant derived from the treated plant element relative to a plant derived from a reference plant element, wherein the endophyte is a member of the genus *Acremonium* and comprises at least one polynucleotide sequence at least 97% identical to a polynucleotide sequence selected from the group consisting of SEQ ID NOs: 46, 47, 48, 49, 50, and 51.

In one aspect, the invention provides a method of improving a trait of agronomic importance in a wheat plant, comprising heterologously disposing an endophyte to a wheat plant element in an amount effective to improve a trait of agronomic importance selected from the group consisting of decreasing grain moisture and increasing yield in the plant derived from the treated plant element relative to a plant derived from a reference plant element, wherein the endophyte is a member of the genus *Acremonium* and comprises at least one polynucleotide sequence at least 97% identical to a polynucleotide sequence selected from the group consisting of SEQ ID NOs: 46, 47, 48, 49, 50, and 51, wherein the wheat plant is a variety selected from the group consisting of SDSU Focus, SDSU Select, and closely related varieties thereof.

In one aspect, the invention provides a method of improving a trait of agronomic importance in a peanut plant, comprising heterologously disposing an endophyte to a peanut plant element in an amount effective to increase yield in the plant derived from the treated plant element relative to a plant derived from a reference plant element, wherein the endophyte is a member of the genus *Acremonium* and comprises at least one polynucleotide sequence at least 97% identical to a polynucleotide sequence selected from the group consisting of SEQ ID NOs: 46, 47, 48, 49, 50, and 51, and the peanut plant is a variety Georgia-06G or a closely related variety.

In one aspect, the invention provides a method of improving a trait of agronomic importance in a rice plant, comprising heterologously disposing an endophyte to a rice plant element in an amount effective to increase dry shoot biomass in the plant derived from the treated plant element relative to a plant derived from a reference plant element, wherein the endophyte is a member of the genus *Acremonium* and comprises at least one polynucleotide sequence at least 97% identical to a polynucleotide sequence selected from the group consisting of SEQ ID NOs: 46, 47, 48, 49, 50, and 51.

In one aspect, the invention provides a method of improving a trait of agronomic importance in a wheat plant, comprising heterologously disposing a first endophyte and a second endophyte to a wheat plant element in an amount effective to improve a trait of agronomic importance selected from the group consisting of plant height, fresh root weight, and fresh shoot weight in the plant derived from the treated plant element relative to a plant derived from a reference plant element, wherein the first endophyte is a member of the genus *Acremonium* and comprises at least one polynucleotide sequence at least 97% identical to a polynucleotide sequence selected from the group consisting of SEQ ID NOs: 46, 47, 48, 49, 50, and 51, and the second endophyte is a member of the genus *Coniochaeta* and comprises at least one polynucleotide sequence at least 97% identical to a polynucleotide sequence selected from the group consisting of SEQ ID NOs: 38, 39, 40, and 41.

In one aspect, the invention provides a method of improving a trait of agronomic importance in a rice plant, comprising heterologously disposing a first endophyte and a second endophyte to a rice plant element in an amount effective to increase yield in the plant derived from the treated plant element relative to a plant derived from a reference plant element, wherein the first endophyte is a member of the genus *Acremonium* and comprises at least one polynucleotide sequence at least 97% identical to a polynucleotide sequence selected from the group consisting of SEQ ID NOs: 46, 47, 48, 49, 50, and 51, and the second endophyte is a member of the genus *Coniochaeta* and comprises at least one polynucleotide sequence at least 97% identical to a polynucleotide sequence selected from the group consisting of SEQ ID NOs: 38, 39, 40, and 41.

In one aspect, the invention provides a method of improving a trait of agronomic importance in a soybean plant, comprising heterologously disposing an endophyte to a soybean plant element in an amount effective to increase yield in the plant derived from the treated plant element relative to a plant derived from a reference plant element, wherein the endophyte is a member of the genus *Cladosporium* and comprises at least one polynucleotide sequence at least 97% identical to SEQ ID NO: 68.

In one aspect, the invention provides a method of improving a trait of agronomic importance in a soybean plant, comprising heterologously disposing an endophyte to a soybean plant element in an amount effective to increase yield in the plant derived from the treated plant element relative to a plant derived from a reference plant element, wherein the endophyte is a member of the genus *Cladosporium* and comprises at least one polynucleotide sequence at least 97% identical to SEQ ID NO: 68, wherein the soybean is a variety selected from the group consisting of Pfister 38R25, Stine 3920, and closely related varieties thereof.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Cladosporium* and comprises at least one polynucleotide sequence at least 97% identical to SEQ ID NO: 68.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Cladosporium* and comprises at least one polynucleotide sequence at least 97% identical to SEQ ID NO: 68, wherein the wheat plant is a variety selected from the group consisting of SDSU Focus, SDSU Select, and closely related varieties thereof.

In one aspect, the invention provides a method of improving a trait of agronomic importance in a peanut plant, comprising heterologously disposing an endophyte to a peanut plant element in an amount effective to increase yield in the plant derived from the treated plant element relative to a plant derived from a reference plant element, wherein the endophyte is a member of the genus *Cladosporium* and comprises at least one polynucleotide sequence at least 97% identical to SEQ ID NO: 68 and the peanut plant is the variety AT-9899 or a closely related variety thereof.

In one aspect, the invention provides a method of improving a trait of agronomic importance in a soybean plant, comprising heterologously disposing a first endophyte and a second endophyte to a soybean plant element in an amount effective to increase dry root biomass in the plant derived from the treated plant element relative to a plant derived from a reference plant element, wherein the first endophyte is a member of the genus *Epicoccum* and comprises at least one polynucleotide sequence at least 97% identical to a polynucleotide sequence selected from the group consisting of SEQ ID NOs: 63, 64, and 71, the second endophyte is a member of the genus *Chaetomium* and comprises at least one polynucleotide sequence at least 97% identical to a polynucleotide sequence selected from the group consisting of SEQ ID NOs: 52, 53, 54, 55, 56, 57, 58, and 59, and soybean plant is variety Stine 33E22 or a closely related variety thereof.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Chaetomium* and comprises at least one polynucleotide sequence at least 97% identical to a polynucleotide sequence selected from the group consisting of SEQ ID NOs: 52, 53, 54, 55, 56, 57, 58, and 59.

In one aspect, the invention provides a method of improving a trait of agronomic importance in a soybean plant, comprising heterologously disposing an endophyte to a soybean plant element in an amount effective to improve a trait of agronomic importance selected from the group consisting of root area, root length, dry shoot biomass, and yield in the plant derived from the treated plant element relative to a plant derived from a reference plant element, wherein the endophyte is a member of the genus *Chaetomium* and comprises at least one polynucleotide sequence at least 97% identical to a polynucleotide sequence selected from the group consisting of SEQ ID NOs: 52, 53, 54, 55, 56, 57, 58, and 59.

In one aspect, the invention provides a method of improving a trait of agronomic importance in a soybean plant, comprising heterologously disposing an endophyte to a soybean plant element in an amount effective to improve a trait of agronomic importance selected from the group consisting of root area, root length, dry shoot biomass, and yield in the plant derived from the treated plant element relative to a plant derived from a reference plant element, wherein the endophyte is a member of the genus *Chaetomium* and comprises at least one polynucleotide sequence at least 97% identical to a polynucleotide sequence selected from the group consisting of SEQ ID NOs: 52, 53, 54, 55, 56, 57, 58, and 59, wherein the trait of agronomic importance is yield and the soybean plant is the variety Pfister 38R25 or a closely related variety thereof.

In one aspect, the invention provides a method of improving a trait of agronomic importance in a wheat plant, comprising heterologously disposing an endophyte to a wheat plant element in an amount effective to improve a trait of agronomic importance selected from the group consisting of root length and yield in the plant derived from the treated plant element relative to a plant derived from a reference plant element, wherein the endophyte is a member of the genus *Chaetomium* and comprises at least one polynucleotide sequence at least 97% identical to a polynucleotide sequence selected from the group consisting of SEQ ID NOs: 52, 53, 54, 55, 56, 57, 58, and 59.

In one aspect, the invention provides a method of improving a trait of agronomic importance in a wheat plant, comprising heterologously disposing an endophyte to a wheat plant element in an amount effective to improve a trait of agronomic importance selected from the group consisting of root length and yield in the plant derived from the treated plant element relative to a plant derived from a reference plant element, wherein the endophyte is a member of the genus *Chaetomium* and comprises at least one polynucleotide sequence at least 97% identical to a polynucleotide sequence selected from the group consisting of SEQ ID NOs: 52, 53, 54, 55, 56, 57, 58, and 59, wherein the wheat plant is a variety selected from the group consisting of SDSU Focus, SDSU Select, and closely related varieties thereof.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Exserohilum* and comprises at least one polynucleotide sequence at least 97% identical to a polynucleotide sequence selected from the group consisting of SEQ ID NOs: 60, 61, and 62, wherein the corn plant element is the variety Stine 9734 or a closely related variety thereof, wherein the plant element is a seed, optionally a modified seed.

In one aspect, the invention provides a method of improving a trait of agronomic importance in a soybean plant, comprising heterologously disposing an endophyte to a soybean plant element in an amount effective to increase yield in the plant derived from the treated plant element relative to a plant derived from a reference plant element, wherein the endophyte is a member of the genus *Exserohilum* and comprises at least one polynucleotide sequence at least 97% identical to a polynucleotide sequence selected from the group consisting of SEQ ID NOs: 60, 61, and 62, wherein the plant element is a seed, optionally a modified seed.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Exserohilum* and comprises at least one polynucleotide sequence at least 97% identical to a polynucleotide sequence selected from the group consisting of SEQ ID NOs: 60, 61, and 62, wherein the plant element is a seed, optionally a modified seed.

In one aspect, the invention provides a method of improving a trait of agronomic importance in a peanut plant, comprising heterologously disposing an endophyte to a peanut plant element in an amount effective to increase yield in the plant derived from the treated plant element relative to a plant derived from a reference plant element, wherein the endophyte is a member of the genus *Exserohilum* and comprises at least one polynucleotide sequence at least 97% identical to a polynucleotide sequence selected from the group consisting of SEQ ID NOs: 60, 61, and 62, wherein the plant element is a seed, optionally a modified seed.

In one aspect, the invention provides a method of improving a trait of agronomic importance in a soybean plant, comprising heterologously disposing an endophyte to a soybean plant element in an amount effective to improve a trait of agronomic importance selected from the group consisting of root area, root length, and root dry weight in the plant derived from the treated plant element relative to a plant derived from a reference plant element, wherein the endophyte is a member of the genus *Epicoccum* and comprises at least one polynucleotide sequence at least 97% identical to a polynucleotide sequence selected from the group consisting of SEQ ID NOs: 63, 64, and 71, wherein the plant element is a seed, optionally a modified seed.

In one aspect, the invention provides a method of improving a trait of agronomic importance in a peanut plant, comprising heterologously disposing an endophyte to a peanut plant element in an amount effective to increase yield in the plant derived from the treated plant element relative to a plant derived from a reference plant element, wherein the endophyte is a member of the genus *Epicoccum* and comprises at least one polynucleotide sequence at least 97% identical to a polynucleotide sequence selected from the group consisting of SEQ ID NOs: 63, 64, and 71, wherein the plant element is a seed, optionally a modified seed.

In one aspect, the invention provides a method of improving a trait of agronomic importance in a rice plant, comprising heterologously disposing an endophyte to a rice plant element in an amount effective to increase root length in the plant derived from the treated plant element relative to a plant derived from a reference plant element, wherein the endophyte is a member of the genus *Epicoccum* and comprises at least one polynucleotide sequence at least 97% identical to a polynucleotide sequence selected from the group consisting of SEQ ID NOs: 63, 64, and 71, wherein the plant element is a seed, optionally a modified seed.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Coniochaeta* and comprises at least one polynucleotide sequence at least 97% identical to a polynucleotide sequence selected from the group consisting of SEQ ID NOs: 38, 39, 40, and 41, wherein the plant element is a seed, optionally a modified seed.

In one aspect, the invention provides a method of improving a trait of agronomic importance in a canola plant, comprising heterologously disposing an endophyte to a canola plant element in an amount effective to increase yield in the plant derived from the treated plant element relative to a plant derived from a reference plant element, wherein the endophyte is a member of the genus *Epicoccum* and comprises at least one polynucleotide sequence at least 97% identical to SEQ ID NO: 70, wherein the canola plant is the variety Brett Young 552 or a closely related variety thereof, wherein the plant element is a seed, optionally a modified seed.

In one aspect, the invention provides a method of improving a trait of agronomic importance in a soybean plant, comprising heterologously disposing an endophyte to a soybean plant element in an amount effective to improve a trait of agronomic importance selected from the group consisting of root area, root length, and yield in the plant derived from the treated plant element relative to a plant derived from a reference plant element, wherein the endophyte is a member of the genus *Curvularia* and comprises at least one polynucleotide sequence at least 97% identical to a polynucleotide sequence selected from the group consisting of SEQ ID NOs: 65 and 66, wherein the plant element is a seed, optionally a modified seed.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Curvularia* and comprises at least one polynucleotide sequence at least 97% identical to a polynucleotide sequence selected from the group consisting of SEQ ID NOs: 65 and 66, wherein the plant element is a seed, optionally a modified seed.

In one aspect, the invention provides a method of improving a trait of agronomic importance in a soybean plant, comprising heterologously disposing an endophyte to a soybean plant element in an amount effective to improve a trait of agronomic importance selected from the group consisting of root area, root length, dry shoot biomass, and yield in the plant derived from the treated plant element relative to a plant derived from a reference plant element, wherein the endophyte is a member of the genus *Curvularia* and comprises at least one polynucleotide sequence at least 97% identical to a polynucleotide sequence selected from the group consisting of SEQ ID NOs: 42, 43, 44, and 45, wherein the plant element is a seed, optionally a modified seed.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Curvularia* and comprises at least one polynucleotide sequence at least 97% identical to a polynucleotide sequence selected from the group consisting of SEQ ID NOs: 42, 43, 44, and 45, wherein the plant element is a seed, optionally a modified seed.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Cladosporium* and comprises at least one polynucleotide sequence at least 97% identical to SEQ ID NO: 67, wherein the corn plant element is the variety Stine 9734 or a closely related variety, wherein the plant element is a seed, optionally a modified seed.

In one aspect, the invention provides a method of improving a trait of agronomic importance in a soybean plant, comprising heterologously disposing an endophyte to a soybean plant element in an amount effective to improve a trait of agronomic importance selected from the group consisting of root area, root length, and yield in the plant derived from the treated plant element relative to a plant derived from a reference plant element, wherein the endophyte is a member of the genus *Cladosporium* and comprises at least one polynucleotide sequence at least 97% identical to SEQ ID NO: 67, wherein the plant element is a seed, optionally a modified seed.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Cladosporium* and comprises at least one polynucleotide sequence at least 97% identical to SEQ ID NO: 67, wherein the plant element is a seed, optionally a modified seed.

In one aspect, the invention provides a method of improving a trait of agronomic importance in a canola plant, comprising heterologously disposing an endophyte to a canola plant element in an amount effective to increase yield in the plant derived from the treated plant element relative to a plant derived from a reference plant element, wherein the endophyte is a member of the genus *Paecilomyces* and comprises at least one polynucleotide sequence at least 97% identical to SEQ ID NO: 69, wherein the plant element is a seed, optionally a modified seed.

In one aspect, the invention provides a method of improving a trait of agronomic importance in a soybean plant, comprising heterologously disposing an endophyte to a soybean plant element in an amount effective to improve a trait of agronomic importance selected from the group consisting of root area, root length, and yield in the plant derived from the treated plant element relative to a plant derived from a reference plant element, wherein the endophyte is a member of the genus *Acremonium* and comprises at least one polynucleotide sequence at least 97% identical to a polynucleotide sequence selected from the group consisting of SEQ ID NOs: 46, 47, 48, 49, 50, and 51, wherein the plant element is a seed, optionally a modified seed.

In one aspect, the invention provides a method of improving a trait of agronomic importance in a wheat plant, comprising heterologously disposing an endophyte to a wheat plant element in an amount effective to improve a trait of agronomic importance selected from the group consisting of decreasing grain moisture and increasing yield in the plant derived from the treated plant element relative to a plant derived from a reference plant element, wherein the endophyte is a member of the genus *Acremonium* and comprises at least one polynucleotide sequence at least 97% identical to a polynucleotide sequence selected from the group consisting of SEQ ID NOs: 46, 47, 48, 49, 50, and 51, wherein the plant element is a seed, optionally a modified seed.

In one aspect, the invention provides a method of improving a trait of agronomic importance in a peanut plant, comprising heterologously disposing an endophyte to a peanut plant element in an amount effective to increase yield in the plant derived from the treated plant element relative to a plant derived from a reference plant element, wherein the endophyte is a member of the genus *Acremonium* and comprises at least one polynucleotide sequence at least 97% identical to a polynucleotide sequence selected from the group consisting of SEQ ID NOs: 46, 47, 48, 49, 50, and 51, and the peanut plant is a variety Georgia-06G or a closely related variety, wherein the plant element is a seed, optionally a modified seed.

In one aspect, the invention provides a method of improving a trait of agronomic importance in a rice plant, comprising heterologously disposing an endophyte to a rice plant element in an amount effective to increase dry shoot biomass in the plant derived from the treated plant element relative to a plant derived from a reference plant element, wherein the endophyte is a member of the genus *Acremonium* and comprises at least one polynucleotide sequence at least 97% identical to a polynucleotide sequence selected from the group consisting of SEQ ID NOs: 46, 47, 48, 49, 50, and 51, wherein the plant element is a seed, optionally a modified seed.

In one aspect, the invention provides a method of improving a trait of agronomic importance in a wheat plant, comprising heterologously disposing a first endophyte and a second endophyte to a wheat plant element in an amount effective to improve a trait of agronomic importance selected from the group consisting of plant height, fresh root weight, and fresh shoot weight in the plant derived from the treated plant element relative to a plant derived from a reference plant element, wherein the first endophyte is a member of the genus *Acremonium* and comprises at least one polynucleotide sequence at least 97% identical to a polynucleotide sequence selected from the group consisting of SEQ ID NOs: 46, 47, 48, 49, 50, and 51, and the second endophyte is a member of the genus *Coniochaeta* and comprises at least one polynucleotide sequence at least 97% identical to a polynucleotide sequence selected from the group consisting of SEQ ID NOs: 38, 39, 40, and 41, wherein the plant element is a seed, optionally a modified seed.

In one aspect, the invention provides a method of improving a trait of agronomic importance in a rice plant, comprising heterologously disposing a first endophyte and a second endophyte to a rice plant element in an amount effective to increase yield in the plant derived from the treated plant element relative to a plant derived from a reference plant element, wherein the first endophyte is a member of the genus *Acremonium* and comprises at least one polynucleotide sequence at least 97% identical to a polynucleotide sequence selected from the group consisting of SEQ ID NOs: 46, 47, 48, 49, 50, and 51, and the second endophyte is a member of the genus *Coniochaeta* and comprises at least one polynucleotide sequence at least 97% identical to a polynucleotide sequence selected from the group consisting of SEQ ID NOs: 38, 39, 40, and 41, wherein the plant element is a seed, optionally a modified seed.

In one aspect, the invention provides a method of improving a trait of agronomic importance in a soybean plant, comprising heterologously disposing an endophyte to a soybean plant element in an amount effective to increase yield in the plant derived from the treated plant element relative to a plant derived from a reference plant element, wherein the endophyte is a member of the genus *Cladosporium* and comprises at least one polynucleotide sequence at least 97% identical to SEQ ID NO: 68, wherein the plant element is a seed, optionally a modified seed.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Cladosporium* and comprises at least one polynucleotide sequence at least 97% identical to SEQ ID NO: 68, wherein the plant element is a seed, optionally a modified seed.

In one aspect, the invention provides a method of improving a trait of agronomic importance in a peanut plant, comprising heterologously disposing an endophyte to a peanut plant element in an amount effective to increase yield in the plant derived from the treated plant element relative to a plant derived from a reference plant element, wherein the endophyte is a member of the genus *Cladosporium* and comprises at least one polynucleotide sequence at least 97% identical to SEQ ID NO: 68 and the peanut plant is the variety AT-9899 or a closely related variety thereof, wherein the plant element is a seed, optionally a modified seed.

In one aspect, the invention provides a method of improving a trait of agronomic importance in a soybean plant, comprising heterologously disposing a first endophyte and a second endophyte to a soybean plant element in an amount effective to increase dry root biomass in the plant derived from the treated plant element relative to a plant derived from a reference plant element, wherein the first endophyte is a member of the genus *Epicoccum* and comprises at least one polynucleotide sequence at least 97% identical to a polynucleotide sequence selected from the group consisting of SEQ ID NOs: 63, 64, and 71, the second endophyte is a member of the genus *Chaetomium* and comprises at least one polynucleotide sequence at least 97% identical to a polynucleotide sequence selected from the group consisting of SEQ ID NOs: 52, 53, 54, 55, 56, 57, 58, and 59, and soybean plant is variety Stine 33E22 or a closely related variety thereof, wherein the plant element is a seed, optionally a modified seed.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Chaetomium* and comprises at least one polynucleotide sequence at least 97% identical to a polynucleotide sequence selected from the group consisting of SEQ ID NOs: 52, 53, 54, 55, 56, 57, 58, and 59, wherein the plant element is a seed, optionally a modified seed.

In one aspect, the invention provides a method of improving a trait of agronomic importance in a soybean plant, comprising heterologously disposing an endophyte to a soybean plant element in an amount effective to improve a trait of agronomic importance selected from the group consisting of root area, root length, dry shoot biomass, and yield in the plant derived from the treated plant element relative to a plant derived from a reference plant element, wherein the endophyte is a member of the genus *Chaetomium* and comprises at least one polynucleotide sequence at least 97% identical to a polynucleotide sequence selected from the group consisting of SEQ ID NOs: 52, 53, 54, 55, 56, 57, 58, and 59, wherein the plant element is a seed, optionally a modified seed.

In one aspect, the invention provides a method of improving a trait of agronomic importance in a wheat plant, comprising heterologously disposing an endophyte to a wheat plant element in an amount effective to improve a trait of agronomic importance selected from the group consisting of root length and yield in the plant derived from the treated plant element relative to a plant derived from a reference plant element, wherein the endophyte is a member of the genus *Chaetomium* and comprises at least one polynucleotide sequence at least 97% identical to a polynucleotide sequence selected from the group consisting of SEQ ID NOs: 52, 53, 54, 55, 56, 57, 58, and 59, wherein the plant element is a seed, optionally a modified seed.

In some embodiments, any of the endophyte is heterologously disposed to the plant element in a formulation, said formulation further comprising one or more of the following: a stabilizer, a preservative, a carrier, a surfactant, a fungicide, a nematicide, a bactericide, an insecticide, or herbicide, or any combination thereof.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Exserohilum* and comprises at least one polynucleotide sequence 97%, at least 98%, at least 99%, or 100% identical to a polynucleotide sequence selected from the group consisting of SEQ ID NOs: 60, 61, and 62, wherein the corn plant element is the variety Stine 9734 or a closely related variety thereof, wherein the percent identify is determined over a region of alignment of at least 100, 200, 300, 400, or at least 500 nucleotides.

In one aspect, the invention provides a method of improving a trait of agronomic importance in a soybean plant, comprising heterologously disposing an endophyte to a soybean plant element in an amount effective to increase yield in the plant derived from the treated plant element relative to a plant derived from a reference plant element, wherein the endophyte is a member of the genus *Exserohilum* and comprises at least one polynucleotide sequence at least 97%, at least 98%, at least 99%, or 100% identical to a polynucleotide sequence selected from the group consisting of SEQ ID NOs: 60, 61, and 62, wherein the percent identify is determined over a region of alignment of at least 100, 200, 300, 400, or at least 500 nucleotides.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Exserohilum* and comprises at least one polynucleotide sequence 97%, at least 98%, at least 99%, or 100% identical to a polynucleotide sequence selected from the group consisting of SEQ ID NOs: 60, 61, and 62, wherein the percent identify is determined over a region of alignment of at least 100, 200, 300, 400, or at least 500 nucleotides.

In one aspect, the invention provides a method of improving a trait of agronomic importance in a peanut plant, comprising heterologously disposing an endophyte to a peanut plant element in an amount effective to increase yield in the plant derived from the treated plant element relative to a plant derived from a reference plant element, wherein the endophyte is a member of the genus *Exserohilum* and comprises at least one polynucleotide sequence at least 97%, at least 98%, at least 99%, or 100% identical to a polynucleotide sequence selected from the group consisting of SEQ ID NOs: 60, 61, and 62, wherein the percent identify is determined over a region of alignment of at least 100, 200, 300, 400, or at least 500 nucleotides.

In one aspect, the invention provides a method of improving a trait of agronomic importance in a soybean plant, comprising heterologously disposing an endophyte to a soybean plant element in an amount effective to improve a trait of agronomic importance selected from the group consisting of root area, root length, and root dry weight in the plant derived from the treated plant element relative to a plant derived from a reference plant element, wherein the endophyte is a member of the genus *Epicoccum* and comprises at least one polynucleotide sequence at least 97%, at least 98%, at least 99%, or 100% identical to a polynucleotide sequence selected from the group consisting of SEQ ID NOs: 63, 64, and 71, wherein the percent identify is determined over a region of alignment of at least 100, 200, 300, 400, or at least 500 nucleotides.

In one aspect, the invention provides a method of improving a trait of agronomic importance in a peanut plant, comprising heterologously disposing an endophyte to a peanut plant element in an amount effective to increase yield in the plant derived from the treated plant element relative to a plant derived from a reference plant element, wherein the endophyte is a member of the genus *Epicoccum* and comprises at least one polynucleotide sequence at least 97%, at least 98%, at least 99%, or 100% identical to a polynucleotide sequence selected from the group consisting of SEQ ID NOs: 63, 64, and 71, wherein the percent identify is determined over a region of alignment of at least 100, 200, 300, 400, or at least 500 nucleotides.

In one aspect, the invention provides a method of improving a trait of agronomic importance in a rice plant, comprising heterologously disposing an endophyte to a rice plant element in an amount effective to increase root length in the plant derived from the treated plant element relative to a plant derived from a reference plant element, wherein the endophyte is a member of the genus *Epicoccum* and comprises at least one polynucleotide sequence at least 97%, at least 98%, at least 99%, or 100% identical to a polynucleotide sequence selected from the group consisting of SEQ ID NOs: 63, 64, and 71, wherein the percent identify is determined over a region of alignment of at least 100, 200, 300, 400, or at least 500 nucleotides.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Coniochaeta* and comprises at least one polynucleotide sequence at least 97%, at least 98%, at least 99%, or 100% identical to a polynucleotide sequence selected from the group consisting of SEQ ID NOs: 38, 39, 40, and 41, wherein the percent identify is determined over a region of alignment of at least 100, 200, 300, 400, or at least 500 nucleotides.

In one aspect, the invention provides a method of improving a trait of agronomic importance in a canola plant, comprising heterologously disposing an endophyte to a canola plant element in an amount effective to increase yield in the plant derived from the treated plant element relative to a plant derived from a reference plant element, wherein the endophyte is a member of the genus *Epicoccum* and comprises at least one polynucleotide sequence at least 97%, at least 98%, at least 99%, or 100% identical to SEQ ID NO: 70, wherein the canola plant is the variety Brett Young 552 or a closely related variety thereof, wherein the percent identify is determined over a region of alignment of at least 100, 200, 300, 400, or at least 500 nucleotides.

In one aspect, the invention provides a method of improving a trait of agronomic importance in a soybean plant, comprising heterologously disposing an endophyte to a soybean plant element in an amount effective to improve a trait of agronomic importance selected from the group consisting of root area, root length, and yield in the plant derived from the treated plant element relative to a plant derived from a reference plant element, wherein the endophyte is a member of the genus *Curvularia* and comprises at least one polynucleotide sequence at least 97%, at least 98%, at least 99%, or 100% identical to a polynucleotide sequence selected from the group consisting of SEQ ID NOs: 65 and 66, wherein the percent identify is determined over a region of alignment of at least 100, 200, 300, 400, or at least 500 nucleotides.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Curvularia* and comprises at least one polynucleotide sequence at least 97%, at least 98%, at least 99%, or 100% identical to a polynucleotide sequence selected from the group consisting of SEQ ID NOs: 65 and 66, wherein the percent identify is determined over a region of alignment of at least 100, 200, 300, 400, or at least 500 nucleotides.

In one aspect, the invention provides a method of improving a trait of agronomic importance in a soybean plant, comprising heterologously disposing an endophyte to a soybean plant element in an amount effective to improve a trait of agronomic importance selected from the group consisting of root area, root length, dry shoot biomass, and yield in the plant derived from the treated plant element relative to a plant derived from a reference plant element, wherein the endophyte is a member of the genus *Curvularia* and comprises at least one polynucleotide sequence at least 97%, at least 98%, at least 99%, or 100% identical to a polynucleotide sequence selected from the group consisting of SEQ ID NOs: 42, 43, 44, and 45, wherein the percent identify is determined over a region of alignment of at least 100, 200, 300, 400, or at least 500 nucleotides.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Curvularia* and comprises at least one polynucleotide sequence at least 97%, at least 98%, at least 99%, or 100% identical to a polynucleotide sequence selected from the group consisting of SEQ ID NOs: 42, 43, 44, and 45, wherein the percent identify is determined over a region of alignment of at least 100, 200, 300, 400, or at least 500 nucleotides.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Cladosporium* and comprises at least one polynucleotide sequence at least 97%, at least 98%, at least 99%, or 100% identical to SEQ ID NO: 67, wherein the corn plant element is the variety Stine 9734 or a closely related variety, wherein the percent identify is determined over a region of alignment of at least 100, 200, 300, 400, or at least 500 nucleotides.

In one aspect, the invention provides a method of improving a trait of agronomic importance in a soybean plant, comprising heterologously disposing an endophyte to a soybean plant element in an amount effective to improve a trait of agronomic importance selected from the group consisting of root area, root length, and yield in the plant derived from the treated plant element relative to a plant derived from a reference plant element, wherein the endophyte is a member of the genus *Cladosporium* and comprises at least one polynucleotide sequence at least 97%, at least 98%, at least 99%, or 100% identical to SEQ ID NO: 67, wherein the percent identify is determined over a region of alignment of at least 100, 200, 300, 400, or at least 500 nucleotides.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Cladosporium* and comprises at least one polynucleotide sequence at least 97%, at least 98%, at least 99%, or 100% identical to SEQ ID NO: 67, wherein the percent identify is determined over a region of alignment of at least 100, 200, 300, 400, or at least 500 nucleotides.

In one aspect, the invention provides a method of improving a trait of agronomic importance in a canola plant, comprising heterologously disposing an endophyte to a canola plant element in an amount effective to increase yield in the plant derived from the treated plant element relative to a plant derived from a reference plant element, wherein the endophyte is a member of the genus *Paecilomyces* and comprises at least one polynucleotide sequence at least 97%, at least 98%, at least 99%, or 100% identical to SEQ ID NO: 69, wherein the percent identify is determined over a region of alignment of at least 100, 200, 300, 400, or at least 500 nucleotides.

In one aspect, the invention provides a method of improving a trait of agronomic importance in a soybean plant, comprising heterologously disposing an endophyte to a soybean plant element in an amount effective to improve a trait of agronomic importance selected from the group consisting of root area, root length, and yield in the plant derived from the treated plant element relative to a plant derived from a reference plant element, wherein the endophyte is a member of the genus *Acremonium* and comprises at least one polynucleotide sequence at least 97%, at least 98%, at least 99%, or 100% identical to a polynucleotide sequence selected from the group consisting of SEQ ID NOs: 46, 47, 48, 49, 50, and 51, wherein the percent identify is determined over a region of alignment of at least 100, 200, 300, 400, or at least 500 nucleotides.

In one aspect, the invention provides a method of improving a trait of agronomic importance in a wheat plant, comprising heterologously disposing an endophyte to a wheat plant element in an amount effective to improve a trait of agronomic importance selected from the group consisting of decreasing grain moisture and increasing yield in the plant derived from the treated plant element relative to a plant derived from a reference plant element, wherein the endophyte is a member of the genus *Acremonium* and comprises at least one polynucleotide sequence at least 97%, at least 98%, at least 99%, or 100% identical to a polynucleotide sequence selected from the group consisting of SEQ ID NOs: 46, 47, 48, 49, 50, and 51, wherein the percent identify is determined over a region of alignment of at least 100, 200, 300, 400, or at least 500 nucleotides.

In one aspect, the invention provides a method of improving a trait of agronomic importance in a peanut plant, comprising heterologously disposing an endophyte to a peanut plant element in an amount effective to increase yield in the plant derived from the treated plant element relative to a plant derived from a reference plant element, wherein the endophyte is a member of the genus *Acremonium* and comprises at least one polynucleotide sequence at least 97%, at least 98%, at least 99%, or 100% identical to a polynucleotide sequence selected from the group consisting of SEQ ID NOs: 46, 47, 48, 49, 50, and 51, and the peanut plant is a variety Georgia-06G or a closely related variety, wherein the percent identify is determined over a region of alignment of at least 100, 200, 300, 400, or at least 500 nucleotides.

In one aspect, the invention provides a method of improving a trait of agronomic importance in a rice plant, comprising heterologously disposing an endophyte to a rice plant element in an amount effective to increase dry shoot biomass in the plant derived from the treated plant element relative to a plant derived from a reference plant element, wherein the endophyte is a member of the genus *Acremonium* and comprises at least one polynucleotide sequence at least 97%, at least 98%, at least 99%, or 100% identical to a polynucleotide sequence selected from the group consisting of SEQ ID NOs: 46, 47, 48, 49, 50, and 51, wherein the percent identify is determined over a region of alignment of at least 100, 200, 300, 400, or at least 500 nucleotides.

In one aspect, the invention provides a method of improving a trait of agronomic importance in a wheat plant, comprising heterologously disposing a first endophyte and a second endophyte to a wheat plant element in an amount effective to improve a trait of agronomic importance selected from the group consisting of plant height, fresh root weight, and fresh shoot weight in the plant derived from the treated plant element relative to a plant derived from a reference plant element, wherein the first endophyte is a member of the genus *Acremonium* and comprises at least one polynucleotide sequence at least 97%, at least 98%, at least 99%, or 100% identical to a polynucleotide sequence selected from the group consisting of SEQ ID NOs: 46, 47, 48, 49, 50, and 51, and the second endophyte is a member of the genus *Coniochaeta* and comprises at least one polynucleotide sequence at least 97%, at least 98%, at least 99%, or 100% identical to a polynucleotide sequence selected from the group consisting of SEQ ID NOs: 38, 39, 40, and 41, wherein the percent identify is determined over a region of alignment of at least 100, 200, 300, 400, or at least 500 nucleotides.

In one aspect, the invention provides a method of improving a trait of agronomic importance in a rice plant, comprising heterologously disposing a first endophyte and a second endophyte to a rice plant element in an amount effective to increase yield in the plant derived from the treated plant element relative to a plant derived from a reference plant element, wherein the first endophyte is a member of the genus *Acremonium* and comprises at least one polynucleotide sequence at least 97%, at least 98%, at least 99%, or 100% identical to a polynucleotide sequence selected from the group consisting of SEQ ID NOs: 46, 47, 48, 49, 50, and 51, and the second endophyte is a member of the genus *Coniochaeta* and comprises at least one polynucleotide sequence at least 97%, at least 98%, at least 99%, or 100% identical to a polynucleotide sequence selected from the group consisting of SEQ ID NOs: 38, 39, 40, and 41, wherein the percent identify is determined over a region of alignment of at least 100, 200, 300, 400, or at least 500 nucleotides.

In one aspect, the invention provides a method of improving a trait of agronomic importance in a soybean plant, comprising heterologously disposing an endophyte to a soybean plant element in an amount effective to increase yield in the plant derived from the treated plant element relative to a plant derived from a reference plant element, wherein the endophyte is a member of the genus *Cladosporium* and comprises at least one polynucleotide sequence at least 97%, at least 98%, at least 99%, or 100% identical to SEQ ID NO: 68, wherein the percent identify is determined over a region of alignment of at least 100, 200, 300, 400, or at least 500 nucleotides.

In one aspect, the invention provides a method of improving a trait of agronomic importance in a wheat plant, comprising heterologously disposing an endophyte to a wheat plant element in an amount effective to increase yield in the plant derived from the treated plant element relative to a plant derived from a reference plant element, wherein the endophyte is a member of the genus *Cladosporium* and comprises at least one polynucleotide sequence at least 97%, at least 98%, at least 99%, or 100% identical to SEQ ID NO: 68, wherein the percent identify is determined over a region of alignment of at least 100, 200, 300, 400, or at least 500 nucleotides.

In one aspect, the invention provides a method of improving a trait of agronomic importance in a peanut plant, comprising heterologously disposing an endophyte to a peanut plant element in an amount effective to increase yield in the plant derived from the treated plant element relative to a plant derived from a reference plant element, wherein the endophyte is a member of the genus *Cladosporium* and comprises at least one polynucleotide sequence at least 97%, at least 98%, at least 99%, or 100% identical to SEQ ID NO: 68 and the peanut plant is the variety AT-9899 or a closely related variety thereof, wherein the percent identify is determined over a region of alignment of at least 100, 200, 300, 400, or at least 500 nucleotides.

In one aspect, the invention provides a method of improving a trait of agronomic importance in a soybean plant, comprising heterologously disposing a first endophyte and a second endophyte to a soybean plant element in an amount effective to increase dry root biomass in the plant derived from the treated plant element relative to a plant derived from a reference plant element, wherein the first endophyte is a member of the genus *Epicoccum* and comprises at least one polynucleotide sequence at least 97%, at least 98%, at least 99%, or 100% identical to a polynucleotide sequence selected from the group consisting of SEQ ID NOs: 63, 64, and 71, the second endophyte is a member of the genus *Chaetomium* and comprises at least one polynucleotide sequence at least 97%, at least 98%, at least 99%, or 100% identical to a polynucleotide sequence selected from the group consisting of SEQ ID NOs: 52, 53, 54, 55, 56, 57, 58, and 59, and soybean plant is variety Stine 33E22 or a closely related variety thereof, wherein the percent identify is determined over a region of alignment of at least 100, 200, 300, 400, or at least 500 nucleotides.

In one aspect, the invention provides a method of improving a trait of agronomic importance in a corn plant, comprising heterologously disposing an endophyte to a corn plant element in an amount effective to increase yield in the plant derived from the treated plant element relative to a plant derived from a reference plant element, wherein the endophyte is a member of the genus *Chaetomium* and comprises at least one polynucleotide sequence at least 97%, at least 98%, at least 99%, or 100% identical to a polynucleotide sequence selected from the group consisting of SEQ ID NOs: 52, 53, 54, 55, 56, 57, 58, and 59, wherein the percent identify is determined over a region of alignment of at least 100, 200, 300, 400, or at least 500 nucleotides.

In one aspect, the invention provides a method of improving a trait of agronomic importance in a soybean plant, comprising heterologously disposing an endophyte to a soybean plant element in an amount effective to improve a trait of agronomic importance selected from the group consisting of root area, root length, dry shoot biomass, and yield in the plant derived from the treated plant element relative to a plant derived from a reference plant element, wherein the endophyte is a member of the genus *Chaetomium* and comprises at least one polynucleotide sequence at least 97%, at least 98%, at least 99%, or 100% identical to a polynucleotide sequence selected from the group consisting of SEQ ID NOs: 52, 53, 54, 55, 56, 57, 58, and 59, wherein the percent identify is determined over a region of alignment of at least 100, 200, 300, 400, or at least 500 nucleotides.

In one aspect, the invention provides a method of improving a trait of agronomic importance in a wheat plant, comprising heterologously disposing an endophyte to a wheat plant element in an amount effective to improve a trait of agronomic importance selected from the group consisting of root length and yield in the plant derived from the treated plant element relative to a plant derived from a reference plant element, wherein the endophyte is a member of the genus *Chaetomium* and comprises at least one polynucleotide sequence at least 97%, at least 98%, at least 99%, or 100% identical to a polynucleotide sequence selected from the group consisting of SEQ ID NOs: 52, 53, 54, 55, 56, 57, 58, and 59, wherein the percent identify is determined over a region of alignment of at least 100, 200, 300, 400, or at least 500 nucleotides.

In one aspect, the invention provides an agrochemically active microbial formulation, comprising at least one oil, surfactant, polymer, and a microbial active ingredient, wherein the microbial active ingredient comprises a first endophyte of the genus *Exserohilum* and comprises at least one polynucleotide sequence at least 97% identical to a polynucleotide sequence selected from the group consisting of SEQ ID NOs: 60, 61, and 62.

In one aspect, the invention provides an agrochemically active microbial formulation, comprising at least one oil, surfactant, polymer, and a microbial active ingredient, wherein the microbial active ingredient comprises a first endophyte of the genus *Epicoccum* and comprises at least one polynucleotide sequence at least 97% identical to a polynucleotide sequence selected from the group consisting of SEQ ID NOs: 63, 64, and 71.

In one aspect, the invention provides an agrochemically active microbial formulation, comprising at least one oil, surfactant, polymer, and a microbial active ingredient, wherein the microbial active ingredient comprises a first endophyte of the genus *Exserohilum* and comprises at least one polynucleotide sequence at least 97% identical to a polynucleotide sequence selected from the group consisting of SEQ ID NOs: 60, 61, and 62 further comprising a second endophyte, wherein the second endophyte is of the genus *Chaetomium* and comprises at least one polynucleotide sequence at least 97% identical to a polynucleotide sequence selected from the group consisting of SEQ ID NOs: 52, 53, 54, 55, 56, 57, 58, and 59.

In one aspect, the invention provides an agrochemically active microbial formulation, comprising at least one oil, surfactant, polymer, and a microbial active ingredient, wherein the microbial active ingredient comprises a first endophyte of the genus *Coniochaeta* and comprises at least one polynucleotide sequence at least 97% identical to a polynucleotide sequence selected from the group consisting of SEQ ID NOs: 38, 39, 40, and 41.

In one aspect, the invention provides an agrochemically active microbial formulation, comprising at least one oil, surfactant, polymer, and a microbial active ingredient, wherein the microbial active ingredient comprises a first endophyte of the genus *Epicoccum* and comprises at least one polynucleotide sequence at least 97% identical to SEQ ID NO: 70.

In one aspect, the invention provides an agrochemically active microbial formulation, comprising at least one oil, surfactant, polymer, and a microbial active ingredient, wherein the microbial active ingredient comprises a first endophyte of the genus *Curvularia* and comprises at least one polynucleotide sequence at least 97% identical to a polynucleotide sequence selected from the group consisting of SEQ ID NOs: 42, 43, 44, 45, 65, and 66.

In one aspect, the invention provides an agrochemically active microbial formulation, comprising at least one oil, surfactant, polymer, and a microbial active ingredient, wherein the microbial active ingredient comprises a first endophyte of the genus *Cladosporium* and comprises at least one polynucleotide sequence at least 97% identical to a polynucleotide sequence selected from the group consisting of SEQ ID NOs: 67 and 68.

In one aspect, the invention provides an agrochemically active microbial formulation, comprising at least one oil, surfactant, polymer, and a microbial active ingredient, wherein the microbial active ingredient comprises a first endophyte of the genus *Paecilomyces* and comprises at least one polynucleotide sequence at least 97% identical to SEQ ID NO: 69.

In one aspect, the invention provides an agrochemically active microbial formulation, comprising at least one oil, surfactant, polymer, and a microbial active ingredient, wherein the microbial active ingredient comprises a first endophyte of the genus *Acremonium* and comprises at least one polynucleotide sequence at least 97% identical to a polynucleotide sequence selected from the group consisting of SEQ ID NOs: 46, 47, 48, 49, 50, and 51.

In one aspect, the invention provides an agrochemically active microbial formulation, comprising at least one oil, surfactant, polymer, and a microbial active ingredient, wherein the microbial active ingredient comprises a first endophyte of the genus *Cladosporium* and comprises at least one polynucleotide sequence at least 97% identical to a polynucleotide sequence selected from the group consisting of SEQ ID NOs: 67 and 68 and wherein the microbial active ingredient further comprises a second endophyte, wherein the second endophyte is of the genus *Coniochaeta* and comprises at least one polynucleotide sequence at least 97% identical to a polynucleotide sequence selected from the group consisting of SEQ ID NOs: 38, 39, 40, and 41.

In one aspect, the invention provides an agrochemically active microbial formulation, comprising at least one oil, surfactant, polymer, and a microbial active ingredient, wherein the microbial active ingredient comprises a first endophyte of the genus *Chaetomium* and comprises at least one polynucleotide sequence at least 97% identical to a polynucleotide sequence selected from the group consisting of SEQ ID NOs: 52, 53, 54, 55, 56, 57, 58, and 59.

In some embodiments, the formulation oil comprises rapeseed, NEEM, or erucic acid, or comprises herbicidal or insecticidal properties. In some embodiments, the formulation surfactant is a non-ionic detergent, Tween 20, or Triton X-100. In some embodiments, the formulation polymer is Flo Rite®, DISCO™, or Kannar® Universal Wonder. In some embodiments, the formulation microbial active ingredient comprises a spore suspension, spray dried spores, or whole cell broth. In some embodiments, the formulation further comprises one or more of the following: fungicide, nematicide, bactericide, insecticide, herbicide, stabilizer, preservative, carrier, anticomplex agent, or any combination thereof. In some embodiments, the endophyte of the formulation is shelf-stable In one aspect, the invention provides an agrochemically active microbial formulation, comprising at least one oil, surfactant, polymer, and a microbial active ingredient, wherein the microbial active ingredient comprises a first endophyte of the genus *Exserohilum* and comprises at least one polynucleotide sequence at least 97%, at least 98%, at least 99%, or 100% identical to a polynucleotide sequence selected from the group consisting of SEQ ID NOs: 60, 61, and 62, wherein the percent identify is determined over a region of alignment of at least 100, 200, 300, 400, or at least 500 nucleotides.

In one aspect, the invention provides an agrochemically active microbial formulation, comprising at least one oil, surfactant, polymer, and a microbial active ingredient, wherein the microbial active ingredient comprises a first endophyte of the genus *Epicoccum* and comprises at least one polynucleotide sequence at least 97%, at least 98%, at least 99%, or 100% identical to a polynucleotide sequence selected from the group consisting of SEQ ID NOs: 63, 64, and 71, wherein the percent identify is determined over a region of alignment of at least 100, 200, 300, 400, or at least 500 nucleotides.

In one aspect, the invention provides an agrochemically active microbial formulation, comprising at least one oil, surfactant, polymer, and a microbial active ingredient, wherein the microbial active ingredient comprises a first endophyte of the genus *Exserohilum* and comprises at least one polynucleotide sequence at least 97%, at least 98%, at least 99%, or 100% identical to a polynucleotide sequence selected from the group consisting of SEQ ID NOs: 60, 61, and 62 further comprising a second endophyte, wherein the second endophyte is of the genus *Chaetomium* and comprises at least one polynucleotide sequence at least 97%, at least 98%, at least 99%, or 100% identical to a polynucleotide sequence selected from the group consisting of SEQ ID NOs: 52, 53, 54, 55, 56, 57, 58, and 59, wherein the percent identify is determined over a region of alignment of at least 100, 200, 300, 400, or at least 500 nucleotides.

In one aspect, the invention provides an agrochemically active microbial formulation, comprising at least one oil, surfactant, polymer, and a microbial active ingredient, wherein the microbial active ingredient comprises a first endophyte of the genus *Coniochaeta* and comprises at least one polynucleotide sequence at least 97%, at least 98%, at least 99%, or 100% identical to a polynucleotide sequence selected from the group consisting of SEQ ID NOs: 38, 39, 40, and 41, wherein the percent identify is determined over a region of alignment of at least 100, 200, 300, 400, or at least 500 nucleotides.

In one aspect, the invention provides an agrochemically active microbial formulation, comprising at least one oil, surfactant, polymer, and a microbial active ingredient, wherein the microbial active ingredient comprises a first endophyte of the genus *Epicoccum* and comprises at least one polynucleotide sequence at least 97%, at least 98%, at least 99%, or 100% identical to SEQ ID NO: 70, wherein the percent identify is determined over a region of alignment of at least 100, 200, 300, 400, or at least 500 nucleotides.

In one aspect, the invention provides an agrochemically active microbial formulation, comprising at least one oil, surfactant, polymer, and a microbial active ingredient, wherein the microbial active ingredient comprises a first endophyte of the genus *Curvularia* and comprises at least one polynucleotide sequence at least 97%, at least 98%, at least 99%, or 100% identical to a polynucleotide sequence selected from the group consisting of SEQ ID NOs: 42, 43, 44, 45, 65, and 66, wherein the percent identify is determined over a region of alignment of at least 100, 200, 300, 400, or at least 500 nucleotides.

In one aspect, the invention provides an agrochemically active microbial formulation, comprising at least one oil, surfactant, polymer, and a microbial active ingredient, wherein the microbial active ingredient comprises a first endophyte of the genus *Cladosporium* and comprises at least one polynucleotide sequence at least 97%, at least 98%, at least 99%, or 100% identical to a polynucleotide sequence selected from the group consisting of SEQ ID NOs: 67 and 68, wherein the percent identify is determined over a region of alignment of at least 100, 200, 300, 400, or at least 500 nucleotides.

In one aspect, the invention provides an agrochemically active microbial formulation, comprising at least one oil, surfactant, polymer, and a microbial active ingredient, wherein the microbial active ingredient comprises a first endophyte of the genus *Paecilomyces* and comprises at least one polynucleotide sequence at least 97%, at least 98%, at least 99%, or 100% identical to SEQ ID NO: 69, wherein the percent identify is determined over a region of alignment of at least 100, 200, 300, 400, or at least 500 nucleotides.

In one aspect, the invention provides an agrochemically active microbial formulation, comprising at least one oil, surfactant, polymer, and a microbial active ingredient, wherein the microbial active ingredient comprises a first endophyte of the genus *Acremonium* and comprises at least one polynucleotide sequence at least 97%, at least 98%, at least 99%, or 100% identical to a polynucleotide sequence selected from the group consisting of SEQ ID NOs: 46, 47, 48, 49, 50, and 51, wherein the percent identify is determined over a region of alignment of at least 100, 200, 300, 400, or at least 500 nucleotides.

In one aspect, the invention provides an agrochemically active microbial formulation, comprising at least one oil, surfactant, polymer, and a microbial active ingredient, wherein the microbial active ingredient comprises a first endophyte of the genus *Cladosporium* and comprises at least one polynucleotide sequence at least 97%, at least 98%, at least 99%, or 100% identical to a polynucleotide sequence selected from the group consisting of SEQ ID NOs: 67 and 68 and wherein the microbial active ingredient further comprises a second endophyte, wherein the second endophyte is of the genus *Coniochaeta* and comprises at least one polynucleotide sequence at least 97%, at least 98%, at least 99%, or 100% identical to a polynucleotide sequence selected from the group consisting of SEQ ID NOs: 38, 39, 40, and 41, wherein the percent identify is determined over a region of alignment of at least 100, 200, 300, 400, or at least 500 nucleotides.

In one aspect, the invention provides an agrochemically active microbial formulation, comprising at least one oil, surfactant, polymer, and a microbial active ingredient, wherein the microbial active ingredient comprises a first endophyte of the genus *Chaetomium* and comprises at least one polynucleotide sequence at least 97%, at least 98%, at least 99%, or 100% identical to a polynucleotide sequence selected from the group consisting of SEQ ID NOs: 52, 53, 54, 55, 56, 57, 58, and 59, wherein the percent identify is determined over a region of alignment of at least 100, 200, 300, 400, or at least 500 nucleotides.

In one aspect, the invention provides a synthetic composition comprising a plant element and a heterologously disposed endophyte, wherein the endophyte is a member of the genus *Exserohilum* and comprises at least one polynucleotide sequence at least 97% identical to a polynucleotide sequence selected from the group consisting of SEQ ID NOs: 60, 61, and 62, wherein the synthetic composition is capable of providing an improved trait of agronomic importance as compared to a reference plant element not further comprising the endophyte.

In one aspect, the invention provides a synthetic composition comprising a plant element and a heterologously disposed endophyte, wherein the endophyte is a member of the genus *Exserohilum* and comprises at least one polynucleotide sequence at least 97% identical to a polynucleotide sequence selected from the group consisting of SEQ ID NOs: 60, 61, and 62, wherein the synthetic composition is capable of providing an improved trait of agronomic importance as compared to a reference plant element not further comprising the endophyte, wherein the plant element is a corn plant element and the improved trait of agronomic importance is yield.

In one aspect, the invention provides a synthetic composition comprising a plant element and a heterologously disposed endophyte, wherein the endophyte is a member of the genus *Exserohilum* and comprises at least one polynucleotide sequence at least 97% identical to a polynucleotide sequence selected from the group consisting of SEQ ID NOs: 60, 61, and 62, wherein the synthetic composition is capable of providing an improved trait of agronomic importance as compared to a reference plant element not further comprising the endophyte, wherein the plant element is a soybean plant element.

In one aspect, the invention provides a synthetic composition comprising a plant element and a heterologously disposed endophyte, wherein the endophyte is a member of the genus *Exserohilum* and comprises at least one polynucleotide sequence at least 97% identical to a polynucleotide sequence selected from the group consisting of SEQ ID NOs: 60, 61, and 62, wherein the synthetic composition is capable of providing an improved trait of agronomic importance as compared to a reference plant element not further comprising the endophyte, wherein the plant element is a soybean variety selected from the group consisting of: Pfister 38R25, Dairyland DSR1808R2Y, Stine 3920, and closely related varieties thereof, and the improved trait of agronomic importance is yield.

In one aspect, the invention provides a synthetic composition comprising a plant element and a heterologously disposed endophyte, wherein the endophyte is a member of the genus *Exserohilum* and comprises at least one polynucleotide sequence at least 97% identical to a polynucleotide sequence selected from the group consisting of SEQ ID NOs: 60, 61, and 62, wherein the synthetic composition is capable of providing an improved trait of agronomic importance as compared to a reference plant element not further comprising the endophyte, wherein the plant element is a wheat plant element and the improved trait of agronomic importance is yield.

In one aspect, the invention provides a synthetic composition comprising a plant element and a heterologously disposed endophyte, wherein the endophyte is a member of the genus *Exserohilum* and comprises at least one polynucleotide sequence at least 97% identical to a polynucleotide sequence selected from the group consisting of SEQ ID NOs: 60, 61, and 62, wherein the synthetic composition is capable of providing an improved trait of agronomic importance as compared to a reference plant element not further comprising the endophyte, wherein the plant element is a peanut plant element and the improved trait of agronomic importance is yield.

In one aspect, the invention provides a synthetic composition comprising a plant element and a heterologously disposed endophyte, wherein the endophyte is a member of the genus *Exserohilum* and comprises at least one polynucleotide sequence at least 97% identical to a polynucleotide sequence selected from the group consisting of SEQ ID NOs: 60, 61, and 62, wherein the synthetic composition is capable of providing an improved trait of agronomic importance as compared to a reference plant element not further comprising the endophyte, wherein the plant element is a peanut variety selected from the group consisting of: AT9899, FloRun 107, Georgia-06G, Tamnut OL06, and closely related varieties thereof.

In one aspect, the invention provides a synthetic composition comprising a plant element and a heterologously disposed endophyte, wherein the endophyte is a member of the genus *Epicoccum* and comprises at least one polynucleotide sequence at least 97% identical to a polynucleotide sequence selected from the group consisting of SEQ ID NOs: 63, 64, and 71, wherein the synthetic composition is capable of providing an improved trait of agronomic importance as compared to a reference plant element not further comprising the endophyte.

In one aspect, the invention provides a synthetic composition comprising a plant element and a heterologously disposed endophyte, wherein the endophyte is a member of the genus *Epicoccum* and comprises at least one polynucleotide sequence at least 97% identical to a polynucleotide sequence selected from the group consisting of SEQ ID NOs: 63, 64, and 71, wherein the synthetic composition is capable of providing an improved trait of agronomic importance as compared to a reference plant element not further comprising the endophyte, wherein the plant element is a soybean plant element and the improved trait of agronomic importance is selected from the group consisting of root area, root length, and root dry weight.

In one aspect, the invention provides a synthetic composition comprising a plant element and a heterologously disposed endophyte, wherein the endophyte is a member of the genus *Epicoccum* and comprises at least one polynucleotide sequence at least 97% identical to a polynucleotide sequence selected from the group consisting of SEQ ID NOs: 63, 64, and 71, wherein the synthetic composition is capable of providing an improved trait of agronomic importance as compared to a reference plant element not further comprising the endophyte, wherein the plant element is a soybean variety Stine 33E22 or a closely related variety thereof.

In one aspect, the invention provides a synthetic composition comprising a plant element and a heterologously disposed endophyte, wherein the endophyte is a member of the genus *Epicoccum* and comprises at least one polynucleotide sequence at least 97% identical to a polynucleotide sequence selected from the group consisting of SEQ ID NOs: 63, 64, and 71, wherein the synthetic composition is capable of providing an improved trait of agronomic importance as compared to a reference plant element not further comprising the endophyte, wherein the plant element is a peanut plant element and the improved trait of agronomic importance is yield.

In one aspect, the invention provides a synthetic composition comprising a plant element and a heterologously disposed endophyte, wherein the endophyte is a member of the genus *Epicoccum* and comprises at least one polynucleotide sequence at least 97% identical to a polynucleotide sequence selected from the group consisting of SEQ ID NOs: 63, 64, and 71, wherein the synthetic composition is capable of providing an improved trait of agronomic importance as compared to a reference plant element not further comprising the endophyte, wherein the plant element is a peanut plant element is selected from the group consisting of the variety FloRun 107, Georgia-06G, and closely related varieties thereof and the improved trait of agronomic importance is yield.

In one aspect, the invention provides a synthetic composition comprising a plant element and a heterologously disposed endophyte, wherein the endophyte is a member of the genus *Epicoccum* and comprises at least one polynucleotide sequence at least 97% identical to a polynucleotide sequence selected from the group consisting of SEQ ID NOs: 63, 64, and 71, wherein the synthetic composition is capable of providing an improved trait of agronomic importance as compared to a reference plant element not further comprising the endophyte, and further comprising a second endophyte, wherein the second endophyte is of the genus *Chaetomium* and comprises at least one polynucleotide sequence at least 97% identical to a polynucleotide sequence selected from the group consisting of SEQ ID NO: 52, 53, 54, 55, 56, 57, 58, and 59, wherein the synthetic composition is capable of providing an improved trait of agronomic importance as compared to a reference plant element not further comprising the endophyte.

In one aspect, the invention provides a synthetic composition comprising a plant element and a heterologously disposed endophyte, wherein the endophyte is a member of the genus *Epicoccum* and comprises at least one polynucleotide sequence at least 97% identical to a polynucleotide sequence selected from the group consisting of SEQ ID NOs: 63, 64, and 71, wherein the synthetic composition is capable of providing an improved trait of agronomic importance as compared to a reference plant element not further comprising the endophyte, wherein the plant element is the soybean variety Stine 33E22 and the trait of agronomic importance is dry root biomass.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a polynucleotide sequence selected from the group consisting of SEQ ID NOs: 38, 39, 40, and 41, wherein the synthetic composition is capable of providing an improved trait of agronomic importance as compared to a reference plant element not further comprising the endophyte.

In one aspect, the invention provides a synthetic composition comprising a plant element and a heterologously disposed endophyte, wherein the endophyte is a member of the genus *Coniochaeta* and comprises at least one polynucleotide sequence at least 97% identical to a polynucleotide sequence selected from the group consisting of SEQ ID NOs: 38, 39, 40, and 41, wherein the synthetic composition is capable of providing an improved trait of agronomic importance as compared to a reference plant element not further comprising the endophyte, wherein the plant element is a wheat plant element and the trait of agronomic importance is yield.

In one aspect, the invention provides a synthetic composition comprising a plant element and a heterologously disposed endophyte, wherein the endophyte is a member of the genus *Epicoccum* and comprises at least one polynucleotide sequence at least 97% identical to SEQ ID NO: 70, wherein the synthetic composition is capable of providing an improved trait of agronomic importance as compared to a reference plant element not further comprising the endophyte.

In one aspect, the invention provides a synthetic composition comprising a plant element and a heterologously disposed endophyte, wherein the endophyte is a member of the genus *Epicoccum* and comprises at least one polynucleotide sequence at least 97% identical to SEQ ID NO: 70, wherein the synthetic composition is capable of providing an improved trait of agronomic importance as compared to a reference plant element not further comprising the endophyte, wherein the plant element is canola variety Brett Young 5525 or a closely related variety In one aspect, the invention provides a synthetic composition comprising a plant element and a heterologously disposed endophyte, wherein the endophyte is a member of the genus *Curvularia* and comprises at least one polynucleotide sequence at least 97% identical to a polynucleotide sequence selected from the group consisting of SEQ ID NOs: 42, 43, 44, 45, 65, and 66, wherein the synthetic composition is capable of providing an improved trait of agronomic importance as compared to a reference plant element not further comprising the endophyte.

In one aspect, the invention provides a synthetic composition comprising a plant element and a heterologously disposed endophyte, wherein the endophyte is a member of the genus *Curvularia* and comprises at least one polynucleotide sequence at least 97% identical to a polynucleotide sequence selected from the group consisting of SEQ ID NOs: 42, 43, 44, 45, 65, and 66, wherein the synthetic composition is capable of providing an improved trait of agronomic importance as compared to a reference plant element not further comprising the endophyte, wherein the plant element is a soybean plant element and the trait of agronomic importance is selected from the group consisting of root area, root length, and yield.

In one aspect, the invention provides a synthetic composition comprising a plant element and a heterologously disposed endophyte, wherein the endophyte is a member of the genus *Curvularia* and comprises at least one polynucleotide sequence at least 97% identical to a polynucleotide sequence selected from the group consisting of SEQ ID NOs: 42, 43, 44, 45, 65, and 66, wherein the synthetic composition is capable of providing an improved trait of agronomic importance as compared to a reference plant element not further comprising the endophyte, wherein the plant element is a soybean variety selected from the group consisting of Pfister 38R25, Stine 3920, and closely related varieties thereof, and the trait of agronomic importance is selected from the group consisting of root area, root length, and yield.

In one aspect, the invention provides a synthetic composition comprising a plant element and a heterologously disposed endophyte, wherein the endophyte is a member of the genus *Curvularia* and comprises at least one polynucleotide sequence at least 97% identical to a polynucleotide sequence selected from the group consisting of SEQ ID NOs: 42, 43, 44, 45, 65, and 66, wherein the synthetic composition is capable of providing an improved trait of agronomic importance as compared to a reference plant element not further comprising the endophyte, wherein the plant element is a wheat plant element and the trait of agronomic importance is yield.

In one aspect, the invention provides a synthetic composition comprising a plant element and a heterologously disposed endophyte, wherein the endophyte is a member of the genus *Curvularia* and comprises at least one polynucleotide sequence at least 97% identical to a polynucleotide sequence selected from the group consisting of SEQ ID NOs: 42, 43, 44, 45, 65, and 66, wherein the synthetic composition is capable of providing an improved trait of agronomic importance as compared to a reference plant element not further comprising the endophyte, wherein the plant element is a wheat variety selected from the group consisting of SDSU Focus, SDSU Select, and closely related varieties thereof, and the trait of agronomic importance is yield.

In one aspect, the invention provides a synthetic composition comprising a plant element and a heterologously disposed endophyte, wherein the endophyte is a member of the genus *Cladosporium* and comprises at least one polynucleotide sequence at least 97% identical to SEQ ID NO: 67, wherein the synthetic composition is capable of providing an improved trait of agronomic importance as compared to a reference plant element not further comprising the endophyte.

In one aspect, the invention provides a synthetic composition comprising a plant element and a heterologously disposed endophyte, wherein the endophyte is a member of the genus *Cladosporium* and comprises at least one polynucleotide sequence at least 97% identical to SEQ ID NO: 67, wherein the synthetic composition is capable of providing an improved trait of agronomic importance as compared to a reference plant element not further comprising the endophyte, wherein the plant element is a soybean plant element and the trait of agronomic importance is selected from the group consisting of root area, root length, and yield.

In one aspect, the invention provides a synthetic composition comprising a plant element and a heterologously disposed endophyte, wherein the endophyte is a member of the genus *Cladosporium* and comprises at least one polynucleotide sequence at least 97% identical to SEQ ID NO: 67, wherein the synthetic composition is capable of providing an improved trait of agronomic importance as compared to a reference plant element not further comprising the endophyte, wherein the plant element is a soybean variety selected from the group consisting of Pfister 38R25, Stine 3920, and closely related varieties thereof, and the trait of agronomic importance is selected from the group consisting of root area, root length, and yield.

In one aspect, the invention provides a synthetic composition comprising a plant element and a heterologously disposed endophyte, wherein the endophyte is a member of the genus *Cladosporium* and comprises at least one polynucleotide sequence at least 97% identical to a polynucleotide sequence selected from the group consisting of SEQ ID NOs: 67 and 68, wherein the synthetic composition is capable of providing an improved trait of agronomic importance as compared to a reference plant element not further comprising the endophyte.

In one aspect, the invention provides a synthetic composition comprising a plant element and a heterologously disposed endophyte, wherein the endophyte is a member of the genus *Cladosporium* and comprises at least one polynucleotide sequence at least 97% identical to a polynucleotide sequence selected from the group consisting of SEQ ID NOs: 67 and 68, wherein the synthetic composition is capable of providing an improved trait of agronomic importance as compared to a reference plant element not further comprising the endophyte, wherein the plant element is a corn plant element and the trait of agronomic importance is yield.

In one aspect, the invention provides a synthetic composition comprising a plant element and a heterologously disposed endophyte, wherein the endophyte is a member of the genus *Cladosporium* and comprises at least one polynucleotide sequence at least 97% identical to a polynucleotide sequence selected from the group consisting of SEQ ID NOs: 67 and 68, wherein the synthetic composition is capable of providing an improved trait of agronomic importance as compared to a reference plant element not further comprising the endophyte, wherein the plant element is corn variety Stine 9734 and the trait of agronomic importance is yield.

In one aspect, the invention provides a synthetic composition comprising a plant element and a heterologously disposed endophyte, wherein the endophyte is a member of the genus *Cladosporium* and comprises at least one polynucleotide sequence at least 97% identical to a polynucleotide sequence selected from the group consisting of SEQ ID NOs: 67 and 68, wherein the synthetic composition is capable of providing an improved trait of agronomic importance as compared to a reference plant element not further comprising the endophyte, wherein the plant element is a soybean plant element and the trait of agronomic importance is selected from the group consisting of root area, root length, and yield.

In one aspect, the invention provides a synthetic composition comprising a plant element and a heterologously disposed endophyte, wherein the endophyte is a member of the genus *Cladosporium* and comprises at least one polynucleotide sequence at least 97% identical to a polynucleotide sequence selected from the group consisting of SEQ ID NOs: 67 and 68, wherein the synthetic composition is capable of providing an improved trait of agronomic importance as compared to a reference plant element not further comprising the endophyte, wherein the plant element is a soybean variety selected from the group consisting of Pfister 38R25, Stine 3920, and closely related varieties thereof and the trait of agronomic importance is yield.

In one aspect, the invention provides a synthetic composition comprising a plant element and a heterologously disposed endophyte, wherein the endophyte is a member of the genus *Cladosporium* and comprises at least one polynucleotide sequence at least 97% identical to a polynucleotide sequence selected from the group consisting of SEQ ID NOs: 67 and 68, wherein the synthetic composition is capable of providing an improved trait of agronomic importance as compared to a reference plant element not further comprising the endophyte, wherein the plant element is a wheat plant element and the trait of agronomic importance is yield.

In one aspect, the invention provides a synthetic composition comprising a plant element and a heterologously disposed endophyte, wherein the endophyte is a member of the genus *Cladosporium* and comprises at least one polynucleotide sequence at least 97% identical to a polynucleotide sequence selected from the group consisting of SEQ ID NOs: 67 and 68, wherein the synthetic composition is capable of providing an improved trait of agronomic importance as compared to a reference plant element not further comprising the endophyte, wherein the plant element is a wheat variety selected from the group consisting of SDSU Focus, SDSU Select, and closely related varieties thereof and the trait of agronomic importance is yield.

In one aspect, the invention provides a synthetic composition comprising a plant element and a heterologously disposed endophyte, wherein the endophyte is a member of the genus *Cladosporium* and comprises at least one polynucleotide sequence at least 97% identical to a polynucleotide sequence selected from the group consisting of SEQ ID NOs: 67 and 68, wherein the synthetic composition is capable of providing an improved trait of agronomic importance as compared to a reference plant element not further comprising the endophyte, wherein the endophyte comprises at least one polynucleotide sequence at least 97% identical to SEQ ID NO: 68, the plant element is a peanut of variety AT9899, and the trait of agronomic importance is yield.

In one aspect, the invention provides a synthetic composition comprising a plant element and a heterologously disposed endophyte, wherein the endophyte is a member of the genus *Paecilomyces* and comprises at least one polynucleotide sequence at least 97% identical to SEQ ID NO: 69, wherein the synthetic composition is capable of providing an improved trait of agronomic importance as compared to a reference plant element not further comprising the endophyte.

In one aspect, the invention provides a synthetic composition comprising a plant element and a heterologously disposed endophyte, wherein the endophyte is a member of the genus *Paecilomyces* and comprises at least one polynucleotide sequence at least 97% identical to SEQ ID NO: 69, wherein the synthetic composition is capable of providing an improved trait of agronomic importance as compared to a reference plant element not further comprising the endophyte, wherein the plant element is canola variety NCC1015 and the trait of agronomic importance is yield.

In one aspect, the invention provides a synthetic composition comprising a plant element and a heterologously disposed endophyte, wherein the endophyte is a member of the genus *Acremonium* and comprises at least one polynucleotide sequence at least 97% identical to a polynucleotide sequence selected from the group consisting of SEQ ID NOs: 46, 47, 48, 49, 50, and 51, and wherein the synthetic composition is capable of providing an improved trait of agronomic importance as compared to a reference plant element not further comprising the endophyte.

In one aspect, the invention provides a synthetic composition comprising a plant element and a heterologously disposed endophyte, wherein the endophyte is a member of the genus *Acremonium* and comprises at least one polynucleotide sequence at least 97% identical to a polynucleotide sequence selected from the group consisting of SEQ ID NOs: 46, 47, 48, 49, 50, and 51, and wherein the synthetic composition is capable of providing an improved trait of agronomic importance as compared to a reference plant element not further comprising the endophyte, wherein the plant element is a soybean plant element and the trait of agronomic importance is dry shoot biomass.

In one aspect, the invention provides a synthetic composition comprising a plant element and a heterologously disposed endophyte, wherein the endophyte is a member of the genus *Acremonium* and comprises at least one polynucleotide sequence at least 97% identical to a polynucleotide sequence selected from the group consisting of SEQ ID NOs: 46, 47, 48, 49, 50, and 51, and wherein the synthetic composition is capable of providing an improved trait of agronomic importance as compared to a reference plant element not further comprising the endophyte, wherein the plant element is a wheat plant element and the trait of agronomic importance is grain moisture or yield.

In one aspect, the invention provides a synthetic composition comprising a plant element and a heterologously disposed endophyte, wherein the endophyte is a member of the genus *Acremonium* and comprises at least one polynucleotide sequence at least 97% identical to a polynucleotide sequence selected from the group consisting of SEQ ID NOs: 46, 47, 48, 49, 50, and 51, and wherein the synthetic composition is capable of providing an improved trait of agronomic importance as compared to a reference plant element not further comprising the endophyte, wherein the plant element is wheat variety SDSU Select and the trait of agronomic importance is yield.

In one aspect, the invention provides a synthetic composition comprising a plant element and a heterologously disposed endophyte, wherein the endophyte is a member of the genus *Acremonium* and comprises at least one polynucleotide sequence at least 97% identical to a polynucleotide sequence selected from the group consisting of SEQ ID NOs: 46, 47, 48, 49, 50, and 51, and wherein the synthetic composition is capable of providing an improved trait of agronomic importance as compared to a reference plant element not further comprising the endophyte, wherein the plant element is peanut variety Georgia-06G and the trait of agronomic importance is yield.

In one aspect, the invention provides a synthetic composition comprising a plant element and a heterologously disposed endophyte, wherein the endophyte is a member of the genus *Acremonium* and comprises at least one polynucleotide sequence at least 97% identical to a polynucleotide sequence selected from the group consisting of SEQ ID NOs: 46, 47, 48, 49, 50, and 51, and wherein the synthetic composition is capable of providing an improved trait of agronomic importance as compared to a reference plant element not further comprising the endophyte, wherein the plant element is a rice plant element and the trait of agronomic importance is dry shoot biomass.

In one aspect, the invention provides a synthetic composition comprising a plant element and a heterologously disposed endophyte, wherein the endophyte is a member of the genus *Acremonium* and comprises at least one polynucleotide sequence at least 97% identical to a polynucleotide sequence selected from the group consisting of SEQ ID NOs: 46, 47, 48, 49, 50, and 51, and wherein the synthetic composition is capable of providing an improved trait of agronomic importance as compared to a reference plant element not further comprising the endophyte, and further comprising a second endophyte, wherein the second endophyte is of the genus *Coniochaeta* and comprises at least one polynucleotide sequence at least 97% identical to a polynucleotide sequence selected from the group consisting of SEQ ID NOs: 38, 39, 40, and 41, wherein the synthetic composition is capable of providing an improved trait of agronomic importance as compared to a reference plant element not further comprising the endophyte.

In one aspect, the invention provides a synthetic composition comprising a plant element and a heterologously disposed endophyte, wherein the endophyte is a member of the genus *Acremonium* and comprises at least one polynucleotide sequence at least 97% identical to a polynucleotide sequence selected from the group consisting of SEQ ID NOs: 46, 47, 48, 49, 50, and 51, and wherein the synthetic composition is capable of providing an improved trait of agronomic importance as compared to a reference plant element not further comprising the endophyte, and further comprising a second endophyte, wherein the second endophyte is of the genus *Coniochaeta* and comprises at least one polynucleotide sequence at least 97% identical to a polynucleotide sequence selected from the group consisting of SEQ ID NOs: 38, 39, 40, and 41, wherein the synthetic composition is capable of providing an improved trait of agronomic importance as compared to a reference plant element not further comprising the endophyte, wherein the plant element is a wheat plant element and the trait of agronomic importance is selected from the group consisting of plant height, fresh root biomass, and fresh shoot weight.

In one aspect, the invention provides a synthetic composition comprising a plant element and a heterologously disposed endophyte, wherein the endophyte is a member of the genus *Acremonium* and comprises at least one polynucleotide sequence at least 97% identical to a polynucleotide sequence selected from the group consisting of SEQ ID NOs: 46, 47, 48, 49, 50, and 51, and wherein the synthetic composition is capable of providing an improved trait of agronomic importance as compared to a reference plant element not further comprising the endophyte, and further comprising a second endophyte, wherein the second endophyte is of the genus *Coniochaeta* and comprises at least one polynucleotide sequence at least 97% identical to a polynucleotide sequence selected from the group consisting of SEQ ID NOs: 38, 39, 40, and 41, wherein the synthetic composition is capable of providing an improved trait of agronomic importance as compared to a reference plant element not further comprising the endophyte, wherein the plant element is a rice plant element and the trait of agronomic importance is yield.

In one aspect, the invention provides a synthetic composition comprising a plant element and a heterologously disposed endophyte, wherein the endophyte is a member of the genus *Chaetomium* and comprises at least one polynucleotide sequence at least 97% identical to a polynucleotide sequence selected from the group consisting of SEQ ID NOs: 52, 53, 54, 55, 56, 57, 58, and 59, wherein the synthetic composition is capable of providing an improved trait of agronomic importance as compared to a reference plant element not further comprising the endophyte.

In one aspect, the invention provides a synthetic composition comprising a plant element and a heterologously disposed endophyte, wherein the endophyte is a member of the genus *Chaetomium* and comprises at least one polynucleotide sequence at least 97% identical to a polynucleotide sequence selected from the group consisting of SEQ ID NOs: 52, 53, 54, 55, 56, 57, 58, and 59, wherein the synthetic composition is capable of providing an improved trait of agronomic importance as compared to a reference plant element not further comprising the endophyte, wherein the plant element is a soybean plant element and the trait of agronomic importance is selected from the group consisting of root area, root length, dry shoot biomass, and yield.

In one aspect, the invention provides a synthetic composition comprising a plant element and a heterologously disposed endophyte, wherein the endophyte is a member of the genus *Chaetomium* and comprises at least one polynucleotide sequence at least 97% identical to a polynucleotide sequence selected from the group consisting of SEQ ID NOs: 52, 53, 54, 55, 56, 57, 58, and 59, wherein the synthetic composition is capable of providing an improved trait of agronomic importance as compared to a reference plant element not further comprising the endophyte, wherein the plant element is a soybean variety selected from the group consisting of Pfister 38R25, Stine 3920, and closely related varieties thereof, and the trait of agronomic importance is yield.

In one aspect, the invention provides a synthetic composition comprising a plant element and a heterologously disposed endophyte, wherein the endophyte is a member of the genus *Chaetomium* and comprises at least one polynucleotide sequence at least 97% identical to a polynucleotide sequence selected from the group consisting of SEQ ID NOs: 52, 53, 54, 55, 56, 57, 58, and 59, wherein the synthetic composition is capable of providing an improved trait of agronomic importance as compared to a reference plant element not further comprising the endophyte, wherein the plant element is a wheat plant element and the trait of agronomic importance is root length or yield.

In one aspect, the invention provides a synthetic composition comprising a plant element and a heterologously disposed endophyte, wherein the endophyte is a member of the genus *Chaetomium* and comprises at least one polynucleotide sequence at least 97% identical to a polynucleotide sequence selected from the group consisting of SEQ ID NOs: 52, 53, 54, 55, 56, 57, 58, and 59, wherein the synthetic composition is capable of providing an improved trait of agronomic importance as compared to a reference plant element not further comprising the endophyte, wherein the plant element is a wheat variety selected from the group consisting of SDSU Focus, SDSU Select, and closely related varieties thereof and the trait of agronomic importance is yield.

In some embodiments, any of the synthetic compositions described herein further comprise a plant element is a seed, optionally wherein the seed is modified. In some embodiments, wherein the improved trait of agronomic importance is conferred under normal watering conditions. In some embodiments, the plant element is placed into a substrate that promotes plant growth, optionally soil. In some embodiments, a plurality of said plant elements are placed in the soil in rows, with substantially equal spacing between each seed within each row.

In some embodiments, any of the synthetic compositions described herein further comprise a formulation that comprising one or more of the following: stabilizer, preservative, carrier, surfactant, anticomplex agent, or any combination thereof and/or one or more of the following: fungicide, nematicide, bactericide, insecticide, or herbicide. In some embodiments, any of the synthetic compositions described herein are confined within an object selected from the group consisting of: bottle, jar, ampule, package, vessel, bag, box, bin, envelope, carton, container, silo, shipping container, truck bed, or case. In some embodiments, any of the synthetic compositions described herein are shelf-stable.

In one aspect, the invention provides a synthetic composition comprising a plant element and a heterologously disposed endophyte, wherein the endophyte is a member of the genus *Exserohilum* and comprises at least one polynucleotide sequence at least 97%, at least 98%, at least 99%, or 100% identical to a polynucleotide sequence selected from the group consisting of SEQ ID NOs: 60, 61, and 62, wherein the synthetic composition is capable of providing an improved trait of agronomic importance as compared to a reference plant element not further comprising the endophyte, wherein the percent identify is determined over a region of alignment of at least 100, 200, 300, 400, or at least 500 nucleotides.

In one aspect, the invention provides a synthetic composition comprising a plant element and a heterologously disposed endophyte, wherein the endophyte is a member of the genus *Epicoccum* and comprises at least one polynucleotide sequence at least 97%, at least 98%, at least 99%, or 100% identical to a polynucleotide sequence selected from the group consisting of SEQ ID NOs: 63, 64, and 71, wherein the synthetic composition is capable of providing an improved trait of agronomic importance as compared to a reference plant element not further comprising the endophyte, wherein the percent identify is determined over a region of alignment of at least 100, 200, 300, 400, or at least 500 nucleotides.

In one aspect, the invention provides a synthetic composition comprising a plant element and a heterologously disposed endophyte, wherein the endophyte is a member of the genus *Coniochaeta* and comprises at least one polynucleotide sequence at least 97%, at least 98%, at least 99%, or 100% identical to a polynucleotide sequence selected from the group consisting of SEQ ID NOs: 38, 39, 40, and 41, wherein the synthetic composition is capable of providing an improved trait of agronomic importance as compared to a reference plant element not further comprising the endophyte, wherein the percent identify is determined over a region of alignment of at least 100, 200, 300, 400, or at least 500 nucleotides.

In one aspect, the invention provides a synthetic composition comprising a plant element and a heterologously disposed endophyte, wherein the endophyte is a member of the genus *Epicoccum* and comprises at least one polynucleotide sequence at least 97%, at least 98%, at least 99%, or 100% identical to SEQ ID NO: 70, wherein the synthetic composition is capable of providing an improved trait of agronomic importance as compared to a reference plant element not further comprising the endophyte, wherein the percent identify is determined over a region of alignment of at least 100, 200, 300, 400, or at least 500 nucleotides.

In one aspect, the invention provides a synthetic composition comprising a plant element and a heterologously disposed endophyte, wherein the endophyte is a member of the genus *Curvularia* and comprises at least one polynucleotide sequence at least 97%, at least 98%, at least 99%, or 100% identical to a polynucleotide sequence selected from the group consisting of SEQ ID NOs: 42, 43, 44, 45, 65, and 66, wherein the synthetic composition is capable of providing an improved trait of agronomic importance as compared to a reference plant element not further comprising the endophyte, wherein the percent identify is determined over a region of alignment of at least 100, 200, 300, 400, or at least 500 nucleotides.

In one aspect, the invention provides a synthetic composition comprising a plant element and a heterologously disposed endophyte, wherein the endophyte is a member of the genus *Cladosporium* and comprises at least one polynucleotide sequence at least 97%, at least 98%, at least 99%, or 100% identical to SEQ ID NO: 67, wherein the synthetic composition is capable of providing an improved trait of agronomic importance as compared to a reference plant element not further comprising the endophyte, wherein the percent identify is determined over a region of alignment of at least 100, 200, 300, 400, or at least 500 nucleotides.

In one aspect, the invention provides a synthetic composition comprising a plant element and a heterologously disposed endophyte, wherein the endophyte is a member of the genus *Cladosporium* and comprises at least one polynucleotide sequence at least 97%, at least 98%, at least 99%, or 100% identical to a polynucleotide sequence selected from the group consisting of SEQ ID NOs: 67 and 68, wherein the synthetic composition is capable of providing an improved trait of agronomic importance as compared to a reference plant element not further comprising the endophyte, wherein the percent identify is determined over a region of alignment of at least 100, 200, 300, 400, or at least 500 nucleotides.

In one aspect, the invention provides a synthetic composition comprising a plant element and a heterologously disposed endophyte, wherein the endophyte is a member of the genus *Paecilomyces* and comprises at least one polynucleotide sequence at least 97%, at least 98%, at least 99%, or 100% identical to SEQ ID NO: 69, wherein the synthetic composition is capable of providing an improved trait of agronomic importance as compared to a reference plant element not further comprising the endophyte, wherein the percent identify is determined over a region of alignment of at least 100, 200, 300, 400, or at least 500 nucleotides.

In one aspect, the invention provides a synthetic composition comprising a plant element and a heterologously disposed endophyte, wherein the endophyte is a member of the genus *Acremonium* and comprises at least one polynucleotide sequence at least 97%, at least 98%, at least 99%, or 100% identical to a polynucleotide sequence selected from the group consisting of SEQ ID NOs: 46, 47, 48, 49, 50, and 51, and wherein the synthetic composition is capable of providing an improved trait of agronomic importance as compared to a reference plant element not further comprising the endophyte, wherein the percent identify is determined over a region of alignment of at least 100, 200, 300, 400, or at least 500 nucleotides.

In one aspect, the invention provides a synthetic composition comprising a plant element and a heterologously disposed endophyte, wherein the endophyte is a member of the genus *Chaetomium* and comprises at least one polynucleotide sequence at least 97%, at least 98%, at least 99%, or 100% identical to a polynucleotide sequence selected from the group consisting of SEQ ID NOs: 52, 53, 54, 55, 56, 57, 58, and 59, wherein the synthetic composition is capable of providing an improved trait of agronomic importance as compared to a reference plant element not further comprising the endophyte, wherein the percent identify is determined over a region of alignment of at least 100, 200, 300, 400, or at least 500 nucleotides.

DETAILED DESCRIPTION

Figure 1A:
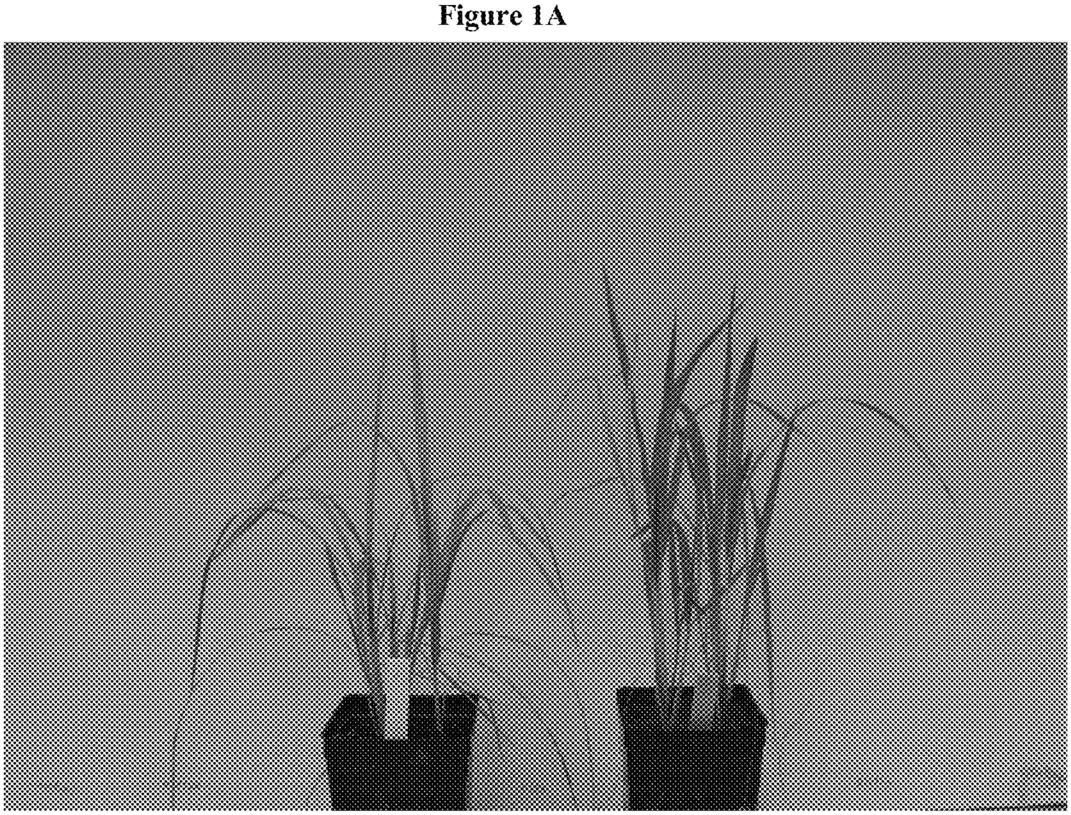
FIG. 1A shows exemplary rice plants grown as described in Example 29. The pot on the left contains untreated control rice plants. The pot on the right shows rice plants treated with MIC-68178.
Figure 2:
FIG. 2 shows the washed roots of exemplary rice plants grown as described in Example 29. The roots of untreated control rice plants are on the left. The roots of rice plants treated with MIC-68178 are on the right.

As demonstrated herein, agricultural plants are heterologously disposed to symbiotic microorganisms, termed endophytes, particularly bacteria and fungi, which contribute to plant survival, performance, and characteristics.

Described herein are endophytes that are capable of living within or otherwise heterologously disposed to plants to improve plant characteristics. Described herein are methods of using endophytes that are heterologously disposed to plants to impart novel characteristics to a host plant, as well as to distinct plant elements of the host plant. In some embodiments, endophyte compositions are isolated and purified from plant or fungal sources, and heterologously disposed with a plant element to impart improved agronomic potential and/or improved agronomic traits to the host plant. In some embodiments, endophytes that are capable of living within plants are isolated and purified from their native source(s) and heterologously disposed, e.g., manually, mechanically, or artificially combined, with a plant element, to impart improved agronomic potential and/or improved agronomic traits to the host plant or the host plant's elements. Such endophytes that are capable of living within plants may be further manipulated or combined with additional elements prior to combining with the plant element(s).

As described herein, endophytes can be robustly derived from heterologous, homologous, or engineered sources, optionally cultured, manually, mechanically or artificially applied heterologously to plant elements, e.g., heterologously disposed, and, as a result of the manual, mechanical or artificial application, confer multiple beneficial properties. This is surprising given the variability observed in the art in endophytic microbe isolation and the previous observations of inefficient plant element pathogen colonization of plant host's tissues.

In part, the present invention provides preparations of endophytes that are capable of living within plants, and the creation of synthetic compositions of plant elements and/or seedlings with heterologously disposed endophytes, and formulations comprising the synthetic compositions, as well as the recognition that such synthetic compositions display a diversity of beneficial and unexpected properties present in the agricultural plants and/or the heterologous endophyte populations. Beneficial properties include, but are not limited to metabolism, transcript expression, proteome alterations, morphology, resilience to a variety of environmental stresses, and any combination of such properties. The present invention also provides methods of using endophytes described herein to benefit the host plant with which they are heterologously disposed.

Definitions

Terms used in the claims and specification are defined as set forth below unless otherwise specified.

It must be noted that, as used in the specification and the appended claims, the singular forms "a," "an" and "the" include plural referents unless the context clearly dictates otherwise.

An "endophyte" is an organism capable of living on a plant element (e.g., rhizoplane or phylosphere) or within a plant element, or on a surface in close physical proximity with a plant element, e.g., the rhizosphere, or e.g., on a seed. A "beneficial" endophytes does not cause disease or harm the host plant otherwise. Endophytes can occupy the intracellular or extracellular spaces of plant tissue, including the leaves, stems, flowers, fruits, seeds, or roots. An endophyte can be, for example, a bacterial or fungal organism, and can confer a beneficial property to the host plant such as an increase in yield, biomass, resistance, or fitness. An endophyte can be a fungus or a bacterium. As used herein, the term "microbe" is sometimes used to describe an endophyte.

A "population" of endophytes, or an "endophyte population", refers to one or more endophytes that share a common genetic derivation, e.g., one or more propagules of a single endophyte, i.e., endophytes grown from a single picked colony. In some embodiments, a population refers to endophytes of identical taxonomy. In some cases, a population of endophytes refers to one or more endophytes of the same genus. In some cases, a population of endophytes refers to one or more endophytes of the same OTU.

A "plurality of endophytes" means two or more types of endophyte entities, e.g., of bacteria or fungi, or combinations thereof. In some embodiments, the two or more types of endophyte entities are two or more individual endophytic organisms, regardless of genetic derivation or taxonomic relationship. In some embodiments, the two or more types of endophyte entities are two or more populations of endophytes. In other embodiments, the two or more types of endophyte entities are two or more species of endophytes. In yet other embodiments, the two or more types of endophyte entities are two or more genera of endophytes. In yet other embodiments, the two or more types of endophyte entities are two or more families of endophytes. In yet other embodiments, the two or more types of endophyte entities are two or more orders of endophytes. In yet other embodiments, the two or more types of endophyte entities are two or more classes of endophytes. In yet other embodiments, the two or more types of endophyte entities are two or more phyla of endophytes. In some embodiments, a plurality refers to three or more endophytes, either distinct individual organisms or distinct members of different genetic derivation or taxa. In some embodiments, a plurality refers to four or more either distinct individual endophytic organisms or distinct members of different genetic derivation or taxa. In some embodiments, a plurality refers to five or more, ten or more, or an even greater number of either distinct individual endophytic organisms or distinct members of different genetic derivation or taxa. In some embodiments, the term "consortium" or "consortia" may be used as a collective noun synonymous with "plurality", when describing more than one population, species, genus, family, order, class, or phylum of endophytes.

As used herein, the term "microbe" or "microorganism" refers to any species or taxon of microorganism, including, but not limited to, archaea, bacteria, microalgae, fungi (including mold and yeast species), mycoplasmas, microspores, nanobacteria, oomycetes, and protozoa. In some embodiments, a microbe or microorganism is an endophyte, for example a bacterial or fungal endophyte, which is capable of living within a plant. In some embodiments, a microbe or microorganism encompasses individual cells (e.g., unicellular microorganisms) or more than one cell (e.g., multi-cellular microorganism). A "population of microorganisms" may thus refer to multiple cells of a single microorganism, in which the cells share common genetic derivation.

As used herein, the term "bacterium" or "bacteria" refers in general to any prokaryotic organism, and may reference an organism from either Kingdom Eubacteria (Bacteria), Kingdom Archaebacteria (Archae), or both. In some cases, bacterial genera have been reassigned due to various reasons (such as, but not limited to, the evolving field of whole genome sequencing), and it is understood that such nomenclature reassignments are within the scope of any claimed genus. For example, certain species of the genus *Erwinia* have been described in the literature as belonging to genus *Pantoea* (Zhang, Y. & Qiu, S. Antonie van Leeuwenhoek (2015) 108: 1037).

The term 16S refers to the DNA sequence of the 16S ribosomal RNA (rRNA) sequence of a bacterium. 16S rRNA gene sequencing is a well-established method for studying phylogeny and taxonomy of bacteria.

As used herein, the term "fungus" or "fungi" refers in general to any organism from Kingdom Fungi. Historical taxonomic classification of fungi has been according to morphological presentation. Beginning in the mid-1800's, it was recognized that some fungi have a pleomorphic life cycle, and that different nomenclature designations were being used for different forms of the same fungus. In 1981, the Sydney Congress of the International Mycological Association laid out rules for the naming of fungi according to their status as anamorph, teleomorph, or holomorph (Taylor J W. One Fungus=One Name: DNA and fungal nomenclature twenty years after PCR. IMA Fungus 2(2):113-120. 2011). With the development of genomic sequencing, it became evident that taxonomic classification based on molecular phylogenetics did not align with morphological-based nomenclature (Shenoy B D, Jeewon R, Hyde K D. Impact of DNA sequence-data on the taxonomy of anamorphic fungi. Fungal Diversity 26(10) 1-54. 2007). As a result, in 2011 the International Botanical Congress adopted a resolution approving the International Code of Nomenclature for Algae, Fungi, and Plants (Melbourne Code) (International Code of Nomenclature for algae, fungi, and plants (Melbourne Code), adopted by the Eighteenth International Botanical Congress Melbourne, Australia, July 2011), with the stated outcome of designating "One Fungus=One Name" (Hawksworth D L. Managing and coping with names of pleomorphic fungi in a period of transition. IMA Fungus 3(1):15-24. 2012). However, systematics experts have not aligned on common nomenclature for all fungi, nor are all existing databases and information resources inclusive of updated taxonomies. As such, many fungi referenced herein may be described by their anamorph form but it is understood that based on identical genomic sequencing, any pleomorphic state of that fungus may be considered to be the same organism. For example, the genus *Alternaria* is the anamorph form of the teleomorph genus *Lewia* (Kwasna H and Kosiak B. *Lewia avenicola* sp. nov. and its *Alternaria* anamorph from oat grain, with a key to the species of *Lewia*. Mycol Res 2003; 107(Pt 3):371-6), ergo both would be understood to be the same organism with the same DNA sequence. For example, it is understood that the genus *Acremonium* is also reported in the literature as genus *Sarocladium* as well as genus *Tilachilidium* (Summerbell R. C., C. Gueidan, H-J. Schroers3, G. S. de Hoog, M. Starink, Y. Arocha Rosete, J. Guano and J. A. Scott. *Acremonium* phylogenetic overview and revision of *Gliomastix, Sarocladium*, and *Trichothecium*. Studies in Mycology 68: 139-162. 2011). For example, the genus *Cladosporium* is an anamorph of the teleomorph genus *Davidiella* (Bensch K, Braun U, Groenewald J Z, Crous P W. The genus *Cladosporium*. Stud Mycol. 2012 Jun. 15; 72(1): 1-401), and is understood to describe the same organism. In some cases, fungal genera have been reassigned due to various reasons, and it is understood that such nomenclature reassignments are within the scope of any claimed genus.

"Internal Transcribed Spacer" (ITS) refers to the spacer DNA (non-coding DNA) situated between the small-subunit ribosomal RNA (rRNA) and large-subunit (LSU) rRNA genes in the chromosome or the corresponding transcribed region in the polycistronic rRNA precursor transcript. ITS gene sequencing is a well-established method for studying phylogeny and taxonomy of fungi. In some cases, the "Large SubUnit" (LSU) sequence is used to identify fungi. LSU gene sequencing is a well-established method for studying phylogeny and taxonomy of fungi. Some fungal endophytes may be described by an ITS sequence and some may be described by an LSU sequence. Both are understood to be equally descriptive and accurate for determining taxonomy.

As used herein with respect to fungi and bacteria, the term "marker gene" refers to a conserved gene comprising sequence variation among related organisms, e.g. an organism's 16S (for bacteria) or ITS (for fungi) polynucleotide sequence, fusA gene, or unique genomic regions, by which a microbe may be specifically identified and assigned taxonomic nomenclature. In some embodiments, marker genes include, but are not limited to, actin, elongation factor G (fusA), tubulin, largest subunit of RNA polymerase II (RPB1), long subunit rRNA gene (LSU), second largest subunit of RNA polymerase II (RPB2), small subunit rRNA gene (SSU), phosphoglycerate kinase, beta-tubulin, and combinations thereof.

The terms "pathogen" and "pathogenic" in reference to a bacterium or fungus includes any such organism that is capable of causing or affecting a disease, disorder or condition of a host comprising the organism.

A "spore" or a population of "spores" refers to bacteria or fungi that are generally viable, more resistant to environmental influences such as heat and bactericidal or fungicidal agents than other forms of the same bacteria or fungi, and typically capable of germination and out-growth. Bacteria and fungi that are "capable of forming spores" are those bacteria and fungi comprising the genes and other necessary abilities to produce spores under suitable environmental conditions.

"Biomass" means the total mass or weight (fresh or dry), at a given time, of a plant tissue, plant tissues, an entire plant, or population of plants. Biomass is usually given as weight per unit area. The term may also refer to all the plants or species in the community (community biomass).

The term "isolated" is intended to specifically reference an organism, cell, tissue, polynucleotide, or polypeptide that is removed from its original source.

As used herein, an isolated endophyte or microbe is an endophyte or microbe that has been removed from its natural milieu. "Pure cultures" or "isolated cultures" are cultures in which the organisms present are only of one particular genus and species. This is in contrast to "mixed cultures," which are cultures in which more than one genus and/or species of microorganism are present. As such, the term "isolated" does not necessarily reflect the extent to which the microbe has been purified. A "substantially pure culture" of the microbe refers to a culture which contains substantially no other endophytes or microbes than the desired endophyte or microbe. In other words, a substantially pure endophyte or microbe culture is substantially free of other contaminants, which can include microbial contaminants. Further, as used herein, "biologically pure" is intended to mean the endophyte or microbe separated from materials with which it is normally found in nature. A microbe or endophyte heterologously disposed to other microbes or endophytes, or with compounds or materials that it is not normally found with in nature, is still defined as "biologically pure." A monoculture is, of course, "biologically pure." As used herein, the term "enriched culture" of an isolated microbe or endophyte refers to a culture that contains more that 50%, 60%, 70%, 80%, 90%, or 95% of the isolated endophyte or microbe.

A "host plant" includes any plant, particularly a plant of agronomic importance, within which or onto which a microbe, such as an endophyte, is heterologously disposed. As used herein, a microbe is said to colonize a plant, plant element, or seed, when it can exist as an endophyte in relationship with a plant or plant element during at least part of either the plant's or the microbe's life cycle. In some embodiments, an endophyte is said to "colonize" a plant or plant element when it can be stably detected within the plant or plant element over a period time, such as one or more days, weeks, months or years. Some of the compositions and methods described herein involve a plurality of microbes in an amount effective to colonize a plant.

A "non-host target" means an organism or chemical compound that is altered in some way after contacting a host plant that comprises an endophyte, as a result of a property conferred to the host plant by the endophyte.

As used herein, a nucleic acid has "homology" or is "homologous" to a second nucleic acid if the nucleic acid sequence has a similar sequence to the second nucleic acid sequence. The terms "identity", "percent identity", "percent sequence identity" or "identical" in the context of nucleic acid sequences refer to the nucleotides in the two sequences that are the same when aligned for maximum correspondence. There are different algorithms known in the art that can be used to measure nucleotide sequence identity. Nucleotide sequence identity can be measured by a local or global alignment, preferably implementing an optimal local or optimal global alignment algorithm. For example, a global alignment may be generated using an implementation of the Needleman-Wunsch algorithm (Needleman, S. B. & Wunsch, C. D. (1970) Journal of Molecular Biology. 48(3): 443-53). For example, a local alignment may be generated using an implementation of the Smith-Waterman algorithm (Smith T. F & Waterman, M. S. (1981) Journal of Molecular Biology. 147(1):195-197). Optimal global alignments using the Needleman-Wunsch algorithm and optimal local alignments using the Smith-Waterman algorithm are implemented in USEARCH, for example USEARCH version v8.1.1756_i86osx32.

A gap is a region of an alignment wherein a sequence does not align to a position in the other sequence of the alignment. In global alignments, terminal gaps are discarded before identity is calculated. For both local and global alignments, internal gaps are counted as differences. A terminal gap is a region beginning at the end of a sequence in an alignment wherein the nucleotide in the terminal position of that sequence does not correspond to a nucleotide position in the other sequence of the alignment and extending for all contiguous positions in that sequence wherein the nucleotides of that sequence do not correspond to a nucleotide position in the other sequence of the alignment. An internal gap is a gap in an alignment which is flanked on the 3' and 5' end by positions wherein the aligned sequences are identical.

In some embodiments, the nucleic acid sequence to be aligned is a complete gene. In some embodiments, the nucleic acid sequence to be aligned is a gene fragment. In some embodiments, the nucleic acid sequence to be aligned is an intergenic sequence. In a preferred embodiment, inference of homology from a sequence alignment is make where the region of alignment is at least 85% of the length of the query sequence.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 76%, 80%, 85%, or at least about 90%, or at least about 95%, 96%, at least 97%, 98%, 99% or 100% of the positions of the alignment, wherein the region of alignment is at least about 50%, 60%, 70%, 75%, 85%, or at least about 90%, or at least about 95%, 96%, 97%, 98%, 99% or 100% of the length of the query sequence. In a preferred embodiment, the region of alignment contains at least 100 positions inclusive of any internal gaps. In some embodiments, the region of alignment comprises at least 100 nucleotides of the query sequence. In some embodiments, the region of alignment comprises at least 200 nucleotides of the query sequence. In some embodiments, the region of alignment comprises at least 300 nucleotides of the query sequence. In some embodiments, the region of alignment comprises at least 400 nucleotides of the query sequence. In some embodiments, the region of alignment comprises at least 500 nucleotides of the query sequence. In some embodiments, the query sequence is selected from the group consisting of SEQ ID NOs 38-59.

As used herein, the terms "operational taxonomic unit," "OTU," "taxon," "hierarchical cluster," and "cluster" are used interchangeably. An operational taxon unit (OTU) refers to a group of one or more organisms that comprises a node in a clustering tree. The level of a cluster is determined by its hierarchical order. In some embodiments, an OTU is a group tentatively assumed to be a valid taxon for purposes of phylogenetic analysis. In another embodiment, an OTU is any of the extant taxonomic units under study. In yet another embodiment, an OTU is given a name and a rank. For example, an OTU can represent a domain, a sub-domain, a kingdom, a sub-kingdom, a phylum, a sub-phylum, a class, a sub-class, an order, a sub-order, a family, a subfamily, a genus, a subgenus, or a species. In some embodiments, OTUs can represent one or more organisms from the kingdoms Eubacteria, Bacteria, Protista, or Fungi, at any level of a hierarchal order. In some embodiments, an OTU represents a prokaryotic or fungal order.

In some embodiments, the present invention contemplates the synthetic compositions comprising the combination of a plant element, seedling, or whole plants and an endophyte population, in which the endophyte population is "heterologously disposed". In some embodiments, one or more endophytes of the synthetic composition are heterologously disposed when they are mechanically or manually applied, artificially inoculated or disposed onto or into a plant element, seedling, plant or onto or into a plant growth medium or onto or into a treatment formulation so that the endophyte exists on or in said plant element, seedling, plant, plant growth medium, or treatment formulation in a manner not found in nature prior to the application of the one or more endophytes, e.g., said combination which is not found in nature. In some embodiments, such a manner is contemplated to be selected from the group consisting of: the presence of the endophyte; presence of the endophyte in a different number of cells, concentration, or amount; the presence of the endophyte in a different plant element, tissue, cell type, or other physical location in or on the plant; the presence of the endophyte at different time period, e.g. developmental phase of the plant or plant element, time of day, time of season, and combinations thereof. In some embodiments, one or more endophytes of a synthetic composition are heterologously disposed when the one or more endophytes are artificially inoculated, e.g., is manually or mechanically inoculated, or artificially applied, e.g. manually or mechanically applied, to a different plant element or at a different developmental stage than that with which the one or more endophytes are naturally found or at a greater concentration, number, or amount than that which is naturally found in or on said plant element, seedling, or plant. In some embodiments, "heterologously disposed" refers to the relationship between the endophyte and the inoculated host plant as compared to the type of host plant with which said endophyte is normally associated. In one example, endophytes used in a synthetic composition can be obtained from a different individual plant of the same variety as that of the host inoculated plant to which it becomes heterologously disposed, a plant of a different variety but the same genus and species, a plant of a different cultivar, or a plant of a different genus. In an embodiment, the endophyte is an endophytic microbe isolated from a different plant than the inoculated plant. For example, in an embodiment, the endophyte is an endophyte isolated from a different plant of the same species as the inoculated plant. In some cases, the endophyte is isolated from a species related to the inoculated plant. In another example, endophytes used in a synthetic composition can be obtained from different individual plants of the same variety, each of which has been subjected to different growth conditions. For example, an endophyte derived from a drought-affected plant of one variety can be isolated and coated onto the plant element that was derived from a plant of the same variety not subjected to drought. In such cases, the endophyte is considered to be heterologously disposed to the plant element onto which it is manually, mechanically, or artificially applied. In some embodiments, "heterologously disposed" means that the endophyte applied to a different tissue or cell type of the plant element than that in which the microbe is naturally found. In some embodiments, an endophyte is heterologously disposed on a seedling if that endophyte is normally found at the flowering stage of a plant and not at a seedling stage. In some embodiments, an endophyte is heterologously disposed the endophyte is normally found in the root tissue of a plant element but not in the leaf tissue, and the endophyte is applied to the leaf. In yet another non-limiting example, if an endophyte is naturally found in the mesophyll layer of leaf tissue but is being applied to the epithelial layer, the endophyte would be considered to be heterologously disposed. In some embodiments, "heterologously disposed" means that the native plant element, seedling, or plant does not contain detectable levels of the microbe in that same plant element, seedling, or plant. For example, if said plant element or seedling or plant does not naturally have the endophyte heterologously disposed to it and the endophyte is applied, the endophyte would be considered to be heterologously disposed. In some embodiments, "heterologously disposed" means that the endophyte being applied is at a greater concentration, number, or amount to the plant element, seedling, or plant, than that which is naturally found in said plant element, seedling, or plant. For example, an endophyte is heterologously disposed when present at a concentration that is at least 1.5 times greater, between 1.5 and 2 times greater, 2 times greater, between 2 and 3 times greater, 3 times greater, between 3 and 5 times greater, 5 times greater, between 5 and 7 times greater, 7 times greater, between 7 and 10 times greater, 10 times greater, or even greater than 10 times higher number, amount, or concentration than the concentration that was present prior to the disposition of said endophyte. In some embodiments, "heterologously disposed" means that the endophyte is applied to a developmental stage of the plant element, seedling, or plant in which said endophyte is not naturally found, but may be associated at other stages. In some embodiments, "heterologously disposed" means that the endophyte was isolated from plants or plant elements under an environmental condition different than that which is normally found (for example but not limited to: different soil pH, different mean air temperature, different soil temperature, different rainfall conditions, different soil nutrient composition, or different environmental salinity). In one example, if an endophyte is normally found at the flowering stage of a plant and no other stage, an endophyte applied at the seedling stage may be considered to be heterologously disposed. In another example, an endophyte that is normally heterologously disposed to leaf tissue of a plant is considered heterologous to a leaf tissue of another plant that naturally lacks said endophyte. In another example, an endophyte that is normally found at low levels in a plant is considered heterologous to that plant if a higher concentration of that endophyte is introduced into the plant. In yet another example, an endophyte that is heterologously disposed to a tropical grass species would be considered heterologous to a different grass species that naturally lacks said endophyte.

An "inoculated" plant or plant element has been artificially introduced to a heterologous endophyte at some point during the plant's or plant element's growth or development (including vegetative or reproductive phases). In some embodiments, the heterologous endophyte is transiently or permanently incorporated into the plant or plant element, and is detectable using methods known in the art or described herein. In some embodiments, a seed is inoculated with an endophyte by manually or mechanically contacting the seed with a formulation comprising said endophyte, which is detectable in or on the seed. In some embodiments, a plant is said to be inoculated with an endophyte if it is grown from a reproductive element (e.g. a seed) that was itself manually or mechanically contacted with a formulation comprising said endophyte, which is subsequently detectable in or on the plant. In some embodiments, a plant is said to be inoculated with an endophyte if any one or more if its plant elements (e.g., leaf, stem, or root) is manually or mechanically contacted with a formulation comprising said endophyte, which is subsequently detectable either in the same plant element that was originally contacted with said formulation or in a different plant element of that plant. The term "inoculation" may also refer to the manual or mechanical contact of an endophyte population to any substance, that is detectable in or on said substance subsequent to endophyte contact. In one example, said substance is soil or other plant growth medium. In another example, said substance is a storage medium such as glycerol. In some cases, "inoculation" may refer to the contact of an endophyte population to a non-plant living organism, for example, but not limited to, an insect or a fungus.

The term "isoline" is a comparative term, and references organisms that are genetically identical, but may differ in treatment. In one example, two genetically identical maize plant embryos may be separated into two different groups, one receiving a treatment (such as transformation with a heterologous polynucleotide, to create a genetically modified plant) and one control, e.g., reference, that does not receive such treatment. Any phenotypic differences between the two groups may thus be attributed solely to the treatment and not to any inherency of the plant's genetic makeup. In another example, two genetically identical soybean seeds may be treated with a formulation, one that introduces an endophyte composition and one that does not. Any phenotypic differences between the plants derived from (e.g., grown from or obtained from) those seeds may be attributed to the endophyte treatment, thus forming an isoline comparison.

Similarly, by the term "reference agricultural plant," it is meant an agricultural plant of the same species, variety, or cultivar to which a treatment, formulation, composition or endophyte preparation as described herein is not administered/contacted. A reference agricultural plant, therefore, is identical to the treated plant with the exception of the presence of the endophyte and can serve as a control for detecting the effects of the endophyte that is conferred to the plant. In some embodiments, the phrase "reference isoline plant" is used herein to describe a reference plant that is genetically identical and subject to the same conditions, i.e., a control plant, to the treated plant.

A "reference environment" refers to the environment, treatment or condition of the plant in which a measurement is made. For example, production of a compound in a plant heterologously disposed to an endophyte can be measured in a reference environment of drought stress, and compared with the levels of the compound in a reference agricultural plant under the same conditions of drought stress. Alternatively, the levels of a compound in plant heterologously disposed to an endophyte and reference agricultural plant can be measured under identical conditions of no stress.

A "plant element" is intended to generically reference either a whole plant or a plant component, including but not limited to plant tissues, parts, and cell types. A plant element is preferably one of the following: whole plant, seedling, meristematic tissue, ground tissue, vascular tissue, dermal tissue, seed, leaf, root, shoot, stem, flower, fruit, stolon, bulb, tuber, corm, keikis, shoot, bud. As used herein, a "plant element" is synonymous to a "portion" of a plant, and refers to any part of the plant, and can include distinct tissues and/or organs, and may be used interchangeably with the term "tissue" throughout.

Similarly, a "plant reproductive element" is intended to generically reference any part of a plant that is able to initiate other plants via either sexual or asexual reproduction of that plant, for example but not limited to: seed, seedling, root, shoot, cutting, scion, graft, stolon, bulb, tuber, corm, keikis, or bud.

A "progeny seed", as used herein, refers to the seed produced by a host plant that has been inoculated with, or heterologously disposed to, an endophyte. For example, in the present invention, a seed, plant element, or whole plant may become heterologously disposed to an endophyte, and the plant that is grown from said seed, or plant that is grown in heterologous association with said endophyte, may itself produce progeny seeds that comprise altered nutritional composition compared to seeds obtained from plants that were not grown from a plant element heterologously disposed to an endophyte or obtained from a parental (host) plant that had become heterologously disposed to an endophyte at some point in its life cycle. In the general sense, the phrase "progeny seed" may be construed to represent any plant propagative unit produced by the host plant that is capable of becoming another individual of that same plant species.

A "population" of plants refers to more than one plant, that are of the same taxonomic category, typically be of the same species, and will also typically share a common genetic derivation.

As used herein, an "agricultural seed" is a seed used to grow a plant typically used in agriculture (an "agricultural plant"). The seed may be of a monocot plant, and may be planted for the production of an agricultural product, for example feed, food, fiber, fuel, industrial uses, etc. As used herein, an agricultural seed is a seed that is prepared for planting, for example, in farms for growing.

"Agricultural plants" or "plants of agronomic importance include plants that are cultivated by humans for food, feed, fiber, fuel, and/or industrial purposes. In some embodiments, plants (including seeds and other plant elements) treated in accordance with the present invention are monocots. In some embodiments, plants (including seeds or other plant elements) treated in accordance with the present invention are dicots, excluding cotton and sorghum. In some embodiments, plants treated in accordance with the present invention include, but are not limited to: agricultural row, agricultural grass plants or other field crops: wheat, rice, barley, buckwheat, beans (soybean, snap, dry), corn (grain, seed, sweet corn, silage, popcorn, high oil), canola, peas (dry, succulent), peanuts, safflower, sunflower, alfalfa hay, forage crops (alfalfa, clover, vetch, and trefoil), berries and small fruits (blackberries, blueberries, currants, elderberries, gooseberries, huckleberries, loganberries, raspberries, strawberries, bananas and grapes), bulb crops (garlic, leeks, onions, shallots, and ornamental bulbs), citrus fruits (citrus hybrids, grapefruit, kumquat, lines, oranges, and pummelos), cucurbit vegetables (cucumbers, melons, gourds, pumpkins, and squash), flowers, bedding plants, ornamentals, fruiting vegetables (eggplant, sweet and hot peppers, tomatillos, and tomatoes), herbs, spices, mints, hydroponic crops (cucumbers, tomatoes, lettuce, herbs, and spices), leafy vegetables and cole crops (arugula, celery, chervil, endive, fennel, lettuce (head and leaf), parsley, radicchio, rhubarb, spinach, Swiss chard, broccoli, Brussels sprouts, cabbage, cauliflower, collards, kale, kohlrabi, and mustard greens), asparagus, legume vegetable and field crops (snap and dry beans, lentils, succulent and dry peas, and peanuts), pome fruit (pears and quince), root crops (beets, sugarbeets, red beets, carrots, celeriac, chicory, horseradish, parsnip, radish rutabaga, salsify, and turnips), deciduous trees (maple and oak), pine, rye, wheat, millet, stone fruits (apricots, cherries, nectarines, peaches, plums, and prunes), tree nuts (almonds, beech nuts, Brazil nuts, butternuts, cashews, chestnuts, filberts, hickory nuts, macadamia nuts, pecans, pistachios, and walnuts), and tuber crops (potatoes, sweet potatoes, yams, artichoke, cassava, and ginger). In a particular embodiment, the agricultural plant is selected from the group consisting of rice (*Oryza sativa* and related varieties), soy (*Glycine max* and related varieties), wheat (*Triticum aestivum* and related varieties), corn (*Zea mays* and related varieties), peanuts (*Arachis hypogaea* and related varieties), canola (*Brassica napus, Brassica rapa* and related varieties), coffee (*Coffea* spp.), cocoa (*Theobroma cacao*), melons, and tomatoes (*Solanum lycopsersicum* and related varieties).

A "closely related variety" comprises a common genetic derivation with a plant variety. In some embodiments, a closely related variety has at least one grandparental line in common with the plant variety. In some embodiments, a closely related variety has at least one parental line in common with the plant variety. In some embodiments, a closely related variety has at least 60%, 70%, 80%, 90%, 91%, 92%, 93%, 94%, 95%, 96%, 97%, 98%, 99%, 99.5%, 99.7%, 99.9%, 99.99% of the same SNPs detected in the plant variety. In some embodiments, a closely related variety has at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or 20 or more of the same SNPs detected in the plant variety. In some embodiments, a closely related variety has at least 20, at least 30, at least 40, at least 50, at least 60, at least 70, at least 80, at least 90, at least 100, at least 200, at least 300, at least 400, at least 500, at least 600, at least 700, at least 800, at least 900, or 100 or more of the same SNPs detected in the plant variety. In some embodiments, a closely related variety has at least 1000, at least 2000, at least 3000, at least 4000, at least 5000, at least 6000, at least 7000, at least 8000, at least 9000, or 10000 or more of the same SNPs detected in the plant variety. In some embodiments, a closely related variety has at least 10000, at least 20000, at least 30000, at least 40000, at least 50000, at least 60000, at least 70000, at least 80000, at least 90000, or 100000 or more of the same SNPs detected in the plant variety.

A "synthetic composition" comprises one or more endophytes combined by human endeavor with a heterologously disposed plant element or a treatment formulation, said combination which is not found in nature. In some embodiments, the term "synthetic composition" means one or more plant elements or formulation components combined by human endeavor with an isolated, purified endophyte composition. In some embodiments, said purified endophyte composition is mechanically or manually applied, artificially inoculated or disposed on a plant element in a manner that is not found on or in the plant element before application of the purified endophyte composition, e.g., said combination or association which is not found in nature.

In some embodiments, "synthetic composition" is used to refer to a treatment formulation comprising an isolated, purified population of endophytes heterologously disposed to a plant element. In some embodiments, "synthetic composition" refers to a purified population of endophytes in a treatment formulation comprising additional compositions with which said endophytes are not found in nature.

A "treatment formulation" refers to a mixture of chemicals that facilitate the stability, storage, and/or application of the endophyte composition(s). Treatment formulations may comprise any one or more agents such as: surfactant, a buffer, a tackifier, a microbial stabilizer, a fungicide, an anticomplex agent, an herbicide, a nematicide, an insecticide, a plant growth regulator, a rodenticide, a desiccant, a nutrient, an excipient, a wetting agent, a salt.

In some embodiments, an "agriculturally compatible carrier" can be used to formulate an agricultural formulation or other composition that includes a purified endophyte preparation. As used herein an "agriculturally compatible carrier" refers to any material, other than water, that can be added to a plant element without causing or having an adverse effect on the plant element (e.g., reducing seed germination) or the plant that grows from the plant element, or the like.

"Plant health" is demonstrated by the presence or improvement of a trait of agronomic importance found in a plant or plant element as compared to a reference plant or plant element. The compositions and methods herein may provide for an improved "agronomic trait" or "trait of agronomic importance" to a host plant, which include, but are not limited to disease resistance, drought tolerance, heat tolerance, cold tolerance, salinity tolerance, metal tolerance, herbicide tolerance, improved water use efficiency, improved nitrogen utilization, improved nitrogen fixation, pest resistance, herbivore resistance, pathogen resistance, yield improvement, health enhancement, vigor improvement, growth improvement, photosynthetic capability improvement, nutrition enhancement, altered protein content, altered oil content, increased biomass, increased shoot length, increased root length, increased root area, improved root architecture, modulation of a metabolite, modulation of the proteome, increased seed weight, altered seed carbohydrate composition, altered seed oil composition, altered seed protein composition, altered seed nutrient composition, and combinations thereof, as compared to reference plant derived from a seed without said seed treatment formulation.

In some embodiments, a treatment is heterologously disposed on a plant element in an amount effective to improve a trait of agronomic importance. In some embodiments, treatments capable of improving plant health are applied in an amount effective to improve a trait of agronomic importance or tolerance by at least 0.1%, at least 0.5%, at least 1%, at least 2%, at least 3%, between 3% and 5%, at least 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, as compared to a reference plant element not further comprising said endophyte.

In some embodiments, an improvement in a trait of agronomic importance is measured by the "win rate". The win rate is the proportion of replicates where the treatment shows an improvement in a trait of agronomic importance relative to reference replicates. In some embodiments, replicates are individual plants. In some embodiments, replicates are plots, e.g. replicated plots within a randomized complete block design field trial. In some embodiments, replicates are field trials conducted at diverse geographies.

In some embodiments, the endophyte is capable of improving a trait of agronomic importance at concentrations detected on or in the treated plant element of at least 10^2 CFU or spores per plant element, between 10^2 and 10^3 CFU or spores per plant element, about 10^3 CFU or spores per plant element, between 10^3 and 10^4 CFU or spores per plant element, about 10^4 CFU or spores per plant element, or between 10^4, of about 10^5 CFU or spores per plant element, at least 10^5 CFU or spores per plant element, between 10^5 and 10^6 CFU or spores per plant element, about 10^6 CFU or spores per plant element, between 10^6 and 10^7 CFU or spores per plant element, about 10^7 CFU or spores per plant element, between 10^7 and 10^8 CFU or spores per plant element, about 10^8 CFU or spores per plant element, or even greater than 10^8 CFU or spores per plant element. In some embodiments, the plant element is a seed.

The phrase "nutritional quality trait" includes any measurable parameter of a seed that either directly or indirectly influences the value (nutritional or economic) of said seed, for example, but not limited to: protein, fat, carbohydrate, ash, moisture, fiber, and calories. In some cases, "nutritional quality trait" is synonymous with "nutritional quality trait" or "seed nutritional quality trait", and can refer to any composition of the associated plant element, most particularly compositions providing benefit to other organisms that consume or utilize said plant element. As used herein, "oil" and "fat" are used interchangeably.

An increased "seed yield" can refer to any increase in seed or fruit weight, size, or abundance per a unit of measure, for example, per plant, per number of plants, per mass of plants, per acre planted, per acre harvested. In some embodiments, seed yield is reported as pounds or bushels of seed produced per acre harvested. The terms seed and grain are used interchangeably herein. Yield may also refer to the recovery of a particular component of a plant tissue upon processing, for example, the amount of oil which can be extracted per unit of seed. Typically, the particular characteristic is designated when referring to increased yield, e.g., increased seed yield or increased oil yield. Where the characteristic is not specified it may be assumed yield refers to seed yield and the terms may be used interchangeably.

As used herein, the terms "water-limited condition" and "drought condition," or "water-limited" and "drought," may be used interchangeably. For example, a method or composition for improving a plant's ability to grow under drought conditions means the same as the ability to grow under water-limited conditions. In such cases, the plant can be further said to display improved tolerance to drought stress.

As used herein, the terms "normal watering" and "well-watered" are used interchangeably, to describe a plant grown under typical growth conditions with no water restriction.

Additionally, "altered metabolic function" or "altered enzymatic function" may include, but not be limited to, the following: altered production of an auxin, altered nitrogen fixation, altered production of an antimicrobial compound, altered production of a siderophore, altered mineral phosphate solubilization, altered production of a cellulase, altered production of a chitinase, altered production of a xylanase, altered production of acetoin, altered utilization of a carbon source.

"Nutrient" or "seed nutrient" refers to any composition of the associated plant element, most particularly compositions providing benefit to other organisms that consume or utilize said plant element.

"Agronomic trait potential" is intended to mean a capability of a plant element for exhibiting a phenotype, preferably an improved agronomic trait, at some point during its life cycle, or conveying said phenotype to another plant element with which it is associated in the same plant. For example, a plant element may comprise an endophyte that will provide benefit to leaf tissue of a plant from which the plant element is grown; in such case, the plant element comprising such endophyte has the agronomic trait potential for a particular phenotype (for example, increased biomass in the plant) even if the plant element itself does not display said phenotype.

In some cases, the present invention contemplates the use of compositions that are "compatible" with agricultural chemicals, including but not limited to, a fungicide, an anticomplex compound, a bactericide, a virucide, an herbicide, a nematicide, a parasiticide, a pesticide, or any other agent widely used in agricultural which has the effect of killing or otherwise interfering with optimal growth of another organism. As used herein, a composition is "compatible" with an agricultural chemical when the organism is modified, such as by genetic modification, e.g., contains a transgene that confers resistance to an herbicide, or is adapted to grow in, or otherwise survive, the concentration of the agricultural chemical used in agriculture. For example, an endophyte disposed on the surface of a plant element is compatible with the fungicide metalaxyl if it is able to survive the concentrations that are applied on the plant element surface.

As used herein, a "colony-forming unit" ("CFU") is used as a measure of viable microorganisms in a sample. A CFU is an individual viable cell capable of forming on a solid medium a visible colony whose individual cells are derived by cell division from one parental cell. In some embodiments, a cell is a fungal spore.

The terms "decreased," "fewer," "slower" and "increased" "faster" "enhanced" "greater" as used herein refers to a decrease or increase in a characteristic of the endophyte treated plant element or resulting plant compared to an untreated plant element or resulting plant. For example, a decrease in a characteristic may be at least 1%, at least 2%, at least 3%, at least 4%, at least 5%, between 5% and 10%, at least 10%, between 10% and 20%, at least 15%, at least 20%, between 20% and 30%, at least 25%, at least 30%, between 30% and 40%, at least 35%, at least 40%, between 40% and 50%, at least 45%, at least 50%, between 50% and 60%, at least about 60%, between 60% and 70%, between 70% and 80%, at least 75%, at least about 80%, between 80% and 90%, at least about 90%, between 90% and 100%, at least 100%, between 100% and 200%, at least 200%, at least about 300%, at least about 400% or more lower than the untreated control and an increase may be at least 1%, at least 2%, at least 3%, at least 4%, at least 5%, between 5% and 10%, at least 10%, between 10% and 20%, at least 15%, at least 20%, between 20% and 30%, at least 25%, at least 30%, between 30% and 40%, at least 35%, at least 40%, between 40% and 50%, at least 45%, at least 50%, between 50% and 60%, at least about 60%, between 60% and 70%, between 70% and 80%, at least 75%, at least about 80%, between 80% and 90%, at least about 90%, between 90% and 100%, at least 100%, between 100% and 200%, at least 200%, at least about 300%, at least about 400% or more higher than the untreated control.

As used herein, a microbe or plant or plant element is "modified" when it comprises an artificially introduced genetic or epigenetic "modification". In some embodiments, the modification is introduced by a genome engineering technology. In some embodiments, the modification is introduced by a targeted nuclease. In some embodiments, targeted nucleases include, but are not limited to, transcription activator-like effector nuclease (TALEN), zinc finger nuclease (ZNF), clustered regulatory interspaced short palindromic repeats (CRISPR), CRISPR/Cas9, CRISPR/CPF1, and combinations thereof. In some embodiments, the modification is an epigenetic modification. In some embodiments, the modification is introduced by treatment with a DNA methyltransferase inhibitor such as 5-azacytidine, or a histone deacetylase inhibitor such as 2-amino-7-methoxy-3H-phenoxazin-3-one. In some embodiments, the modification is introduced via tissue culture. In some embodiments, a modified microbe or plant or plant element comprises a transgene.

Endophyte Compositions

The endophytes described herein provide several unexpected and significant advantages to agricultural plants over other plant-associated microbes, as demonstrated in the Examples.

Novel endophyte compositions are described herein. In some embodiments, the endophyte is selected from Table 4. In some embodiments, the endophyte is selected from Table 6.

In some embodiments, the endophyte comprises a polynucleotide sequence that is at least 97% identical to at least one sequence selected from the group consisting of SEQ ID NOs: 67. In some embodiments, the endophyte comprises a polynucleotide sequence that is between 97% and 98% identical, at least 98% identical, between 98.0% identical and 99.5% identical, at least 99.5% identical, or 100% identical to at least one sequence selected from the group consisting of SEQ ID NOs: 67.

In some embodiments, the endophyte comprises a polynucleotide sequence that is at least 97% identical to at least one sequence selected from the group consisting of SEQ ID NOs: 68. In some embodiments, the endophyte comprises a polynucleotide sequence that is between 97% and 98% identical, at least 98% identical, between 98.0% identical and 99.5% identical, at least 99.5% identical, or 100% identical to at least one sequence selected from the group consisting of SEQ ID NOs: 68.

In some embodiments, the endophyte comprises a polynucleotide sequence that is at least 97% identical to at least one sequence selected from the group consisting of SEQ ID NOs: 69. In some embodiments, the endophyte comprises a polynucleotide sequence that is between 97% and 98% identical, at least 98% identical, between 98.0% identical and 99.5% identical, at least 99.5% identical, or 100% identical to at least one sequence selected from the group consisting of SEQ ID NOs: 69.

In some embodiments, the endophyte comprises a polynucleotide sequence that is at least 97% identical to at least one sequence selected from the group consisting of SEQ ID NOs: 70. In some embodiments, the endophyte comprises a polynucleotide sequence that is between 97% and 98% identical, at least 98% identical, between 98.0% identical and 99.5% identical, at least 99.5% identical, or 100% identical to at least one sequence selected from the group consisting of SEQ ID NOs: 70.

In some embodiments, the endophyte comprises a polynucleotide sequence that is at least 97% identical to at least one sequence selected from the group consisting of SEQ ID NOs: 65 and 66. In some embodiments, the endophyte comprises a polynucleotide sequence that is between 97% and 98% identical, at least 98% identical, between 98.0% identical and 99.5% identical, at least 99.5% identical, or 100% identical to at least one sequence selected from the group consisting of SEQ ID NOs: 65 and 66. In some embodiments, the endophyte comprises at least two polynucleotide sequences that are at least 97% identical to at least two sequences selected from the group consisting of SEQ ID NOs: 65 and 66. In some embodiments, the endophyte comprises at least two polynucleotide sequences that are between 97% and 98% identical, at least 98% identical, between 98.0% identical and 99.5% identical, or at least 99.5% identical, or 100% identical to at least two sequences selected from the group consisting of SEQ ID NOs: 65 and 66.

In some embodiments, the endophyte comprises a polynucleotide sequence that is at least 97% identical to at least one sequence selected from the group consisting of SEQ ID NOs: 63, 64, and 71. In some embodiments, the endophyte comprises a polynucleotide sequence that is between 97% and 98% identical, at least 98% identical, between 98.0% identical and 99.5% identical, at least 99.5% identical, or 100% identical to at least one sequence selected from the group consisting of SEQ ID NOs: 63, 64, and 71. In some embodiments, the endophyte comprises at least two polynucleotide sequences that are at least 97% identical to at least two sequences selected from the group consisting of SEQ ID NOs: 63, 64, and 71. In some embodiments, the endophyte comprises at least two polynucleotide sequences that are between 97% and 98% identical, at least 98% identical, between 98.0% identical and 99.5% identical, or at least 99.5% identical, or 100% identical to at least two sequences selected from the group consisting of SEQ ID NOs: 63, 64, and 71. In some embodiments, the endophyte comprises at least three polynucleotide sequences that are at least 97% identical to at least three sequences selected from the group consisting of SEQ ID NOs: 63, 64, and 71. In some embodiments, the endophyte comprises at least three polynucleotide sequences that are between 97% and 98% identical, at least 98% identical, between 98.0% identical and 99.5% identical, or at least 99.5% identical, or 100% identical to at least three sequences selected from the group consisting of SEQ ID NOs: 63, 64, and 71.

In some embodiments, the endophyte comprises a polynucleotide sequence that is at least 97% identical to at least one sequence selected from the group consisting of SEQ ID NOs: 60, 61, and 62. In some embodiments, the endophyte comprises a polynucleotide sequence that is between 97% and 98% identical, at least 98% identical, between 98.0% identical and 99.5% identical, at least 99.5% identical, or 100% identical to at least one sequence selected from the group consisting of SEQ ID NOs: 60, 61, and 62. In some embodiments, the endophyte comprises at least two polynucleotide sequences that are at least 97% identical to at least two sequences selected from the group consisting of SEQ ID NOs: 60, 61, and 62. In some embodiments, the endophyte comprises at least two polynucleotide sequences that are between 97% and 98% identical, at least 98% identical, between 98.0% identical and 99.5% identical, or at least 99.5% identical, or 100% identical to at least two sequences selected from the group consisting of SEQ ID NOs: 60, 61, and 62. In some embodiments, the endophyte comprises at least three polynucleotide sequences that are at least 97% identical to at least three sequences selected from the group consisting of SEQ ID NOs: 60, 61, and 62. In some embodiments, the endophyte comprises at least three polynucleotide sequences that are between 97% and 98% identical, at least 98% identical, between 98.0% identical and 99.5% identical, or at least 99.5% identical, or 100% identical to at least three sequences selected from the group consisting of SEQ ID NOs: 60, 61, and 62.

In some embodiments, the endophyte comprises a polynucleotide sequence that is at least 97% identical to at least one sequence selected from the group consisting of SEQ ID NOs: 38, 39, 40, and 41. In some embodiments, the endophyte comprises a polynucleotide sequence that is between 97% and 98% identical, at least 98% identical, between 98.0% identical and 99.5% identical, at least 99.5% identical, or 100% identical to at least one sequence selected from the group consisting of SEQ ID NOs: 38, 39, 40, and 41. In some embodiments, the endophyte comprises at least two polynucleotide sequences that are at least 97% identical to at least two sequences selected from the group consisting of SEQ ID NOs: 38, 39, 40, and 41. In some embodiments, the endophyte comprises at least two polynucleotide sequences that are between 97% and 98% identical, at least 98% identical, between 98.0% identical and 99.5% identical, or at least 99.5% identical, or 100% identical to at least two sequences selected from the group consisting of SEQ ID NOs: 38, 39, 40, and 41. In some embodiments, the endophyte comprises at least three polynucleotide sequences that are at least 97% identical to at least three sequences selected from the group consisting of SEQ ID NOs: 38, 39, 40, and 41. In some embodiments, the endophyte comprises at least three polynucleotide sequences that are between 97% and 98% identical, at least 98% identical, between 98.0% identical and 99.5% identical, or at least 99.5% identical, or 100% identical to at least three sequences selected from the group consisting of SEQ ID NOs: 38, 39, 40, and 41. In some embodiments, the endophyte comprises at least four polynucleotide sequences that are at least 97% identical to at least four sequences selected from the group consisting of SEQ ID NOs: 38, 39, 40, and 41. In some embodiments, the endophyte comprises at least four polynucleotide sequences that are between 97% and 98% identical, at least 98% identical, between 98.0% identical and 99.5% identical, or at least 99.5% identical, or 100% identical to at least four sequences selected from the group consisting of SEQ ID NOs: 38, 39, 40, and 41.

In some embodiments, the endophyte comprises a polynucleotide sequence that is at least 97% identical to at least one sequence selected from the group consisting of SEQ ID NOs: 42, 43, 44, and 45. In some embodiments, the endophyte comprises a polynucleotide sequence that is between 97% and 98% identical, at least 98% identical, between 98.0% identical and 99.5% identical, at least 99.5% identical, or 100% identical to at least one sequence selected from the group consisting of SEQ ID NOs: 42, 43, 44, and 45. In some embodiments, the endophyte comprises at least two polynucleotide sequences that are at least 97% identical to at least two sequences selected from the group consisting of SEQ ID NOs: 42, 43, 44, and 45. In some embodiments, the endophyte comprises at least two polynucleotide sequences that are between 97% and 98% identical, at least 98% identical, between 98.0% identical and 99.5% identical, or at least 99.5% identical, or 100% identical to at least two sequences selected from the group consisting of SEQ ID NOs: 42, 43, 44, and 45. In some embodiments, the endophyte comprises at least three polynucleotide sequences that are at least 97% identical to at least three sequences selected from the group consisting of SEQ ID NOs: 42, 43, 44, and 45. In some embodiments, the endophyte comprises at least three polynucleotide sequences that are between 97% and 98% identical, at least 98% identical, between 98.0% identical and 99.5% identical, or at least 99.5% identical, or 100% identical to at least three sequences selected from the group consisting of SEQ ID NOs: 42, 43, 44, and 45. In some embodiments, the endophyte comprises at least four polynucleotide sequences that are at least 97% identical to at least four sequences selected from the group consisting of SEQ ID NOs: 42, 43, 44, and 45. In some embodiments, the endophyte comprises at least four polynucleotide sequences that are between 97% and 98% identical, at least 98% identical, between 98.0% identical and 99.5% identical, or at least 99.5% identical, or 100% identical to at least four sequences selected from the group consisting of SEQ ID NOs: 42, 43, 44, and 45.

In some embodiments, the endophyte comprises a polynucleotide sequence that is at least 97% identical to at least one sequence selected from the group consisting of SEQ ID NOs: 46, 47, 48, 49, 50, and 51. In some embodiments, the endophyte comprises a polynucleotide sequence that is between 97% and 98% identical, at least 98% identical, between 98.0% identical and 99.5% identical, at least 99.5% identical, or 100% identical to at least one sequence selected from the group consisting of SEQ ID NOs: 46, 47, 48, 49, 50, and 51. In some embodiments, the endophyte comprises at least two polynucleotide sequences that are at least 97% identical to at least two sequences selected from the group consisting of SEQ ID NOs: 46, 47, 48, 49, 50, and 51. In some embodiments, the endophyte comprises at least two polynucleotide sequences that are between 97% and 98% identical, at least 98% identical, between 98.0% identical and 99.5% identical, or at least 99.5% identical, or 100% identical to at least two sequences selected from the group consisting of SEQ ID NOs: 46, 47, 48, 49, 50, and 51. In some embodiments, the endophyte comprises at least three polynucleotide sequences that are at least 97% identical to at least three sequences selected from the group consisting of SEQ ID NOs: 46, 47, 48, 49, 50, and 51. In some embodiments, the endophyte comprises at least three polynucleotide sequences that are between 97% and 98% identical, at least 98% identical, between 98.0% identical and 99.5% identical, or at least 99.5% identical, or 100% identical to at least three sequences selected from the group consisting of SEQ ID NOs: 46, 47, 48, 49, 50, and 51. In some embodiments, the endophyte comprises at least four polynucleotide sequences that are at least 97% identical to at least four sequences selected from the group consisting of SEQ ID NOs: 46, 47, 48, 49, 50, and 51. In some embodiments, the endophyte comprises at least four polynucleotide sequences that are between 97% and 98% identical, at least 98% identical, between 98.0% identical and 99.5% identical, or at least 99.5% identical, or 100% identical to at least four sequences selected from the group consisting of SEQ ID NOs: 46, 47, 48, 49, 50, and 51. In some embodiments, the endophyte comprises at least five polynucleotide sequences that are at least 97% identical to at least five sequences selected from the group consisting of SEQ ID NOs: 46, 47, 48, 49, 50, and 51. In some embodiments, the endophyte comprises at least five polynucleotide sequences that are between 97% and 98% identical, at least 98% identical, between 98.0% identical and 99.5% identical, or at least 99.5% identical, or 100% identical to at least five sequences selected from the group consisting of SEQ ID NOs: 46, 47, 48, 49, 50, and 51. In some embodiments, the endophyte comprises at least six polynucleotide sequences that are at least 97% identical to at least six sequences selected from the group consisting of SEQ ID NOs: 46, 47, 48, 49, 50, and 51. In some embodiments, the endophyte comprises at least six polynucleotide sequences that are between 97% and 98% identical, at least 98% identical, between 98.0% identical and 99.5% identical, or at least 99.5% identical, or 100% identical to at least six sequences selected from the group consisting of SEQ ID NOs: 46, 47, 48, 49, 50, and 51.

In some embodiments, the endophyte comprises a polynucleotide sequence that is at least 97% identical to at least one sequence selected from the group consisting of SEQ ID NOs: 52, 53, 54, 55, 56, 57, 58, and 59. In some embodiments, the endophyte comprises a polynucleotide sequence that is between 97% and 98% identical, at least 98% identical, between 98.0% identical and 99.5% identical, at least 99.5% identical, or 100% identical to at least one sequence selected from the group consisting of SEQ ID NOs: 52, 53, 54, 55, 56, 57, 58, and 59. In some embodiments, the endophyte comprises at least two polynucleotide sequences that are at least 97% identical to at least two sequences selected from the group consisting of SEQ ID NOs: 52, 53, 54, 55, 56, 57, 58, and 59. In some embodiments, the endophyte comprises at least two polynucleotide sequences that are between 97% and 98% identical, at least 98% identical, between 98.0% identical and 99.5% identical, or at least 99.5% identical, or 100% identical to at least two sequences selected from the group consisting of SEQ ID NOs: 52, 53, 54, 55, 56, 57, 58, and 59. In some embodiments, the endophyte comprises at least three polynucleotide sequences that are at least 97% identical to at least three sequences selected from the group consisting of SEQ ID NOs: 52, 53, 54, 55, 56, 57, 58, and 59. In some embodiments, the endophyte comprises at least three polynucleotide sequences that are between 97% and 98% identical, at least 98% identical, between 98.0% identical and 99.5% identical, or at least 99.5% identical, or 100% identical to at least three sequences selected from the group consisting of SEQ ID NOs: 52, 53, 54, 55, 56, 57, 58, and 59. In some embodiments, the endophyte comprises at least four polynucleotide sequences that are at least 97% identical to at least four sequences selected from the group consisting of SEQ ID NOs: 52, 53, 54, 55, 56, 57, 58, and 59. In some embodiments, the endophyte comprises at least four polynucleotide sequences that are between 97% and 98% identical, at least 98% identical, between 98.0% identical and 99.5% identical, or at least 99.5% identical, or 100% identical to at least four sequences selected from the group consisting of SEQ ID NOs: 52, 53, 54, 55, 56, 57, 58, and 59. In some embodiments, the endophyte comprises at least five polynucleotide sequences that are at least 97% identical to at least five sequences selected from the group consisting of SEQ ID NOs: 52, 53, 54, 55, 56, 57, 58, and 59. In some embodiments, the endophyte comprises at least five polynucleotide sequences that are between 97% and 98% identical, at least 98% identical, between 98.0% identical and 99.5% identical, or at least 99.5% identical, or 100% identical to at least five sequences selected from the group consisting of SEQ ID NOs: 52, 53, 54, 55, 56, 57, 58, and 59. In some embodiments, the endophyte comprises at least six polynucleotide sequences that are at least 97% identical to at least six sequences selected from the group consisting of SEQ ID NOs: 52, 53, 54, 55, 56, 57, 58, and 59. In some embodiments, the endophyte comprises at least six polynucleotide sequences that are between 97% and 98% identical, at least 98% identical, between 98.0% identical and 99.5% identical, or at least 99.5% identical, or 100% identical to at least six sequences selected from the group consisting of SEQ ID NOs: 52, 53, 54, 55, 56, 57, 58, and 59. In some embodiments, the endophyte comprises at least seven polynucleotide sequences that are at least 97% identical to at least seven sequences selected from the group consisting of SEQ ID NOs: 52, 53, 54, 55, 56, 57, 58, and 59. In some embodiments, the endophyte comprises at least seven polynucleotide sequences that are between 97% and 98% identical, at least 98% identical, between 98.0% identical and 99.5% identical, or at least 99.5% identical, or 100% identical to at least seven sequences selected from the group consisting of SEQ ID NOs: 52, 53, 54, 55, 56, 57, 58, and 59.

In some embodiments, the endophyte is a *Exserohilum rostrata*. In some embodiments, the endophyte is a *Curvularia spicifera*. In some embodiments, the endophyte is a *Curvularia protuberata*. In some embodiments, the endophyte is an *Acremonium alternatum*. In some embodiments, the endophyte is a *Cladosporium oxysporum*. In some embodiments, the endophyte is a *Chaetomium globosum*. In some embodiments, the endophyte is a *Epicoccum nigrum*. In some embodiments, the endophyte is a *Paecilomyces inflatus*. In some embodiments, the endophyte is of the taxonomy *Coniochaeta prunicola*.

In some cases, the endophyte, or one or more components thereof, is of monoclonal origin, providing high genetic uniformity of the endophyte population in an agricultural formulation or within a plant element or synthetic combination with the endophyte.

In some embodiments, the endophyte can be cultured on a culture medium or can be adapted to culture on a culture medium.

The synthetic compositions provided herein are preferably stable. The endophyte may be shelf-stable, where at least 0.01%, of the CFUs are viable after storage in desiccated form (i.e., moisture content of 30% or less) for 1, 2, 3, 4, 5, 6, 7, 8, 9, 10 or greater than 10 weeks at 4° C. or at room temperature. Optionally, a shelf-stable formulation is in a dry formulation, a powder formulation, or a lyophilized formulation. In some embodiments, the formulation is formulated to provide stability for the population of endophytes. In an embodiment, the formulation is substantially stable at temperatures between about −20° C. and about 50° C. for at least about 1, 2, 3, 4, 5, or 6 days, or 1, 2, 3 or 4 weeks, or 1, 2, 3, 4, 5, 6, 7, 8, 9, 10, 11 or 12 months, or one or more years. In another embodiment, the formulation is substantially stable at temperatures between about 4° C. and about 37° C. for at least about 5, 10, 15, 20, 25, 30 or greater than 30 days.

Endophytes and Synthetic Compositions with Plants and Plant Elements

It is contemplated that the methods and synthetic compositions may be used to improve a characteristic of agronomic importance to a plant.

The methods described herein can also be used with transgenic plants comprising one or more exogenous transgenes, for example, to yield additional trait benefits conferred by the newly introduced endophytic microbes.

For example, the endophyte may provide an improved benefit or tolerance to a plant that is of at least 3%, between 3% and 5%, at least 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, when compared with uninoculated plants grown under the same conditions.

In one embodiment, it is contemplated that the plant of the present invention is rice (*Oryza* spp.), in particular *O. sativa* and *O. glaberrima*, and members of the major *O. sativa* subspecies *japonica, javanica*, and *indica*. In one embodiment, it is contemplated that the plant of the present invention is the rice variety Rex, and closely related varieties thereof. In some embodiments, the present invention contemplates the use of endophytes that can confer a beneficial agronomic trait upon a rice plant element or rice plant to which it is heterologously disposed.

In one embodiment, it is contemplated that the plant of the present invention is corn (*Zea* spp.), in particular *Zea mays* ssp. such as *Zea mays indenata, Zea mays indurata, Zea mays amylacea, Zea mays saccharata*, and *Zea mays everta*. In one embodiment, it is contemplated that the plant of the present invention is the corn variety Stine 9734, and closely related varieties thereof. In some embodiments, the present invention contemplates the use of endophytes that can confer a beneficial agronomic trait upon a corn plant element or corn plant to which it is heterologously disposed.

In one embodiment, it is contemplated that the plant of the present invention is wheat (*Triticum* spp.) including species *T. aestivum* and *T. durum*. In one embodiment, it is contemplated that the plant of the present invention is hard red winter (HRW), hard red spring (HRS), hard white (HW), durum, soft white (SW), or soft red winter (SRW). In one embodiment, it is contemplated that the plant of the present invention is the wheat variety SDSU Focus, SDSU Select, and closely related varieties thereof. In some embodiments, the present invention contemplates the use of endophytes that can confer a beneficial agronomic trait upon a wheat plant element or wheat plant to which it is heterologously disposed.

In one embodiment, it is contemplated that the plant of the present invention is soy (*Glycine max*). In one embodiment, it is contemplated that the plant of the present invention is the soy variety Dairyland DSR1808R2Y, Pfister 38R25, Stine 3920, Stine 33E22, or closely related varieties thereof.

In some embodiments, the present invention contemplates the use of endophytes that can confer a beneficial agronomic trait upon a soy plant element or soy plant to which it is heterologously disposed.

In one embodiment, it is contemplated that the plant of the present invention is peanut (*Arachis hypogaea*). In one embodiment, it is contemplated that the plant of the present invention is the peanut variety AT9899, FloRun 107, Georgia-06G, Tamnut OL06, or closely related varieties thereof. In some embodiments, the present invention contemplates the use of endophytes that can confer a beneficial agronomic trait upon a peanut plant element or peanut plant to which it is heterologously disposed.

In one embodiment, it is contemplated that the plant of the present invention is a member of the genus *Brassica*. In one embodiment, it is contemplated that the plant of the present invention is *Brassica napus*. In one embodiment, it is contemplated that the plant of the present invention is a low erucic acid and low glucosinolate cultivar of *Brassica napus*. In one embodiment, it is contemplated that the plant of the present invention is canola. In one embodiment, it is contemplated that the plant of the present invention is the canola variety Brett Young 5525, NCC1015, or closely related varieties thereof. In some embodiments, the present invention contemplates the use of endophytes that can confer a beneficial agronomic trait upon a canola plant element or canola plant to which it is heterologously disposed.

In some cases, the endophytes described herein are capable of moving from one tissue type to another. For example, the present invention's detection and isolation of endophytes within the mature tissues of plants after coating on the exterior of a plant element demonstrates their ability to move from the plant element into the vegetative tissues of a maturing plant. Therefore, in some embodiments, the population of endophytes is capable of moving from the plant element exterior into the vegetative tissues of a plant. In some embodiments, the endophyte that is coated onto the plant element of a plant is capable, upon germination of the plant element into a vegetative state, of localizing to a different tissue of the plant. For example, endophytes can be capable of localizing to any one of the tissues in the plant, including: the root, adventitious root, seminal root, root hair, shoot, leaf, flower, bud, tassel, meristem, pollen, pistil, ovaries, stamen, fruit, stolon, rhizome, nodule, tuber, trichome, guard cells, hydathode, petal, sepal, glume, rachis, vascular cambium, phloem, and xylem. In an embodiment, the endophyte is capable of localizing to the root and/or the root hair of the plant. In another embodiment, the endophyte is capable of localizing to the photosynthetic tissues, for example, leaves and shoots of the plant. In other cases, the endophyte is localized to the vascular tissues of the plant, for example, in the xylem and phloem. In still another embodiment, the endophyte is capable of localizing to the reproductive tissues (flower, pollen, pistil, ovaries, stamen, fruit) of the plant. In another embodiment, the endophyte is capable of localizing to the root, shoots, leaves and reproductive tissues of the plant. In still another embodiment, the endophyte colonizes a fruit or plant element tissue of the plant. In still another embodiment, the endophyte is able to colonize the plant such that it is present in the surface of the plant (i.e., its presence is detectably present on the plant exterior, or the episphere of the plant). In still other embodiments, the endophyte is capable of localizing to substantially all, or all, tissues of the plant. In certain embodiments, the endophyte is not localized to the root of a plant. In other cases, the endophyte is not localized to the photosynthetic tissues of the plant.

In some cases, endophytes are capable of replicating within the host plant and colonizing the plant.

The endophyte populations described herein are capable of colonizing a host plant. Successful colonization can be confirmed by detecting the presence of the endophyte population within the plant. For example, after applying the endophyte to the plant elements, high titers of the endophyte can be detected in the roots and shoots of the plants that germinate from the plant elements. Detecting the presence of the endophyte inside the plant can be accomplished by measuring the viability of the endophyte after surface sterilization of the plant element or the plant: endophyte colonization results in an internal localization of the endophyte, rendering it resistant to conditions of surface sterilization. The presence and quantity of endophyte can also be established using other means known in the art, for example, immunofluorescence microscopy using microbe-specific antibodies, or fluorescence in situ hybridization. Alternatively, specific nucleic acid probes recognizing conserved sequences from an endophyte can be employed to amplify a region, for example by quantitative PCR, and correlated to CFUs by means of a standard curve.

In another embodiment, the endophyte is heterologously disposed, for example, on the surface of a reproductive element of an agricultural plant, in an amount effective to be detectable in the mature agricultural plant. In some embodiments, the endophyte is heterologously disposed in an amount effective to be detectable in an amount of at least about 100 CFU between 100 and 200 CFU, at least about 200 CFU, between 200 and 300 CFU, at least about 300 CFU, between 300 and 400 CFU, at least about 500 CFU, between 500 and 1,000 CFU, at least about 1,000 CFU, between 1,000 and 3,000 CFU, at least about 3,000 CFU, between 3,000 and 10,000 CFU, at least about 10,000 CFU, between 10,000 and 30,000 CFU, at least about 30,000 CFU, between 30,000 and 100,000 CFU, at least about 100,000 CFU or more in the mature agricultural plant.

In some cases, the endophyte is capable of colonizing particular plant elements or tissue types of the plant. In an embodiment, the endophyte is heterologously disposed on the plant element or seedling in an amount effective to be detectable within a target tissue of the mature agricultural plant selected from a fruit, a seed, a leaf, or a root, or portion thereof. For example, the endophyte can be detected in an amount of at least about 100 CFU, at least about 200 CFU, at least about 300 CFU, at least about 500 CFU, at least about 1,000 CFU, at least about 3,000 CFU, at least about 10,000 CFU, at least about 30,000 CFU, at least about 100,000 CFU or more, in the target tissue of the mature agricultural plant.

Endophytes Compatible with Agrichemicals

In certain embodiments, the endophyte is selected on the basis of its compatibility with commonly used agrichemicals. As described herein, plants, particularly agricultural plants, can be treated with a vast array of agrichemicals, including fungicides, biocides (anticomplex agents), herbicides, insecticides, nematicides, rodenticides, bactericides, virucides, fertilizers, and other agents.

In some embodiments, the endophytes display tolerance to an agrichemical selected from the group consisting of: Aeris®, Avicta® DuoCot 202, Cruiser®, Syntenta CCB® (A), Clariva®, Albaugh, Dynasty®, Apron®, Maxim®, Gaucho®, Provoke® ST, Syngenta CCB®, Trilex®, WG Purple, WG Silver, Azoxystrobin, Carboxin, Difenoconazole, Fludioxonil, fluxapyroxad, Ipconazole, Mefenoxam, Metalaxyl, Myclobutanil, Penflufen, pyraclostrobin, Sedaxane, TCMTB, Tebuconazole, Thiram, Triadimenol (Baytan®), Trifloxystrobin, Triticonazole, Tolclofos-methyl, PCNB, Abamectin, Chlorpyrifos, Clothianidin, Imidacloprid, Thiamethoxam, Thiodicarb.

In some cases, it can be important for the endophyte to be compatible with agrichemicals, particularly those with anticomplex properties, in order to persist in the plant although, as described herein, there are many such anticomplex agents that do not penetrate the plant, at least at a concentration sufficient to interfere with the endophyte. Therefore, where a systemic anticomplex agent is used in the plant, compatibility of the endophyte to be inoculated with such agents will be an important criterion.

In an embodiment, natural isolates of endophytes that are compatible with agrichemicals can be used to inoculate the plants according to the methods described herein. For example, endophytes that are compatible with agriculturally employed anticomplex agents can be isolated by plating a culture of endophytes on a petri dish comprising an effective concentration of the anticomplex agent, and isolating colonies of endophytes that are compatible with the anticomplex agent. In another embodiment, an endophyte that is compatible with an anticomplex agent is used for the methods described herein.

Bactericide-compatible endophyte can also be isolated by selection on liquid medium. The culture of endophytes can be plated on petri dishes without any forms of mutagenesis; alternatively, endophytes can be mutagenized using any means known in the art. For example, endophyte cultures can be exposed to UV light, gamma-irradiation, or chemical mutagens such as ethylmethanesulfonate (EMS), ethidium bromide (EtBr) dichlovos (DDVP, methyl methane sulphonale (MMS), triethylphosphate (TEP), trimethylphosphate (TMP), nitrous acid, or DNA base analogs, prior to selection on fungicide comprising media. Finally, where the mechanism of action of a particular bactericide is known, the target gene can be specifically mutated (either by gene deletion, gene replacement, site-directed mutagenesis, etc.) to generate an endophyte that is resilient against that particular chemical. It is noted that the above-described methods can be used to isolate endophytes that are compatible with both bacteriostatic and bactericidal compounds.

It will also be appreciated by one skilled in the art that a plant may be exposed to multiple types of anticomplex compounds, either simultaneously or in succession, for example at different stages of plant growth. Where the target plant is likely to be exposed to multiple anticomplex agents, an endophyte that is compatible with many or all of these agrichemicals can be used to inoculate the plant. An endophyte that is compatible with several agents can be isolated, for example, by serial selection. An endophyte that is compatible with the first agent can be isolated as described above (with or without prior mutagenesis). A culture of the resulting endophyte can then be selected for the ability to grow on liquid or solid media comprising the second agent (again, with or without prior mutagenesis). Colonies isolated from the second selection are then tested to confirm its compatibility to both agents.

Likewise, endophytes that are compatible to biocides (including herbicides such as glyphosate or anticomplex compounds, whether bacteriostatic or bactericidal) that are agriculturally employed can be isolated using methods similar to those described for isolating compatible endophytes. In some embodiments, mutagenesis of the endophyte population can be performed prior to selection with an anticomplex agent. In another embodiment, selection is performed on the endophyte population without prior mutagenesis. In still another embodiment, serial selection is performed on an endophyte: the endophyte is first selected for compatibility to a first anticomplex agent. The isolated compatible endophyte is then cultured and selected for compatibility to the second anticomplex agent. Any colony thus isolated is tested for compatibility to each, or both anticomplex agents to confirm compatibility with these two agents.

Compatibility with an antimicrobial agent can be determined by a number of means known in the art, including the comparison of the minimal inhibitory concentration of the unmodified and modified endophytes. In some embodiments, the present invention discloses an isolated modified endophyte, wherein the endophyte is modified such that it exhibits at least 3 fold greater, for example, at least 5 fold greater, between 5 and 10 fold greater, at least 10 fold greater, between 10 and 20 fold greater, at least 20 fold greater, between 20 and 30 fold greater, at least 30 fold greater or more minimal inhibitory concentration to an antimicrobial agent when compared with the unmodified endophyte.

In a particular embodiment, disclosed herein are endophytes with enhanced compatibility to the herbicide glyphosate. In some embodiments, the endophyte has a doubling time in growth medium comprising at least 1 mM glyphosate, for example, between 1 mM and 2 mM glyphosate, at least 2 mM glyphosate, between 2 mM and 5 mM glyphosate, at least 5 mM glyphosate, between 5 mM and 10 mM glyphosate, at least 10 mM glyphosate, between 10 mM and 15 mM glyphosate, at least 15 mM glyphosate or more, that is no more than 250%, between 250% and 100%, for example, no more than 200%, between 200% and 175%, no more than 175%, between 175% and 150%, no more than 150%, between 150% and 125%, or no more than 125%, of the doubling time of the endophyte in the same growth medium comprising no glyphosate. In one particular embodiment, the endophyte has a doubling time in growth medium comprising 5 mM glyphosate that is no more than 150% the doubling time of the endophyte in the same growth medium comprising no glyphosate.

In another embodiment, the endophyte has a doubling time in a plant tissue comprising at least 10 ppm glyphosate, between 10 and 15 ppm, for example, at least 15 ppm glyphosate, between 15 and 10 ppm, at least 20 ppm glyphosate, between 20 and 30 ppm, at least 30 ppm glyphosate, between 30 and 40 ppm, at least 40 ppm glyphosate or more, that is no more than 250%, between 250% and 200%, for example, no more than 200%, between 200% and 175%, no more than 175%, between 175% and 150%, no more than 150%, between 150% and 125%, or no more than 125%, of the doubling time of the endophyte in a reference plant tissue comprising no glyphosate. In one particular embodiment, the endophyte has a doubling time in a plant tissue comprising 40 ppm glyphosate that is no more than 150% the doubling time of the endophyte in a reference plant tissue comprising no glyphosate.

The selection process described above can be repeated to identify isolates of endophytes that are compatible with a multitude of agents.

Candidate isolates can be tested to ensure that the selection for agrichemical compatibility did not result in loss of a desired bioactivity. Isolates of endophytes that are compatible with commonly employed agents can be selected as described above. The resulting compatible endophyte can be compared with the parental endophyte on plants in its ability to promote germination.

The agrichemical compatible endophytes generated as described above can be detected in samples. For example, where a transgene was introduced to render the endophyte compatible with the agrichemical(s), the transgene can be used as a target gene for amplification and detection by PCR. In addition, where point mutations or deletions to a portion of a specific gene or a number of genes results in compatibility with the agrichemical(s), the unique point mutations can likewise be detected by PCR or other means known in the art. Such methods allow the detection of the endophyte even if it is no longer viable. Thus, commodity plant products produced using the agrichemical compatible endophytes described herein can readily be identified by employing these and related methods of nucleic acid detection.

Beneficial Attributes of Synthetic Compositions of Plant Elements and Endophytes The present invention contemplates the establishment of a relationship between a symbiont and a plant element. In some embodiments, endophyte association results in a detectable change to the plant element, or the whole plant. The detectable change can be an improvement in a number of agronomic traits (e.g., improved general health, increased response to biotic or abiotic stresses, or enhanced properties of the plant or a plant element, including fruits and grains). Alternatively, the detectable change can be a physiological or biological change that can be measured by methods known in the art. The detectable changes are described in more detail in the sections below. As used herein, an endophyte is considered to have conferred an improved agricultural trait whether or not the improved trait arose from the plant, the endophyte, or the concerted action between the plant and endophyte. Therefore, for example, whether a beneficial hormone or chemical is produced by the plant or the endophyte, for purposes, the endophyte will be considered to have conferred an improved agronomic trait upon the host plant, as compared to an isoline plant that has not been heterologously disposed to said endophyte.

In some embodiments, provided herein, are methods for producing a plant element of a plant with a heritably altered trait. The trait of the plant can be altered without known genetic modification of the plant genome, and comprises the following steps. First, a preparation of an isolated endophyte that is heterologously disposed to the plant element of the plant is provided, and optionally processed to produce an endophyte formulation. The endophyte formulation is then contacted with the plant. The plants are then allowed to go to seed, and the seeds are collected.

Improved General Health

Also described herein are plants, and fields of plants, that are heterologously disposed to beneficial endophytes, such that the overall fitness, productivity or health of the plant or a portion thereof, is maintained, increased and/or improved over a period of time. Improvement in overall plant health can be assessed using numerous physiological parameters including, but not limited to, height, overall biomass, root and/or shoot biomass, emergence, seed germination, seedling survival, photosynthetic efficiency, transpiration rate, seed/fruit number or mass, plant grain yield, leaf chlorophyll content, photosynthetic rate, root length, or any combination thereof.

Drought Tolerance

In some cases, a plant resulting from seeds or other plant elements treated with an endophyte can exhibit a physiological change, such as a compensation of the stress-induced reduction in photosynthetic activity. Fv/Fm tests whether or not plant stress affects photosystem II in a dark adapted state. Fv/Fm is one of the most commonly used chlorophyll fluorescence measuring parameter. The Fv/Fm test is designed to allow the maximum amount of the light energy to take the fluorescence pathway. It compares the dark-adapted leaf pre-photosynthetic fluorescent state, called minimum fluorescence, or Fo, to maximum fluorescence called Fm. In maximum fluorescence, the maximum number of reaction centers have been reduced or closed by a saturating light source. In general, the greater the plant stress, the fewer open reaction centers available, and the Fv/Fm ratio is lowered. Fv/Fm is a measuring protocol that works for many types of plant stress. For example, there would be a difference in the Fv/Fm after exposure of an endophyte treated plant that had been subjected to heat shock or drought conditions, as compared to a corresponding control, a genetically identical plant that does not contain the endophytes grown in the same conditions. In some cases, the inoculated plant as disclosed herein can exhibit an increased change in photosynthetic activity ΔFv(ΔFv/Fm) after heat-shock or drought stress treatment, for example 1, 2, 3, 4, 5, 6, 7 days or more after the heat-shock or drought stress treatment, or until photosynthesis ceases, as compared with corresponding control plant of similar developmental stage but not comprising endophytes. For example, a plant having an endophyte able to confer heat and/or drought-tolerance can exhibit a ΔFv/Fm of from about 0.1 to about 0.8 after exposure to heat-shock or drought stress or a ΔFv/Fm range of from about 0.03 to about 0.8 under one day, or 1, 2, 3, 4, 5, 6, 7, or over 7 days post heat-shock or drought stress treatment, or until photosynthesis ceases. In some embodiments, stress-induced reductions in photosynthetic activity can be compensated by at least about 0.25% (for example, at least about 0.5%, between 0.5% and 1%, at least about 1%, between 1% and 2%, at least about 2%, between 2% and 3%, at least about 3%, between 3% and 5%, at least about 5%, between 5% and 10%, at least about 8%, at least about 10%, between 10% and 15%, at least about 15%, between 15% and 20%, at least about 20%, between 20$ and 25%, at least about 25%, between 25% and 30%, at least about 30%, between 30% and 40%, at least about 40%, between 40% and 50%, at least about 50%, between 50% and 60%, at least about 60%, between 60% and 75%, at least about 75%, between 75% and 80%, at least about 80%, between 80% and 85%, at least about 85%, between 85% and 90%, at least about 90%, between 90% and 95%, at least about 95%, between 95% and 99%, at least about 99% or at least 100%) as compared to the photosynthetic activity decrease in a corresponding reference agricultural plant following heat shock conditions. Significance of the difference between inoculated and reference agricultural plants can be established upon demonstrating statistical significance, for example at $p<0.05$ with an appropriate parametric or non-parametric statistic, e.g., Chi-square test, Student's t-test, Mann-Whitney test, or F-test based on the assumption or known facts that the inoculated plant and reference agricultural plant have identical or near identical genomes (isoline comparison).

In some embodiments, the plants comprise endophytes able to increase heat and/or drought-tolerance in sufficient quantity, such that increased growth or improved recovery from wilting under conditions of heat or drought stress is observed. For example, an endophyte population described herein can be present in sufficient quantity in a plant, resulting in increased growth as compared to a plant that does not contain endophytes, when grown under drought conditions or heat shock conditions, or following such conditions. Increased heat and/or drought tolerance can be assessed with physiological parameters including, but not limited to, increased height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, wilt recovery, turgor pressure, or any combination thereof, as compared to a reference agricultural plant grown under similar conditions. For example, the endophyte may provide an improved benefit or tolerance to a plant that is of at least 3%, between 3% and 5%, at least 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, when compared with uninoculated plants grown under the same conditions.

In various embodiments, endophytes heterologously disposed to the plant can confer various benefits to the plant, including but not limited to: thermal tolerance, herbicide tolerance, drought resistance, insect resistance, fungus resistance, virus resistance, bacteria resistance, male sterility, cold tolerance, salt tolerance, increased yield, enhanced nutrient use efficiency, increased nitrogen use efficiency, increased protein content, increased fermentable carbohydrate content, reduced lignin content, increased antioxidant content, enhanced water use efficiency, increased vigor, increased germination efficiency, earlier or increased flowering, increased biomass, altered root-to-shoot biomass ratio, enhanced soil water retention, or a combination thereof. A difference between the inoculated plant (e.g., a plant to which one or more endophytes have been heterologously disposed) and a reference agricultural plant can also be measured using other methods known in the art.

Formulations for Agricultural Use

The endophyte populations described herein are intended to be useful in the improvement of agricultural plants, and as such, may be formulated with other compositions as part of an agriculturally compatible carrier. It is contemplated that such carriers can include, but not be limited to: seed treatment, root wash, seedling soak, foliar application, soil inocula, in-furrow application, sidedress application, soil pre-treatment, wound inoculation, drip tape irrigation, vector-mediation via a pollinator, injection, osmopriming, hydroponics, aquaponics, aeroponics. The carrier composition with the endophyte populations, may be prepared for agricultural application as a liquid, a solid, or a gas formulation. Application to the plant may be achieved, for example, as a powder for surface deposition onto plant leaves, as a spray to the whole plant or selected plant element, as part of a drip to the soil or the roots, or as a coating onto the plant element prior to planting. Such examples are meant to be illustrative and not limiting to the scope of the invention.

The formulation useful for these embodiments generally and typically include at least one member selected from the group consisting of a buffer, a tackifier, a microbial stabilizer, a fungicide, an anticomplex agent, an herbicide, a nematicide, an insecticide, a bactericide, a virucide, a plant growth regulator, a rodenticide, a desiccant, and a nutrient.

The carrier can be a solid carrier or liquid carrier, and in various forms including microspheres, powders, emulsions and the like. The carrier may be any one or more of a number of carriers that confer a variety of properties, such as increased stability, wettability, or dispersability. Wetting agents such as natural or synthetic surfactants, which can be nonionic or ionic surfactants, or a combination thereof can be included in a composition of the invention. Water-in-oil emulsions can also be used to formulate a composition that includes the purified population (see, for example, U.S. Pat. No. 7,485,451). Suitable formulations that may be prepared include wettable powders, granules, gels, agar strips or pellets, thickeners, biopolymers, and the like, microencapsulated particles, and the like, liquids such as aqueous flowables, aqueous suspensions, water-in-oil emulsions, etc. The formulation may include grain or legume products, for example, ground grain or beans, broth or flour derived from grain or beans, starch, sugar, or oil.

In some embodiments, the agricultural carrier may be soil or a plant growth medium. Other agricultural carriers that may be used include water, fertilizers, plant-based oils, humectants, or combinations thereof. Alternatively, the agricultural carrier may be a solid, such as diatomaceous earth, loam, silica, alginate, clay, bentonite, vermiculite, seed cases, other plant and animal products, or combinations, including granules, pellets, or suspensions. Mixtures of any of the aforementioned ingredients are also contemplated as carriers, such as but not limited to, pesta (flour and kaolin clay), agar or flour-based pellets in loam, sand, or clay, etc. Formulations may include food sources for the cultured organisms, such as barley, rice, wheat or other biological materials such as seed, plant elements, sugar cane bagasse, hulls or stalks from grain processing, ground plant material or wood from building site refuse, sawdust or small fibers from recycling of paper, fabric, or wood. Other suitable formulations will be known to those skilled in the art.

In an embodiment, the formulation can include a tackifier or adherent. Such agents are useful for combining the complex population of the invention with carriers that can contain other compounds (e.g., control agents that are not biologic), to yield a coating composition. Such compositions help create coatings around the plant or plant element to maintain contact between the endophyte and other agents with the plant or plant element. In some embodiments, adherents are selected from the group consisting of: alginate, gums, starches, lecithins, formononetin, polyvinyl alcohol, alkali formononetinate, hesperetin, polyvinyl acetate, cephalins, Gum Arabic, Xanthan Gum, carragennan, PGA, other biopolymers, Mineral Oil, Polyethylene Glycol (PEG), Polyvinyl pyrrolidone (PVP), Arabino-galactan, Methyl Cellulose, PEG 400, Chitosan, Polyacrylamide, Polyacrylate, Polyacrylonitrile, Glycerol, Triethylene glycol, Vinyl Acetate, Gellan Gum, Polystyrene, Polyvinyl, Carboxymethyl cellulose, Gum Ghatti, and polyoxyethylene-polyoxybutylene block copolymers. Other examples of adherent compositions that can be used in the synthetic preparation include those described in EP 0818135, CA 1229497, WO 2013090628, EP 0192342, WO 2008103422 and CA 1041788.

It is also contemplated that the formulation may further comprise an anti-caking agent.

The formulation can also contain a surfactant, wetting agent, emulsifier, stabilizer, or anti-foaming agent. Non-limiting examples of surfactants include nitrogen-surfactant blends such as Prefer 28 (Cenex), Surf-N (US), Inhance (Brandt), P-28 (Wilfarm) and Patrol (Helena); esterified seed oils include Sun-It II (AmCy), MSO (UAP), Scoil (Agsco), Hasten (Wilfarm) and Mes-100 (Drexel); and organo-silicone surfactants include Silwet L77 (UAP), Silikin (Terra), Dyne-Amic (Helena), Kinetic (Helena), Sylgard 309 (Wilbur-Ellis) and Century (Precision), polysorbate 20, polysorbate 80, Tween 20, Tween 80, Scattics, Alktest TW20, Canarcel, Peogabsorb 80, Triton X-100, Conco NI, Dowfax 9N, Igebapl CO, Makon, Neutronyx 600, Nonipol NO, Plytergent B, Renex 600, Solar NO, Sterox, Serfonic N, T-DET-N, Tergitol NP, Triton N, IGEPAL CA-630, Nonident P-40, Pluronic. In some embodiments, the surfactant is present at a concentration of between 0.01% v/v to 10% v/v. In another embodiment, the surfactant is present at a concentration of between 0.1% v/v to 1% v/v. An example of an anti-foaming agent would be Antifoam-C.

In certain cases, the formulation includes a microbial stabilizer. Such an agent can include a desiccant. As used herein, a "desiccant" can include any compound or mixture of compounds that can be classified as a desiccant regardless of whether the compound or compounds are used in such concentrations that they in fact have a desiccating effect on the liquid inoculant. Such desiccants are ideally compatible with the population used, and should promote the ability of the endophyte population to survive application on the seeds and to survive desiccation. Examples of suitable desiccants include one or more of trehalose, sucrose, glycerol, and methylene glycol. Other suitable desiccants include, but are not limited to, non-reducing sugars and sugar alcohols (e.g., mannitol or sorbitol). The amount of desiccant introduced into the formulation can range from about 5% to about 50% by weight/volume, for example, between about 10% to about 40%, between about 15% and about 35%, or between about 20% and about 30%. In some embodiments, components of a sugar-based microbial stabilizer include, but are not limited to, glucose, sucrose, polyvinylpyrrolidone K 30 (PVP30K), mineral oil, soy lecithin, peptone, monopotassium phosphate (KH2PO4) and dipotassium phosphate (K2HPO4). In an alternate embodiment, components of a non-sugar based microbial stabilizer include, but are not limited to, polyvinylpyrrolidone K 30 (PVP30K), polyvinylpyrrolidone/vinyl acetate (PVP-VA), soy lecithin, peptone, mineral oil, hydroxypropyl-guar (HP-Guar), monopotassium phosphate (KH2PO4) and dipotassium phosphate (K2HPO4). Components of exemplary microbial stabilizers for use with the invention described herein are depicted in Table 1 and Table 2.

TABLE 1

Exemplary Sugar Based Microbial Stabilizer

| Component | Percentage (%), by weight |
|---|---|
| Glucose | 11.4 |
| Sucrose | 11.4 |
| PVP30K | 2.8 |
| Mineral oil | 5.7 |

TABLE 1-continued

| Exemplary Sugar Based Microbial Stabilizer | |
|---|---|
| Component | Percentage (%), by weight |
| Soy lecithin | 0.3 |
| Peptone | 11.4 |
| KH2PO4 | 0.78 |
| K2HPO4 | 0.99 |
| Non-chlorinated water | 55 |

TABLE 2

| Exemplary Non-sugar Based Microbial Stabilizer | |
|---|---|
| Component | Percentage (%), by weight |
| PVP30K | 3.8 |
| PVP-VA | 3.8 |
| Soy lecithin | 0.4 |
| Peptone | 15.4 |
| Mineral oil | 6.0 |
| HP-Guar | 0.2 |
| KH2PO4 | 0.96 |
| K2HPO4 | 1.23 |
| Non-chlorinated water | 68 |

In some cases, it is advantageous for the formulation to contain agents such as a fungicide, an anticomplex agent, an herbicide, a nematicide, an insecticide, a plant growth regulator, a rodenticide, a bactericide, a virucide, or a nutrient. Such agents are ideally compatible with the agricultural plant element or seedling onto which the formulation is applied (e.g., it should not be deleterious to the growth or health of the plant). Furthermore, the agent is ideally one which does not cause safety concerns for human, animal or industrial use (e.g., no safety issues, or the compound is sufficiently labile that the commodity plant product derived from the plant contains negligible amounts of the compound).

In the liquid form, for example, solutions or suspensions, endophyte populations can be mixed or suspended in water or in aqueous solutions. Suitable liquid diluents or carriers include water, aqueous solutions, petroleum distillates, or other liquid carriers.

Solid compositions can be prepared by dispersing the endophyte populations of the invention in and on an appropriately divided solid carrier, such as peat, wheat, bran, vermiculite, clay, talc, bentonite, diatomaceous earth, fuller's earth, pasteurized soil, and the like. When such formulations are used as wettable powders, biologically compatible dispersing agents such as non-ionic, anionic, amphoteric, or cationic dispersing and emulsifying agents can be used.

In some cases, a flowability polymer, also referred to as a plantability polymer such as Flo Rite® e.g., Flo-Rite® 1706 (BASF, Ludwigshafen, Germany). In some embodiments, a flowability or plantability polymer is DISCO™ AG (Incotec, Enkhuizen, the Netherlands). In some embodiments, a flowability or plantability polymer is Kannar® Universal Wonder (Kannar Earth Science, Ltd., Buford, Ga.).

The solid carriers used upon formulation include, for example, mineral carriers such as kaolin clay, pyrophyllite, bentonite, montmorillonite, diatomaceous earth, acid white soil, vermiculite, and pearlite, and inorganic salts such as ammonium sulfate, ammonium phosphate, ammonium nitrate, urea, ammonium chloride, and calcium carbonate. Also, organic fine powders such as wheat flour, wheat bran, and rice bran may be used. The liquid carriers include vegetable oils such as soybean oil, neem oil, cottonseed oil, and other compositions such as glycerol, ethylene glycol, polyethylene glycol, propylene glycol, polypropylene glycol, etc.

In an embodiment, the formulation is ideally suited for coating of a population of endophytes onto plant elements. The endophytes populations described in the present invention are capable of conferring many fitness benefits to the host plants. The ability to confer such benefits by coating the populations on the surface of plant elements has many potential advantages, particularly when used in a commercial (agricultural) scale.

The endophyte populations herein can be combined with one or more of the agents described above to yield a formulation suitable for combining with an agricultural plant element, seedling, or other plant element. Endophyte populations can be obtained from growth in culture, for example, using a synthetic growth medium. In addition, endophytes can be cultured on solid media, for example on petri dishes, scraped off and suspended into the preparation. Endophytes at different growth phases can be used. For example, endophytes at lag phase, early-log phase, mid-log phase, late-log phase, stationary phase, early death phase, or death phase can be used. Endophytic spores may be used for the present invention, for example but not limited to: arthospores, sporangispores, conidia, chlamadospores, pycnidiospores, endospores, zoospores.

The formulations comprising endophyte populations typically contains between about 0.1 to 95% by weight, for example, between about 1% and 90%, between about 3% and 75%, between about 5% and 60%, between about 10% and 50% in wet weight of the population. It is preferred that the formulation contains at least about 10^3 CFU per ml of formulation, for example, at least about 10^4, at least about 10^5, at least about 10^6, at least about 10^7 CFU, at least about 10^8 CFU per ml of formulation. It is preferred that the formulation be applied to the plant element at about 10^2 CFU/seed, between 10^2 and 10^3 CFU, at least about 10^3 CFU, between 10^3 and 10^4 CFU, at least about 10^4 CFU, between 10^4 and 10^5 CFU, at least about 10^5 CFU, between 10^5 and 10^6 CFU, at least about 10^6 CFU, between 10^6 and 10^7 CFU, at least about 10^7 CFU, between 10^7 and 10^8 CFU, or even greater than 10^8 CFU per seed.

Populations of Plant Elements

In another embodiment, the invention provides for a substantially uniform population of synthetic compositions comprising plant elements (PEs), comprising two or more PEs comprising the endophytic population, as described herein above. Substantial uniformity can be determined in many ways. In some cases, at least 10%, between 10% and 20%, for example, at least 20%, between 20% and 30%, at least 30%, between 30% and 40%, at least 40%, between 40% and 50%, at least 50%, between 50% and 60%, at least 60%, between 60% and 70%, at least 70%, between 70% and 75%, at least 75%, between 75% and 80%, at least 80%, between 80% and 90%, at least 90%, between 90% and 95%, at least 95% or more of the PEs in the population, comprises the endophytic population in an amount effective to colonize a plant, or plants, derived from said PEs when disposed on the surface of the PEs. In other cases, at least 10%, between 10% and 20%, for example, at least 20%, between 20% and 30%, at least 30%, between 30% and 40%, at least 40%, between 40% and 50%, at least 50%, between 50% and 60%, at least 60%, between 60% and 70%, at least 70%, between 70% and 75%, at least 75%, between 75% and 80%, at least 80%, between 80% and 90%, at least 90%, between 90% and 95%, at least 95% or more of the plant element s in the population, contains at least 1, between 10 and 10, 10, between 10 and 100, or 100 CFU on the plant element surface or per gram of plant element, for example, between 100 and 200 CFU, at least 200 CFU, between 200 and 300 CFU, at least 300 CFU, between 300 and 1,000 CFU, at least 1,000 CFU, between 1,000 and 3,000 CFU, at least 3,000 CFU, between 3,000 and 10,000 CFU, at least 10,000 CFU, between 10,000 and 30,000 CFU, at least 30,000 CFU, between 30,000 and 100,000 CFU, at least 100,000 CFU, between 100,000 and 300,000 CFU, at least 300,000 CFU, between 300,000 and 1,000,000 CFU, or at least 1,000,000 CFU per plant element or more.

In a particular embodiment, the population of plant elements is packaged in a bag or container suitable for commercial sale. Such a bag contains a unit weight or count of the plant elements comprising the endophytic population as described herein, and further comprises a label. In an embodiment, the bag or container contains at least 100 plant elements, between 100 and 1,000 plant elements, 1,000 plant elements, between 1,000 and 5,000 plant elements, for example, at least 5,000 plant elements, between 5,000 and 10,000 plant elements, at least 10,000 plant elements, between 10,000 and 20,000 plant elements, at least 20,000 plant elements, between 20,000 and 30,000 plant elements, at least 30,000 plant elements, between 30,000 and 50,000 plant elements, at least 50,000 plant elements, between 50,000 and 70,000 plant elements, at least 70,000 plant elements, between 70,000 and 80,000 plant elements, at least 80,000 plant elements, between 80,000 and 90,000, at least 90,000 plant elements or more. In another embodiment, the bag or container can comprise a discrete weight of plant elements, for example, at least 1 lb, between 1 and 2 lbs, at least 2 lbs, between 2 and 5 lbs, at least 5 lbs, between 5 and 10 lbs, at least 10 lbs, between 10 and 30 lbs, at least 30 lbs, between 30 and 50 lbs, at least 50 lbs, between 50 and 70 lmbs, at least 70 lbs or more. The bag or container comprises a label describing the plant elements and/or said endophytic population. The label can contain additional information, for example, the information selected from the group consisting of: net weight, lot number, geographic origin of the plant elements, test date, germination rate, inert matter content, and the amount of noxious weeds, if any. Suitable containers or packages include those traditionally used in plant seed commercialization. The invention also contemplates other containers with more sophisticated storage capabilities (e.g., with microbiologically tight wrappings or with gas- or water-proof containments).

In some cases, a sub-population of seeds comprising the endophytic population is further selected on the basis of increased uniformity, for example, on the basis of uniformity of microbial population. For example, individual plant elements of pools collected from individual cobs, individual plants, individual plots (representing plants inoculated on the same day) or individual fields can be tested for uniformity of microbial density, and only those pools meeting specifications (e.g., at least 80% of tested plant elements have minimum density, as determined by quantitative methods described elsewhere) are combined to provide the agricultural seed sub-population.

The methods described herein can also comprise a validating step. The validating step can entail, for example, growing some plant elements collected from the inoculated plants into mature agricultural plants, and testing those individual plants for uniformity. Such validating step can be performed on individual seeds collected from cobs, individual plants, individual plots (representing plants inoculated on the same day) or individual fields, and tested as described above to identify pools meeting the required specifications.

In some embodiments, methods described herein include planting a synthetic composition described herein. Suitable planters include an air seeder and/or fertilizer apparatus used in agricultural operations to apply particulate materials including one or more of the following, seed, fertilizer and/or inoculants, into soil during the planting operation. Seeder/fertilizer devices can include a tool bar having ground-engaging openers thereon, behind which is towed a wheeled cart that includes one or more containment tanks or bins and associated metering means to respectively contain and meter therefrom particulate materials.

In certain embodiments, a composition described herein may be in the form of a liquid, a slurry, a solid, or a powder (wettable powder or dry powder). In another embodiment, a composition may be in the form of a seed coating. Compositions in liquid, slurry, or powder (e.g., wettable powder) form may be suitable for coating plant elements. When used to coat plant elements, the composition may be applied to the plant elements and allowed to dry. In embodiments wherein the composition is a powder (e.g., a wettable powder), a liquid, such as water, may need to be added to the powder before application to a seed.

In still another embodiment, the methods can include introducing into the soil an inoculum of one or more of the endophyte populations described herein. Such methods can include introducing into the soil one or more of the compositions described herein. The inoculum(s) or compositions may be introduced into the soil according to methods known to those skilled in the art. Non-limiting examples include in-furrow introduction, spraying, coating seeds, foliar introduction, etc. In a particular embodiment, the introducing step comprises in-furrow introduction of the inoculum or compositions described herein.

In an embodiment, plant elements may be treated with composition(s) described herein in several ways but preferably via spraying or dripping. Spray and drip treatment may be conducted by formulating compositions described herein and spraying or dripping the composition(s) onto a seed(s) via a continuous treating system (which is calibrated to apply treatment at a predefined rate in proportion to the continuous flow of seed), such as a drum-type of treater. Batch systems, in which a predetermined batch size of seed and composition(s) as described herein are delivered into a mixer, may also be employed.

In another embodiment, the treatment entails coating plant elements. One such process involves coating the inside wall of a round container with the composition(s) described herein, adding plant elements, then rotating the container to cause the plant elements to contact the wall and the composition(s), a process known in the art as "container coating." Plant elements can be coated by combinations of coating methods. Soaking typically entails using liquid forms of the compositions described. For example, plant elements can be soaked for about 1 minute to about 24 hours (e.g., for at least 1 min, between 1 and 5 min, 5 min, between 5 and 10 min, 10 min, between 10 and 20 min, 20 min, between 20 and 40 min, 40 min, between 40 and 80 min, 80 min, between 80 min and 3 hrs, 3 hrs, between 3 hrs and 6 hrs, 6 hr, between 6 hrs and 12 hrs, 12 hr, between 12 hrs and 24 hrs, 24 hrs).

Population of Plants/Agricultural Fields

A major focus of crop improvement efforts has been to select varieties with traits that give, in addition to the highest return, the greatest homogeneity and uniformity. While inbreeding can yield plants with substantial genetic identity, heterogeneity with respect to plant height, flowering time, and time to seed, remain impediments to obtaining a homogeneous field of plants. The inevitable plant-to-plant variability is caused by a multitude of factors, including uneven environmental conditions and management practices. Another possible source of variability can, in some cases, be due to the heterogeneity of the endophyte population inhabiting the plants. By providing endophyte populations onto plant reproductive elements, the resulting plants generated by germinating the plant reproductive elements have a more consistent endophyte collection, and thus are expected to yield a more uniform population of plants.

Therefore, in another embodiment, the invention provides a substantially uniform population of plants. The population can include at least 5 plants, between 5 and 10 plants at least 10 plants, between 10 and 100 plants, for example, at least 100 plants, between 100 and 300 plants, at least 300 plants, between 300 and 1,000 plants, at least 1,000 plants, between 1,000 and 3,000 plants, at least 3,000 plants, between 3,000 and 10,000 plants, at least 10,000 plants, between 10,000 and 30,000 plants, at least 30,000 plants, between 30,000 and 100,000 plants, at least 100,000 plants or more. The plants may be derived from plant reproductive elements comprising endophyte populations as described herein. The plants are cultivated in substantially uniform groups, for example in rows, groves, blocks, circles, or other planting layout.

The uniformity of the plants can be measured in a number of different ways. In some embodiments, there is an increased uniformity with respect to endophytes within the plant population. For example, in some embodiments, a substantial portion of the population of plants, for example at least 10%, between 10% and 20%, at least 20%, between 20% and 30%, at least 30%, between 30% and 40%, at least 40%, between 40% and 50%, at least 50%, between 50% and 60%, at least 60%, between 60% and 70%, at least 70%, between 70% and 75%, at least 75%, between 75% and 80%, at least 80%, between 80% and 90%, at least 90%, between 90% and 95%, at least 95% or more of the plant elements or plants in a population, contains a threshold number of an endophyte population. The threshold number can be at least 10 CFU, between 10 and 100 CFU, at least 100 CFU, between 100 and 300 CFU, for example at least 300 CFU, between 300 and 1,000 CFU, at least 1,000 CFU, between 1,000 and 3,000 CFU, at least 3,000 CFU, between 3,000 and 10,000 CFU, at least 10,000 CFU, between 10,000 and 30,000 CFU, at least 30,000 CFU, between 30,000 and 100,000 CFU, at least 100,000 CFU or more, in the plant or a part of the plant. Alternatively, in a substantial portion of the population of plants, for example, in at least 1%, between 1% and 10%, at least 10%, between 10% and 20%, at least 20%, between 20% and 30%, at least 30%, between 30% and 40%, at least 40%, between 40% and 50%, at least 50%, between 50% and 60%, at least 60%, between 60% and 70%, at least 70%, between 70% and 75%, at least 75%, between 75% and 80%, at least 80%, between 80% and 90%, at least 90%, between 90% and 95%, at least 95% or more of the plants in the population, the endophyte population that is provided to the seed or seedling represents at least 0.1%, between 0.1% and 1% at least 1%, between 1% and 5%, at least 5%, between 5% and 10%, at least 10%, between 10% and 20%, at least 20%, between 20% and 30%, at least 30%, between 30% and 40%, at least 40%, between 40% and 50%, at least 50%, between 50% and 60%, at least 60%, between 60% and 70%, at least 70%, between 70% and 80%, at least 80%, between 80% and 90%, at least 90%, between 90% and 95%, at least 95%, between 95% and 99%, at least 99%, between 99% and 100%, or 100% of the total endophyte population in the plant/seed.

In an embodiment, there is increased genetic uniformity of a substantial proportion or all detectable endophytes within the taxa, genus, or species of a component relative to an uninoculated control. This increased uniformity can be a result of the endophyte being of monoclonal origin or otherwise deriving from a population comprising a more uniform genome sequence and plasmid repertoire than would be present in the endophyte population a plant that derives its endophyte community largely via assimilation of diverse soil symbionts.

In another embodiment, there is an increased uniformity with respect to a physiological parameter of the plants within the population. In some cases, there can be an increased uniformity in the height of the plants when compared with a population of reference agricultural plants grown under the same conditions. For example, there can be a reduction in the standard deviation in the height of the plants in the population of at least 5%, between 5% and 10%, for example, at least 10%, between 10% and 15%, at least 15%, between 15% and 20%, at least 20%, between 20% and 30%, at least 30%, between 30% and 40%, at least 40%, between 40% and 50%, at least 50%, between 50% and 60%, at least 60% or more, when compared with a population of reference agricultural plants grown under the same conditions. In other cases, there can be a reduction in the standard deviation in the flowering time of the plants in the population of at least 5%, between 5% and 10%, for example, at least 10%, between 10% and 15%, at least 15%, between 15% and 20%, at least 20%, between 20% and 30%, at least 30%, between 30% and 40%, at least 40%, between 40% and 50%, at least 50%, between 50% and 60%, at least 60% or more, when compared with a population of reference agricultural plants grown under the same conditions.

Commodity Plant Products

The present invention provides a commodity plant product, as well as methods for producing a commodity plant product, that is derived from a plant. As used herein, a "commodity plant product" refers to any composition or product that is comprised of material derived from a plant, seed, plant cell, or plant element of the present invention. Commodity plant products may be sold to consumers and can be viable or nonviable. Nonviable commodity products include but are not limited to nonviable plant elements and grains; processed seeds, seed parts, and plant elements; dehydrated plant tissue, frozen plant tissue, and processed plant tissue; seeds and plant elements processed for animal feed for terrestrial and/or aquatic animal consumption, oil, meal, flour, flakes, bran, fiber, paper, tea, coffee, silage, crushed of whole grain, and any other food for human or animal consumption such as the fruit or other edible portion of the plant; and biomasses and fuel products; and raw material in industry.

Industrial uses of oils derived from the agricultural plants described herein include ingredients for paints, plastics, fibers, detergents, cosmetics, lubricants, and biodiesel fuel. Plant oils may be split, inter-esterified, sulfurized, epoxidized, polymerized, ethoxylated, or cleaved. Designing and producing plant oil derivatives with improved functionality and improved oleochemistry is a rapidly growing field. For example, a mixture of triglycerides is usually split and separated into pure fatty acids, which are then combined with petroleum-derived alcohols or acids, nitrogen, sulfonates, chlorine, or with fatty alcohols derived from fats and oils to produce the desired type of oil or fat. Commodity plant products also include industrial compounds, such as a wide variety of resins used in the formulation of adhesives, films, plastics, paints, coatings and foams.

Methods of Using Endophytes and Synthetic Compositions Comprising Endophytes

As described herein, purified endophyte populations and synthetic compositions comprising the same (e.g., formulations) can be used to confer beneficial traits to the host plant.

The invention will be further described in the following examples, which do not limit the scope of the invention described in the claims. Each patent application, journal article, citation, and other references are herein incorporated by reference in their entirety, as if each has been incorporated by reference individually.

EXAMPLES

Example 1. Isolation and Identification of Endophytes

Isolation and cultivation of endophytic microbes from agricultural plants was performed using methods well known in the art. DNA was extracted from the ground tissues using the DNeasy DNA extraction kit (Qiagen, Hilden, Germany) according to the manufacturer's instructions. The endophytes were characterized by the sequences of genomic regions, these sequences are listed in Table 4. Primers that amplify genomic regions of the endophytes of the present invention are listed in Table 3.

TABLE 3

Primer sequences useful in identifying microbes of the present invention

| Primers | Genomic locus |
|---|---|
| 27f (5' - AGAGTTTGATYMTGGCTCAG- 3')(SEQ ID NO: 1)<br>1492r (5' - GGTTACCTTGTTACGACTT - 3')(SEQ ID NO: 2) | 16S |
| 515f (5' - GTGYCAGCMGCCGCGGTAA - 3')(SEQ ID NO: 3)<br>806r (5' - GGACTACNVGGGTWTCTAAT - 3')(SEQ ID NO: 4) | 16S |
| ITS_1 (5' - CTTGGTCATTTAGAGGAAGTAA - 3')(SEQ ID NO: 5)<br>LRS (5' - TCCTGAGGGAAACTTCG - 3')(SEQ ID NO: 8) | ITS |
| ITS_2 (5' -GCTGCGTTCTTCATCGATGC - 3')(SEQ ID NO: 6)<br>ITS_3 (5' - GCATCGATGAAGAACGCAGC - 3')(SEQ ID NO: 7) | ITS |
| MIC-19994, unique genomic region, primer - amplicon F (5' - TGCTGGTAGTGCGAATGAAA - 3')(SEQ ID NO: 9),<br>MIC-19994, unique genomic region, primer - amplicon R (5' - CTTTCGGGTTCCATCAGGT - 3')(SEQ ID NO: 10) | unique genomic region |
| MIC-31593, unique genomic region, primer - amplicon F (5' - CTACCGCAAGAGCAACTGTG - 3')(SEQ ID NO: 11)<br>MIC-31593, unique genomic region, primer - amplicon R (5' - ACTTCCTCCTCCTCCTCCTC - 3')(SEQ ID NO: 12) | unique genomic region |
| MIC-96038, unique genomic region, primer - amplicon F (5' - GTCCTCGCCTAATCAGGAGTC -3')(SEQ ID NO: 13)<br>MIC-96038, unique genomic region, primer - amplicon R (5' - TCCTATTCCCTGACGTGCTAC -3')(SEQ ID NO: 14) | unique genomic region |
| MIC-33414, unique genomic region, primer - amplicon F (5' - GAGGAGGAGGAGGAGAGGTT - 3')(SEQ ID NO: 15)<br>MIC-33414, unique genomic region, primer - amplicon R (5' - CGTCCGTCTCCCAGACTATT - 3')(SEQ ID NO: 16) | unique genomic region |
| MIC-68178, primer - amplicon F (5' - CTCCTCCTCCTCCTCCTGAT - 3') (SEQ ID NO: 36)<br>MIC-68178, primer - amplicon R (5' - TCACAGAGCTACGCGACTTG - 3')(SEQ ID NO: 37) | unique genomic region |
| MIC-68390 (5' - CTTCCAGGCATAGTAATGTGGA - 3')(SEQ ID NO: 34)<br>MIC-68390 (5' - ACTTCCACTACCATGAGCAATTC - 3')(SEQ ID NO: 35) | unique genomic region |
| PGK (5' - GTYGAYTTCAAYGTYCC - 3')(SEQ ID NO: 32)<br>PGK (5' - ACACCDGGDGGRCCGTTCCA - 3')(SEQ ID NO: 33) | Phosphoglycerate kinase |
| ACT512f, Actin, primer - amplicon F (5' - ATGTGCAAGGCCGGTTTCG - 3')(SEQ ID NO: 17)<br>ACT783r, Actin, primer - amplicon R (5' - TACGAGTCCTTCTGGCCCAT - 3')(SEQ ID NO: 18) | Actin |
| fusA-f2, elongation factor G, primer - amplicon F (5' - TCGCGTTCGTTAACAAAATGGACCGTAT -3')(SEQ ID NO: 19)<br>fusA-R2, elongation factor G, primer - amplicon R (5' - TCGCCAGACGGCCCAGAGCCAGACCCAT - 3')(SEQ ID NO: 20) | elongation factor G |

TABLE 3-continued

| Primer sequences useful in identifying microbes of the present invention | |
|---|---|
| **Primers** | **Genomic locus** |
| RPB1-Af, largest subunit of RNA polymerase II, primer - amplicon F (5' - GARTGYCCDGGDCAYTTYGG - 3')(SEQ ID NO: 21)<br>RPB1-Cr, largest subunit of RNA polymerase II, primer - amplicon R (5' - CCNGCDATNTCRTTRTCCATRTA - 3')(SEQ ID NO: 22) | largest subunit of RNA polymerase II |
| LR0R, long subunit rRNA gene, primer - amplicon F (5' - ACCCGCTGAACTTAAGC - 3')(SEQ ID NO: 23)<br>LR5, long subunit rRNA gene, primer - amplicon R (5' - TCCTGAGGGAAACTTCG - 3')(SEQ ID NO: 24) | long subunit rRNA gene |
| bRPB2-7.1R, second largest subunit of RNA polymerase II, primer - amplicon R (5' - CCCATRGCYTGYTTMCCCATDGC - 3')(SEQ ID NO: 25)<br>fRPB2-5F, second largest subunit of RNA polymerase II, primer - amplicon F (5' - GAYGAYMGWGATCAYTTYGG - 3')(SEQ ID NO: 26) | second largest subunit of RNA polymerase II |
| NS1 (5'- GTAGTCATATGCTTGTCTC -3')(SEQ ID NO: 27)<br>NS4 (5' - CTTCCGTCAATTCCTTTAAG -3')(SEQ ID NO: 28) | SSU, small subunit rRNA gene |
| SR1R (5' - TACCTGGTTGATQCTGCCAGT - 3')(SEQ ID NO: 29)<br>NS4 (5' - CTTCCGTCAATTCCTTTAAG -3')(SEQ ID NO: 28) | SSU, small subunit rRNA gene |
| Btub2Fd, beta-tubulin, primer - amplicon F (5' - GTBCACCTYCARACCGGYCARTG - 3')(SEQ ID NO: 30)<br>Btub4Rd, beta-tubulin, primer - amplicon R (5' - CCRGAYTGRCCRAARACRAAGTTGTC - 3')(SEQ ID NO: 31) | Beta-tubulin |

TABLE 4

Exemplary sequences of endophytes of the present invention

| SEQ ID | MIC ID | Gene/ Locus | Sequence |
|---|---|---|---|
| 38 | MIC-19994 | ITS | TCTTGGTCATTTAGAGGAAGTAAAAGTCGTAACAAGGTCTCCGTTGGTGAACCAGCGGAGGGATCATTACAAGAAG CCGAAAGGCTACTTCAAACCATCGTGAACTTATCCAAGTTGCTTCGGCGGCGCGGCTCCCCTCGCGGGGTGCCGCA GCCCCGCCCCCTCGGGGGTGGTGGGCGCCCGCCGGAGGTATTAAACTCTCCCGTATTATAGTGGTATTTCTGAGTA AAAACAAATAAGTTAAAACTTTCAACAACGGATCTCTTGGTTCTGGCATCGATGAAGAACGCAGCGAAATGCGATA AGTAATGTGAATTGCAGAATTCAGTGAATCATCGAATCTTTGAACGCACATTGCGCCCGCTAGTATTCTAGCGGGC ATGCCTGTTCGAGCGTCATTTCAACCCTCAAGCCCTGCTTGGTGTTGGGGCCCTACGGCTGCCGTAGGCCCTGAAA AGAAGTGGCGGGCTCGCTGCAACTCCGAGCGTAGTAATTCATTATCTCGCTAGGGAGGCGCGGCGGTGCTCCTGCC GTTAAAGACCATCTTTAACCAAAGGTTGACCTCGGATCAGGTAGGAATACCCGCTGAACTTAAGCATATCAATAAG CGGAGGAAAAGAAACCAACAGGGATTGCCCTAGTAACGGCGAGTGAAGCGGCAACAGCTCAAATTTGAAATCTGGC TTCGGCCCGAGTTGTAATTTGTAGAGGATGCTTTTGGTGAGGTGCCTTCTGAGTTCCCTGGAACGGGACGCCAGAG AGGGTGAGAGCCCCGTATAGTCGGCCACCGATCCTCTGTAAAGCTCCTTCGACGAGTCGAGTAGTTTGGGAATGCT GCTCAAAATGGGAGGTATATCTCTTCTAAAGCTAAATATAGGCCAGAGACCGATAGCGCACAAGTAGAGTGATCGA AAGATGAAAAGCACTTTGAAAAGAGGGTTAAATAGCACGTGAAATTGTTGAAAGGGAAGCGCTTGTGACCAGACTT GCGCCGGGCTGATCATCCAGTGTTCTCACTGGTGCACTCGACCCGGCTCAGGCCAGCGTCGGTTCTCGCAGGGGGA TAAAAGCTTCGGGAACGTGGCACCTTCGGGTGTGTTATAGCCCGCTGCTTAATACCCCGGTGGGGACCGAGGTTCG CGCTCTGCAAGGACGCTGGCATAATGGTCATCAGCGACCCGTCTTGAAACACGGACCAAGGAGTCGAGGTTTTGCG CGAGTGTTTGGGTGTAAAACCCGCACGCGTAATGAAAGTGAACGTAGGTGAGAGCTTCGGCGCATCATCGACCGAT CCTGATGTATTCGGATGGATTTGAGTAAGAGCGTATAGCCTCGGACCCGAAAGATGGTGAACTATGCCTGAATAGG GGGAAGCCAGAGGAAACTCTGGTGGAGGCTCGCAGCGGTTCTGACGTGCAAATCGATCGTCAAATTTGGGCA |
| 39 | MIC-19994 | LSU | TCCTGAGGGAAACTTCGGCGGTAACCAGCTACTAGATGGTTCGATTAGTCTTTCGCCCCCATGCCCAAATTTGACG ATCGATTTGCACGTCAGAACCGCTGCGAGCCTCCACCAGAGTTTCCTCTGGCTTCACCCTATTCAGGCATAGTTCA CCATCTTTCGGGTCCGAGGCTATACGCTCTTACTCAAATCCATCCGAATACATCAGGATCGGTCGATGATGCGCCG AAGCTCTCACCTACGTTCACTTTCATTACGCGTGCGGGTTTTACACCCAAACACTCGCGCAAAACCTCGACTCCTT GGTCCGTGTTTCAAGACGGGTCGCTGATGACCATTATGCCAGCGTCCTTGCAGAGCGCGAACCTCGGTCCCCACAG GGGTATTAAGCAGCGGGCTATAACACACCCGAAGGTGCCACGTTCCCGAAGCTTTTATCCCCCTGCGAGAACCGAC GCTGGCCTGAGCCGGGTCGAGTGCACCAGTGAGAACACTGGATGATCAGCCCGGCGCAAGTCTGGTCACAAGCGCT TCCCTTTCAACAATTTCACGTGCTATTTAACCCTCTTTTCAAAGTGCTTTTCATCTTTCGATCACTCTACTTGTGC GCTATCGGTCTCTGGCCTATATTTAGCTTTAGAAGAGATATACCTCCCATTTTGAGCAGCATTCCCAAACTACTCG ACTCGTCGAAGGAGCTTTACAGAGGATCGGTGGCCGACTATACGGGGCTCTCACCCTCTCTGGCGTCCCGTTCCAG GGAACTCAGAAGGCACCTCACCAAAAGCATCCTCTACAAATTACAACTCGGGCCGAAGCCAGATTTCAAATTTGAG CTGTTGCCGCTTCACTCGCCGTTACTAGGGCAATCCCTGTTGGTTTCTTTTCCTCCGCTTATTGATATGCTTAAGT TCAGCGGGTA |
| 40 | MIC-19994 | SSU | CTTCCGTCAATTTCTTTAAGTTTCAGCCTTGCGACCATACTCCCCCCAGAACCCAGAAACTTTACTTTCGTGTAAG GTGCCGAACGAGTCAAAATATAACATCGTCCGATCCCTAGTCGGCATAGTTTATGGTTAAGACTACGACGGTATCT GATCGTCTTCGATCCCCTAACTTTCGTTCCTGATTAATGAAAACATCCTTGGCAAATGCTTTCGCAGTAGTTAGTC |

TABLE 4-continued

Exemplary sequences of endophytes of the present invention

| SEQ ID | MIC ID | Gene/ Locus | Sequence |
|---|---|---|---|
| | | | TTCAATAAATCCAAGAATTTCACCTCTGACAATTGAATACTGATGCCCCCGACTGTCCCTATTAATCATTACGGCGGTCCTAGAAACCAACAAAATAGAACCACACGTCCTATTCTATTATTCCATGCTAATGTATTCGAGCATAGGCCTTCTTTAAGCGATCTAATTTGTTCAAAGTAAAAGTCCTGGTTCCCCGACACACCCAGTGAAGGGCATGCGGTTCCCCAGAGGGAAAGGCCCGGCCGGACCAGTGCACGCGGTGAGGCGGACCGGCCAGCCAGGCCCAAGGTTCAACTACGAGCTTTTTAACTGCAACAACTTTAATATACGCTATTGGAGCTGGAATTACCGCGGCTGCTGGCACCAGACTTGCCCTCCAATTGTTCCTCGTTAAGGGATTTAAATTGTACTCATTCCAATTACAAGACCCAAAAGAGCCCTGTATCAGTATTTATTGTCACTACCTCCCCGAATCGGGATTGGGTAATTTGCGCGCCTGCTGCCTTCCTTGGATGTAGTAGCCGTTTCTCAGGCTCCTTCTCCGGGGTCGAGCCCTAACCCTCCGTTACCCGTTGTCACCATGGCTGGCCAAGACCCAGCCGTCGAAAGTTGATAGGGCAGAAATTTGAATGAACCATCGCCGGCGCAAGGCCGTGCGATTCGAGAAGTTATTATGAATCACCAGAGAGCCCCGAAGGGCATTGGTTTTTAATCTAATAAATACATCCCTTCCGAAGTCGGGATTTTTAGCATGTATTAGCTCTAGAATTACCACGGTTATCCAAGTAGTAAGGTACTATCAAATAAACGATAACTGATTTAATGAGCCATTCGCAGTTTCGCGGTATAATTGCTTATACTTAGACATGCATGGCTTAATCTTTGAGACAAGCATATGACTACTGGCAGAATCAACCAGGTAA |
| 41 | MIC-19994 | Unique genomic region | TGCTGGTAGTGCGAATGAAAATGGCTGGTTCCAGGATATAACGGGTAATCGACTGCACTTTAACAAGGCTATGCGAGTACTTTGCGACCATGGTCTTGCAGAAGCAGATCCGCCGACGAAAGAGCACGGTTCGGAGTCTGGAGGGTACAGTGTGCACGGATGTGTGCACTCCTGGATGGTAAACGTCCTCAACCAGACAGGAGATGCGGAGATGGCACGTCTGGCTTTGAGGTGTGTGGCTAGCCATGTGCCAAGCACGGAGGAGGGTGAGTATTGGCGGGTACAGCGGCGCCTCCTTCTGCACGCAGACCAATGCTTGAAATTGATGGAAGAGGGTCAGGAGGAGGAAGGCAATGGATGGGTATTCCATAATCTAGGAGATCTCTACAAAGCCCAAGGGCGGTTCAAGGAAGCAGAAGCCATGTACGAGCGGGCGCTTCGAGGCAAGGAGAAGGCATGGGGACCAGACCACACGTCGACACTCGACACAGTCAACAATCTGGGTCTCGTCGCCGACAACAAAGCCAGCCACACCAAACATCAAGTTCCATTCTCGTTCCCCGTCTTTGTCGTGTGGCAGACAAAACCTGATGGAACCCGAAAG |
| 42 | MIC-31593 | ITS | AGGTGAACCTGCGGAGGGATCATTACACAATAAAATACGAAGGCCGTTCGCGGCTGGACTATTTATTACCCTTGTCTTTTGCGCACTTGTTGTTTCCTGGGCGGGTTCGCTCGCCACCAGGACCACAATATAAACCTTTTTTATGCAGTTGCAATCAGCGTCAGTATAACAAATGTAAATCATTTACAACTTTCAACAACGGATCTCTTGGTTCTGGCATCGATGAAGAACGCAGCGAAATGCGATACGTAGTGTGAATTGCAGAATTCAGTGAATCATCGAATCTTTGAACGCACATTGCGCCCTTTGGTATTCCAAAGGGCATGCCTGTTCGAGCGTCATTTGTACCCTCAAGCTTTGCTTGGTGTTGGGCGTTTTTGTCTTTGGCCCGCCAAAGACTCGCCTTAAAATGATTGGCAGCCGGCCTACTGGTTTCGCAGCGCAGCACATTTTTGCGCTTGCAATCAGCAAAAGAGGACGGCAATCCATCAAGACTCCTTCTCACGTTTGACCTCGGATCAGGTAGGGATACCCGCTGAACTTAAGCATATCAATAAGCGGAGGAAAAGAAACCAACAGGGATTGCCCTAGTAACGGCGAGTGAAGCGGCAACAGCTCAAATTTGAAATCTGGCTCTTTCAGAGTCCGAGTTGTAATTTGCAGAGGGCGCTTTGGCTTTGGCAGCGGTCCAAGTTCCTTGGAACAGGACGTCACAGAGGGTGAGAATCCCGTACGTGGTCGCTAGCTATTGCCGTGTAAAGCCCCTTCGACGAGTCGAGTTGTTTGGGAATGCAGCTCTAAATGGGAGGTAAATTTCTTCTAAAGCTAAATATTGGCCAGAGACCGATAGCGCACAAGTAGAGTGATCGAAAGATGAAAAGCACTTTGGAAAGAGAGTCAAACAGCACGTGAAATTGTTGAAAGGGAAGCGCTTGCAGCCAGACTTGCTTGCAGTTGCTCATCCGGGCTTTTGCCCGGTGCACTCTTCTGCAGGCAGGCCAGCATCAGTTTGGGCGGTGGGATAAAGGTCTCTGTCACGTACCTTCCTTCGGGTTGGCCTTATAGGGGAGACGCCATACCACCAGCCTGGACTGAGGTCCGCGCATCTGCTAGGATGCTGGCGTAATGGCTGTAAGCGGCCCGTCTTGAAACACGGACCAAGGAGTCTAACATCTATGCGAGTGTTTGGGTGTCAAGCCCGAGCGCGTAATGAAAGTGAACGGAGGTGGGAACCCGCAAGGGTGCACCATCGACCGATCCTGAAGTTTACGGAAGGATTTGAGTAAGAGCATGGCTGTTGGGACCCGAAAGATGGTGAACTATGCTTGAATAGGGTGAAGCCAGAGGAAACTCTGGTGGAGGCTCGCAGCGGTTCTGACGTGCAAATCGATCGTCAAATTTGGGCATAGGGGCGAAAGACTAATCGAA |
| 43 | MIC-31593 | RPB2 | CCCATAGCTTGCTTACCCATAGCAGATTGGTATGTGTTACGGGGCGACTGGTTGTGATCTGGGAAGGGAATGATACTGGCGCAAATACCCAAGATCATAGCTGGGTGAATCTCACAATGGGTGTAGGCGTGGATGCGAGGATCCGGTAGTGGCTTGAGACGGCGGAGTCGATCCTTGCCTTCAGTAGATCGCTCAGCTGCAGGCAAGCCCATCTTCATTTCTCGCCATTCTTCCAAGTCCTCGGGAGAGAATGTTATCATTGCAGTTTCTTCTTCCTCGGCATCGAGGTATTCAACGACACCGTCTTGAATGAGACCTCTCCAGCCGTATGTAGCCTGCTCGACTTCCTCTTGACTCCAGCCTTGTCTTGTACTGGTCTCTTGCTGTTCAGCCTTGAGCTTGTTGCTGATTTCCTTGGTAAAGATGAGGTGGTTCCGGTTTGGCTTTCGAATATCGTTTTCTACAACGAACAAAGGCCTCATGACACGACCCGCATCTGTGAATATCTTGAACTCTCTGTCGCGAATATCACGAATCAAACTCATCTCGTAAGACAGAGTACCATTGCGGCGAAGCTCCTGCACGACTGTGACAAGCTGCTGAGCATTTGAATGAACACCAACCCAGACACCGTTAACGAAGACCTTGGTCGCATCCGGGTTCTGGTTCTGGTCGTACTCCTCGAGAAGTTGCATGTTACGTTGTGTCATGAAGTCGATAATGGGCGATGCATCGCTACCAACACTGACATAACACATAAGAGACAAGTTCTTGACCAGACCGCAAGCCTGTCCTTCGGGCGTCTCAGCAGGGCAGACAAGACCCCAATGAGAGTTGTGAAGCTGTCGCGGCTTTGCCAACTTACCATCACGTCCAACGGGGGTGTTCGTTCGACGCAGATGGGATAGTGTGGAGGCATAGGTGTATCGGTTCAACACCTGCGAAACACCAGCCTTGGCAGATGCAGCCTTCTTCTGATCACCCCAATTGCCTGTAGCCAGAGAGTACTTCAGGCCGTTTGTGATGATGCTGGCTTTCACAGCCATTTGAACATTGAAGTCTTGGTTGTTTTCCACGCACCGCTGGAGGTACTTGTAGACATCCTTGGTGAGCTTCAGGAACAAGATTCGGAACAAGTTGGCAATCAGAGGTCCAGCCAGATCTAGTCGCTTCTTTCCAAAGTGATCACGATCGTCC |
| 44 | MIC-31593 | Beta-tubulin | GTTCACCTCCAGACCGGTCAATGCGTAAGTCTCGCGCCGCCTGAAAACACCACGGGAACGACTGCTAACAGCCGCTACAGGGTAACCAAATTGGTGCCGCCTTCTGGCAGACCATTTCCGGCGAGCATGGCCTCGACGGCTCTGGTGTCTACAACGGCACCTCTGACCTTCAGCTCGAGCGCATGAACGTCTACTTCAACGAAGTACGTCCCTCGGTGAAGCTCCAACAGACAAAAGACCAATACTGATGTGCAGCAGGCTTCCAACAACAAGTTCGTGCCCCGTGCCGTCCTCGTCGATCTCGAGCCTGGTACTATGGACGCTGTCCGCGCTGGTCCCTTTGGTCAGCTCTTCCGCCCCGACAACTTCGTCTTCGGCCAGTCGGGT |
| 45 | MIC-31593 | Unique genomic region | CTACCGCAAGAGCAACTGTGCAAGTCCAGCTTCAGTCCCTTTCGATCCCCCTCGCCCAGGAAGAGATTCACCCACGAGCGCAACCAGTCCGAGGCGGTCCAGCGTCCACGTCCTATGAGCGTTTGCAGCAACTCGCCAGCAGTTCAGCACACCAAAAGAGCCTCCATCTACGTCTCCGACGCTTCCATCATCCTAGCGCAACGCTCACCCATGGCTTCTCCGGTTTCCCCACCAGACTCCATGTCCTCCCCCATCCATGAATCGTCTGATGCCGTCGACCACTATGCTATCCTGGAGATCACCCCTAGAGCAACTACCGATGAGGTCAAGGCTGCCTACCGCCGACTACGGGTCGTCTACTTCTCAAGTGACGCGAAGAAGTACCGAGCACTGCAGGCGGCCTTCGACGTCTTGATGGACCCGCAATCCCGCGAAGCTTACGACGCAACCTATCAACCAACTGCCGCAGCACCAGTATCGCTCGCTAGCATTGGTGAGATCCTGGACTCGGGGAAGCTATGGCGACAGGACAGCGCCCACGGAGACGACCCAGTAATCCCAGAAGAGGAAGAGGAGGAGGAGGAGGAAGT |

TABLE 4-continued

Exemplary sequences of endophytes of the present invention

| SEQ ID | MIC ID | Gene/ Locus | Sequence |
|---|---|---|---|
| 46 | MIC-96038 | ITS | TCTTGGTCATTTAGAGGAAGTAAAAGTCGTAACAAGGTCTCCGTTGGTGAACCAGCGGAGGGATCATTACCGAGTG<br>TAAAAACTCCCAAACCATTGTGAACTTACCACTGTTGCTTCGGCGGCCTCGCCCCGGGCGCGTTCGCGCGGCCCGG<br>ACCCAGGCGTCCGCCGGAGGCTCCAAACTCTTGTCTTTTAGTGTATTTCTGAGTGGCATAAGCAAATAAATCAAAA<br>CTTTCAGCAACGGATCTCTTGGTTCTGGCATCGATGAAGAACGCAGCAAAATGCGATAAGTAATGTGAATTGCAGA<br>ATTCAGTGAATCATCGAATCTTTGAACGCACATTGCGCCCGCCAGTATTCTGGCGGGCATGCCTGTCTGAGCGTCA<br>TTTCAACCCTCAGGACCCGTTCGCGGGACCTGGCGTTGGGGATCAGCCTGCCCCTGGCGGCGGCTGGCCCTGAAAT<br>CCAGTGGCGGTTCCCTCGCGAACTCCTCCGTGCAGTAATTAAACCTCTCGCGGCAGGATAGCGGTTGAACCACGCC<br>GTTAAACCCCCCACTTCTCAAGGTTGACCTCAGATCAGGTAGGAATACCCGCTGAACTTAAGCATATCAATAAGCG<br>GAGGAAAAGAAACCAACAGGGATTGCCCTAGTAACGGCGAGTGAAGCGGCAACAGCTCAAATTTGAAATCTGGCCT<br>CACGGTCCGAATTGTAATTTGTAGAGGATGTTTCTGGCGACGTGTCTTCCGAGTTCCCTGGAACGGGACGCCATAG<br>AGGGTGAGAGCCCCGTCCGGTCGTACACCTAGCCTCTGTGAAACTCCTTCGACGAGTCGAGTAGTTTGGGAATGCT<br>GCTCTAAATGGGAGGTATACGTCTTCTAAAGCTAAATACCGGCCAGAGACCGATAGCGCACAAGTAGAGTGATCGA<br>AAGATGAAAAGCACTTTGAAAAGAGGGTTAAATAGTACGTGAAATTGCTGAAAGGGAAGCGCTTATGACCAGACTT<br>GGGCTCGGTGAATCATCCGGCGTTCTCGCCGGTGCACTTTGCCGTCCCAGGCCAGCATCAGTTCGCGCCGGGGGAT<br>AAAGGTTTCGGGAATGTAGCTCCTTCGGGAGTGTTATAGCCCGTTGCGTAATACCCTGGCGTGGACTGAGGTCCGC<br>GCTCTGCAAGGATGCTGGCGTAATGGTCATCAGTGACCCGTCTTGAAACACGGACCAAGGAGTCGTCTTCGTATGC<br>GAGTGTTCGGGTGTCAAACCCCTACGCGTAATGAAAGTGAACGTAGGAGAGAGCTTCGGCGCATCTCCGACCGATC<br>CTGATGTTCTCGGATGGATTTGAGTAAGAGCATACGGGGCCGGACCCGAAAGAAGGTGAACTATGCCTGTATAGGG<br>TGAAGCCAGAGGAAACTCTGGTGGAGGCTCGCAGCGGTTCTGACGTGCAAATCGATCGTCAAATATGGGCATGGGG<br>GCGAAAGACTAATC |
| 47 | MIC-96038 | Actin | ATGTGCAAGGCCGGTTTCGCCGGTGACGATGCTCCCCGAGCTGTTTTCCGTAAGTCAACCCCACTTTCGCTTCCCA<br>AGCTCCTAATCGCCCACACCTGGCGATATGGGCTTTGGGGGCCTGTAAGCAGCCGACACAAGACTAACGCGATGCG<br>CCAGCTTCCATTGTCGGTCGCCCCCGTCACCATGGGTAAGTACGCGCGCAAATGACACCTGTCAGCCCCCTCGACG<br>AGCGGCACAGGCTCTGACCATTCGATAGTATCATGATTGGTATGGGACAGAAGGACTCGTAC |
| 48 | MIC-96038 | Beta-tubulin | CCGGACTGGCCGAAGACGAAGTTGTCGGGACGGAAGAGCTGACCGAAAGGACCGGCGCGGACGGCATCCATGGTAC<br>CGGGCTCGAGATCGACGAGGACAGCGCGAGGAACGTACTTGTTGCCAGAGGCCTACAGAGGGTCAGCTTGGCCACA<br>GACTGCGGGATACTCCAAATTGCTCACCTCGTTGAAGTAGACGCTCATGCGCTCGAGCTGGAGCTCAGAGGTGCCG<br>TTGTAGACACCGTTGCTGTCGAGGCCATGCTCGCCAGAGATGGTCTGCCAGAAGGCAGCACCAATCTGGTTACCCT<br>GCTCGGAGGTTAGACATGGTAGGCGATATCACATATGGCGGAAGTACTTACGCACTGACCGGTCTGGAGGTGAACC |
| 49 | MIC-96038 | RPB2 | GATGATCGTGATCACTTCGGGAAAAAGCGCCTTGACCTGGCTGGGCCCCTCTTAGCTAAATTGTTCCGCAACATTA<br>TTCGCAGGATCAACAACGAGCTGTCGACCTACCTCAGGCGATGTGTCGAGGGCGGCAGGAACTTCAACCTCGCTGT<br>CGGCATCAAGCCTGGCACACTGTCGAACGGGTTGAAGTACTCTTTGGCAACAGGCAACTGGGGAGACCAAAAGAAG<br>GCAATGAGCTCGGTTGCTGGAGTGTCCCAGGTTCTCAACCGCTACACATTTGCGTCAACCTTGTCTCATTTGAGGC<br>GCACCAACACCCCCATTGGCCGTGATGGAAAGCTGGCGAAGCCTCGGCAGCTACACAACACGCATTGGGGTCTTGT<br>GTGTCCCGCCGAGACCCCCGAGGGTCAGGCTTGTGGTTTGGTGAAGAACCTGTCACTGATGTGTCACGTTTCCGTT<br>GGCACACCTAGCGAACCTCTCTACGGATACTTCATCAACCGTGGCATGGAAGTGCTCGAAGAGTACGAGCCCCAGC<br>GGTTCCCCAACGCCACCAAGGTGTTCATCAACGGTGCCTGGGTCGGTGTGCACACAAGCCCGAAAGATCTCGTGGA<br>TAGCATCATGCATCTGCGGCGCTATGGTGACCTGAACCATGAAGCTTCCGTCATCCGCGACATTCGGGATCGAGAG<br>TTCAGGGTCGTCACGGATGCTGGTCGTGTTATGCGCCCAGTATTCACCGTGCAGCAAGAAGACAAGCTAGACGGGC<br>CCGAGAAGGGCTCGTTGTGCATGACCAAGGAGCATCTTGCCGGTTTGGATGACTGGCATCTGGTCAACGAGGAGAG<br>GGAAGAGATGGCCACGGGCTGGGAGTACCTCGTGAAGAGTGGGTGTATTGAGTACTTGGACGCCGAAGAAGAAGAG<br>ACGGCAATGATTTGCATGACACCAGAAGACTTGGAGTCTTACCGCAAGGAGAAGTACCTCGATCAGAAACCCCAGG<br>AGCACAACGTGGAAGCCGAGCCCAACAAGCGACTCAAGACGAAGACCAACCCGACGACACACATGTACACCCACTG<br>CGAGATTCATCCCAGTATGATCCTCGGTATCTGCGCCAGCATCATCCCCTTCCCGGATCATAACCAGGCATGTCTC<br>TACGCCACCAGACCTCGAGATTACTTACTAATATTGCATCTAGTCGCCCCGTAATACTTACCAATCTGCCATGGGC<br>AAGCAGGCCATGGGC |
| 50 | MIC-96038 | RPB1 | GAATGCCCCGGTCATTTTGGTCACATCGAGCTGGCAAAGCCCGTTTACCACCCCGGCTTCATCAAGAAAGTCAAGA<br>AGATTTTGGAGATTGTCTGCCACAACTGCAGCAAGGTCTTGGCCGATGAAGTTGGTCTCACCTGATCCATGTCTTG<br>TTCCTTAGATGCTAACATGGACCTCTCAGAGCGACCCCGAGTTTGTCACTGCGATCCGTACGCGCGACCCGAAAGT<br>CCGCTTCCAGCGAGTCTGGGCTGTGTGCAAGAAGAAGCGGAAGTGTGAGAACGAGGATCGCCAAGACAAGAAGGAA<br>GAGGAGTTCGCGCCCGGCATGAAGCCGCAGACGCACAACCACGGCGGCTGTGGAAACGAGATGCCCGCGGTTCGTC<br>AAGCTGGTTTGCGTCTCAACGCGCAGTTCGAGATCAAGGAAGAGGGCGGAGCTAAGCGCAAGGATACTCAAGTTAT<br>CCTGCCCGACCAAGCTCACACAATCCTGCGGCGGATATCGGAACAGGACCTCCGACACATGGGCCTCAACTCAGAG<br>TATGCCCGCCCAGAGTGGATGGTTCTTACCGTCCTTCCGGTCCCCCCGCCTCCCGTTCGTCCAAGTATTTCCATGG<br>ACGGCACTGGCACGGGAATGCGGAACGAGGATGATTTGACTTACAAGCTTGGTGATATCATCCGAGCCAACGGAAA<br>CGTCAAGCAGGCTATCCGCGAAGGCTCGCCGGCCCACATTGCTCGCGATTTCGAAGAGCTGCTCCAGTACCATGTA<br>GCCACCTACATGGATAATGATATTGCTGGA |
| 51 | MIC-96038 | Unique genomic region | GTCCTCGCCTAATCAGGAGTCACTAGACGACATACCCGAGGACGACATGATGGGCGACCTTGCGCTTGGCCTTTCG<br>AGCAGCTTCAAGCAACACGCCCTCCGGAACTCAAAGGGCAAGACCTTCTGGGATACCTTCTCCGAGACGAGCAGTG<br>TCGCAGGACCGAGAACCACGCCACCTCCGCCGGGAGTGATGGCTCGACGTCCATCGTCCGGCAGGAGTGAGGATGT<br>GACCATGGATTCGCCGCTCCAGCAAAGCAGCATGCCTTGGCTACAAACACGGCACCTTTCCGACTCCCAGCGCTCG<br>GACTCGGCACCTGCGGCCAAGGAGAAGGACTCCCCGGCCCAGCCACCCACCGCTGCAGAGATAACGCGCCGAATCA<br>ACAACAAACGCCGCCGTGACGATGACTTCGACCCGGTGAGCTTCAAACGCCGCGCAGTGAGTCCCGGGCTCAGCGT<br>CCACAACTCGCCGCTCCCGCAGAGCCCAATGCAGCAGAGCGGTGCGCCATGGGGTTCCAGGCCGGGAAGCAATGGG<br>GGCGACAAGGCGGGAAGCAGTGCACCTAGCGAATCTGGTGGTAGCACGTCAGGGAATAGGA |
| 52 | MIC-33414 | ITS | TCTTGGTCATTTAGAGGAAGTAAAAGTCGTAACAAGGTCTCCGTTGGTGAACCAGCGGAGGGATCATTACAGAGTT<br>GCAAAACTCCCTAAACCATTGTGAACGTTACCTATACCGTTGCTTCGGCGGGCGGCCCCGGGGTTTACCCCCCGGG<br>CGCCCCTGGGCCCCACCGCGGGCGCCCGCCGGAGGTCACCAAACTCTTGATAATTTATGGCCTCTCTGAGTCTTCT<br>GTACTGAATAAGTCAAAACTTTCAACAACGGATCTCTTGGTTCTGGCATCGATGAAGAACGCAGCGAAATGCGATA<br>AGTAATGTGAATTGCAGAATTCAGTGAATCATCGAATCTTTGAACGCACATTGCGCCCGCCAGCATTCTGGCGGGC |

TABLE 4-continued

Exemplary sequences of endophytes of the present invention

| SEQ ID | MIC ID | Gene/ Locus | Sequence |
|---|---|---|---|
| | | | ATGCCTGTTCGAGCGTCATTTCAACCATCAAGCCCCCGGGCTTGTGTTGGGGACCTGCGGCTGCCGCAGGCCCTGAAAAGCAGTGGCGGGCTCGCTGTCGCACCGAGCGTAGTAGCATACATCTCGCTCTGGTCGCGCCGCGGGTTCCGGCCGTTAAACCACCTTTTAACCCAAGGTTGACCTCGGATCAGGTAGGAAGACCCGCTGAACTTAAGCATATCAATAAGCGGAGGAAAAGAAACCAACAGGGATTGCCCTAGTAACGGCGAGTGAAGCGGCAACAGCTCAAATTTGAAATCTGGCTTCGGCCCGAGTTGTAATTTGCAGAGGAAGCTTTAGGCGCGGCACCTTCTGAGTCCCCTGGAACGGGGCGCCATAGAGGGTGAGAGCCCCGTATAGTTGGATGCCTAGCCTGTGTAAAGCTCCTTCGACGAGTCGAGTAGTTTGGGAATGCTGCTCAAAATGGGAGGTAAATTTCTTCTAAAGCTAAATACCGGCCAGAGACCGATAGCGCACAAGTAGAGTGATCGAAAGATGAAAAGCACTTTGAAAAGAGGGTTAAATAGCACGTGAAATTGTTGAAAGGGAAGCGCTTGTGACCAGACTTGCGCCGGGCGGATCATCCGGTGTTCTCACCGGTGCACTCCGCCCGGCTCAGGCCAGCATCGGTTCTCGCGGGGGGATAAAGGTCCTGGGAACGTAGCTCCTCCGGGAGTGTTATAGCCCGGGGCGTAATGCCCTCGCGGGGACCGAGGTTCGCGCATCTGCAAGGATGCTGGCGTAATGGTCATCAGCGACCCGTCTTGAAACACGGACCAAGGAGTCAAGGTTTTGCGCGAGTGTTTGGGTGTAAAACCCGCACGCGTAATGAAAGTGAACGTAGGTGAGAGCTTCGGCGCATCATCGACCGATCCTGATGTTTTCGGATGGATTTGAGTAGGAGCGTTAAGCCTTGGACCCGAAAGATGGTGAACTATGCTTGGATAGGGTGAAGCCAGAGGAAACTCTGGTGGAGGCTCGCAGCGGTTCTGACGTGCAAATCGATCGTCAAATCTGAGCATGGGGGCGAAAGA |
| 53 | MIC-33414 | Actin | ATGTGCAAGGCCGGTTTCGCCGGTGATGATGCACCCCGCGCTGTTTTCCGTAAGTCTCCCAGCCCCGGCCCCGGCCCGGTCGGCGATAAGCCGAGCTCCGGACGCTCGTTGGCACAAACAGACAAGCTAACAGCGCCGTTTAGCGTCGATTGTCGGTCGTCCCCGTCACCATGGGTAGGCTTTCAGTTCCGGTATCTCTGCGATATGGGGTCGCTGGCTAACGCGCCGCTAGTATTATGATCGGTATGGGGCAGAAGGACTCGTAC |
| 54 | MIC-33414 | LSU | TCCTGAGGGAAACTTCGGCGGTAACCAGCTACTAGATGGTTCGATTAGTCTTTCGCCCCCATGCTCAGATTTGACGATCGATTTGCACGTCAGAACCGCTGCGAGCCTCCACCAGAGTTTCCTCTGGCTTCACCCTATCCAAGCATAGTTCACCATCTTTCGGGTCCAAGGCTTAACGCTCCTACTCAAATCCATCCGAAAACATCAGGATCGGTCGATGATGCGCCGAAGCTCTCACCTACGTTCACTTTCATTACGCGTGCGGGTTTTACACCCAAACACTCGCGCAAAACCTTGACTCCTTGGTCCGTGTTTCAAGACGGGTCGCTGATGACCATTACGCCAGCATCCTTGCAGATGCGCGAACCTCGGTCCCCGCGAGGGCATTACGCCCCGGGCTATAACACTCCCGGAGGAGCTACGTTCCCAGGACCTTTATCCCCCCGCGAGAACCGATGCTGGCCTGAGCCGGGCGGAGTGCACCGGTGAGAACACCGGATGATCCGCCCGGCGCAAGTCTGGTCACAAGCGCTTCCCTTTCAACAATTTCACGTGCTATTTAACCCTCTTTTCAAAGTGCTTTTCATCTTTCGATCACTCTACTTGTGCGCTATCGGTCTCTGGCCGGTATTTAGCTTTAGAAGAAATTTACCTCCCATTTTGAGCAGCATTCCCAAACTACTCGACTCGTCGAAGGAGCTTTACACAGGCTAGGCATCCAACTATACGGGGCTCTCACCCTCTATGGCGCCCCGTTCCAGGGGACTCAGAAGGTGCCGCGCCTAAAGCTTCCTCTGCAAATTACAACTCGGGCCGAAGCCAGATTTCAAATTTGAGCTGTTGCCGCTTCACTCGCCGTTACTAGGGCAATCCCTGTTGGTTTCTTTTCCTCCGCTTATTGATATGCTTAAGTTCAGCGGGTC |
| 55 | MIC-33414 | RPB1 | GAGTGTCCAGGTCACTTTGGCCACATTGAGCTATCCAGACCCGTTTTCCACCCCGGGTTCATCAGGCGTGTCAAAAAGTTGCTCGAGATGGTCTGCCACAACTGCAGCAAGGTGTTGGCTGATCGTGTTAGTGCACCTTGCCTGACCGAGTGATGATTTGTTTTGGCATGCTAACTCTTCACCAGGAGGACGAGCAATATGCTGCTGCCATGCGGATTCGGGACCCCAAAGTACGCTTCAAGCGAGTTTGGGATATTTGCAAGAGTAAGAAGCGCTGCGAAAACGAAGTGCGCAAGGGGAAAGATGGCGAGTTCAAACCCGACAGCGAAAACCAAGCCGCAGAGGGTGGCCATGGAGGATGTGGCAACACGCAGCCAGTCATTCGCCAGCAGGCTCTCACCCTGTGGGGCAGCGTCGAGACCAAGGACGAGGATGGTGTGAAGACCAAGGAGAAGAAGGTCATCACCCCAGAAATGGCCCTGAACATCTTCCGTCGCATGTCGGACGACGAGATGATTGACATTGGCCTCAATATTTCCCAAGCTCGTCCGGAATGGATGATCATCACGGTTCTTCCTGTCCCGCCTCCTCCGGTGCGCCCCAGTATTTCCATGGACGGAACTGGAACAGGCTTGCGGAATGAGGACGATCTGACGTATAAACTCGGCGATATCATCCGCGCCAATGGCAACGTCCGCCAGGCTATTGCCGAGGGCTCTCCTCAGCATATCATCACCGACTTTGAGAACCTACTCCAGTACCACGTCGCTACGTACATGGATAATGACATCGCCGGT |
| 56 | MIC-33414 | SSU | CTTCCGTCAATTTCTTTAAGTTTCAGCCTTGCGACCATACTCCCCCAGGAGCCCAAACATTTTGATTTATCGTAAGGTGCCGAACGGGTCAAAAAATAACGCCGTCCGATCCCTAATCGGCATAGTTTAGGTTAAGACTACGACGGTATCTGATCGTATTCGATCCCCTAACTTTCGTTCCTGATTAATGAAAACATCCTTGGCAAATGCTTTCGCAGTAGTTAGTCTTCAATAAATCCAAGAATTTCACCTCTGACAATTGAATACTGATGCCCCCGACTGTCCCTATTAATCATTACGGCGGTCCTAGAAACCAACAAAATAGAACCACACGTCCTATTCTATTATTCCATGCTAATGTATTCGAGCATAGGCCTTCTTTAAGCGATCTAATTTGTTCAGAGTAAAAGTCCTGGTTCCCCGGCACACCCAGTGAAGGGCATGCGGTTCTCCAGAAGGAAAGACCCAGCCGAGCCAGTGCACGCGGTGAGGCGGACCGGCCGGCTAGGCCCAAGGTTCAACTACGAGCTTTTTAACCTCAACAACTTTAATATACGCTATTGGAGCTGGAATTACCGCGGCTGCTGGCACCAGACTTGCCCTCCAATTGTTCCTCGTTAAGGGATTTAAATTGTACTCATTCCAATTACAAGACCCGAAAGAGCCCTGTATCAGTATTTATTGTCACTACCTCCCCGTGTCGGGATTGGGTAATTTGCGCGCCTGCTGCCTTCCTTTGGATGTAGTAGCCGTTTCTCAGGCTCCTTCTCCGGGGTCGAGCCCTAACCCTCCGTTACCCGTTGTCACCACGGCTGGCCAAGACCCAGCCGTCGAAAGTTGATAGGGCAGAAATTTGAATGAACCATCGCCGGCGCAAGGCCGTGCGATTCGAGAAGTTATTATGAATCACCAGAGAGCCCCGAAGGGCATTGGTTTTTAATCTAATAAATACATCCCTTCCGAAGTCGGGATTTTTAGCATGTATTAGCTCTAGAATTACCACGGTTATCCATGTAGTAAGGTACTATCAAATAAACGATAACTGATTTAATGAGCCATTCGCAGTTTCGCGGTATAATTGCTTATACTTAGACATGCATGGCTTAATCTTTGAGACAAGCATATGACTACT |
| 57 | MIC-33414 | SSU | CTTCCGTCAATTTCTTTAAGTTTCAGCCTTGCGACCATACTCCCCCAGGAGCCCAAACATTTTGATTTATCGTAAGGTGCCGAACGGGTCAAAAAATAACGCCGTCCGATCCCTAATCGGCATAGTTTAGGTTAAGACTACGACGGTATCTGATCGTATTCGATCCCCTAACTTTCGTTCCTGATTAATGAAAACATCCTTGGCAAATGCTTTCGCAGTAGTTAGTCTTCAATAAATCCAAGAATTTCACCTCTGACAATTGAATACTGATGCCCCCGACTGTCCCTATTAATCATTACGGCGGTCCTAGAAACCAACAAAATAGAACCACACGTCCTATTCTATTATTCCATGCTAATGTATTCGAGCATAGGCCTTCTTTAAGCGATCTAATTTGTTCAGAGTAAAAGTCCTGGTTCCCCGGCACACCCAGTGAAGGGCATGCGGTTCTCCAGAAGGAAAGACCCAGCCGAGCCAGTGCACGCGGTGAGGCGGACCGGCCGGCTAGGCCCAAGGTTCAACTACGAGCTTTTTAACCTCAACAACTTTAATATACGCTATTGGAGCTGGAATTACCGCGGCTGCTGGCACCAGACTTGCCCTCCAATTGTTCCTCGTTAAGGGATTTAAATTGTACTCATTCCAATTACAAGACCCGAAAGAGCCCTGTATCAGTATTTATTGTCACTACCTCCCCGTGTCGGGATTGGGTAATTTGCGCGCCTGCTGCCTTCCTTTGGATGTAGTAGCCGTTTCTCAGGCTCCTTCTCCGGGGTCGAGCCCTAACCCTCCGTTACCCGTTGTCACCACGGCTGGCCAAGACCCAGCCGTCGAAAGTTGATAGGGCAGAAATTTGAATGAACCATCGCCGGCGCAAGGCCGTGCGATTCGAGAAGTTATTATGAATCACCAGAGAGCCCCGAAG |

TABLE 4-continued

Exemplary sequences of endophytes of the present invention

| SEQ ID | MIC ID | Gene/ Locus | Sequence |
|---|---|---|---|
| 58 | MIC-33414 | Beta-tubulin | GTTCACCTCCAGACCGGCCAGTGCGTAAGTTGGACCGAATCGAACATTACGACCGACCGGCCGCGCAGGATAACTG<br>ACATGGAGCTCTCTAGGGTAACCAAATCGGTGCCGCTTTCTGGTACGTCCAAGCAAAGCAAACACTCTTGGCTGAT<br>GACAATCGAGACTGACTTCTTTTCAGGCAGACCATCTCTGGCGAGCACGGCCTCGACAGCAATGGCGTGTATGTGG<br>GCATGACAGTTCCCAACCGATAAATCCCCGCTCACCGCTTCGATAGGTACAACGGCACCTCCGAGCTCCAGCTCGA<br>GCGTATGAACGTGTACTTCAACGAGGTCAGTCGGGTCAAATAATTTTACACGACCGAGTGATGGCGTGCTCATAGT<br>ATTATACAGGCTTCCGGCAACAAGTATGTTCCTCGCGCTGTCCTCGTCGACTTGGAGCCCGGCACCATGGATGCCG<br>TCCGTGCCGGCCCCTTCGGCCAGCTCTTCCGCCCGGACAACTTCGTCTTCGGCCAGTCGGGT |
| 59 | MIC-33414 | Unique genomic region | GAGGAGGAGGAGGAGAGGTTGGAGAGGGAGGCGTTGCGTGCCGAGGCGCTTTGTGAGGTCAGGCGGGTTATGGCGC<br>TGCTGGAGGATACGCTGCTTGCGGACGGGCGGGAGTGGGTTTTGGGCGGTGGTGGTGGCGGTGATGGTGGTGGCAG<br>TGAGGGTGCGAGAAAAGGGCCGACGTTGGCGGATATCGAGGCCGTGTGGGTGCTTCACTGGATGATTGGCATTCCT<br>GGTGCGCTGTTCAACGCCGGGTATGTGAGCGCCGAGCGGTTTCCGCGGGTGTATGCGTGGGTGGCGCGGTTTCAGG<br>CGGCGGTTGGGGCGGCGAAGGCCGGGGTGGTGGTGAAGGGCATGAGCGGGGAGGAGGCGGCGGTAGTGTTGAAGGG<br>GCAGAGAGAAGGGGTAGGATATTTTGAGAAGGAGGGGGAGGTGGACGCCGCGGACCCGATCGTCAAGGTGTACGGA<br>TTGGAGAAAGGGAGCAGGGTCGAGGTGTGGCCGACGGACTCCGGGGCTGGGCATCGGGATCAGGGCTGCCTGGTGA<br>GCCTCGACGCCGAGGAAATAGTCTGGGAGACGGACG |
| 60 | MIC-68390 | ITS | TCTTGGTCATTTAGAGGAAGTAAAAGTCGTAACAAGGTCTCCGTAGGTGAACCTGCGGAGGGATCATTACACAACA<br>AAAATATGAGGGTGTGGTTTGCTGGCAACAGCGTCCGCCCCAAGTATTTTTCACCCATGTCTTTTGCGCACTTTTT<br>GTTTCCTGGGCGAGTTCGCTCGCCACCAGGACCCAACCATAAACCTTTTTTTATGCAGTTGCAATCAGCGTCAGTA<br>TAATAATTCAATTTATTAAAACTTTCAACAACGGATCTCTTGGTTCTGGCATCGATGAAGAACGCAGCGAAATGCG<br>ATACGTAGTGTGAATTGCAGAATTCAGTGAATCATCGAATCTTTGAACGCACATTGCGCCCTTTGGTATTCCAAAG<br>GGCATGCCTGTTCGAGCGTCATTTGTACCCTCAAGCTTTGCTTGGTGTTGGGCGTCTTTTTGTCTCTCCCCTTGTT<br>GGGGGAGACTCGCCTTAAAACGATTGGCAGCCGACCTACTGGTTTTCGGAGCGCAGCACAAATTTGCGCCTTCCAA<br>TCCACGGGGCGGCATCCAGCAAGCCTTTGTTTTCTATAACAAATCCACATTTTGACCTCGGATCAGGTAGGGATAC<br>CCGCTGAACTTAAGCATATCAATAAGCGGAGGAAAAGAAACCAACAGGGATTGCCCTAGTAACGGCGAGTGAAGCG<br>GCAACAGCTCAAATTTGAAATCTGGCTCTTTCAGAGTCCGAGTTGTAATTTGCAGAGGGCGCTTTGGCTTTGGCAG<br>CGGTCCAAGTTCCTTGGAACAGGACGTCACAGAGGGTGAGAATCCCGTACGTGGTCGCTAGCTATTGCCGTGTAAA<br>GCCCCTTCGACGAGTCGAGTTGTTTGGGAATGCAGCTCTAAATGGGAGGTAAATTTCTTCTAAAGCTAAATATTGG<br>CCAGAGACCGATAGCGCACAAGTAGAGTGATCGAAAGATGAAAAGCACTTTGGAAAGAGAGTCAAACAGCACGTGA<br>AATTGTTGAAAGGGAAGCGCTTGCAGCCAGACTTGCTTGCAGTTGCTCATCCGGGCTTTTGCCCGGTGCACTCTTC<br>TGCAGGCAGGCCAGCATCAGTTTGGGCGGTGGGATAAAGGTCTCTGTCATGTACCTCTCTTCGGGGAGGCCTTATA<br>GGGGAGGCGACATACCACCAGCCTAGACTGAGGTCCGCGCATCTGCTAGGATGCTGGCGTAATGGCTGTAAGCGGC<br>CCGTCTTGAAACACGGACCAAGGAGTCTAACATCTATGCGAGTGTTTGGGTGTCAAGCCCGAGCGCGTAATGAAAG<br>TGAACGGAGGTGGGAACCCGCAAGGGTGCACCATCGACCGATCCTGAAGTTTACGGAAGGATTTGAGTAAGAGCAT<br>GGCTGTTGGGACCCGAAAGATGGTGAACTATGCTTGAATAGGGTGAAGCCAGAGGAAACTCTGGTGGAGGCTCGCA<br>GCGGTTCTGACGTGCAAATCGATCGTCAAATTTGGGCATAGGGGCGAAAGACTAATCGA |
| 61 | MIC-68390 | second largest subunit of RNA poly-merase II | CCCATGGCTTGCTTGCCCATAGCAGATTGGTAGGTGTTACGAGGCGACTGGTTGTGATCTGGGAAAGGAATGATAC<br>TGGCGCAAATACCCAGAATCATGGCCGGATGGATTTCACAGTGAGTGTAGGCATGGATACGAGGATCTGGTAGGGG<br>CTTGAGACGGCGAAGACGGTCCTTACCCTCTGTGGAGCGCTCCGCTGCAGGTAGGCCCATCTTCATCTCTCGCCAT<br>TCTTCTAAGTCCTCGGGAGAGAATGTAATCATGGCAGTCTCTTCCTCCTCAGCATCGAGGTATTCGACAACACCAT<br>CTTGGATAAGACCTCTCCAGCCATAAGTAGCCTGCTCAACCTCCTCCTGACTCCATCCTTGCCTTGTGCTAGTCTC<br>TTGTTGTTCAGCCTTGAGCTTGTTACTAATCTCCTTGGTGAAGATGAGGTGGTTTCGGTTTGGCTTTCGAATATCG<br>TTCTCTACAACAAATAGAGGTCTCATGACACGACCAGCATCTGTGAAGATCTTGAACTCTCGGTCACGAATGTCAC<br>GAATCAAACTCATCTCGTAAGATAGAGTTCCGTTTCGTCGAAGCTCCTGCACGACCGTAACAAGTTGTTGAGCATT<br>GGAATGAACCCCAACCCAAACACCATTAACGAAAACCTTGGTCGCATCGGGGTTTTGGTTCTGGTCGTATTCCTCG<br>AGCAGCTGCATGTTACGTTGCGTCATGAAGTCGATAATGGGCGACGCATCGCTACCGACACTGACGTAACACATGA<br>GAGACAAGTTCTTGACCAGACCGCAAGCCTGTCCTTCAGGCGTCTCAGCAGGGCAGACAAGACCCCAGTGGGAGTT<br>GTGCAGTTGACGGGGCTTGGCCAATTTACCATCACGTCCAACAGGAGTATTTGTTCGACGAAGATGGGACAATGTG<br>GAGGCGTAAGTGTATCGGTTCAACACCTGCGAGACACCAGCCTTGGCAGATGCTGCCTTCTTCTGGTCACCCCAGT<br>TGCCTGTAGCCAGAGAGTACTTCAATCCGTTCGTGATGATGCTGGCTTTTACAGCCATCTGAACGTTAAAGTCCTG<br>GTTGTTCTCAACGCACCGCTGGAGGTACTTGTAGACGTCCTTGGTAAGCTTCAAGAAGAGGATACGGAACAAGTTG<br>GCGATTAAAGGTCCAGCAAGATCCAGGCGCTTCTTTCCGAAATGATCACGGTCATCC |
| 62 | MIC-68390 | unique genomic region | CTTCCAGGCATAGTAATGTGGATATTAGGTGAGAGCGAAATATAAGTGTCCCTAGAAGTGATAGTGAGAAGGCTAT<br>GGTGAGGTTGAAGAAGGTAGATGGCATATTGGTAATTATGAACATCATCATAATCTAATGAGTCGAAATCATTAAT<br>TTTTTTTTAAACTAATTACCATTTACTCTGTTCATTCTAATCCTTTTTGTGTTCATTCATATGCTAGGCCTAGAGA<br>TAGAATTGTGACTAGAATAAAGGCTATAATTATTATAGTAGAGGTTTTAATTGTTTGAATTGCTCATGGTAGTGGA<br>AGT |
| 63 | MIC-68178 | ITS | TCTTGGTCATTTAGAGGAAGTAAAAGTCGTAACAAGGTTTCCGTAGGTGAACCTGCGGAAGGATCATTACCTAGAG<br>TTTGTGGACTTCGGTCTGCTACCTCTTACCCATGTCTTTTGAGTACCTTCGTTTCCTCGGCGGGTCCGCCCGCCGG<br>TTGGACAACATTCAAACCCTTTGCAGTTGCAATCAGCGTCTGAAAAAACTTAATAGTTACAACTTTCAACAACGGA<br>TCTCTTGGTTCTGGCATCGATGAAGAACGCAGCGAAATGCGATAAGTAGTGTGAATTGCAGAATTCAGTGAATCAT<br>CGAATCTTTGAACGCACATTGCGCCCCTTGGTATTCCATGGGGCATGCCTGTTCGAGCGTCATTTGTACCTTCAAG<br>CTCTGCTTGGTGTTGGGTGTTTTGTCTCGCCTCCGCGCAGACTCGCCTTAAAACAATTGGCAGCCGGCGTATTG<br>ATTTCGGAGCGCAGTACATCTCGCGCTTTGCACTCATAACGACGACGTCCAAAAGTACATTTTTACACTCTTGACC<br>TCGGATCAGGTAGGGATACCCGCTGAACTTAAGCATATCAATAAGCGGAGGAAAAGAAACCAACAGGGATTGCCCT<br>AGTAACGGCGAGTGAAGCGGCAACAGCTCAAATTTGAAATCTGGCGTCTTTGGCGTCCGAGTTGTAATTTGCAGAG<br>GGCGCTTTGGCATTGGCAGCGGTCCAAGTTCCTTGGAACAGGACGTCACAGAGGGTGAGAATCCCGTACGTGGTCG<br>CTAGCCTTTACCGTGTAAAGCCCCTTCGACGAGTCGAGTTGTTTGGGAATGCAGCTCTAAATGGGAGGTAAATTTC<br>TTCTAAAGCTAAATACTGGCCAGAGACCGATAGCGCACAAGTAGAGTGATCGAAAGATGAAAAGCACTTTGGAAAG<br>AGAGTTAAAAAGCACGTGAAATTGTTGAAAGGGAAGCGCTTGCAGCCAGACTTGCCTGTAGTTGCTCATCCGGGTT<br>TCTACCCGGTGCACTCTTCTACGGGCAGGCCAGCATCAGTTTGGGCGGTTGGATAAAGGTCTCTGTCATGTACCTC |

TABLE 4-continued

Exemplary sequences of endophytes of the present invention

| SEQ ID | MIC ID | Gene/ Locus | Sequence |
|---|---|---|---|
| | | | CCTTCGGGGAGATCTTATAGGGGAGACGACATGCAACCAGCCTGGACTGAGGTCCGCGCATCTGCTAGGATGCTGG<br>CGTAATGGCTGTAAGCGGCCCGTCTTGAAACACGGACCAAGGAGTCTAACATCTATGCGAGTGTTTGGGTGTCAAG<br>CCCGAGCGCGTAATGAAAGTGAACGGAGGTGGGAACCTTTCGGGGTGCACCATCGACCGATCCTGATGTCTTCGGA<br>TGGATTTGAGTAAGAGCATAGCTGTTGGGACCCGAAAGATGGTGAACTATGCTTGAATAGGGTGAAGCCAGAGGAA<br>ACTCTGGTGGAGGCTCGCAGCGGTTCTGACGTGCAAATCGATCGTCAAATTTGGGCATAGGGGCGAAAGAC |
| 64 | MIC-68178 | Tubulin | CCAGACTGGCCGAAGACGAAGTTATCGGGACGGAAGAGCTGGCCGAAGGGGCCGGCGCGGACAGCGTCCATTGTAC<br>CGGGCTCCAAGTCGACGAGGACGGCACGGGGAACGAACTTGTTGCCAGAGGCCTGCGGGAGGTCAGCACTCGCAGT<br>CCGTCTCAGGAAAGCGTGTCGTTTCTAGTACCTCGTTGAAGTAGACGTTCATGCGCTCGAGCTGGAGGTCCGAGGT<br>GCCGTTGTAGACACCGGAGCCGTCGAGGCCATGCTCGCCGGAGATGGTCTGCCAGAAGGCAGCACCGATTTGGTTA<br>CCCTGTCCCTTGTGAGCTGCCGTCCATGAGAGAACATGCAAGTGGTGTACTTACGCACTGACCGGTCTGGAGGTGA<br>ACC |
| 65 | MIC-07010 | ITS | TCTTGGTCATTTAGAGGAAGTAAAAGTCGTAACAAGGTCTCCGTAGGTGAACCTGCGGAGGGATCATTACACAATA<br>ACATATGAAGGCTGTACGCCGCTGCGCCCCCGGGCCAGTTGGCTGAGGCTGGATTATTTATTACCCTTGTCTTTTG<br>CGCACTTGTTGTTTCCTGGGCGGGTTCGCCCGCCTCCAGGACCACACCATAAACCTTTTTTATGCAGTTGCAATCA<br>GCGTCAGTACAACAAATGTAAATCATTTACAACTTTCAACAACGGATCTCTTGGTTCTGGCATCGATGAAGAACGC<br>AGCGAAATGCGATACGTAGTGTGAATTGCAGAATTCAGTGAATCATCGAATCTTTGAACGCACATTGCGCCCTTTG<br>GTATTCCAAAGGGCATGCCTGTTCGAGCGTCATTTGTACCCTCAAGCTTTGCTTGGTGTTGGGCGTTTTTGTCTTT<br>GGTTTGCCAAAGACTCGCCTTAAAACGATTGGCAGCCGGCCTCCTGGTTACGCAGCGCAGCACATTTTTGCGCTTG<br>CAATCAGCAAGAGGGCGGCACTCCATCAAGACTCCTTCTCACGTTTGACCTCGGATCAGGTAGGGATACCCGCTGA<br>ACTTAAGCATATCAATAAGCGGAGGAAAAGAAACCAACAGGGATTGCCCTAGTAACGGCGAGTGAAGCGGCAACAG<br>CTCAAATTTGAAATCTGGCTCTTTAGGGTCCGAGTTGTAATTTGCAGAGGGCGCTTTGGCTTTGGCAGCGGTCCA<br>AGTTCCTTGGAACAGGACGTCACAGAGGGTGAGAATCCCGTACGTGGTCGCTAGCTATTGCCGTGTAAAGCCCCTT<br>CGACGAGTCGAGTTGTTTGGGAATGCAGCTCTAAATGGGAGGTAAATTTCTTCTAAAGCTAAATATTGGCCAGAGA<br>CCGATAGCGCACAAGTAGAGTGATCGAAAGATGAAAAGCACTTTGGAAAGAGAGTCAAACAGCACGTGAAATTGTT<br>GAAAGGGAAGCGCTTGCAGCCAGACTTGCTTGCAGTTGCTCATCCGGGCTTTTGCCCGGTGCACTCTTCTGTAGGC<br>AGGCCAGCATCAGTTTGGGCGGTGGGATAAAGGTCTCTGACACGTTCCTTCCTTCGGGTTGGCCATATAGGGGAGA<br>CGTCATACCACCAGCCTGGACTGAGGTCCGCGCATCTGCTAGGATGCTGGCGTAATGGCTGTAAGCGGCCCGTCTT<br>GAAACACGGACCAAGGAGTCTAACATCTATGCGAGTGTTTGGGTGTCAAGCCCGAGCGCGTAATGAAAGTGAACGG<br>AGGTGGGAACCCGCAAGGGCGCACCATCGACCGATCCTGAAGTTTACGGAAGGATTTGAGTAAGAGCATGGCTGTT<br>GGGACCCGAAAGATGGTGAACTATGCTTGAATAGGGTGAAGCCAGAGGAAACTCTGGTGGAGGCTCGCAGCGGTTC<br>TGACGTGCAAATCGATCGTCAAATTTGGGCATAGGGGCGAAAGACTAATCGA |
| 66 | MIC-07010 | phospho-glyce-rate kinase | ACACCGGCAGGGCCGTTCCAGAGGATGGTCTGCGCCTCATCGATGGCCTCCTTGTAAAGCTTGATCGACTTCTCTC<br>CACAGTCGAGACCCATCCAGCCATCTGGGATACCATCCTTGTCCTCGGCATAACCGACGTTGGCGTCCTTGTCGAA<br>CTTGTCGGCGGTGATGTAGTCAACAGGCAGCACAATCTTGACATTGTTCTTCTTCGCCTTCTCCACGAGGTCCTTG<br>ACGGTCTTGCTACCAGCCTCATCGAACAAGCTTTCACCAATCTTGACGCCCTCGAGAGTCTTCTTGAAGGTGAAGG<br>ACATGCCTCCGCAAATGATCAGGCTGTTGACCTTGCCAAGCAGGTTGTCGATCAATTGAATCTTGTCAGAGACCTT<br>GGCACCACCAAGGATGGCGAGGAAAGGTCGCTTGGGGTTCTCAAGCGCTTGTGCAAAGTAATCAAGCTCCTTCTTG<br>ACAAGGAAGCCAGAGGCCTTTTGTGGGAGGTCGACACCGACCATGGAGCTGTGCGCGCGGTGAGCAGTACCAAAAG<br>CGTCGTCTGTAAACCGTCAGCCTCGTGCTTTCGCCCATGAATTCATAGTTACTTACTAATGTAGACGTCGCCCAGA<br>GCAGTCAGTCCCTTCCTAAACTCATCGACCTTGCTCTTGTCGACCTTCTGCTTCTTGCCCGCATCATCCTTGTAGC<br>TACCCTCCTCCTCAGCGTGGAAGCGCAGGTTCTCGAGGAGGATGACCTGACCACCGCTAGCGTTGTTGACGGTATC<br>CTCTACCGACTTGCCGACGCAGTCGTCGGTGAAGGTAACGCTCTTGCCGAGGAGCTTCTCGAGTTCGGGAACAACC<br>GGCTTGAGGCTGTACTTCGCATTGGGCTTACCGTCTGGCCGGCCAAGGTGGGACATGAGAATGACGGCCTTGGCGC<br>CATTGTCGACGGCGTACTTGATTGTGGGAAGTGCGCCAACAATGCGCTGGTTGTTGGTGATCTTCTTGTCGGCGTC<br>GAGAGGGACGTTGAAGTCGACC |
| 67 | MIC-48747 | ITS | TCTTGGTCATTTAGAGGAAGTAAAAGTCGTAACAAGGTCTCCGTAGGTGAACCTGCGGAGGGATCATTACAAGTGA<br>CCCCGGTCTAACCACCGGGATGTTCATAACCCTTTGTTGTCCGACTCTGTTGCCTCCGGGGCGACCCTGCCTTCGG<br>GCGGGGGCTCCGGGTGGACACTTCAAACTCTTGCGTAACTTTGCAGTCTGAGTAAACTTAATTAATAAATTAAAAC<br>TTTTAACAACGGATCTCTTGGTTCTGGCATCGATGAAGAACGCAGCGAAATGCGATAAGTAATGTGAATTGCAGAA<br>TTCAGTGAATCATCGAATCTTTGAACGCACATTGCGCCCCCTGGTATTCCGGGGGGCATGCCTGTTCGAGCGTCAT<br>TTCACCACTCAAGCCTCGCTTGGTATTGGGCATCGCGGTCCGCCGCGTGCCTCAAATCGACCGGCTGGGTCTTCTG<br>TCCCCTAAGCGTTGTGGAAACTATTCGCTAAAGGGTGTTCGGGAGGCTACGCCGTAAAACAACCCCATTTCTAAGG<br>TTGACCTCGGATCAGGTAGGGATACCCGCTGAACTTAAGCATATCAATAAGCGGAGGAAAAGAAACCAACAGGGAT<br>TGCTCTAGTAACGGCGAGTGAAGCAGCAATAGCTCAAATTTGAAATCTGGCGTCTTCGACGTCCGAGTTGTAATTT<br>GTAGAGGATGCTTCTGAGTAACCACCGACCTAAGTTCCTTGGAACAGGACGTCATAGAGGGTGAGAATCCCGTATG<br>CGGTCGGAAAGGTGCTCTATACGTAGCTCCTTCGACGAGTCGAGTTGTTTGGGAATGCAGCTCTAAATGGGAGGTA<br>AATTTCTTCTAAAGCTAAATATTGGCCAGAGACCGATAGCGCACAAGTAGAGTGATCGAAAGATGAAAAGCACTTT<br>GGAAAGAGAGTTAAAAAGCACGTGAAATTGTTAAAAGGGAAGGGATTGCAACCAGACTTGCTCGCGGTGTTCCGCC<br>GGTCTTCTGACCGGTCTACTCGCCGCGTTGCAGGCCAGCATCGTCTGGTGCCGCTGGATAAGACTTGAGGAATGTA<br>GCTCCTTCGGGAGTGTTATAGCCTCTTGTGATGCAGCGAGCGCCGGGCGAGGTCCGCGCTTCGGCTAGGATGCTGG<br>CGTAATGGTCGTAATCCGCCCGTCTTGAAACACGGACCAAGGAGTCTAACATCTATGCGAGTGTTCGGGTGTCAAA<br>CCCCTACGCGTAATGAAAGTGAACGGAGGTGAGAACCGCAAGGTGCATCATCGACCGATCCTGATGTCTTCGGATG<br>GATTTGAGTAAGAGCATAGCTGTTGGGACCCGAAAGATGGTGAACTATGCCTGAATAGGGTGAAGCCAGAGGAAAC<br>TCTGGTGGAGGCTCGCAGCGGTTCTGACGTGCAAATCGATCGTCAAATTTGGGTATAGGGGCGAAAGACTAATCG |
| 68 | MIC-50414 | ITS | TCTTGGTCATTTAGAGGAAGTAAAAGTCGTAACAAGGTCTCCGTAGGTGAACCTGCGGAGGGATCATTACAAGTGA<br>CCCCGGTCTAACCACCGGGATGTTCATAACCCTTTGTTGTCCGACTCTGTTGCCTCCGGGGCGACCCTGCCTTCGG<br>GCGGGGGCTCCGGGTGGACACTTCAAACTCTTGCGTAACTTTGCAGTCTGAGTAAACTTAATTAATAAATTAAAAC<br>TTTTAACAACGGATCTCTTGGTTCTGGCATCGATGAAGAACGCAGCGAAATGCGATAAGTAATGTGAATTGCAGAA<br>TTCAGTGAATCATCGAATCTTTGAACGCACATTGCGCCCCCTGGTATTCCGGGGGGCATGCCTGTTCGAGCGTCAT<br>TTCACCACTCAAGCCTCGCTTGGTATTGGGCAACGCGGTCCGCCGCGTGCCTCAAATCGACCGGCTGGGTCTTCTG<br>TCCCCTAAGCGTTGTGGAAACTATTCGCTAAAGGGTGCTCGGGAGGCTACGCCGTAAAACAAACCCATTTCTAAGG |

TABLE 4-continued

Exemplary sequences of endophytes of the present invention

| SEQ ID | MIC ID | Gene/ Locus | Sequence |
|---|---|---|---|
| | | | TTGACCTCGGATCAGGTAGGGATACCCGCTGAACTTAAGCATATCAATAAGCGGAGGAAAAGAAACCAACAGGGAT<br>TGCTCTAGTAACGGCGAGTGAAGCAGCAATAGCTCAAATTTGAAATCTGGCGTCTTCGACGTCCGAGTTGTAATTT<br>GTAGAGGATGCTTCTGAGTAACCACCGACCTAAGTTCCTTGGAACAGGACGTCATAGAGGGTGAGAATCCCGTATG<br>CGGTCGGAAAGGTGCTCTATACGTAGCTCCTTCGACGAGTCGAGTTGTTTGGGAATGCAGCTCTAAATGGGAGGTA<br>AATTTCTTCTAAAGCTAAATATTGGCCAGAGACCGATAGCGCACAAGTAGAGTGATCGAAAGATGAAAAGCACTTT<br>GGAAAGAGAGTTAAAAAGCACGTGAAATTGTTAAAAGGGAAGGGATTGCAACCAGACTTGCTCGCGGTGTTCCGCC<br>GGTCTTCTGACCGGTCTACTCGCCGCGTTGCAGGCCAGCATCGTCTGGTGCCGCTGGATAAGACTTGAGGAATGTA<br>GCTCCCTCGGGAGTGTTATAGCCTCTTGTGATGCAGCGAGCGCCGGGCGAGGTCCGCGCTTCGGCTAGGATGCTGG<br>CGTAATGGTCGTAATCCGCCCGTCTTGAAACACGGACCAAGGAGTCTAACATCTATGCGAGTGTTCGGGTGTCAAA<br>CCCCTACGCGTAATGAAAGTGAACGGAGGTGAGAACCGCAAGGTGCATCATCGACCGATCCTGATGTCTTCGGATG<br>GATTTGAGTAAGAGCATAGCTGTTGGGACCCGAAAGATGGTGAACTATGCCTGAATAGGGTGAAGCCAGAGGAAAC<br>TCTGGTGGAGGCTCGCAGCGGTTCTGACGTGCAAATCGATCGTCAAATTTGGGTATAGGGGCGAAAG |
| 69 | MIC-50989 | ITS | TCTTGGTCATTTAGAGGAAGTAAAAGTCGTAACAAGGTCTCCGTTGGTGAACCAGCGGAGGGATCATTACAGAGTT<br>TAACGACTCCCAAACCACTGTGAACATACCCGTACCGTTGCCTCGGCGGGCGGCCCCAGGGCGGGGCCGCAGCCTC<br>CCCAGCGGAGGCGCCCGCCGCAGGTCGCAAAACTATAACTATATTTAGTGGCATCTCTGAGTAACTTCCAAACAAT<br>CAAAACTTTCAACAACGGATCTCTTGGTTCTGGCATCGATGAAGAACGCAGCGAAATGCGATAAGTAATGTGAATT<br>GCAGAATTCAGTGAATCATCGAATCTTTGAACGCACATTGCGCCCGCCAGCATTCTGGCGGGCATGCCTGTCCGAG<br>CGTCATTTCAACCCTCAAGCCCTGCTTGGTGTTGGGGCACTACGCGCGAGCGTAGGCCCTCAAAATCAGTGGCGGA<br>CCCGCTGGAGGTCCGGGCGTAGTAACACATCTCGCCCGAGGTCCCCAGCGTGCCCCTGCCGTTAAACCCCCAAATT<br>TACAGAAGGTTGACCTCGGATCAGGTAGGAATACCCGCTGAACTTAAGCATATCAATAAGCGGAGGAAAAGAAACC<br>AACAGGGATTGCCCTAGTAACGGCGAGTGAAGCGGCAACAGCTCGAATTTGAAATCTGGCCTCGGCCCGAGTTGTA<br>ATCTGTAGAGGATGCTTTTGGCGCGGTGCCTTCCGAGTGCCCTGGAACGGGACGCCACAGAGGGTGAGAGCCCCGT<br>ATGGTCGGACACCAAGCCTGTGTAAAGCTCCTTCGACGAGTCGGGTAGCTTGGGAATGCTGCTCTAAGTGGGAGGT<br>AAACTTCTTCTAAAGCTAAATACTGGCCAGAGACCGATAGCGCACAAGTAGAGTGATCGAAAGATGAAAAGCACTT<br>TGAAAAGAGGGTCAAATAGTACGTGAAATTGTTGAAAGGGAAGCGCTCATGACCAGACTTGCGCCGGGCTGATCAT<br>CCAGTGGTCTCCACTGGTGCACTCTGCCCGGCTCAGGCCAGCGTCGGCTGTCACGGGGGGACAAAAGCACTGGGAA<br>AGTAGCTCTCTCCGGGGAGTGTTATAGCCCTATGCAGAATACCCCCGCGGCGGCCGAGGTCCGCGCTCTGCAAGGA<br>CGCTGGCGTAATGGTCATCAGCGACCCGTCTTGAAACACGGACCAAGGAGTCGAGGTTTTGCGCGAGTGTTCGGGT<br>GCAAAGCCCCAGCGCGTAATTAAAGTGAACGTAGGTGAGAGCTTCGGCGCATCATCGACCGATCCTGATGTATTCG<br>GATGGATTTGAGTAGGAGCGTAAAGCCTCGGACCCGAAAGATGGTGAACTATGCCTGTATAGGGTGAAGCCAGAGG<br>AAACTCTGGTGGAGGCTCGCAGCGGTTCTGACGTGCAAATCGATCGTCAAATATGGGCATGGGGGCGAAAG |
| 70 | MIC-85555 | ITS | TCTTGGTCATTTAGAGGAAGTAAAAGTCGTAACAAGGTTTCCGTAGGTGAACCTGCGGAAGGATCATTACCTAGAG<br>TTTGTGGACTTCGGTCTGCTACCTCTTACCCATGTCTTTTGAGTACCTTCGTTTCCTCGGCGGGTCCGCCCGCCGG<br>TTGGACAACATTCAAACCCTTTGCAGTTGCAATCAGCGTCTGAAAAAACTTAATAGTTACAACTTTCAACAACGGA<br>TCTCTTGGTTCTGGCATCGATGAAGAACGCAGCGAAATGCGATAAGTAGTGTGAATTGCAGAATTCAGTGAATCAT<br>CGAATCTTTGAACGCACATTGCGCCCCTTGGTATTCCATGGGGCATGCCTGTTCGAGCGTCATTTGTACCTTCAAG<br>CTCTGCTTGGTGTTGGGTGTTTTGTCTCGCCTCCGCGCGCAGACTCGCCTTAAAACAATTGGCAGCCGGCGTATTG<br>ATTTCGGAGCGCAGTACATCTCGCGCTTTGCACTCATAACGACGACGTCCAAAAGTACATTTTTACACTCTTGACC<br>TCGGATCAGGTAGGGATACCCGCTGAACTTAAGCATATCAATAAGCGGAGGAAAAGAAACCAACAGGGATTGCCCT<br>AGTAACGGCGAGTGAAGCGGCAACAGCTCAAATTTGAAATCTGGCGTCTTTGGCGTCCGAGTTGTAATTTGCAGAG<br>GGCGCTTTGGCATTGGCAGCGGTCCAAGTTCCTTGGAACAGGACGTCACAGAGGGTGAGAATCCCGTACGTGGTCG<br>CTAGCCTTTACCGTGTAAAGCCCCTTCGACGAGTCGAGTTGTTTGGGAATGCAGCTCTAAATGGGAGGTAAATTTC<br>TTCTAAAGCTAAATACTGGCCAGAGACCGATAGCGCACAAGTAGAGTGATCGAAAGATGAAAAGCACTTTGGAAAG<br>AGAGTTAAAAAGCACGTGAAATTGTTGAAAGGGAAGCGCTTGCAGCCAGACTTGCCTGTAGTTGCTCATCCGGGTT<br>TCTACCCGGTGCACTCTTCTACGGGCAGGCCAGCATCAGTTTGGGCGGTTGGATAAAGGTCTCTGTCATGTACCTC<br>CCTTCGGGGAGATCTTATAGGGGAGACGACATGCAACCAGCCTGGACTGAGGTCCGCGCATCTGCTAGGATGCTGG<br>CGTAATGGCTGTAAGCGGCCCGTCTTGAAACACGGACCAAGGAGTCTAACATCTATGCGAGTGTTTGGGTGTCAAG<br>CCCGAGCGCGTAATGAAAGTGAACGGAGGTGGGAACCTTTCGGGGTGCACCATCGACCGATCCTGATGTCTTCGGA<br>TGGATTTGAGTAAGAGCATAGCTGTTGGGACCCGAAAGATGGTGAACTATGCTTGAATAGGGTGAAGCCAGAGGAA<br>ACTCTGGTGGAGGCTCGCAGCGGTTCTGACGTGCAAATCGATCGTCAAATTTGGGCATAGGGGCGAAAGACTAAT |
| 71 | MIC-68178 | Unique genomic region | CTCCTCCTCCTCCTCCTGATCGAACTCGCCCCCCACCAACTCCACCAGCCCACCCAGCCGCCCAAAAACCTCCCCA<br>TCCCCGCTAGCCGCCCCCATGGCCCGGACAAGCAGCNNNNNNNNNNNNNNGTCCGGGATGGCCTTAGGTTCGCTCT<br>CGAGCTGCTCCAGCCGCGACAGGACATGCAGCAGCTCCCTGCGCAGCGAGTCCGGCGCCGGCATGCGGCCCCGCAG<br>CGGCTGGTCGGCGATGTATGTCTTGAGCGGGAGCGCGGCGCGCAGGATGAGGTAGGGCGCCGCTGCCTGGGCGAGT<br>TTGATGTGCGAGTGCGAGGGCGAGGGCGAGGTACTGGCGGGGCGTGCGGCCACGAGGGCGAAGAGGGAGGCCGTGC<br>AGGTGTAGCTCATCTTTGTGCGCAAGGTGGCGGGGAGGACGGCCGTCTGGCCGGTGCGGACGGAGAGGAGGTTGGC<br>GAGGGGCGAGGTGGTGATGGGAGGGAGTTCTCCTTGTACGGGAGTGTGGATGAGGGAGGTGGTGAAGAGGTTGCGG<br>GCGTATGTCCTGCGGAGGGTGTCGGGGAGGGAGGGGGAGTTTAGAGGGCCGCTGATCAAGTCGCGTAGCTCTGTGA |

Example 2: Isolation and Identification of Endophytes Using Marker Gene Sequences The fungal endophytes of the present invention can be identified by the sequence of one or more of the following loci: long subunit rRNA (LSU), small subunit rRNA (SSU), largest subunit of RNA polymerase II (RPB1), second largest subunit of RNA polymerase II (RPB2), beta-tubulin, actin, phosphoglycerate kinase (PGK). PCR amplification of the largest subunit of RNA polymerase I (RPB1) using primer sequences RPB1-Af (SEQ ID NO: 21) and RPB1-Cr (SEQ ID NO: 22) is described in Cendejas-Bueno E, Kolecka A, Alastruey-Izquierdo A, et al. Reclassification of the *Candida haemulonii* Complex as *Candida haemulonii* (*C. haemulonii* Group I), *C. duobushaemulonii* sp. nov. (*C. haemulonii* Group II), and *C. haemulonii* var. *vulnera* var. nov.: Three Multiresistant Human Pathogenic Yeasts. Journal of Clinical Microbiology. 2012; 50(11):3641-3651. PCR amplification of second largest subunit of RNA polymerase II (RPB2) using primer sequences fRPB2-5F (SEQ ID NO: 26) and fRPB2-7.1R (SEQ ID NO: 25) is described in Riess K, Oberwinkler F, Bauer R, Garnica S. High genetic diversity at the regional scale and possible speciation in *Sebacina epigaea* and *S. incrustans*. BMC Evolutionary Biology. 2013; 13:102. doi:10.1186/1471-2148-13-102. PCR amplification of beta-tubulin using primer sequences Btub2Fd (SEQ ID NO: 30) and Btub4Rd (SEQ ID NO: 31) is described in Aveskamp et al. (2009) DNA phylogeny reveals polyphyly of *Phoma* section *Peyronellaea* and multiple taxonomic novelties Mycologia, 101(3):363-382. PCR amplification of the LSU using primer sequences LR0R (SEQ ID NO: 23) and LR5 (SEQ ID NO: 24) is described in Stielow J B, Lëvesque C A, Seifert K A, et al. One fungus, which genes? Development and assessment of universal primers for potential secondary fungal DNA barcodes. *Persoonia: Molecular Phylogeny and Evolution of Fungi.* 2015; 35:242-263. doi:10.3767/003158515X689135. PCR amplification of the SSU using primer sequences SR1R (SEQ ID NO: 29) and NS4 (SEQ ID NO: 28) is described in Zhu et al. (2016) *Helminthosporium velutinum* and *H. aquaticum* sp. nov. from aquatic habitats in Yunnan Province, China. Phytotaxa 253 (3): 179-190. PCR amplification of Actin using primer sequences ACT512f (SEQ ID NO: 17) and ACT783r (SEQ ID NO: 18) is described in Carbone, I. & Kohn, L. M. (1999) A method for designing primer sets for speciation studies in filamentous ascomycetes. Mycologia, 91(3):552-556. PCR amplification of largest subunit of RNA polymerase II (RPB1) using primer sequences RPB1-Af (SEQ ID NO: 21) and RPB1-Cr (SEQ ID NO: 22) is described in Urbina H, Blackwell M (2012) Multilocus Phylogenetic Study of the *Scheffersomyces* Yeast Clade and Characterization of the N-Terminal Region of Xylose Reductase Gene. PLoS ONE 7(6): e39128.

MIC-68390 can be identified by one or more of the following exemplary sequences: RPB2 sequence (SEQ ID NO: 61). MIC-68178 can be identified by one or more of the following exemplary sequences: beta-tubulin sequence (SEQ ID NO: 64). MIC-07010 can be identified by one or more of the following exemplary sequences: phosphoglycerate kinase sequence (SEQ ID NO: 66). MIC-96038 can be identified by one or more of the following exemplary sequences: actin sequence (SEQ ID NO: 47), beta-tubulin sequence (SEQ ID NO: 48), RPB2 sequence (SEQ ID NO: 49), RPB1 sequence (SEQ ID NO: 50). MIC-33414 can be identified by one or more of the following exemplary sequences: its Actin sequence (SEQ ID NO: 53), RPB1 sequence (SEQ ID NO: 55), beta-tubulin sequence (SEQ ID NO: 58), LSU sequence (SEQ ID NO: 54), SSU sequence (SEQ ID NO: 56), SSU sequence (SEQ ID NO: 57). MIC-31593 can be identified by one or more of the following exemplary sequences: its RPB2 sequence (SEQ ID NO: 43), beta-tubulin sequence (SEQ ID NO: 44). Exemplary LSU and SSU sequences of MIC-19994 are SEQ ID NO: 39 and SEQ ID NO: 40, respectively.

Example 3: Isolation and Identification of Bacterial and Fungal Endophytes Using ITS Sequence Classification of the fungal strain using ITS sequences was done by the following methodology.

Total genomic DNA was extracted from individual fungal isolates, using the DNeasy Plant Mini Kit (Qiagen, Germantown, Md.). Polymerase Chain Reaction (PCR) was used to amplify a genomic region including the nuclear ribosomal internal transcribed spacers (ITS) using a primer pair ITS_1 (5'-CTTGGTCATTTAGAGGAAGTAA-3') (SEQ ID NO: 5) and LR5 (5'-TCCTGAGGGAAACTTCG-3') (SEQ ID NO: 8). Each 25 microliter-reaction mixture included 22.5 microliters of Invitrogen Platinum Taq supermix, 0.5 microliter of each primer (10 uM), and 1.5 microliters of DNA template (~2-4 ng). Cycling reactions were run with MJ Research PTC thermocyclers and consisted of 94° C. for 5 min, 35 cycles of 94° C. for 30 s, 54° C. for 30 s, and 72° C. for 1 min, and 72° C. for 10 min. Sanger sequencing of was performed at Genewiz (South Plainfield, N.J.) using primers: ITS_1 (5'-CTTGGTCATTTAGAGGAAGTAA-3') (SEQ ID NO: 5), ITS_2 (5'-GCTGCGTTCTTCATCGATGC-3') (SEQ ID NO: 6), ITS_3 (5'-GCATCGATGAAGAACGCAGC-3') (SEQ ID NO: 7), and LR5 (5'-TCCTGAGGGAAACTTCG-3') (SEQ ID NO: 8). Sequencing primers were chosen so that overlapping regions were sequenced. Raw chromatograms were converted to sequences, and corresponding quality scores were assigned using TraceTuner v3.0.6beta (U.S. Pat. No. 6,681,186). These sequences were quality filtered, aligned and a consensus sequence generated using Geneious v 8.1.8 (Biomatters Limited, Auckland NZ).

Taxonomic classifications were assigned to the sequences using the highest probability of assignment based on the results of industry standard taxonomic classification tools: LCA (runs USEARCH (Edgar, R. C. (2010) Bioinformatics. 26(19):2460-2461) with option search_global, then for all best match hits, returns lowest taxonomic rank shared by all best hits for a query), SPINGO (Allard et al. (2015) BMC Bioinformatics. 16: 324), and UTAX (Edgar, R. C., 2016), using the WARCUP Fungal ITS trainset 1 (Deshpande et al. (2016) Mycologia 108(1):1-5) and UNITE (Koljalg et al. (2013) Molecular Ecology, 22: 5271-5277). The classifier and database combinations listed in Table 5 were used to assign taxonomy to fungal sequences.

TABLE 5

The classifier and database combinations used to classify ITS sequences

| Classifier | Database |
|---|---|
| LCA | UNITE, Fungal ITS trainset 07/04/2014 |
| RDP | UNITE, Fungal ITS trainset 07/04/2014 |
| | WARCUP, Fungal ITS trainset 1 |
| SPINGO | UNITE, Fungal ITS trainset 07/04/2014 |
| UTAX | UNITE, Fungal ITS trainset 07/04/2014 |
| | WARCUP, Fungal ITS trainset 1 |

TABLE 6

Taxonomic classification of endophytes of the present invention

| MIC ID | Phylum | Class | Order | Family | Genus | Species |
|---|---|---|---|---|---|---|
| MIC-68390 | Ascomycota | Dothidiomycetes | Pleosporales | Pleosporaceae | *Exserohilum* | *rostrata* |
| MIC-68178 | Ascomycota | Dothidiomycetes | Pleosporales | Pleosporaceae | *Epicoccum* | *nigrum* |
| MIC-07010 | Ascomycota | Dothidiomycetes | Pleosporales | Pleosporaceae | *Curvularia* | *protuberata* |
| MIC-31593 | Ascomycota | Dothidiomycetes | Pleosporales | Pleosporaceae | *Curvularia* | *spicifera* |
| MIC-48747 | Ascomycota | Dothidiomycetes | Capnodiales | Cladosporiaceae | *Cladosporium* | *cladosporioides* |

TABLE 6-continued

| Taxonomic classification of endophytes of the present invention | | | | | | |
|---|---|---|---|---|---|---|
| MIC ID | Phylum | Class | Order | Family | Genus | Species |
| MIC-96038 | Ascomycota | Sordariomycetes | Hypocreales | Hypocreaceae | *Acremonium* | *alternatum* |
| MIC-50414 | Ascomycota | Dothidiomycetes | Capnodiales | Cladosporiaceae | *Cladosporium* | *oxysporum* |
| MIC-33414 | Ascomycota | Sordariomycetes | Sordariales | Chaetomiaceae | *Chaetomium* | *globosum* |
| MIC-85555 | Ascomycota | Dothidiomycetes | Pleosporales | Pleosporaceae | *Epicoccum* | *nigrum* |
| MIC-50989 | Ascomycota | Sordariomycetes | Sordariales | Cephalothecaceae | *Paecilomyces* | *inflatus* |
| MIC-19994 | Ascomycota | Sordariomycetes | Coniochaetales | Coniochaetaceae | *Coniochaeta* | *prunicola* |

MIC-68390 can be identified by the sequence of its ITS sequence (SEQ ID NO: 60). MIC-68178 can be identified by the sequence of its ITS sequence (SEQ ID NO: 63). MIC-07010 can be identified by the sequence of its ITS sequence (SEQ ID NO: 65). MIC-31593 can be identified by the sequence of its ITS sequence (SEQ ID NO: 42). MIC-48747 can be identified by the sequence of its ITS sequence (SEQ ID NO: 67). MIC-96038 can be identified by the sequence of its ITS sequence (SEQ ID NO: 46). MIC-50414 can be identified by the sequence of its ITS sequence (SEQ ID NO: 68). MIC-33414 can be identified by the sequence of its ITS sequence (SEQ ID NO: 52). MIC-85555 can be identified by the sequence of its ITS sequence (SEQ ID NO: 70). MIC-50989 can be identified by the sequence of its ITS sequence (SEQ ID NO: 69).

Example 4. Assessment of Improved Plant Characteristics, Seedling Vigor

Assay of Soy Seedling Vigor

Seed preparation: The lot quality of soybean seeds was first assessed by testing germination of 100 seeds. Seeds were placed, 8 seeds per petri dish, on filter paper in petri dishes, 12 mL of water was added to each plate and plates are incubated for 3 days at 24° C. The percent germination was greater than 95%. One thousand soybean seeds were then surface sterilized by co-incubation with chlorine gas in a 20×30 cm container placed in a chemical fume hood for 16 hours. Percent germination of 50 seeds, per sterilization batch, was tested as above and confirmed to be greater than 95%.

Preparation and heterologous disposition of endophytes: Spore solutions were made by rinsing and scraping spores from agar slants which have been growing for about 1 month. Rinsing was done with 0.05% Silwet. Solutions were passed through Miracloth to filter out mycelia. Spores per ml were counted under a microscope using a hemocytometer. The stock suspension was then diluted into 10ˆ6 spores/ml utilizing water. 3 μl of spore suspension was used per soy seed (~10ˆ3 CFUs/seed is obtained). Control treatments were prepared by adding equivalent volumes of sterile water to seeds.

Assay of seedling vigor: Two rolled pieces of germination paper were placed in a sterile glass gar with 50 mL sterile water, then removed when completely saturated. Then the papers were separated and inoculated seeds were placed at approximately 1 cm intervals along the length of one sheet of moistened germination paper, at least 2.5 cm from the top of the paper and 3.8 cm from the edge of the paper. The second sheet of was placed on top of the soy seeds and the layered papers and seeds were loosely rolled into a tube. Each tube was secured with a rubber band around the middle and placed in a single sterile glass jar and covered loosely with a lid. For each treatment, three jars with 15 seeds per jar were prepared. The position of jars with the growth chamber was randomized. Jars were incubated at 60% relative humidity, and 22° C. day, 18° C. night with 12 hours light and 12 hours dark for 4 days and then the lids were removed and the jars incubated for an additional 7 days. Then the germinated soy seedlings were weighed and photographed and root length and root surface area scored as follows.

Dirt, excess water, seed coats and other debris was removed from seedlings to allow accurate scanning of the roots. Individual seedlings were laid out on clear plastic trays and trays are arranged on an Epson Expression 11000XL scanner (Epson America, Inc., Long Beach Calif.). Roots were manually arranged to reduce the amount of overlap. For root measurements, shoots were removed if the shape of the shoot causes it to overlap the roots.

The WinRHIZO software version *Arabidopsis* Pro2016a (Regents Instruments, Quebec Canada) was used with the following acquisition settings: greyscale 4000 dpi image, speed priority, overlapping (1 object), Root Morphology: Precision (standard), Crossing Detection (normal). The scanning area was set to the maximum scanner area. When the scan was completed, the root area was selected and root length and root surface area were measured.

Statistical analysis was performed using R (R Core Team, 2016. R: A language and environment for statistical computing. R Foundation for Statistical Computing, Vienna, Austria. R-project.org/). Results are summarized in Tables 7 and 8.

TABLE 7

| Root traits of endophyte treated and untreated soybean seedlings. | | | | | | |
|---|---|---|---|---|---|---|
| MIC ID | Average Root Length | Standard Deviation, Root Length | Average Root Area | Standard Deviation, Root Area | Root Length % difference NT | Root Area % difference NT |
| Untreated control (NT) | 79.4 | 32.5 | 8.9 | 4.1 | 0.0 | 0.0 |
| MIC-68178 | 81.2 | 34.6 | 9.8 | 3.4 | 2.2 | 9.6 |
| MIC-07010 | 94.1 | 29.5 | 10.5 | 3.2 | 18.5 | 17.7 |
| MIC-31593 | 85.6 | 29.7 | 10.1 | 3.4 | 7.7 | 12.9 |

TABLE 7-continued

| Root traits of endophyte treated and untreated soybean seedlings. | | | | | | |
|---|---|---|---|---|---|---|
| MIC ID | Average Root Length | Standard Deviation, Root Length | Average Root Area | Standard Deviation, Root Area | Root Length % difference NT | Root Area % difference NT |
| MIC-48747 | 96.7 | 26.0 | 11.7 | 3.0 | 21.7 | 31.4 |
| MIC-96038 | 88.5 | 33.1 | 10.7 | 4.0 | 11.4 | 19.8 |

TABLE 8

| Percent increase in soybean seedling root length of endophyte treatment relative to untreated controls. | |
|---|---|
| Treatment | % Gain over Control Vigor Soy |
| MIC-33414 | 27.8 |

Assay of Corn Seedling Vigor

Seed preparation: The lot quality of corn seeds is first evaluated for germination by transfer of 100 seeds and with 3.5 mL of water to a filter paper lined petri dish. Seeds are incubated for 3 days at 24° C., and to ensure that percent germination is greater than 95%. One thousand corn seeds are then surface sterilized by co-incubation with chlorine gas in a 20×30 cm container in a chemical fume hood for 12 hours. Percent germination of 50 seeds, per sterilization batch, is tested as above and confirmed to be greater than 95%.

Optional reagent preparation: 7.5% PEG 6000 (Calbiochem, San Diego, Calif.) is prepared by adding 75 g of PEG to 1000 mL of water, then stirred on a warm hot plate until the PEG is fully dissolved. The solution is then autoclaved.

Preparation and heterologous disposition of endophytes: Spore solutions are made by rinsing and scraping spores from agar slants which have been growing for about 1 month. Rinsing is done with 0.05% Silwet. Solutions are passed through Miracloth to filter out mycelia. Spores per ml are counted under a microscope using a hemocytometer. The stock suspension is then diluted into 10^6 spores/ml utilizing water. 3 μl of spore suspension is used per corn seed (~10^3 CFUs/seed is obtained). Control treatments are prepared by adding equivalent volumes of sterile water to seeds.

Assay of seedling vigor: Either 25 ml of sterile water (or optionally, 25 ml of PEG solution as prepared above) is added to each Cyg™ germination pouch (Mega International, Newport, Minn.) and place into pouch rack (Mega International, Newport, Minn.). Sterile forceps are used to place corn seeds prepared as above into every other perforation in the germination pouch. Seeds are fitted snugly into each perforation to ensure they did not shift when moving the pouches. Before and in between treatments forceps are sterilized using ethanol and flame and workspace wiped down with 70% ethanol. For each treatment, three pouches with 15 seeds per pouch are prepared. The germination racks with germination pouches are placed into plastic tubs, and covered with perforated plastic wrap to prevent drying. Tubs are incubated at 60% relative humidity, and 22° C. day, 18° C. night with 12 hours light and 12 hours dark for 6 days to allow for germination and root length growth. Placement of pouches within racks and racks/tubs within the growth chamber is randomized to minimize positional effect. At the end of 6 days the corn seeds are scored manually for germination, root and shoot length.

Statistical analysis is performed using R (R Core Team, 2016. R: A language and environment for statistical computing. R Foundation for Statistical Computing, Vienna, Austria. R-project.org/).

Assay of Wheat Seedling Vigor

Seed preparation: The lot of wheat seeds was first evaluated for germination by transfer of 100 seeds and with 8 mL of water to a filter paper lined petri dish. Seeds were incubated for 3 days at 24° C., and percent germination was greater than 95%. Wheat seeds were then surface sterilized by co-incubation with chlorine gas in a 20×30 cm container in a chemical fume hood for 12 hours. Percent germination of 50 seeds, per sterilization batch, was tested as above and confirmed to be greater than 95%.

Reagent preparation: 7.5% polyethylene glycol (PEG) was prepared by adding 75 g of PEG to 1000 mL of water, then stirring on a warm hot plate until the PEG is fully dissolved. The solution was then autoclaved.

Preparation and heterologous disposition of endophytes: Spore solutions were made by rinsing and scraping spores from agar slants which had been growing for about 1 month. Rinsing was done with 0.05% Silwet. Solutions were passed through Miracloth to filter out mycelia. Spores per ml were counted under a microscope using a hemocytometer. The stock suspension was then diluted into 10^6 spores/ml utilizing water. 3 μl of spore suspension was used per wheat seed (~10^3 CFUs/seed was obtained). Seeds and spores were combined a 50 mL falcon tube and gently shaken for 5-10 seconds until thoroughly coated. Control treatments were prepared by adding equivalent volumes of sterile water to seeds.

Assay of seedling vigor: Petri dishes were prepared by adding four sheets of sterile heavy weight seed germination paper, then adding 50 mL of PEG solution as prepared above to each plate then allowing the liquid to thoroughly soak into all sheets. The sheets were positioned and then creased so that the back of the plate and one side wall were covered, two sheets were then removed and placed on a sterile surface. Along the edge of the plate across from the covered side wall 15 inoculated wheat seeds were placed evenly at least one inch from the top of the plate and half an inch from the sides. Seeds were placed smooth side up and with the pointed end of the seed pointing toward the side wall of the plate covered by germination paper. The seeds were then covered by the two reserved sheets, and the moist paper layers smoothed together to remove air bubbles and secure the seeds, and then the lid was replaced. For each treatment, at least three plates with 15 seeds per plate were prepared. The plates were then randomly distributed into stacks of 8-12 plates and a plate without seeds was placed on the top. The stacks were incubated at 60% relative humidity, and 22° C. day, 18° C. night with 12 hours light and 12 hours dark for 24 hours, then each plate was turned to a semi-vertical position with the side wall covered by paper at the bottom.

The plates were incubated for an additional 5 days, then wheat seeds scored manually for germination, root and shoot length.

Statistical analysis was performed using R (R Core Team, 2016. R: A language and environment for statistical computing. R Foundation for Statistical Computing, Vienna, Austria. R-project.org/). Results are summarized in Table 9.

TABLE 9

Percent increase in wheat seedling root length of endophyte treatment relative to untreated controls.

| | % Gain over Control Vigor |
|---|---|
| SYM | Wheat |
| MIC-33414 | 6.5 |

Example 5: Culture Preparations and Heterologous Disposition of Endophytes for Greenhouse Experiments Strains may be cultured by the methods described herein and methods well known in the art.

Preparation of Fungal Biomass

Method 1

Biomass for MIC-19994 and MIC-96038 was produced by growing for two weeks in liquid medium (PDB). The resulting biomass was homogenized by sonication (50% amplitude for 30 seconds) or in a FastPrep-24 (MP Biomedicals, Santa Ana, Calif., USA) set to 4.5 m/s for 30 seconds.

Method 2

Spore solutions were made by rinsing and scraping spores from agar slants which have been growing for about 1 month. Rinsing was done with 0.05% Silwet. Solutions were passed through Miracloth to filter out mycelia. Spores per ml were counted under a microscope using a hemocytometer. The stock suspension was then diluted into 10^6 spores/ml utilizing water. 3 μl of spore suspension was used per seed (~10^3 CFUs/seed is obtained). Control treatments were prepared by adding equivalent volumes of sterile water to seeds.

Method 3

Preparation: Molasses broth was prepared by dissolving 30 g molasses and 5 g yeast extract per liter deionized water in an autoclavable container and autoclaving (15 psi, 121° C.) for 45 min. Potato dextrose agar (PDA) plates were prepared by dissolving 39.0 g PDA powder per liter deionized water in an autoclavable container and autoclaving (15 psi, 121° C.) for 45 min. The agar was allowed to cool to 50-60° C., before pouring into sterile petri plates (30 mL per 90 mm plate).

Liquid biomass: All equipment and consumables were thoroughly sterilized and procedures performed in a biosafety cabinet. The inoculant is prepared by placing 1 plug from a cryopreserved stock on a fresh PDA plate, sealing the plate with Parafilm® and incubating at room temperature in the dark for 5-10 days. Then ~5×5 mm plugs were cut from the PDA plates and 10-12 plugs were transferred into flasks containing the sterile molasses broth, covered, secured in a shaker and incubated for at least 10 days with shaking at ~130 rpm. Then the culture was placed in a blender for 5 seconds and 1 mL of the blended was centrifuged and the supernatant was discarded and the pellet resuspended in 0.5 mL 1× Phosphate Buffered Saline (PBS) to generate inoculum.

Dry biomass: All equipment and consumables were thoroughly sterilized and procedures performed in a biosafety cabinet. The inoculant is prepared by placing 1 plug from a cryopreserved stock on a fresh PDA plate, sealing the plate with Parafilm® and incubating at room temperature in the dark for 5-10 days. Then ~5×5 mm plugs were cut from the PDA plates and 10-12 plugs were transferred into flasks containing the sterile molasses broth, covered, secured in a shaker and incubated for at least 10 days with shaking at ~130 rpm. In sterile conditions, the liquid culture was carefully decanted using 150 mm sterile filter paper on a sterilized Buchner funnel over a sterile flask. Once all liquid had passed through the funnel, the pellet was rinsed with sterile water until the filtrate ran clear. When dry, the pellet was transferred to a drying cabinet and dried until brittle. The pellet was then ground into a fine powder, and sample used to generate CFU counts.

Seed Inoculation

Unless otherwise specified, inoculum was added to seeds to reach a targeted dose of 10^4 CFU. Where low, medium and high doses are indicated, and in not specified otherwise, a high dose is 10^5 CFU/seed, a medium dose is 10^4 CFU/seed, and a low dose 10^3 CFU/seed. The seeds were agitated to disperse the inoculum evenly on the seeds. Formulation control treatments were prepared using equivalent volumes of PBS. The seeds were allowed to dry for approximately 2 mins, then 2 fluid ounces per kg of seed of Flo-Rite® 1706 (BASF, Ludwigshafen, Germany) was added and the seeds were agitated to disperse the powder evenly on the seeds.

Example 6. Assessment of Improved Plant Characteristics: Greenhouse

Rice

Rice seeds of variety Rex were treated with commercial fungicidal and insecticidal treatment CruiserMaxx® Rice (Syngenta, Basel, Switzerland). Seeds were heterologously disposed with the endophyte formulations and formulation control (lacking any endophyte) as described in Example 28, untreated seeds (lacking formulation and endophyte) were also planted. The loaded dose of each microbe is shown in Table 42. The endophyte treatment MIC-68178/MIC-33414 was co-inoculated with MIC-68178 and MIC-33414. In the co-inoculation treatment, MIC-68178 made up 17.45% of the loaded dose, and MIC-33414 made up 82.55% of the loaded dose.

TABLE 10

Loaded doses (CFU per seed) of soybean seeds treated with endophytes.

| | Loaded doses, CFU per seed |
|---|---|
| MIC-68178 | 1.64E+03 |
| MIC-33414 | 2.39E+03 |
| MIC-68178/MIC-33414 | 1.44E+03 |

Each pot was filled with Cahaba/Wickham type, fine sandy loam soil, and two seeds were sown evenly spaced in each pot. Ten pots were planted per treatment/control. The experimental design called for a completely randomized pattern of each treatment within each block/replicate. Plants were watered twice daily. Upon emergence of true leaves, plants were fertilized weekly at 250 PPM N using Peter's Peat-Lite 20-1020 water-soluble fertilizer.

At day 7, pots were thinned to 1 seedling/pot. Root tissue was harvested from the experiment six weeks post-planting, and the soil was washed from the roots. The tissues from each plant was placed in an unlined paper bag. The tissue was dried in an oven set to 85° C. for 3 days. Once completely dried, the root biomass of individual plants were weighed and recorded.

MIC-68178 demonstrated an increase of 51.5% in dry root weight compared to the untreated control, with over 80% confidence by Bayesian analysis.

TABLE 11

Percent difference in root dry weight in rice variety Rex in greenhouse conditions

| | Rice variety Rex % difference Untreated control, root dry weight |
|---|---|
| Untreated control | 0 |
| Formulation control | 52.0 |
| MIC-68178 | 51.5 |

Soy

Sandy loam was mixed in a ratio of 60% loam and 40% mortar sand. Prior to mixing, both planting media were sifted through a ⅜" square steel mesh screen to remove larger particles and debris. Soy seeds of variety Stine 33E22 were treated with commercial fungicidal and insecticidal treatment CruiserMaxx® Soy (Syngenta, Basel, Switzerland). Seeds were heterologously disposed with the endophyte formulations and formulation control (lacking any endophyte) as described in Example 28, untreated seeds (lacking formulation and endophyte) were also planted.

Each pot was filled with 1000 mL of soil, watered with 225 mL of water and one seed sown per pot. Ten pots were planted per treatment/control. The experimental design called for a completely randomized pattern of each treatment within each block/replicate. Environmental conditions were set at 12 h photoperiod, at 23/20° C. temperature for day/night period and light intensity was set at 550 μMol $m^{-2}$ $s^{-1}$. Post-planting, the seeds were watered to maintain approximately 75% soil capacity.

Root tissue was harvested from the experiment three weeks post-planting, and the soil was washed from the roots. The tissues from each plant was placed in an unlined paper bag. The tissue was dried in an oven set to 85° C. for 3 days. Once completely dried, the root biomass of individual plants were weighed and recorded.

Figure 3:
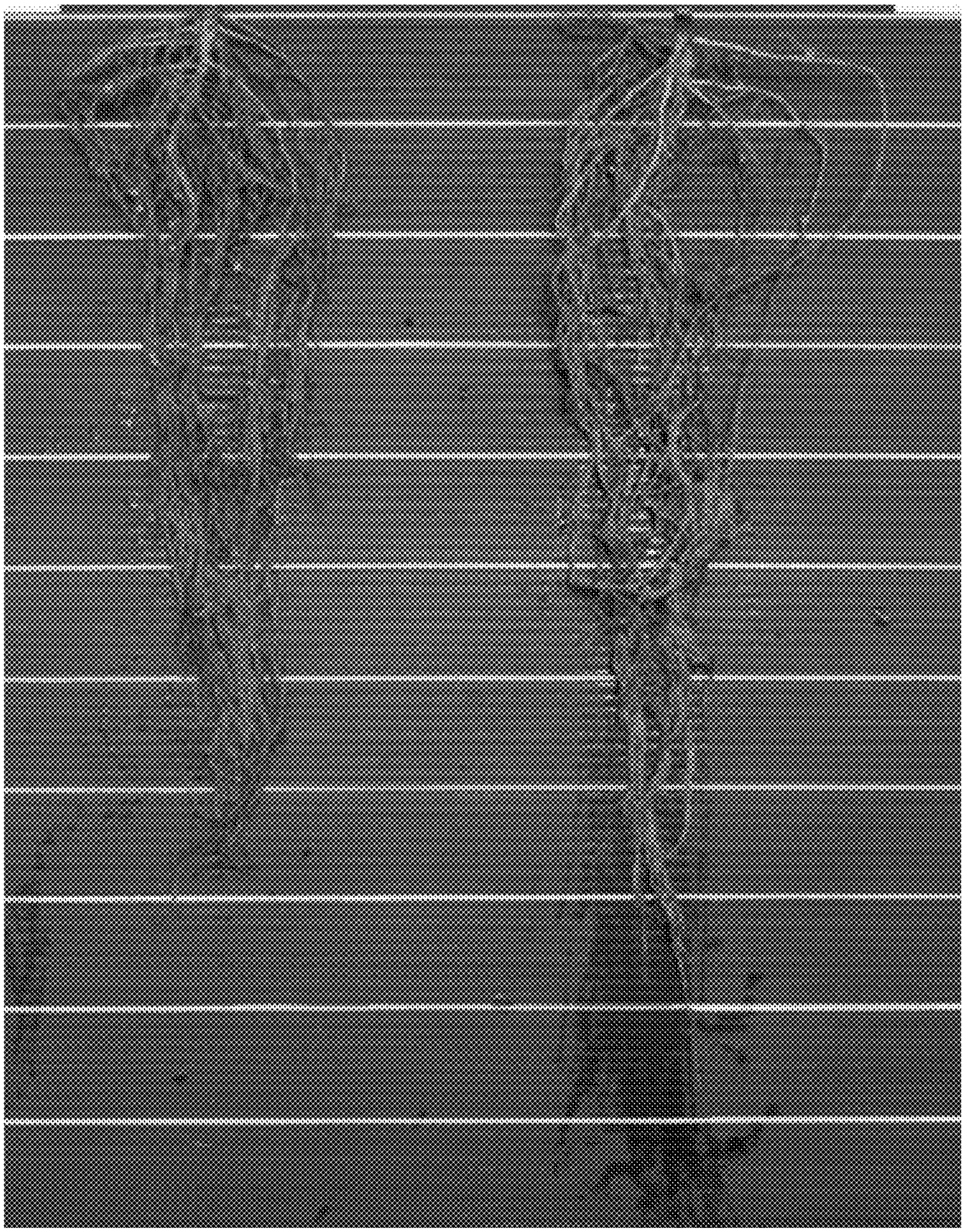
FIG. 3 shows exemplary soybean roots of soybean plants grown as described in Example 29. The roots of untreated control rice plants are on the left. The roots of soybean plants treated with a combination of MIC-68178 and MIC-33414 are on the right.
Figure 4:
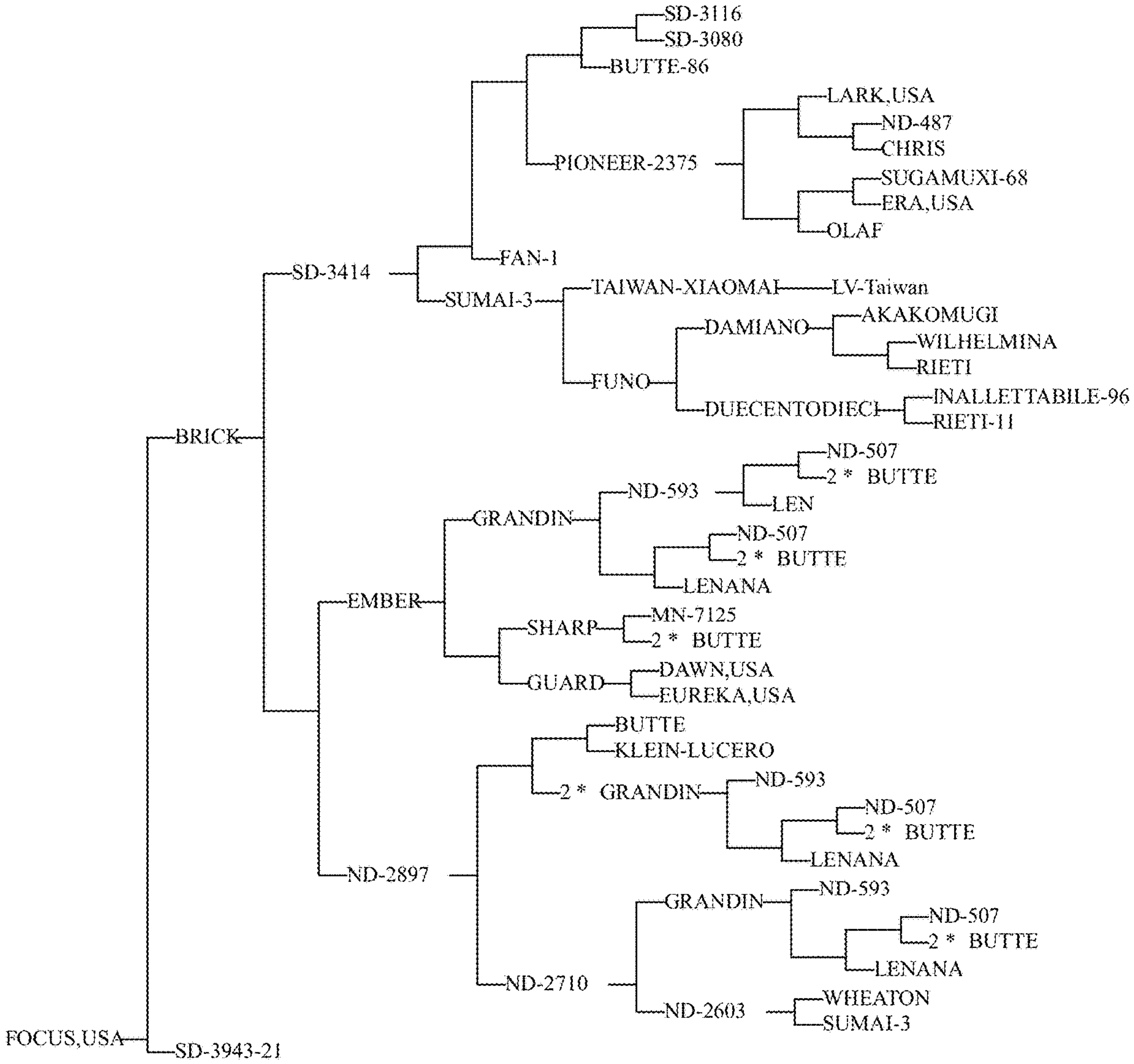
FIG. 4 shows the pedigree of the wheat variety SDSU Focus.
Figure 5:
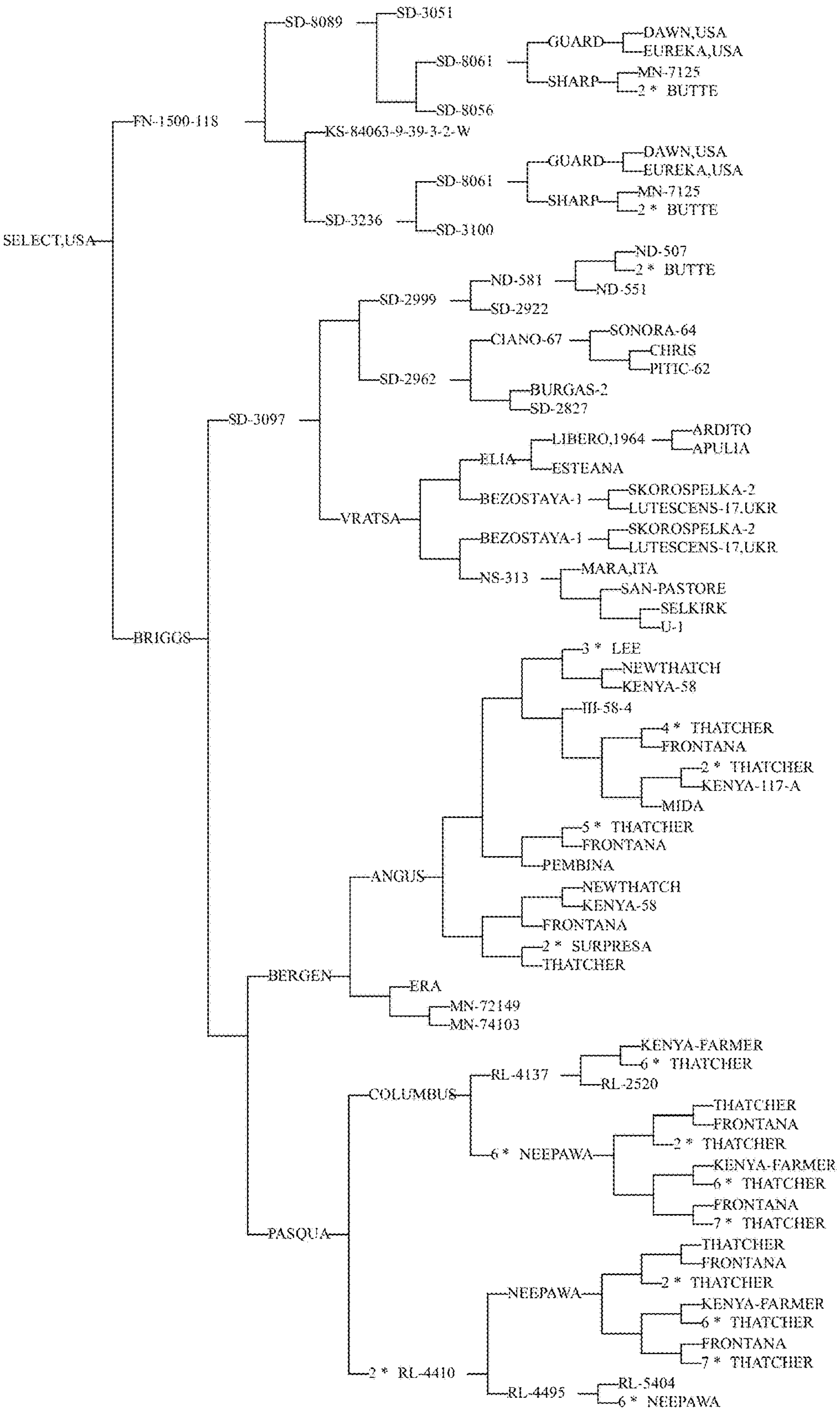
FIG. 5 shows the pedigree of the wheat variety SDSU Select.

Roots treated with the endophyte MIC-68178 demonstrated an increase of 16.9% in dry root weight compared to the untreated control, but with less than 80% confidence by Bayesian analysis. Roots treated with the endophyte MIC-33414 demonstrated a decrease of 23.5% in dry root weight compared to the untreated control, but with less than 80% confidence by Bayesian analysis. However, the endophyte formulation comprising both MIC-68178 and MIC-33414 demonstrated an increase in dry root weight of 36.8% compared to the untreated control, with over 80% confidence by Bayesian analysis. A photo taken prior to drying of exemplary untreated control and MIC-68178 and MIC-33414 treated soybean roots is shown in FIG. 3.

TABLE 12

Percent difference in root dry weight in soybean variety Stine 33E22 in greenhouse conditions.

| | Soybean variety Stine 33E22 % difference Untreated control, root dry weight |
|---|---|
| Untreated control | 0 |
| Formulation control | 7.4 |
| MIC-68178 | 16.9 |
| MIC-68178/MIC-33414 | 36.8 |
| MIC-33414 | −23.5 |

Example 7: Cultivation of Endophyte-Treated Plants in Greenhouse Experiment 1

Wheat

A sandy loam and a commercial potting soil (Farfard®, Agawam, Mass.) were used in this experiment. Sandy loam was mixed in a ratio of 60% loam and 40% mortar sand (Northeast Nursery, Peabody, Mass.). Prior to mixing, both planting media were sifted through a ⅜" square steel mesh screen to remove larger particles and debris. Wheat seeds were treated with commercial fungicidal and insecticidal treatment. Seeds were heterologously disposed with the endophyte formulations and formulation control (lacking any endophyte) as described in Example 5, untreated seeds (lacking formulation and endophyte) were also planted. Endophyte treatments were applied to seed in three target doses: high (10^5 CFU/seed), medium (10^4 CFU/seed), low (10^3 CFU/seed). Each pot was filled with 600 mL of its respective soil, watered with 200 mL of water and then, nine seeds were sown evenly spaced in each pot (in a 3×3 pattern). Soil was then overlaid atop the seeds (estimated average planting depth of 1 inch) and an additional 110 mL of water was added to moisten the overlaying soil substrate. The experimental design called for a completely randomized pattern of each treatment within each block/replicate. Environmental conditions were set at 12 h photoperiod, at 22/18° C. temperature for day/night period and light intensity was set at 650 μMol m−2 s−1. Post-planting, the seeds were watered to maintain approximately 80% soil capacity.

Wheat seedlings emergence was recorded on days 4, 5, and 7 after planting, with days 4 and 5 representing early emergence percentage and day 7 representing final emergence percentage. At day 7, all pots were thinned to 3 seedlings/pot. Above ground tissue was harvested from the experiment three weeks post-planting. The tissues from individual replicate treatments (pots) were pooled and placed in an unlined paper bag. All tissues were dried in an oven set to 85° C. for 3 days. Once completely dried, the shoot biomass of individual treatment replicates (pots) was weighed and recorded MIC-96038, MIC-96038/MIC-19994 co-cultured, and MIC-19994 treatments all increased dry plant shoot biomass at the medium dose. The MIC-19994 treatment resulted in a 6% ($p<0.05$) increase in dry shoot biomass at 10^4 CFU/seed.

TABLE 13

| Dry shoot biomass of endophyte treated wheat | Avg dry shoot biomass (g) | Standard deviation | Standard error of the mean | % change over untreated control | % change over formulatio control |
|---|---|---|---|---|---|
| Untreated control | 0.949 | 0.0852 | 0.011 | 0 | 0.21 |
| Formulation control | 0.947 | 0.072 | 0.0093 | −0.2 | 0.00 |
| MIC-19994, 10^3 | 0.97 | 0.0684 | 0.0153 | 2.2 | 2.43 |
| MIC-96038, 10^4 | 1.009 | 0.0539 | 0.0121 | 6.32 | 6.55 |
| MIC-96038, 10^5 | 0.941 | 0.0865 | 0.0193 | −0.79 | −0.63 |
| MIC-96038 pure, 10^3 | 0.962 | 0.0631 | 0.0141 | 1.41 | 1.58 |
| MIC-96038 pure, 10^4 | 0.992 | 0.0831 | 0.0186 | 4.57 | 4.75 |
| MIC-96038 pure, 10^5 | 0.934 | 0.0891 | 0.0199 | −1.55 | −1.37 |
| MIC-96038/MIC-19994, 10^3 | 0.943 | 0.0644 | 0.0144 | −0.65 | −0.42 |
| MIC-96038/MIC-19994, 10^4 | 0.989 | 0.0775 | 0.0173 | 4.27 | 4.44 |
| MIC-96038/MIC-19994, 10^5 | 0.898 | 0.089 | 0.0199 | −5.38 | -5.17 |

Soy

A sandy loam growth substrate was mixed in the greenhouse and consisting of 60% loam and 40% mortar sand (Northeast Nursery, Peabody, Mass.). Prior to mixing, loam was sifted through a ⅜" square steel mesh screen to remove larger particles and debris. Soybean seeds were treated with commercial fungicidal and insecticidal treatment CruiserMaxx® Vibrance (Syngenta, Basel, Switzerland) according to the manufacturer's instructions. Seeds were heterologously disposed with the endophyte formulations and formulation control (lacking any endophyte) as described in Example 11, untreated seeds (lacking formulation and endophyte) were also planted. Endophyte treatments were applied to seed in three target doses: high (10^5 CFU/seed), medium (10^4 CFU/seed), low (10^3 CFU/seed). Each pot was filled with 600 mL of its respective soil, watered with 200 mL of water and then, nine seeds were sown evenly spaced in each pot (in a 3×3 pattern). Soil was then overlaid atop the seeds (estimated average planting depth of 1 inch) and an additional 110 mL of water was added to moisten the overlaying soil substrate. The experimental design called for a completely randomized pattern of each treatment within each block/replicate. Environmental conditions were set at 12 h photoperiod, at 22/18 C temperature for day/night period and light intensity was set at 650 μMol $m^{-2}$ $s^{-1}$. Post-planting, the seeds grown in normal watering conditions were watered to maintain approximately 80% soil capacity and the seeds grown in drought conditions were watered to maintain approximately 40% soil capacity. Above ground tissue was harvested from the experiment three weeks post-planting. The tissues from individual replicate treatments (pots) were pooled and placed in an unlined paper bag. All tissues were dried in an oven set to 85° C. for 3 days. Once completely dried, the shoot biomass of individual treatment replicates (pots) was weighed and recorded.

TABLE 14

Endophyte treatments associated with increases in dry shoot biomass under normal wateringconditions relative to formulmation for endophyte treated soybeans

| | Normal watering | | Limited watering | |
|---|---|---|---|---|
| | Dry weight (g) | % change over formulation control | Dry weight (g) | % change over formulation control |
| MIC-96038 | 1.987 | 7.3% | 1.145 | −0.72% |
| MIC-960338/MIC-19994 | 1.945 | 5.07% | 1.155 | 0.17% |
| MIC-19994 | 1.937 | 4.64% | 1.106 | −4.11% |

Rice

A sandy loam growth substrate was mixed in the greenhouse and consisting of 60% sifted loam and 40% mortar sand (Northeast Nursery, Peabody, Mass.). Prior to mixing, loam was sifted through a ⅜ inch. square steel mesh screen to remove larger particles and debris.

Endophyte treated seeds and control (no endophyte) seeds prepared in Example 26 were planted in a growth room experiment. For each treatment or control 20 replicates were prepared as follows. Each pot was filled with 600 mL of soil, watered with 200 mL of water and then, six seeds were sown evenly spaced in two rows (in a 2×3 pattern). Soil was then overlaid atop the seeds (estimated average planting depth of 0.5 inches) and an additional 100 mL of water was added to moisten the overlaying substrate. The experimental design called for a completely randomized pattern of each treatment within each block/replicate. Environmental conditions were set at 12 h photoperiod, at 22/18 C temperature for day/night period and light intensity was set at 650 μMol $m^{-2}$ $s^{-1}$. Post-planting, the seeds were watered with 200 mL of water every other day. Pots were thinned down to 3 seedlings at approximately 9 days post-planting.

Emergence was recorded on days 4, 5, 7, 8 and 9 days after planting, with days 4 and 5 representing early emergence percentage and day 9 representing final emergence percentage. Above ground tissue was harvested from the experiment three weeks post-planting. The tissues from individual replicate treatments (pots) were pooled and placed in an unlined paper bag. All tissues were dried in an oven set to 85° C. for 3 days. Once completely dried, the shoot biomass of individual treatment replicates (pots) was weighed and recorded.

TABLE 15

Shown are mean dry biomass (g) of seeds treated with Flo Rite ®

| Treatment | Dose | Mean dry biomass (g) | Std Dev | Std Err of the mean | % vs untreated control | % vs formulation control |
|---|---|---|---|---|---|---|
| Untreated control | | 0.107 | 0.0323 | 0.00417 | 0 | 6.82 |
| Formulation control | | 0.1002 | 0.0294 | 0.0038 | −6.38 | 0 |
| MIC-68178 | Low | 0.1053 | 0.0542 | 0.01211 | −1.61 | 5.09 |
| | Medium | 0.1195 | 0.0263 | 0.00588 | 11.61 | 19.21 |
| | High | 0.0967 | 0.0229 | 0.00513 | −9.67 | −3.51 |
| MIC-96038 | Low | 0.1302 | 0.0204 | 0.00456 | 21.65 | 29.94 |
| | Medium | 0.1244 | 0.0244 | 0.00545 | 16.19 | 24.1 |
| | High | 0.1298 | 0.0241 | 0.00538 | 21.26 | 29.53 |

TABLE 16

Shown are mean dry biomass (g) of seeds not treated with Flo Rite ®

| Treatment | Dose | Mean dry biomass (g) | Standard deviation | Standard error of the mean | % over un-treated control | % over formul-ation control |
|---|---|---|---|---|---|---|
| Untreated control | | 0.107 | 0.0323 | 0.00417 | 0.0 | 6.8 |
| Formul-ation control | | 0.1002 | 0.02945 | 0.0038 | −6.4 | 0.0 |
| MIC-68178 | Low | 0.0891 | 0.04152 | 0.00928 | −16.7 | −11.1 |
| | Medium | 0.0653 | 0.0156 | 0.00349 | −39.0 | −34.9 |
| | High | 0.1294 | 0.01668 | 0.00373 | 20.9 | 29.1 |
| MIC-96038 | Low | 0.144 | 0.03537 | 0.00791 | 34.5 | 43.7 |
| | Medium | 0.1203 | 0.02521 | 0.00564 | 12.4 | 20.1 |
| | High | 0.1187 | 0.02709 | 0.00606 | 10.9 | 18.4 |

Example 8: Oil-based Formulation of Endophyte Seed Treatments

Endophyte compositions were generated comprising an oil high in erucic acid, a non-ionic surfactant, and a plantability polymer. MIC-31593 and MIC-33414 were prepared in three different formulations (A_2, B_2, C_2) and MIC-96038 was prepared in formulation A_1, described in Table 15.

TABLE 17

Components of endophyte compositions, volumes per 50 g of seed

| Formulation | Oil | Oil volume (mL) | 0.5% Triton X-100 volume (mL) | Flo Rite ® (mL) |
|---|---|---|---|---|
| A_2 | Rapeseed | 0.2545 | 0.12727 | 0.049 |
| B_2 | Rapeseed | 0.1273 | 0.2545 | 0.049 |
| C_2 | None | 0 | 0.38182 | 0.049 |
| A_1 | Rapeseed | 0.1273 | 0.2545 | 0.049 |
| A_4 | None | 0 | 0 | 0.049 |

Example 9. Vigor Assessment in Greenhouse Experiment 2

Wheat

Endophyte inocula as prepared in Example 5 was applied to wheat seeds which had not previously been treated with chemical insecticide or fungicide. Endophyte treated seeds were prepared at 5 target doses: 10^1, 10^2, 10^3, 10^4, 10^5 CFU/seed. Ten biological replicates each were planted for each treatment and control condition (no endophyte) in individual containers containing commercial potting media.

Emergence was recorded at 7 days post planting, and plant height (cm) scored at 7, 14, 21 and 28 days post planting. Above and below ground tissue was harvested from the experiment four weeks post-planting. The fresh weight of roots and shoots were recorded, then the samples were dried in an oven set to 85° C. for 3 days. Once completely dried, the shoot and root biomass was weighed and recorded.

TABLE 18

Germination percentage, plant height and weight of endophyte treated wheat formulation controls. DAP = Days after planting

| | | Formulation control | MIC-96038/MIC-19994, 10 CFU/seed | MIC-96038/MIC-19994, 10^2 CFU/seed | MIC-96038/MIC-19994, 10^3 CFU/seed | MIC-96038/MIC-19994, 10^4 CFU/seed | MIC-96038/MIC-19994, 10^5 CFU/seed |
|---|---|---|---|---|---|---|---|
| % Germ | 7 DAP | 100 | 100 | 100 | 100 | 90 | 90 |
| Plant height (cm) | 7 DAP | 10.4 | 11.1 | 10.8 | 11.2 | 11 | 11.6 |
| Plant height (cm) | 14 DAP | 15.3 | 16.2 | 17.1 | 17.2 | 16.9 | 17.7 |
| Plant height (cm) | 21 DAP | 16.1 | 17.2 | 17.3 | 17.8 | 17.2 | 18.5 |
| Plant height (cm) | 28 DAP | 16.29 | 17.21 | 17.66 | 18 | 17.767 | 18.74 |
| Fresh Root Weight (g) | Wt (g) | 0.367 | 0.419 | 0.41 | 0.437 | 0.413 | 0.429 |

TABLE 18-continued

Germination percentage, plant height and weight of endophyte treated wheat formulation controls. DAP = Days after planting

| | | Formulation control | MIC-96038/MIC-19994, 10 CFU/seed | MIC-96038/MIC-19994, 10^2 CFU/seed | MIC-96038/MIC-19994, 10^3 CFU/seed | MIC-96038/MIC-19994, 10^4 CFU/seed | MIC-96038/MIC-19994, 10^5 CFU/seed |
|---|---|---|---|---|---|---|---|
| Fresh Top Weight (g) | Wt (g) | 0.21 | 0.2406 | 0.253 | 0.265 | 0.276 | 0.267 |
| Fresh Total Weight (g) | Wt (g) | 0.577 | 0.6596 | 0.663 | 0.702 | 0.689 | 0.696 |
| Dry Root Weight (g) | Wt (g) | 0.0627 | 0.0729 | 0.0713 | 0.0756 | 0.07 | 0.074 |
| Dry Top Weight (g) | Wt (g) | 0.0582 | 0.0688 | 0.0695 | 0.0733 | 0.071 | 0.074 |
| Dry Total Weight (g) | Wt (g) | 0.1209 | 0.1417 | 0.1408 | 0.1489 | 0.141 | 0.149 |

TABLE 19

Percent change over formulation control of germination percentage, plant height and weight in endophyte treated wheat. DAP = Days after planting

| | | MIC-96038/MIC-19994, 10 CFU/seed, % change over formulation control | MIC-96038/MIC-19994, 10^2 CFU/seed, % change over formulation control | MIC-96038/MIC-19994, 10^3 CFU/seed, % change over formulation control | MIC-96038/MIC-19994, 10^4 CFU/seed, % change over formulation control | MIC-96038/MIC-19994, 10^5 CFU/seed, % change over formulation control |
|---|---|---|---|---|---|---|
| % Germination | 7 DAP | 0.0 | 0.0 | 0.0 | −10.0 | −10.0 |
| Plant height (cm) | 7 DAP | 6.7 | 3.8 | 7.7 | 5.8 | 11.5 |
| Plant height (cm) | 14 DAP | 5.9 | 11.8 | 12.4 | 10.5 | 15.7 |
| Plant height (cm) | 21 DAP | 6.8 | 7.5 | 10.6 | 6.8 | 14.9 |
| Plant height (cm) | 28 DAP | 5.6 | 8.4 | 10.5 | 9.1 | 15.1 |
| Fresh Root Weight (g) | Wt (g) | 14.2 | 11.7 | 19.1 | 12.6 | 16.9 |
| Fresh Top Weight (g) | Wt (g) | 14.6 | 20.5 | 26.2 | 31.2 | 27.0 |
| Fresh Total Weight (g) | Wt (g) | 14.3 | 14.9 | 21.7 | 19.4 | 20.5 |
| Dry Root Weight (g) | Wt (g) | 16.3 | 13.7 | 20.6 | 11.1 | 18.6 |
| Dry Top Weight (g) | Wt (g) | 18.2 | 19.4 | 25.9 | 22.0 | 27.9 |
| Dry Total Weight (g) | Wt (g) | 17.2 | 16.5 | 23.2 | 16.3 | 23.1 |

Rice

Endophyte inocula as prepared in Example 4 was applied to rice seeds which had not previously been treated with chemical insecticide or fungicide. Endophyte treated seeds were prepared at 5 target doses: 10^1, 10^2, 10^3, 10^4, 10^5 CFU/seed. Ten biological replicates each were planted for each treatment and control condition (no endophyte) in individual containers containing commercial potting media.

Emergence was recorded at 7 days post planting, and plant height (cm) scored at 7, 14, 21 and 28 days post planting. Above and below ground tissue was harvested from the experiment four weeks post-planting. The fresh weight of roots and shoots were recorded, then the samples were dried in an oven set to 85° C. for 3 days. Once completely dried, the shoot and root biomass was weighed and recorded.

TABLE 20

Germination percentage, plant height and weight of endophyte treated rice formulation controls. DAP = Days after planting

| | | Formulation control | MIC-96038/MIC-19994, 10 CFU/seed | MIC-96038/MIC-19994, 10^2 CFU/seed | MIC-96038/MIC-19994, 10^3 CFU/seed | MIC-96038/MIC-19994, 10^4 CFU/seed | MIC-96038/MIC-19994, 10^5 CFU/seed |
|---|---|---|---|---|---|---|---|
| % Germ | 7 DAP | 90 | 100 | 100 | 100 | 80 | 90 |
| Plant height (cm) | 7 DAP | 7.1 | 7.1 | 7.7 | 7.7 | 7.3 | 7.3 |
| Plant height (cm) | 14 DAP | 11.7 | 11.5 | 12.9 | 13.1 | 14 | 12.6 |
| Plant height (cm) | 21 DAP | 14.1 | 13.5 | 14.9 | 15.2 | 15.7 | 14.4 |
| Plant height (cm) | 28 DAP | 14.57 | 13.99 | 15.35 | 15.67 | 15.8875 | 15.325 |
| Fresh Root Weight (g) | Wt (g) | 0.189 | 0.196 | 0.218 | 0.2056 | 0.245 | 0.222125 |
| Fresh Top Weight (g) | Wt (g) | 0.0879 | 0.0862 | 0.0993 | 0.1057 | 0.1135 | 0.108125 |
| Fresh Total Weight (g) | Wt (g) | 0.277 | 0.2828 | 0.3173 | 0.3113 | 0.3585 | 0.33025 |
| Dry Root Weight (g) | Wt (g) | 0.031 | 0.0291 | 0.0321 | 0.0335 | 0.036625 | 0.035875 |
| Dry Top Weight (g) | Wt (g) | 0.022 | 0.0211 | 0.0233 | 0.025 | 0.0275 | 0.0265 |
| Dry Total Weight (g) | Wt (g) | 0.053 | 0.0502 | 0.0554 | 0.0585 | 0.064125 | 0.062375 |

TABLE 21

Percent change over formulation control of germination percentage, plant height and weight in endophyte treated rice. DAP = Days after planting

| | | MIC-96038/MIC-19994, 10 CFU/seed, % change over formulation control | MIC-96038/MIC-19994, 10^2 CFU/seed, % change over formulation control | MIC-96038/MIC-19994, 10^3 CFU/seed, % change over formulation control | MIC-96038/MIC-19994, 10^4 CFU/seed, % change over formulation control | MIC-96038/MIC-19994, 10^5 CFU/seed, % change over formulation control |
|---|---|---|---|---|---|---|
| % Germination | 7 DAP | 11% | 11% | 11% | −11% | 0% |
| Plant height (cm) | 7 DAP | 0% | 8% | 8% | 3% | 3% |
| Plant height (cm) | 14 DAP | −2% | 10% | 12% | 20% | 8% |
| Plant height (cm) | 21 DAP | −4% | 6% | 8% | 11% | 2% |
| Plant height (cm) | 28 DAP | −4% | 5% | 8% | 9% | 5% |
| Fresh Root Weight (g) | Wt (g) | 4% | 15% | 9% | 30% | 18% |
| Fresh Top Weight (g) | Wt (g) | −2% | 13% | 20% | 29% | 23% |
| Fresh Total Weight (g) | Wt (g) | 2% | 15% | 12% | 30% | 19% |
| Dry Root Weight (g) | Wt (g) | −6% | 3% | 8% | 18% | 15% |
| Dry Top Weight (g) | Wt (g) | −5% | 5% | 13% | 24% | 20% |
| Dry Total Weight (g) | Wt (g) | −6% | 4% | 10% | 20% | 17% |

Example 10: Cultivation and of Endophyte-Treated Plants in Greenhouse Experiment 2

A sandy loam growth substrate was mixed in the greenhouse and consisting of 60% loam and 40% mortar sand (Northeast Nursery, Peabody, Mass.). Prior to mixing, loam was sifted through a ⅜" square steel mesh screen to remove larger particles and debris. Soybean seeds were treated with commercial fungicidal and insecticidal treatment CruiserMaxx® Vibrance (Syngenta, Basel, Switzerland) according to the manufacturer's instructions. Seeds were heterologously disposed with the endophyte formulations and formulation control (lacking any endophyte) as described in Example 14, untreated seeds (lacking formulation and endophyte) were also planted. Each pot was filled with 600 mL of its respective soil, watered with 200 mL of water and then, nine seeds were sown evenly spaced in each pot (in a 3x3 pattern). Soil was then overlaid atop the seeds (estimated average planting depth of 1 inch) and an additional 110 mL of water was added to moisten the overlaying soil substrate. The experimental design called for a completely randomized pattern of each treatment within each block/replicate. Environmental conditions were set at 12 h photoperiod, at 22/18 C temperature for day/night period and light intensity was set at 650 μMol $m^{-2}$ $s^{-1}$. Post-planting, the seeds were watered to maintain approximately 80% soil capacity. Above ground tissue was harvested from the experiment three weeks post-planting. The tissues from individual replicate treatments (pots) were pooled and placed in an unlined paper bag. All tissues were dried in an oven set to 85° C. for 3 days. Once completely dried, the shoot biomass of individual treatment replicates (pots) was weighed and recorded Results All Formulations tested in soybean resulted in a less than 5% change in dry shoot biomass. Formulation C2 was neutral (−0.09%). Formulations A2 and A4 had a slight negative effect on dry shoot biomass (−3.57% and −1.8%, respectively). The difference between formulation that had slight beneficial (B_2) and slight negative effect (A_2) was in concentrators of oil and Triton X-100. MIC-31593 was the best overall performer with the formulations tested in this experiment; the greatest effect was observed with "B_2 low dose", "A2 medium dose" and "C_2 low dose", in that order, with an increase of dry shoot biomass by 6.9%, 6.87% and 5.26%; respectively, compared to the control. MIC-33414 demonstrated the largest positive effect when paired with C_2 Formulation at "medium dose", followed by "A_2 medium dose", "A_2 high dose" and "A_2 low dose", in that order of magnitude, with an increase of dry shoot biomass by 6.52%, 5.27% and 3.96% and 3.23; respectively, compared to the non-treated control. MIC-96038 paired with Formulation A_fl, exhibited a slight increase in biomass at doses High and Low (2.05% and 4.25%, respectively).

TABLE 22

Dry shoot biomass of endophyte treated soybeans grown in sandy loam soil, using three different formulations

| MIC ID | Formulation | Dose | Average dry biomass (g) | % change over untreated | Standard deviation | Standard error of the mean |
|---|---|---|---|---|---|---|
| | Untreated control | | 1.19 | 0 | 0.1027 | 0.0236 |
| | Formulation control-A_2 | | 1.15 | −3.57 | 0.1485 | 0.0332 |
| | Formulation control-B_2 | | 1.22 | 2.88 | 0.1047 | 0.024 |
| | Formulation control-C_2 | | 1.19 | −0.09 | 0.0957 | 0.022 |
| | Formulation control-A_1 | | 1.2 | 0.76 | 0.1039 | 0.0245 |
| | Formulation control-A_4 | | 1.17 | −1.8 | 0.0899 | 0.0206 |

TABLE 22-continued

Dry shoot biomass of endophyte treated soybeans grown in sandy loam soil, using three different formulations

| MIC ID | Formulation | Dose | Average dry biomass (g) | % change over untreated | Standard deviation | Standard error of the mean |
|---|---|---|---|---|---|---|
| MIC-31593 | A_2 | low | 1.23 | 3.45 | 0.1082 | 0.0248 |
| | | medium | 1.27 | 6.87 | 0.1069 | 0.0245 |
| | | high | 1.24 | 3.9 | 0.1218 | 0.0279 |
| | B_2 | low | 1.27 | 6.9 | 0.0959 | 0.022 |
| | | medium | 1.23 | 3.12 | 0.1038 | 0.0238 |
| | | high | 1.2 | 0.47 | 0.1162 | 0.0267 |
| | C_2 | low | 1.25 | 5.26 | 0.1279 | 0.0301 |
| | | medium | 1.22 | 2.78 | 0.0872 | 0.0206 |
| | | high | 1.21 | 1.68 | 0.1079 | 0.0247 |
| MIC-96038 | A_1 | low | 1.24 | 4.25 | 0.1273 | 0.0292 |
| | | medium | 1.2 | 0.88 | 0.0776 | 0.0178 |
| | | high | 1.21 | 2.05 | 0.1117 | 0.0256 |
| MIC-33414 | A_2 | low | 1.23 | 3.23 | 0.1099 | 0.0252 |
| | | medium | 1.25 | 5.27 | 0.0985 | 0.0226 |
| | | high | 1.24 | 3.96 | 0.0903 | 0.0207 |
| | B_2 | low | 1.21 | 1.38 | 0.0716 | 0.0169 |
| | | medium | 1.22 | 2.2 | 0.1161 | 0.0266 |
| | | high | 1.21 | 1.58 | 0.084 | 0.0193 |
| | C_2 | low | 1.17 | −1.45 | 0.1148 | 0.0263 |
| | | medium | 1.27 | 6.52 | 0.1044 | 0.0246 |
| | | high | 1.18 | −0.6 | 0.1076 | 0.0247 |

Example 11: Cultivation and of Endophyte-Treated Plants in Greenhouse Experiment 3

A sandy loam growth substrate was mixed in the greenhouse and consisting of 60% loam and 40% mortar sand (Northeast Nursery, Peabody, Mass.). Prior to mixing, loam was sifted through a ⅜" square steel mesh screen to remove larger particles and debris. Soybean seeds were treated with commercial fungicidal and insecticidal treatment CruiserMaxx® Vibrance (Syngenta, Basel, Switzerland) according to the manufacturer's instructions. Seeds were heterologously disposed with the endophyte formulations and formulation control (lacking any endophyte) as described in Example 11, untreated seeds (lacking formulation and endophyte) were also planted. Endophyte treatments were applied to seed in two target doses: high (10^5 CFU/seed), medium (10^4 CFU/seed). Each pot was filled with 600 mL of its respective soil, watered with 200 mL of water and then, nine seeds were sown evenly spaced in each pot (in a 3×3 pattern). Soil was then overlaid atop the seeds (estimated average planting depth of 1 inch) and an additional 110 mL of water was added to moisten the overlaying soil substrate. The experimental design called for a completely randomized pattern of each treatment within each block/replicate. Environmental conditions were set at 12 h photoperiod, at 22/18 C temperature for day/night period and light intensity was set at 650 μMol $m^{-2}$ $s^{-1}$. Post-planting, the seeds grown in normal watering conditions were watered to maintain approximately 80% soil capacity and the seeds grown in drought conditions were watered to maintain approximately 40% soil capacity. Above ground tissue was harvested from the experiment three weeks post-planting. The tissues from individual replicate treatments (pots) were pooled and placed in an unlined paper bag. All tissues were dried in an oven set to 85° C. for 3 days. Once completely dried, the shoot biomass of individual treatment replicates (pots) was weighed and recorded.

TABLE 23

Dry shoot biomass of endophyte treated wheat seedlings grown in sandy loam soil under normal conditions

| Treatment | Average dry biomass (g) | % change over untreated | % change over formulation |
|---|---|---|---|
| Formulation control | 1.852 | −3.46 | 0 |
| Untreated control | 1.918 | 0 | 3.59 |
| MIC-96038 10^4 | 1.987 | 3.58 | 7.3 |
| MIC-96038 10^5 | 1.843 | −3.91 | -0.46 |
| MIC-96038/MIC-19994 10^4 | 1.945 | 1.43 | 5.07 |
| MIC-96038/MIC-19994 10^5 | 1.885 | −1.72 | 1.8 |
| MIC-19994 10^4 | 1.937 | 1.01 | 4.64 |
| MIC-19994 10^5 | 1.915 | −0.14 | 3.44 |

Example 12. Methods of Preparing Fungal Biomass and Treating Seeds for Field Experiments Preparation of Fungal Endophytes Preparation of molasses broth and potato dextrose agar: Molasses broth was prepared by dissolving 30 g molasses and 5 g yeast extract per liter deionized water in an autoclavable container and autoclaving (15 psi, 121° C.) for 45 min. Potato dextrose agar (PDA) plates were prepared by dissolving 39.0 g PDA powder per liter deionized water in an autoclavable container and autoclaving (15 psi, 121° C.) for 45 min. The agar was allowed to cool to 50-60° C., before pouring into sterile petri plates (30 mL per 90 mm plate).

Liquid biomass: All equipment and consumables were thoroughly sterilized and procedures performed in a biosafety cabinet. The inoculant is prepared by placing 1 plug from a cryopreserved stock on a fresh PDA plate, sealing the plate with Parafilm® and incubating at room temperature in the dark for 5-10 days. Then ~5×5 mm plugs were cut from the PDA plates and 10-12 plugs were transferred into flasks containing the sterile molasses broth, covered, secured in a shaker and incubated for at least 10 days with shaking at ~130 rpm. Then the culture was placed in a blender for 5 seconds and 1 mL of the blended was centrifuged and the supernatant was discarded and the pellet resuspended in 0.5 mL 1× Phosphate Buffered Saline (PBS) to generate inoculum.

Dry biomass: All equipment and consumables were thoroughly sterilized and procedures performed in a biosafety cabinet. The inoculant is prepared by placing 1 plug from a cryopreserved stock on a fresh PDA plate, sealing the plate with Parafilm® and incubating at room temperature in the dark for 5-10 days. Then ~5×5 mm plugs were cut from the PDA plates and 10-12 plugs were transferred into flasks containing the sterile molasses broth, covered, secured in a shaker and incubated for at least 10 days with shaking at ~130 rpm. In sterile conditions, the liquid culture was carefully decanted using 150 mm sterile filter paper on a sterilized Buchner funnel over a sterile flask. Once all liquid had passed through the funnel, the pellet was rinsed with sterile water until the filtrate ran clear. When dry, the pellet was transferred to a drying cabinet and dried until brittle. The pellet was then ground into a fine powder, and sample used to generate CFU counts.

Preparation of Sodium Alginate and Talc for Seed Treatments

A 2% weight/volume solution of sodium alginate for the seed coatings is prepared by the following method. An Erlenmeyer flask is filled with the appropriate volume of deionized water and warmed to 50 degrees Celsius on a heat plate with agitation using a stir bar. The appropriate mass of sodium alginate powder for the desired final concentration solution is slowly added until dissolved. The solution is autoclaved at 121 degrees Celsius at 15 PSI for 30 minutes to sterilize.

Talcum powder for the powdered seed coatings is prepared by the following method. Talcum powder is aliquoted into Ziploc bags or 50 mL Falcon tubes, and autoclaved in dry cycle (121 degrees Celsius at 15 PSI for 30 minutes) to sterilize.

Seeds were heterologously disposed to each endophyte according to the following seed treatment protocol.

Liquid formulation: The 2% sodium alginate solution prepared above added to the seeds at a rate of 15 ml per kg of seeds. Liquid fungal culture as prepared in Example 10 was added to the seeds at a rate of 8.3 ml per kg of seeds. Control treatments were prepared using equivalent volumes of sterile broth. The seeds were then agitated to disperse the solution evenly on the seeds.

Then 12.5 g of talc powder per kg of seed was added and the seeds were agitated to disperse the powder evenly on the seeds. Then 17 ml per kg of seed of Flo-Rite® 1706 (BASF, Ludwigshafen, Germany) was added and the seeds were agitated to disperse the powder evenly on the seeds. The final concentration of endophyte was targeted to be at least 10^4 CFU. Treated seeds were allowed to dry overnight in a well-ventilated space before planting.

Dry formulation: The 2% sodium alginate solution prepared above was added to the seeds at a rate of 20 ml per kg of seeds. Equal parts of the fungal powder prepared and the talc prepared in above were mixed. The solution is applied to the prepared seeds so that an equivalent of 12.5 g of fungal powder was applied per kg of seeds. Control treatments were prepared using equivalent volumes of talc. The seeds were then agitated to disperse the solution evenly on the seeds.

Then 17 ml per kg of seed of Flo-Rite® 1706 (BASF, Ludwigshafen, Germany) was added and the seeds were agitated to disperse the powder evenly on the seeds. The final concentration of endophyte was targeted to be at least 10^4 CFU. Treated seeds were allowed to dry overnight in a well-ventilated space before planting.

Heterologous Disposition of Endophytes on Soy or Peanut Seeds

Seeds were heterologously disposed to each endophyte according to the following seed treatment protocol.

Liquid formulation: The 2% sodium alginate solution prepared in Example 10 was added to the seeds at a rate of 8.3 ml per kg of seeds. Liquid fungal culture as prepared in Example 9 was added to the seeds at a rate of 8.3 ml per kg of seeds. Control treatments were prepared using equivalent volumes of sterile broth. The seeds were then agitated to disperse the solution evenly on the seeds.

Then 15 g per kg of seed of the talc powder prepared in Example 10 was added and the seeds were agitated to disperse the powder evenly on the seeds. Then 13.3 ml per kg of seed of Flo-Rite® 1706 (BASF, Ludwigshafen, Germany) was added and the seeds were agitated to disperse the powder evenly on the seeds. The final concentration of endophyte was targeted to be at least 10^4 CFU. Treated seeds were allowed to dry overnight in a well-ventilated space before planting.

Dry formulation: The 2% sodium alginate solution prepared in Example 10 was added to the seeds at a rate of 16.6 ml per kg of seeds. Equal parts of the fungal powder prepared in Example 9 and the talc prepared in Example 10 were mixed. The solution was applied so that an equivalent of 10 g of fungal powder was applied per kg of seeds. Control treatments were prepared using equivalent volumes of talc. The seeds were then agitated to disperse the solution evenly on the seeds.

Then 13.3 ml per kg of seed of Flo-Rite® 1706 (BASF, Ludwigshafen, Germany) was added and the seeds were agitated to disperse the powder evenly on the seeds. The final concentration of endophyte was targeted to be at least 10^4 CFU. Treated seeds were allowed to dry overnight in a well-ventilated space before planting.

Heterologous Disposition of Endophytes on Corn Seeds

Seeds were heterologously disposed to each endophyte according to the following seed treatment protocol.

Dry formulation: The 2% sodium alginate solution prepared as above was added to the seeds at a rate of 23 ml per kg of seeds. Equal parts of the fungal powder and the talc as prepared above were mixed. The solution was applied so that an equivalent of 10 g of fungal powder was applied per kg of seeds. Control treatments were prepared using equivalent volumes of talc. The seeds were then agitated to disperse the solution evenly on the seeds.

Then 16.6 ml per kg of seed of Flo-Rite® 1706 (BASF, Ludwigshafen, Germany) was added and the seeds were agitated to disperse the powder evenly on the seeds. The final concentration of endophyte was targeted to be at least 10^4 CFU. Treated seeds were allowed to dry overnight in a well-ventilated space before planting.

Heterologous Disposition of Endophytes on Rice

Seeds were treated with the commercial fungicidal and insecticidal product Sativa® IMF MAX (Nufarm Americas, Alsip, Ill.) per manufacturer's instructions (3.4 oz/cwt). Chemically treated rice seeds were heterologously disposed to each endophyte according to one of two different formulation protocols (Formulation Protocol A, Formulation Protocol B). A corresponding seed formulation control, lacking any endophyte, was also prepared included for each type of formulation. Further seeds lacking any formulation and endophyte were planted as a non-treated baseline control. Formulation A included only diluent 0.05% silwet and microbial preparations. Formulation B included the same diluent and the seed plantability polymer Flo Rite® 1706 applied at 2.0 oz/cwt seed per the manufacturer. Microbe and polymer were applied sequentially.

For endophytes formulated by Formulation Protocol A, microbial preparations were applied to the seeds at a rate of 14/seed and the seeds were agitated for at least 20 seconds to disperse the microbe.

For endophytes formulated by Formulation Protocol B, microbial preparations were applied to the seeds at a rate of 14/seed. Then Flo Rite® 1706 plantability polymer was applied to seeds per the manufacturer's suggestion (2.0 oz/cwt of seed) and agitated for 20 seconds to disperse the polymer.

Example 13: Cultivation of Endophyte-Treated Plants in Field Experiment 1

Assay of Seed Yield Under Field Conditions, Soy

Field trials were conducted under non-irrigated (dryland) conditions at multiple locations, preferably in diverse geographic regions. Seeds were prepared with the endophyte formulations as described in Example 12 and untreated seeds (lacking formulation and endophyte) were also planted. At the end of the field trial employing endophyte treatment and control treatment plants, plots were machine harvested with a 5-ft research combine and yield calculated by the on-board computer. Only the middle two rows of the 4 row plots were harvested to present border effects. Seeds were sown in regularly spaced rows in soil at 40,000 seeds/acre seeding density. At each location, at least 3 replicate plots were planted per endophyte or control treatment in a randomized complete block design. Each plot consisted of four 15.24 m (40 ft.) rows, each separated by 76.2 cm (30 in).

At the end of the field trial employing endophyte treatment and control treatment plants, plots were machine harvested with a 5-ft research combine and yield calculated by the on-board computer. Only the middle two rows of the 4 row plots were harvested to prevent border effects.

TABLE 24

Yield of treated endophyte treated soybeans and untreated and formulation controls, Field Experiment 1

| | Location 1 yield (bu/ac) | Location 2 yield (bu/ac) | Location 3 yield (bu/ac) | Location 4 yield (bu/ac) | Overall yield (bu/ac) | Overall % Δ untreated control | Overall % Δ formulation control |
|---|---|---|---|---|---|---|---|
| Condition | Severe water stress | Water stress | Good moisture, some weed pressure | Weed pressure | | | |
| Days between treatment and planting | 9 | 13 | 28 | 28 | | | |
| Untreated control | 27.7 | 68.4 | 61 | 41.6 | 49.7 | | −1.4 |
| Formulation control | 27.1 | 68.9 | 64.8 | 42.5 | 50.4 | 1.4 | 0 |
| MIC-31593 | 27.9 | 70.2 | 62.1 | 48 | 52.1 | 4.8 | 3.4 |
| MIC-96038 | 27 | 69.5 | 63.4 | 43.4 | 50.8 | 2.2 | 0.8 |
| MIC-33414 | 27.9 | 72 | 67.2 | 43.6 | 52.1 | 4.8 | 3.4 |
| Trial Average | 25.7 | 68.1 | 62.5 | 45.1 | 50.4 | | |

Assay of Seed Yield Under Field Conditions, Wheat

Field trials were conducted under non-irrigated (dryland) conditions at multiple locations, preferably in diverse geographic regions. Wheat seeds were treated with commercial fungicidal and insecticidal treatment. Seeds were heterologously disposed with the endophyte formulations described above in Example 12 and untreated seeds (lacking formulation and endophyte) were also planted. Seeds were sown in regularly spaced rows in soil at 1.2 million seeds/acre seeding density. At each location, at least 3 replicate plots were planted for each endophyte or control treatment in a randomized complete block design. Each plot consisted of seven, 15.24 m (40 ft.) rows.

At the end of the field trial employing endophyte treatment and control treatment plants, plots were machine harvested with a 5-ft research combine and yield calculated by the on-board computer.

TABLE 25

Average yield of endophyte treated spring wheat and untreated and formulation controls by location, Field Experiment 1

| | Location 1 yield (bu/ac) | Location 2 yield (bu/ac) | Location 3 yield (bu/ac) | Location 4 yield (bu/ac) | Overall yield (bu/ac) | Overall % Δ untreated control | Overall % Δ formulation control |
|---|---|---|---|---|---|---|---|
| Untreated control | 25.73 | 39.50 | 38.95 | 47.02 | 37.80 | | −2.0 |
| Formulation control | 29.72 | 41.76 | 35.15 | 48.17 | 38.57 | 2.0 | |

TABLE 25-continued

Average yield of endophyte treated spring wheat and untreated and formulation controls by location, Field Experiment 1

| | Location 1 yield (bu/ac) | Location 2 yield (bu/ac) | Location 3 yield (bu/ac) | Location 4 yield (bu/ac) | Overall yield (bu/ac) | Overall % Δ untreated control | Overall % Δ formulation control |
|---|---|---|---|---|---|---|---|
| MIC-96038 | 28.00 | 40.37 | 37.63 | 50.95 | 39.24 | 3.8 | 1.7 |
| Trial Average | 28.75 | 41.60 | 38.10 | 47.97 | 39.10 | | |

TABLE 26

Average yield of endophyte treated spring wheat and untreated and formulation controls by plant variety, Field Experiment 1

| | Variety 1, yield (bu/ac) | Variety 2, yield (bu/ac) | Variety 3, yield (bu/ac) | Variety 4, yield (bu/ac) | Overall yield (bu/ac) | Overall % Δ untreated control | Overall % Δ formulation control |
|---|---|---|---|---|---|---|---|
| Untreated | 24.83 | 26.63 | 40.96 | 42.69 | 37.80 | | −2.0 |
| Formulation control | 31.22 | 28.22 | 38.83 | 44.23 | 38.57 | 2.0 | |
| MIC-96038 | 32.54 | 23.46 | 42.60 | 43.37 | 39.24 | 3.8 | 1.7 |
| Variety Average | 30.62 | 28.44 | 40.77 | 43.95 | | | |

Assay of Seed Yield Under Field Conditions, Rice

Seeds were prepared with the endophyte formulations and formulation control (lacking any endophyte) as described in Example 12. Seeds were sown with a research sized grain drill at a planting rate of 45 pounds per acre. Four replicate, 30×175 ft plots were planted per endophyte or control treatment in a randomized complete block design. Plots were flooded, weeds and insects were controlled with local standard practices.

At the end of the field trial employing endophyte treatment and control treatment plants, plots were machine harvested with a 5-ft research combine and yield calculated by the on-board computer.

TABLE 27

Yield of treated endophyte rice and untreated controls, Field Experiment 1

| | % emergence | Grain moisture | Weight (lb/ bushel) | Yield (lb/ plot) | Yield (bushel/ acre) | % change over control |
|---|---|---|---|---|---|---|
| Control treatment | 65.3 | 19.33 | 43.95 | 16.405 | 119.6 | 0 |
| MIC-96038 + MIC-19994 | 67.8 | 18.88 | 41.33 | 17.165 | 125.9 | 5.27 |

Example 14: Cultivation of Endophyte-Treated Plants in Field Experiment 2

Assay of Seed Yield Under Field Conditions, Wheat

Field trials were conducted under non-irrigated (dryland) conditions. Two varieties of spring wheat seeds were treated with commercial fungicidal and insecticidal treatment. Seeds were heterologously disposed with the endophyte formulations and formulation control (lacking any endophyte) as described in Example 12, untreated seeds (lacking formulation and endophyte) were also planted. Seeds were sown in regularly spaced rows in soil at 1.2 million seeds/acre seeding density. At each location replicate plots were planted for each endophyte or control treatment in a randomized complete block design). Each plot consisted of seven, 15.24 m (40 ft.) rows.

At the end of the field trial employing endophyte treatment and control treatment plants, plots were machine harvested with a 5-ft research combine and yield and grain percent moisture were calculated by the on-board computer.

TABLE 28

Percent emergence of endophyte treated spring wheat and untreated and formulation controls by location, Field Experiment 2

| | Variety 1, % emergence | Variety 2, % emergence | Overall, % emergence | Overall % Δ untreated control | Overall % Δ formulation control |
|---|---|---|---|---|---|
| Untreated control | 98.3 | 96.7 | 97.5 | | −0.8 |
| Formulation control | 98.3 | 98.3 | 98.3 | 0.8 | |
| MIC-96038 | 98.3 | 98.3 | 98.3 | 0.8 | 0 |
| MIC-19994 | 98.3 | 93.3 | 95.8 | −1.7 | −2.5 |

TABLE 29

Grain moisture of endophyte treated spring wheat and untreated and formulation controls by location, Field Experiment 2

| | Variety 1, grain moisture (%) | Variety 2, grain moisture (%) | Overall, grain moisture (%) | Overall % Δ untreated control | Overall % Δ formulation control |
|---|---|---|---|---|---|
| Untreated control | 19.049 | 16.657 | 17.85 | | 1.0 |
| Formulation control | 19.397 | 15.970 | 17.68 | −0.9 | |
| MIC-96038 | 13.573 | 16.567 | 15.07 | −15.6 | −14.8 |
| MIC-19994 | 18.657 | 16.930 | 17.79 | −0.3 | 0.6 |

TABLE 30

Percent protein of endophyte treated spring wheat and untreated and formulation controls by location, Field Experiment 2

| | Variety 1, % protein | Variety 2, % protein | Overall, % protein | Overall % Δ untreated control | Overall % Δ formulation control |
|---|---|---|---|---|---|
| Untreated control | 14.55087 | 14.76347 | 14.657 | | 0.2 |
| Formulation control | 14.68427 | 14.56693 | 14.626 | −0.2 | |
| MIC-96038 | 14.90133 | 14.71067 | 14.806 | 1.0 | 1.2 |
| MIC-19994 | 14.30587 | 14.21200 | 14.259 | −2.7 | −2.5 |

TABLE 31

Yield of endophyte treated spring wheat and untreated and formulation controls by location, Field Experiment 2

| | Variety 1, yield (bu/acre) | Variety 2, yield (bu/acre) | Overall, yield (bu/acre) | Overall % Δ untreated control | Overall % Δ formulation control |
|---|---|---|---|---|---|
| Untreated control | 24.832 | 26.631 | 25.731 | | −13.3 |
| Formulation control | 31.172 | 28.217 | 29.694 | 15.4 | |
| MIC-96038 | 32.539 | 23.457 | 27.998 | 8.8 | −5.7 |
| MIC-19994 | 31.172 | 26.892 | 29.032 | 12.8 | −2.2 |

Example 15. Cultivation of Endophyte-Treated Plants in Field Experiment 3

Field trials were conducted in 2016, under non-irrigated (dryland) conditions. Wheat seeds were treated with commercial fungicidal and insecticidal treatment. Seeds were heterologously disposed with the endophyte formulations and formulation control (lacking any endophyte) as described in Example 12, untreated seeds (lacking formulation and endophyte) were also planted. Seeds were sown in regularly spaced rows in soil at 1.2 million seeds/acre seeding density. At each location replicate plots were planted for each endophyte or control treatment in a randomized complete block design). Each plot consisted of seven, 15.24 m (40 ft.) rows.

At the end of the field trial employing endophyte treatment and control treatment plants, plots were machine harvested with a 5-ft research combine and yield calculated by the on-board computer.

TABLE 32

Yield of endophyte treated wheat and untreated and formulation controls by location, field experiment 3

| | Variety 1, yield (bu/ac) | Variety 2, yield (bu/ac) | Variety 3, yield (bu/ac) | Variety 4, yield (bu/ac) | Overall, yield (bu/ac) | Overall % Δ untreated control | Overall % Δ formulation control |
|---|---|---|---|---|---|---|---|
| Untreated control | 27.9 | 27.4 | 39.8 | 43.2 | 34.6 | | −3.0 |
| Formulation control | 31.2 | 28.2 | 39.0 | 44.2 | 35.7 | 3.1 | |
| MIC-96038 | 32.5 | 23.5 | 42.6 | 43.4 | 35.5 | 2.7 | −0.4 |
| MIC-19994 | 31.2 | 26.9 | 40.4 | 43.9 | 35.6 | 3.0 | −0.1 |

Example 16. Assessment of Improved Plant Characteristics: Field Conditions

Assay of Seed Yield Under Field Conditions, Wheat

Field trials were conducted under non-irrigated (dryland) conditions at multiple locations, preferably in diverse geographic regions. Wheat seeds were treated with commercial fungicidal and insecticidal treatment. Seeds were heterologously disposed with the dry endophyte formulations as described in Example 12 and untreated seeds (lacking formulation and endophyte) were also planted. Seeds were sown in regularly spaced rows in soil at 1.2 million seeds/acre seeding density. At each location, at least 3 replicate plots were planted for each endophyte or control treatment in a randomized complete block design. Each plot consisted of seven, 15.24 m (40 ft.) rows.

At the end of the field trial employing endophyte treatment and control treatment plants, plots were machine harvested with a 5-ft research combine and yield calculated by the on-board computer.

The endophyte treatments, each comprising one of the following microbes: MIC-68390, MIC-68178, MIC-07010, MIC-31593, MIC-48747, MIC-96038, MIC-50414 or MIC-33414, resulted in average increases in yield of 7-16% in the wheat variety SDSU Focus. The endophyte treatments, each comprising one of the following microbes: MIC-68390, MIC-68178, MIC-07010, MIC-31593, MIC-48747, MIC-96038, MIC-50414 or MIC-33414, resulted in average increases in yield of 14-22% in the wheat variety SDSU Select.

TABLE 33

Average yield of wheat treated with endophytes in field trials

| | SDSU Focus, Variety 3 | | SDSU Select, Variety 4 | |
|---|---|---|---|---|
| | Average yield (BU/acre) | % difference Untreated | Average yield (BU/acre) | % difference Untreated |
| Untreated control | 36.9 | 0 | 37.7 | 0% |
| MIC-68390 | 39.3 | 7% | 45.0 | 19% |
| MIC-68178 | 40.9 | 11% | 46.1 | 22% |
| MIC-07010 | 41.1 | 11% | 43.9 | 16% |
| MIC-31593 | 42.1 | 14% | 44.3 | 18% |
| MIC-48747 | 42.8 | 16% | 44.1 | 17% |
| MIC-96038 | 42.6 | 15% | 43.4 | 15% |
| MIC-50414 | 40.0 | 8% | 45.7 | 21% |
| MIC-33414 | 41.6 | 13% | 42.9 | 14% |

Assay of Seed Yield Under Field Conditions, Corn

Field trials were conducted at multiple locations, preferably in diverse geographic regions. Plots were non-irrigated (dryland) or maintained with suboptimal irrigation at a rate to target approximately 25% reduction in yield. Seeds were prepared with the endophyte formulations (dry) and formulation control (dry, lacking any endophyte) as described in Example 12, untreated seeds (lacking formulation and endophyte) were also planted. Seeds were sown in regularly spaced rows in soil at planting densities typical for each region. At each location 3 replicate plots were planted per endophyte or control treatment in a randomized complete block design. Each plot consisted of four 15.24 m (40 ft.) rows, each separated by 76.2 cm (30 in).

At the end of the field trial employing endophyte treatment and control treatment plants, plots were machine harvested with a 5-ft research combine and yield calculated by the on-board computer. Only the middle two rows of the 4 row plots were harvested to prevent border effects.

The endophyte treatments, each comprising one of the following microbes: MIC-68390, MIC-48747, or MIC-33414, resulted in average increases in yield of 0.9-1.5% relative to formulation control and average increases in yield of 1.0-1.6% relative to the untreated control, in the corn variety Stine 9734.

TABLE 34

Average yield of corn variety Stine 9734 treated with endophytes in field trials

| | Stine 9734 Variety 2 | | |
|---|---|---|---|
| | Average yield (BU/acre) | % difference Formulation control | % difference Untreated control |
| Untreated | 185.5 | | 0.0% |
| Formulation control (dry) | 185.7 | 0.0% | |
| MIC-68390 | 187.4 | 0.9% | 1.0% |
| MIC-48747 | 187.7 | 1.1% | 1.2% |
| MIC-33414 | 188.5 | 1.5% | 1.6% |

Assay of Seed Yield Under Field Conditions, Soy

Field trials were conducted under non-irrigated (dryland) conditions at multiple locations, preferably in diverse geographic regions. Seeds were prepared with the endophyte formulations as described in Example 12 and untreated seeds (lacking formulation and endophyte) were also planted. MIC-68178 and MIC-33414 were formulated with the dry formulation; MIC-68390, MIC-07010, MIC-31593, MIC-48747, MIC-96038, and MIC-50414 were formulated with the liquid formulation.

Seeds were sown in regularly spaced rows in soil at 40,000 seeds/acre seeding density. At each location, at least 3 replicate plots were planted per endophyte or control treatment in a randomized complete block design. Each plot consisted of four 15.24 m (40 ft.) rows, each separated by 76.2 cm (30 in).

At the end of the field trial employing endophyte treatment and control treatment plants, plots were machine harvested with a 5-ft research combine and yield calculated by the on-board computer. Only the middle two rows of the 4 row plots were harvested to prevent border effects.

The endophyte treatments, each comprising one of the following microbes: MIC-68390 MIC-31593, or MIC-33414, resulted in average increases in yield of 1.5-6.2% in the soy variety Dairyland DSR1808R2Y. The endophyte treatments, each comprising one of the following microbes: MIC-68390, MIC-31593, or MIC-33414, resulted in average increases in yield of 1.5-6.2% in the soy variety Dairyland DSR1808R2Y. The endophyte treatments, each comprising one of the following microbes: MIC-68390, MIC-68178, MIC-07010, MIC-31593, MIC-48747, MIC-96038, MIC-50414, or MIC-33414, resulted in average increases in yield of 2.5-15% in the soy variety Pfister 38R25. The endophyte treatments, each comprising one of the following microbes: MIC-68390, MIC-68178, MIC-07010, MIC-31593, MIC-48747, MIC-50414, or MIC-33414, resulted in average increases in yield of 1.1-6% in the soy variety Stine 3920.

TABLE 35

Average yield of soy variety Dairyland DSR1808R2Y treated with endophytes in field trials

| | Dairyland DSR1808R2Y, Variety 1 | |
|---|---|---|
| | Average yield (pounds/acre) | % difference Untreated control |
| Untreated control | 33.9 | 0.0% |
| MIC-68390 | 35.1 | 3.5% |
| MIC-31593 | 34.4 | 1.5% |
| MIC-33414 | 36.0 | 6.2% |

TABLE 36

Average yield of soy variety Pfister 38R25 treated with endophytes in field trials

| | Pfister 38R25, Variety 2 | |
|---|---|---|
| Row Labels | Average yield (pounds/acre) | % difference Untreated control |
| Untreated control | 56.8 | 0% |
| MIC-68390 | 58.8 | 3.5% |
| MIC-68178 | 60.0 | 5.6% |
| MIC-07010 | 60.0 | 5.6% |
| MIC-31593 | 65.3 | 15.0% |
| MIC-48747 | 58.2 | 2.5% |
| MIC-96038 | 61.2 | 7.7% |
| MIC-50414 | 62.6 | 10.2% |
| MIC-33414 | 63.9 | 12.5% |

TABLE 37

Average yield of soy variety Stine 3920 treated with endophytes in field trials

| | Stine 3920, Variety 4 | |
|---|---|---|
| Row Labels | Average yield (pounds/acre) | % difference Untreated control |
| Untreated control | 56.9 | 0% |
| MIC-68390 | 58.4 | 2.6% |
| MIC-68178 | 59.7 | 4.9% |
| MIC-07010 | 58.9 | 3.5% |
| MIC-31593 | 60.3 | 6.0% |
| MIC-48747 | 57.5 | 1.1% |
| MIC-50414 | 57.5 | 1.1% |
| MIC-33414 | 60.2 | 5.8% |

Assay of Seed Yield Under Field Conditions, Canola

Field trials were conducted at multiple locations, preferably in diverse geographic regions. Plots were non-irrigated (dryland) or maintained with suboptimal irrigation at a rate to target approximately 25% reduction in yield. Canola seeds were treated with commercial fungicidal and insecticidal treatment. Seeds were prepared with the liquid endophyte formulations and liquid formulation control (lacking any endophyte) as described in Example 12 and untreated seeds (lacking formulation and endophyte) were also planted. At each location, at least 3 replicate plots were planted for each endophyte or control treatment in a randomized complete block design.

At the end of the field trial employing endophyte treatment and control treatment plants, plots were machine harvested with a 5-ft research combine and yield calculated by the on-board computer.

The endophyte treatments comprising MIC-85555 resulted in an average increase in yield of 0.3% relative to formulation control and an average increase in yield of 0.2% relative to the untreated control, in the canola variety Brett Young 5525. The endophyte treatments comprising MIC-50989 resulted in an average increase in yield of 8.2% relative to formulation control and an average increase in yield of 10.3% relative to the untreated control, in the canola variety NCC1015.

TABLE 38

Average yield of canola variety Brett Young 5525 treated with endophytes in field trials

| | Brett Young 5525, Variety 1 | | |
|---|---|---|---|
| | Average yield (pounds/acre) | % difference Formulation control | % difference Untreated control |
| Untreated | 1111.0 | | 0.0% |
| Formulation control (liquid) | 1109.5 | 0.0% | |
| MIC-85555 | 1112.7 | 0.3% | 0.2% |

TABLE 39

Average yield of canola variety NCC1015 treated with endophytes in field trials

| | NCC1015, Variety 2 | | |
|---|---|---|---|
| | Average yield (pounds/acre) | % difference Formulation control | % difference Untreated control |
| Untreated | 1120.3 | | 0.0% |
| Formulation control (liquid) | 1142.8 | 0.0% | |
| MIC-50989 | 1236.1 | 8.2% | 10.3% |

Assay of Seed Yield Under Field Conditions, Peanut

Field trials were conducted at multiple locations, preferably in diverse geographic regions. Plots were non-irrigated (dryland) or maintained with suboptimal irrigation at a rate to target approximately 25% reduction in yield. Peanut seeds were treated with commercial fungicidal and insecticidal treatment. Seeds were prepared with either the endophyte formulations and formulation control (lacking any endophyte) as described in Example 12 and untreated seeds (lacking formulation and endophyte) were also planted. MIC-68390 was formulated with both the dry and liquid formulation; MIC-50414, MIC-68178, and MIC-96038 were formulated with the liquid formulation. At each location, at least 3 replicate plots were planted for each endophyte or control treatment in a randomized complete block design.

At the end of the field trial employing endophyte treatment and control treatment plants, plots were machine harvested with a 5-ft research combine and yield calculated by the on-board computer.

In dry formulation, the endophyte treatments comprising MIC-68390 resulted in an average increase in yield of 9.1% relative to formulation control and an average increase in yield of 0.7% relative to the untreated control, in the peanut variety AT-9899. In liquid formulation, the endophyte treatments comprising MIC-50414 resulted in an average increase in yield of 3.8% relative to formulation control and an average increase in yield of 0.7% relative to the untreated control, in the peanut variety AT-9899. In liquid formulation, the endophyte treatments, each comprising one of the following microbes: MIC-68390 or MIC-68178, resulted in an average increase in yield of 4.1-4.5% relative to formulation control and an average increase in yield of 10.0-10.5% relative to the untreated control, in the peanut variety FloRun 107. However, in dry formulation, endophyte treatments comprising MIC-68390 resulted in an average decrease in yield of 6.3% in the peanut variety FloRun 107. In liquid formulation, the endophyte treatments, each comprising one of the following microbes: MIC-68390, MIC-68178, or MIC-96038, resulted in an average increase in yield of 0.2-3.6% relative to the formulation control and an average increase in yield of 6.4-10.0% relative to untreated control, in the peanut variety Georgia-06G. However, in dry formulation, endophyte treatments comprising MIC-68390 resulted in an average decrease in yield of 4.9% in the peanut variety Georgia-06G. In liquid formulation, the endophyte treatments comprising MIC-68390 resulted in an average increase in yield of 11.2% relative to formulation control and an average increase in yield of 4.9% relative to the untreated control, in the peanut variety Tamnut OL06. However, in dry formulation, endophyte treatments comprising MIC-68390 resulted in an average decrease in yield of 0.4% in the peanut variety Tamnut OL06.

TABLE 40

Average yield of peanut variety AT-9899 treated with endophytes in dry formulation in field trials

| | AT-9899, Variety 2 | | |
|---|---|---|---|
| | Average yield (pounds/acre) | % difference Formulation control | % difference Untreated control |
| Untreated control | 3567.8 | | 0.0% |
| Formulation control (dry) | 3294.0 | 0.0% | |
| MIC-68390 | 3592.7 | 9.1% | 0.7% |

TABLE 41

Average yield of peanut variety AT-9899 treated with endophytes in liquid formulation in field trials

| | AT-9899, Variety 2 | | |
|---|---|---|---|
| | Average yield (pounds/acre) | % difference Formulation control | % difference Untreated control |
| Untreated control | 3567.8 | | 0.0% |
| Formulation control (liquid) | 3459.9 | 0.0% | |
| MIC-50414 | 3592.7 | 3.8% | 0.7% |

TABLE 42

Average yield of peanut variety FloRun 107 treated with endophytes in liquid formulation in field trials

| | FloRun 107, Variety 3 | | |
|---|---|---|---|
| | Average yield (pounds/acre) | % difference Formulation control | % difference Untreated control |
| Untreated control | 4140.7 | | 0.0% |
| Formulation control (liquid) | 4375.1 | 0.0% | |
| MIC-68390 | 4555.7 | 4.1% | 10.0% |
| MIC-68178 | 4574.0 | 4.5% | 10.5% |

TABLE 43

Average yield of peanut variety Georgia-06G treated with endophytes in liquid formulation in field trials

| | Georgia-06G, Variety 4 | | |
|---|---|---|---|
| | Average yield (pounds/acre) | % difference Formulation control | % difference Untreated control |
| Untreated control | 4592.3 | | 0.0% |
| Formulation control (liquid) | 4876.3 | 0.0% | |
| MIC-68390 | 5053.2 | 3.6% | 10.0% |
| MIC-68178 | 4884.1 | 0.2% | 6.4% |
| MIC-96038 | 4966.5 | 1.9% | 8.2% |

TABLE 44

Average yield of peanut variety Tamnut OL06 treated with endophytes in liquid formulation in field trials

| | Tamnut OL06, Variety 5 | | |
|---|---|---|---|
| | Average yield (pounds/acre) | % difference Formulation control | % difference Untreated control |
| Untreated control | 4098.8 | | 0.0% |
| Formulation control | 3866.5 | 0.0% | |
| MIC-68390 | 4297.9 | 11.2% | 4.9% |

Example 17. Identification of Sequence Variants Across Core Genes

Phylogenomic analysis of whole genome sequences of endophytes can be used to identify distinguishing sequence variants. Sets of genes suitable for phylogenomic analysis as well as methods for identifying the same are well known in the art, for example Floutas et al. (2012) The Paleozoic origin of enzymatic lignin decomposition reconstructed from 31 fungal genomes. Science, 336(6089):1715-9. doi: 10.1126/science.1221748 and James T Y, Pelin A, Bonen L, Ahrendt S, Sain D, Corradi N, Stajich J E. Shared signatures of parasitism and phylogenomics unite Cryptomycota and microsporidia. Curr Biol. 2013; 23(16):1548-53. doi: 10.1016/j.cub.2013.06.057. Orthologous genes to the reference set are identified in protein data bases derived from the genome of each species. Orthologous genes can be identified in the genomes using methods well known including reciprocal best hits (Ward N, Moreno-Hagelsieb G. Quickly Finding Orthologs as Reciprocal Best Hits with BLAT, LAST, and UBLAST: How Much Do We Miss? de Crécy-Lagard V, ed. *PLoS ONE.* 2014; 9(7):e101850. doi:10.1371/journal.pone.0101850) and Hidden Markov Models (HMMs). The best hits are extracted and a multiple sequence alignment generated for each set of orthologous genes. The alignments are used to build phylogenetic trees using methods well known in the art including Bayesian inference and maximum likelihood methods, for example using software tools MrBayes (Huelsenbeck, J. P. & Ronquist (2001) MRBAYES: Bayesian inference of phylogenetic trees. Bioinformatics, 17(8):754-755) and RAxML (Stamatakis, A. (2014) RAxML version 8: a tool for phylogenetic analysis and post-analysis of large phylogenies. *Bioinformatics,* 30 (9): 1312-1313. doi: 10.1093/bioinformatics/btu033). Sequence variants which distinguish between closely related species are identified.

Example 18. Identification of Unique Genes in an Endophyte of Interest

Whole genome analysis of endophytes can be used to identify genes whose presence, absence or over or under representation ("differential abundance") are associated with desirable phenotypes. To identify genes with differential abundance in the genome of an endophyte of interest, protein sequences predicted from the genomes of the endophyte and closely related species compared in an all-vs-all pairwise comparison (for example, using BLAST) followed by clustering of the protein sequences based on alignment scores (for example, using MCL: Enright A. J., Van Dongen S., Ouzounis C. A. An efficient algorithm for large-scale detection of protein families. Nucleic Acids Research 30(7): 1575-1584 (2002)). Additional software tools useful for this analysis are well known in the art and include OMA, OrthoMCL and TribeMCL (Roth A C, Gonnet G H, Dessimoz C. Algorithm of OMA for large-scale orthology inference. BMC Bioinformatics. 2008; 9:518. doi: 10.1186/1471-2105-9-518, Enright A J, Kunin V, Ouzounis C A. Protein families and TRIBES in genome sequence space. Nucleic Acids Res. 2003; 31(15):4632-8; Chen F, Mackey A J, Vermunt J K, Roos D S. Assessing performance of orthology detection strategies applied to eukaryotic genomes. PLoS One. 2007; 2(4):e383). The protein clusters are queried to identify clusters with differential abundance of proteins derived from endophytes having desirable phenotypes. Proteins of these clusters define the unique properties of these endophytes, and the abundance of genes encoding these proteins may be used to identify endophytes of the present invention.

Having illustrated and described the principles of the present invention, it should be apparent to persons skilled in the art that the invention can be modified in arrangement and detail without departing from such principles. It is to be understood that while the invention has been described in conjunction with the detailed description thereof, the foregoing description is intended to illustrate and not limit the scope of the invention, which is defined by the scope of the appended claims. Other embodiments, advantages, and modifications are within the scope of the following claims.

I claim:

1. A synthetic composition comprising a soybean plant seed and an endophyte manually or mechanically disposed to the soybean plant seed, wherein the endophyte is a member of the genus *Acremonium* that is heterologous to the soybean plant seed and comprises the polynucleotide sequence as set forth in SEQ ID NO: 51, wherein the endophyte is manually or mechanically disposed to the soybean plant seed in an amount effective to colonize a soybean plant germinated from the synthetic composition and to improve a trait of agronomic importance, wherein said trait of agronomic importance is selected from the group consisting of increase in dry shoot biomass, increase in root area, and increase in yield in the soybean plant germinated from the inoculated soybean seed as compared to a reference soybean plant germinated from a reference soybean plant seed lacking the colonized endophyte of the genus *Acremonium* comprising the polynucleotide sequence as set forth in SEQ ID NO: 51, wherein the synthetic composition comprises an adherent comprising mineral oil, wherein said trait of agronomic importance further comprises increase in root length in said soybean plant germinated from said inoculated soybean seed as compared to said reference soybean plant, and wherein the effective amount is effective to increase average root length by at least 10% as measured by an in vitro seedling germination paper assay in a soybean plant seedling germinated from said inoculated soybean seed as compared to a soybean plant seedling germinated from said reference soybean plant seed lacking the colonized endophyte of the genus *Acremonium* comprising the polynucleotide sequence having 100% nucleotide sequence identity to the nucleotide sequence of SEQ ID NO: 51.

2. The synthetic composition of claim 1, wherein the improved trait of agronomic importance is conferred under normal watering conditions.

3. The synthetic composition of claim 1 further comprising a formulation that comprises one or more of the following: stabilizer, preservative, surfactant, a fungicide, a nematicide, a bactericide, an insecticide, an herbicide, or any combination thereof.

4. The synthetic composition of claim 1, wherein the synthetic composition is shelf-stable.

5. The synthetic composition of claim 1, wherein the trait of agronomic importance is an increase in yield.

6. The synthetic composition of claim 1, wherein the soybean plant is variety Pfister 38R25.

7. The synthetic composition of claim 1, wherein the in vitro seedling germination paper assay-comprises incubating the inoculated soybean plant seed in moistened germination paper at 60% relative humidity, 22 degrees Celsius day temperature, 18 degrees Celsius night temperature, and with 12 hours of light and 12 hours of dark periods for 4 days.

8. The synthetic composition of claim 7, wherein the incubating further comprises incubating within a covered sterile glass jar, and wherein incubation period comprises an additional seven days following uncovering of said glass jar.

9. The synthetic composition of claim 3, wherein the formulation comprises talc.

10. The synthetic composition of claim 1, wherein the amount effective to colonize the soybean plant is at least $10^3$ CFU/seed.

* * * * *

SEQUENCE LISTING

```
<160> NUMBER OF SEQ ID NOS: 71

<210> SEQ ID NO 1
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 1

agagtttgat ymtggctcag                                                  20


<210> SEQ ID NO 2
<211> LENGTH: 19
<212> TYPE: DNA
<213> ORGANISM: Artificial sequence
<220> FEATURE:
<223> OTHER INFORMATION: Synthetic Polynucleotide

<400> SEQUENCE: 2

ggttaccttg ttacgactt                                                   19


<210> SEQ ID NO 3
<211> LENGTH: 19
<212> TYPE: DNA
<213> ORGANISM: Artificial sequence
<220> FEATURE:
<223> OTHER INFORMATION: Synthetic Polynucleotide

<400> SEQUENCE: 3

gtgycagcmg ccgcggtaa                                                   19


<210> SEQ ID NO 4
<211> LENGTH: 20
<212> TYPE: DNA
<213> ORGANISM: Artificial sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t

<400> SEQUENCE: 4
```

ggactacnvg ggtwtctaat 20

<210> SEQ ID NO 5
<211> LENGTH: 22
<212> TYPE: DNA
<213> ORGANISM: Artificial sequence
<220> FEATURE:
<223> OTHER INFORMATION: Synthetic Polynucleotide

<400> SEQUENCE: 5
cttggtcatt tagaggaagt aa 22

<210> SEQ ID NO 6
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 6
gctgcgttct tcatcgatgc 20

<210> SEQ ID NO 7
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 7
gcatcgatga agaacgcagc 20

<210> SEQ ID NO 8
<211> LENGTH: 17
<212> TYPE: DNA
<213> ORGANISM: Artificial sequence
<220> FEATURE:
<223> OTHER INFORMATION: Synthetic Polynucleotide

<400> SEQUENCE: 8
tcctgaggga aacttcg 17

<210> SEQ ID NO 9
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 9
tgctggtagt gcgaatgaaa 20

<210> SEQ ID NO 10
<211> LENGTH: 19
<212> TYPE: DNA
<213> ORGANISM: Artificial sequence
<220> FEATURE:
<223> OTHER INFORMATION: Synthetic Polynucleotide

<400> SEQUENCE: 10
ctttcgggtt ccatcaggt 19

<210> SEQ ID NO 11
<211> LENGTH: 20
<212> TYPE: DNA
<213> ORGANISM: Artificial sequence -continued
<220> FEATURE:
<223> OTHER INFORMATION: Synthetic Polynucleotide

<400> SEQUENCE: 11
ctaccgcaag agcaactgtg 20

<210> SEQ ID NO 12
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 12
acttcctcct cctcctcctc 20

<210> SEQ ID NO 13
<211> LENGTH: 21
<212> TYPE: DNA
<213> ORGANISM: Artificial sequence
<220> FEATURE:
<223> OTHER INFORMATION: Synthetic Polynucleotide

<400> SEQUENCE: 13
gtcctcgcct aatcaggagt c 21

<210> SEQ ID NO 14
<211> LENGTH: 21
<212> TYPE: DNA
<213> ORGANISM: Artificial sequence
<220> FEATURE:
<223> OTHER INFORMATION: Synthetic Polynucleotide

<400> SEQUENCE: 14
tcctattccc tgacgtgcta c 21

<210> SEQ ID NO 15
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 15
gaggaggagg aggagaggtt 20

<210> SEQ ID NO 16
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 16
cgtccgtctc ccagactatt 20

<210> SEQ ID NO 17
<211> LENGTH: 19
<212> TYPE: DNA
<213> ORGANISM: Artificial sequence
<220> FEATURE:
<223> OTHER INFORMATION: Synthetic Polynucleotide

<400> SEQUENCE: 17
atgtgcaagg ccggtttcg 19

<210> SEQ ID NO 18
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 18
tacgagtcct tctggcccat 20

<210> SEQ ID NO 19
<211> LENGTH: 28
<212> TYPE: DNA
<213> ORGANISM: Artificial sequence
<220> FEATURE:
<223> OTHER INFORMATION: Synthetic Polynucleotide

<400> SEQUENCE: 19
tcgcgttcgt taacaaaatg gaccgtat 28

<210> SEQ ID NO 20
<211> LENGTH: 28
<212> TYPE: DNA
<213> ORGANISM: Artificial sequence
<220> FEATURE:
<223> OTHER INFORMATION: Synthetic Polynucleotide

<400> SEQUENCE: 20
tcgccagacg gcccagagcc agacccat 28

<210> SEQ ID NO 21
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 21
gartgyccdg gdcayttygg 20

<210> SEQ ID NO 22
<211> LENGTH: 23
<212> TYPE: DNA
<213> ORGANISM: Artificial sequence
<220> FEATURE:
<223> OTHER INFORMATION: Synthetic Polynucleotide
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 22
ccngcdatnt crttrtccat rta 23

<210> SEQ ID NO 23
<211> LENGTH: 17
<212> TYPE: DNA
<213> ORGANISM: Artificial sequence
<220> FEATURE:
<223> OTHER INFORMATION: Synthetic Polynucleotide

<400> SEQUENCE: 23
acccgctgaa cttaagc 17

<210> SEQ ID NO 24
<211> LENGTH: 17
<212> TYPE: DNA
<213> ORGANISM: Artificial sequence
<220> FEATURE:
<223> OTHER INFORMATION: Synthetic Polynucleotide

<400> SEQUENCE: 24
tcctgaggga aacttcg 17

<210> SEQ ID NO 25
<211> LENGTH: 23
<212> TYPE: DNA
<213> ORGANISM: Artificial sequence
<220> FEATURE:
<223> OTHER INFORMATION: Synthetic Polynucleotide

<400> SEQUENCE: 25
cccatrgcyt gyttmcccat dgc 23

<210> SEQ ID NO 26
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 26
gaygaymgwg atcayttygg 20

<210> SEQ ID NO 27
<211> LENGTH: 19
<212> TYPE: DNA
<213> ORGANISM: Artificial sequence
<220> FEATURE:
<223> OTHER INFORMATION: Synthetic Polynucleotide

<400> SEQUENCE: 27
gtagtcatat gcttgtctc 19

<210> SEQ ID NO 28
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 28
cttccgtcaa ttcctttaag 20

<210> SEQ ID NO 29
<211> LENGTH: 21
<212> TYPE: DNA
<213> ORGANISM: Artificial sequence
<220> FEATURE:
<223> OTHER INFORMATION: Synthetic Polynucleotide
<220> FEATURE:
<221> NAME/KEY: misc_feature
<222> LOCATION: (13)..(13)
<223> OTHER INFORMATION: n is Queuosine

<400> SEQUENCE: 29
tacctggttg atnctgccag t 21

<210> SEQ ID NO 30

<211> LENGTH: 23
<212> TYPE: DNA
<213> ORGANISM: Artificial sequence
<220> FEATURE:
<223> OTHER INFORMATION: Synthetic Polynucleotide

<400> SEQUENCE: 30
gtbcacctyc araccggyca rtg 23

<210> SEQ ID NO 31
<211> LENGTH: 26
<212> TYPE: DNA
<213> ORGANISM: Artificial sequence
<220> FEATURE:
<223> OTHER INFORMATION: Synthetic Polynucleotide

<400> SEQUENCE: 31
ccrgaytgrc craaracraa gttgtc 26

<210> SEQ ID NO 32
<211> LENGTH: 17
<212> TYPE: DNA
<213> ORGANISM: Artificial sequence
<220> FEATURE:
<223> OTHER INFORMATION: Synthetic Polynucleotide

<400> SEQUENCE: 32
gtygayttca aygtycc 17

<210> SEQ ID NO 33
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 33
acaccdggdg grccgttcca 20

<210> SEQ ID NO 34
<211> LENGTH: 22
<212> TYPE: DNA
<213> ORGANISM: Artificial sequence
<220> FEATURE:
<223> OTHER INFORMATION: Synthetic Polynucleotide

<400> SEQUENCE: 34
cttccaggca tagtaatgtg ga 22

<210> SEQ ID NO 35
<211> LENGTH: 23
<212> TYPE: DNA
<213> ORGANISM: Artificial sequence
<220> FEATURE:
<223> OTHER INFORMATION: Synthetic Polynucleotide

<400> SEQUENCE: 35
acttccacta ccatgagcaa ttc 23

<210> SEQ ID NO 36
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 36
ctcctcctcc tcctcctgat 20

<210> SEQ ID NO 37
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 37
tcacagagct acgcgacttg 20

<210> SEQ ID NO 38
<211> LENGTH: 1440
<212> TYPE: DNA
<213> ORGANISM: Coniochaeta prunicola

<400> SEQUENCE: 38
tcttggtcat ttagaggaag taaaagtcgt aacaaggtct ccgttggtga accagcggag 60
ggatcattac aagaagccga aaggctactt caaaccatcg tgaacttatc caagttgctt 120
cggcggcgcg gctcccctcg cggggtgccg cagccccgcc ccctcggggg tggtgggcgc 180
ccgccggagg tattaaactc tcccgtatta tagtggtatt tctgagtaaa aacaaataag 240
ttaaaacttt caacaacgga tctcttggtt ctggcatcga tgaagaacgc agcgaaatgc 300
gataagtaat gtgaattgca gaattcagtg aatcatcgaa tctttgaacg cacattgcgc 360
ccgctagtat tctagcgggc atgcctgttc gagcgtcatt tcaaccctca agccctgctt 420
ggtgttgggg ccctacggct gccgtaggcc ctgaaaagaa gtggcgggct cgctgcaact 480
ccgagcgtag taattcatta tctcgctagg gaggcgcggc ggtgctcctg ccgttaaaga 540
ccatctttaa ccaaaggttg acctcggatc aggtaggaat acccgctgaa cttaagcata 600
tcaataagcg gaggaaaaga aaccaacagg gattgcccta gtaacggcga gtgaagcggc 660
aacagctcaa atttgaaatc tggcttcggc ccgagttgta atttgtagag gatgcttttg 720
gtgaggtgcc ttctgagttc cctggaacgg gacgccagag agggtgagag ccccgtatag 780
tcggccaccg atcctctgta aagctccttc gacgagtcga gtagtttggg aatgctgctc 840
aaaatgggag gtatatctct tctaaagcta aatataggcc agagaccgat agcgcacaag 900
tagagtgatc gaaagatgaa aagcactttg aaaagagggt taaatagcac gtgaaattgt 960
tgaaagggaa gcgcttgtga ccagacttgc gccgggctga tcatccagtg ttctcactgg 1020
tgcactcgac ccggctcagg ccagcgtcgg ttctcgcagg gggataaaag cttcgggaac 1080
gtggcacctt cgggtgtgtt atagcccgct gcttaatacc ccggtgggga ccgaggttcg 1140
cgctctgcaa ggacgctggc ataatggtca tcagcgaccc gtcttgaaac acggaccaag 1200
gagtcgaggt tttgcgcgag tgtttgggtg taaaacccgc acgcgtaatg aaagtgaacg 1260
taggtgagag cttcggcgca tcatcgaccg atcctgatgt attcggatgg atttgagtaa 1320
gagcgtatag cctcggaccc gaaagatggt gaactatgcc tgaatagggg gaagccagag 1380
gaaactctgg tggaggctcg cagcggttct gacgtgcaaa tcgatcgtca aatttgggca 1440

<210> SEQ ID NO 39
<211> LENGTH: 922
<212> TYPE: DNA
<213> ORGANISM: Coniochaeta prunicola

<400> SEQUENCE: 39

-continued

```
tcctgaggga aacttcggcg gtaaccagct actagatggt tcgattagtc tttcgccccc     60

atgcccaaat ttgacgatcg atttgcacgt cagaaccgct gcgagcctcc accagagttt    120

cctctggctt caccctattc aggcatagtt caccatcttt cgggtccgag gctatacgct    180

cttactcaaa tccatccgaa tacatcagga tcggtcgatg atgcgccgaa gctctcacct    240

acgttcactt tcattacgcg tgcgggtttt acacccaaac actcgcgcaa aacctcgact    300

ccttggtccg tgtttcaaga cgggtcgctg atgaccatta tgccagcgtc cttgcagagc    360

gcgaacctcg gtccccacag gggtattaag cagcgggcta taacacaccc gaaggtgcca    420

cgttccccgaa gcttttatcc ccctgcgaga accgacgctg gcctgagccg ggtcgagtgc    480

accagtgaga acactggatg atcagcccgg cgcaagtctg gtcacaagcg cttccctttc    540

aacaatttca cgtgctattt aaccctcttt tcaaagtgct tttcatcttt cgatcactct    600

acttgtgcgc tatcggtctc tggcctatat ttagctttag aagagatata cctcccattt    660

tgagcagcat tcccaaacta ctcgactcgt cgaaggagct ttacagagga tcggtggccg    720

actatacggg gctctcaccc tctctggcgt cccgttccag ggaactcaga aggcacctca    780

ccaaaagcat cctctacaaa ttacaactcg ggccgaagcc agatttcaaa tttgagctgt    840

tgccgcttca ctcgccgtta ctagggcaat ccctgttggt ttcttttcct ccgcttattg    900

atatgcttaa gttcagcggg ta                                             922
```

<210> SEQ ID NO 40
<211> LENGTH: 1151
<212> TYPE: DNA
<213> ORGANISM: Coniochaeta prunicola

<400> SEQUENCE: 40

```
cttccgtcaa tttctttaag tttcagcctt gcgaccatac tccccccaga acccagaaac     60

tttactttcg tgtaaggtgc cgaacgagtc aaaatataac atcgtccgat ccctagtcgg    120

catagtttat ggttaagact acgacggtat ctgatcgtct tcgatcccct aactttcgtt    180

cctgattaat gaaaacatcc ttggcaaatg ctttcgcagt agttagtctt caataaatcc    240

aagaatttca cctctgacaa ttgaatactg atgcccccga ctgtccctat taatcattac    300

ggcggtccta gaaaccaaca aaatagaacc acacgtccta ttctattatt ccatgctaat    360

gtattcgagc ataggccttc tttaagcgat ctaatttgtt caaagtaaaa gtcctggttc    420

cccgacacac ccagtgaagg gcatgcggtt ccccagaggg aaaggcccgg ccggaccagt    480

gcacgcggtg aggcggaccg gccagccagg cccaaggttc aactacgagc tttttaactg    540

caacaacttt aatatacgct attggagctg gaattaccgc ggctgctggc accagacttg    600

ccctccaatt gttcctcgtt aagggattta aattgtactc attccaatta caagacccaa    660

aagagccctg tatcagtatt tattgtcact acctccccga atcgggattg ggtaatttgc    720

gcgcctgctg ccttccttgg atgtagtagc cgtttctcag gctccttctc cggggtcgag    780

ccctaaccct ccgttacccg ttgtcaccat ggctggccaa gacccagccg tcgaaagttg    840

atagggcaga aatttgaatg aaccatcgcc ggcgcaaggc cgtgcgattc gagaagttat    900

tatgaatcac cagagagccc cgaagggcat tggtttttaa tctaataaat acatcccttc    960

cgaagtcggg atttttagca tgtattagct ctagaattac cacggttatc caagtagtaa   1020

ggtactatca aataaacgat aactgattta atgagccatt cgcagtttcg cggtataatt   1080

gcttatactt agacatgcat ggcttaatct ttgagacaag catatgacta ctggcagaat   1140

caaccaggta a                                                        1151
```

<210> SEQ ID NO 41
<211> LENGTH: 604
<212> TYPE: DNA
<213> ORGANISM: Coniochaeta prunicola

<400> SEQUENCE: 41
tgctggtagt gcgaatgaaa atggctggtt ccaggatata acgggtaatc gactgcactt 60
taacaaggct atgcgagtac tttgcgacca tggtcttgca gaagcagatc cgccgacgaa 120
agagcacggt tcggagtctg gagggtacag tgtgcacgga tgtgtgcact cctggatggt 180
aaacgtcctc aaccagacag gagatgcgga gatggcacgt ctggctttga ggtgtgtggc 240
tagccatgtg ccaagcacgg aggagggtga gtattggcgg gtacagcggc gcctccttct 300
gcacgcagac caatgcttga aattgatgga agagggtcag gaggaggaag gcaatggatg 360
ggtattccat aatctaggag atctctacaa agcccaaggg cggttcaagg aagcagaagc 420
catgtacgag cgggcgcttc gaggcaagga gaaggcatgg ggaccagacc acacgtcgac 480
actcgacaca gtcaacaatc tgggtctcgt cgccgacaac aaagccagcc acaccaaaca 540
tcaagttcca ttctcgttcc ccgtctttgt cgtgtggcag acaaaacctg atggaacccg 600
aaag 604

<210> SEQ ID NO 42
<211> LENGTH: 1428
<212> TYPE: DNA
<213> ORGANISM: Curvularia spicifera

<400> SEQUENCE: 42
aggtgaacct gcggagggat cattacacaa taaaatacga aggccgttcg cggctggact 60
atttattacc cttgtctttt gcgcacttgt tgtttcctgg gcgggttcgc tcgccaccag 120
gaccacaata taaacctttt ttatgcagtt gcaatcagcg tcagtataac aaatgtaaat 180
catttacaac tttcaacaac ggatctcttg gttctggcat cgatgaagaa cgcagcgaaa 240
tgcgatacgt agtgtgaatt gcagaattca gtgaatcatc gaatctttga acgcacattg 300 cgcccctttgg tattccaaag ggcatgcctg ttcgagcgtc atttgtaccc tcaagctttg 360
cttggtgttg ggcgtttttg tctttggccc gccaaagact cgccttaaaa tgattggcag 420
ccggcctact ggtttcgcag cgcagcacat ttttgcgctt gcaatcagca aaagaggacg 480
gcaatccatc aagactcctt ctcacgtttg acctcggatc aggtagggat acccgctgaa 540
cttaagcata tcaataagcg gaggaaaaga aaccaacagg gattgcccta gtaacggcga 600
gtgaagcggc aacagctcaa atttgaaatc tggctctttc agagtccgag ttgtaatttg 660
cagagggcgc tttggctttg gcagcggtcc aagttccttg gaacaggacg tcacagaggg 720
tgagaatccc gtacgtggtc gctagctatt gccgtgtaaa gccccttcga cgagtcgagt 780
tgtttgggaa tgcagctcta aatgggaggt aaatttcttc taaagctaaa tattggccag 840
agaccgatag cgcacaagta gagtgatcga aagatgaaaa gcactttgga aagagagtca 900
aacagcacgt gaaattgttg aaagggaagc gcttgcagcc agacttgctt gcagttgctc 960
atccgggctt ttgcccggtg cactcttctg caggcaggcc agcatcagtt tgggcggtgg 1020
gataaaggtc tctgtcacgt accttccttc gggttggcct tataggggag acgccatacc 1080
accagcctgg actgaggtcc gcgcatctgc taggatgctg gcgtaatggc tgtaagcggc 1140
ccgtcttgaa acacggacca aggagtctaa catctatgcg agtgtttggg tgtcaagccc 1200

-continued

```
gagcgcgtaa tgaaagtgaa cggaggtggg aacccgcaag ggtgcaccat cgaccgatcc   1260

tgaagtttac ggaaggattt gagtaagagc atggctgttg ggacccgaaa gatggtgaac   1320

tatgcttgaa tagggtgaag ccagaggaaa ctctggtgga ggctcgcagc ggttctgacg   1380

tgcaaatcga tcgtcaaatt tgggcatagg ggcgaaagac taatcgaa               1428
```

<210> SEQ ID NO 43
<211> LENGTH: 1197
<212> TYPE: DNA
<213> ORGANISM: Curvularia spicifera

<400> SEQUENCE: 43

```
cccatagctt gcttacccat agcagattgg tatgtgttac ggggcgactg gttgtgatct     60

gggaagggaa tgatactggc gcaaataccc aagatcatag ctgggtgaat ctcacaatgg    120

gtgtaggcgt ggatgcgagg atccggtagt ggcttgagac ggcggagtcg atccttgcct    180

tcagtagatc gctcagctgc aggcaagccc atcttcattt ctcgccattc ttccaagtcc    240

tcgggagaga atgttatcat tgcagtttct tcttcctcgg catcgaggta ttcaacgaca    300

ccgtcttgaa tgagacctct ccagccgtat gtagcctgct cgacttcctc ttgactccag    360

ccttgtcttg tactggtctc ttgctgttca gccttgagct tgttgctgat ttccttggta    420

aagatgaggt ggttccggtt tggctttcga atatcgtttt ctacaacgaa caaaggcctc    480

atgacacgac ccgcatctgt gaatatcttg aactctctgt cgcgaatatc acgaatcaaa    540

ctcatctcgt aagacagagt accattgcgg cgaagctcct gcacgactgt gacaagctgc    600

tgagcatttg aatgaacacc aacccagaca ccgttaacga agaccttggt cgcatccggg    660

ttctggttct ggtcgtactc ctcgagaagt tgcatgttac gttgtgtcat gaagtcgata    720

atgggcgatg catcgctacc aacactgaca taacacataa gagacaagtt cttgaccaga    780

ccgcaagcct gtccttcggg cgtctcagca gggcagacaa gaccccaatg agagttgtga    840

agctgtcgcg gctttgccaa cttaccatca cgtccaacgg gggtgttcgt tcgacgcaga    900

tgggatagtg tggaggcata ggtgtatcgg ttcaacacct gcgaaacacc agccttggca    960

gatgcagcct tcttctgatc accccaattg cctgtagcca gagagtactt caggccgttt   1020

gtgatgatgc tggctttcac agccatttga acattgaagt cttggttgtt ttccacgcac   1080

cgctggaggt acttgtagac atccttggtg agcttcagga acaagattcg gaacaagttg   1140

gcaatcagag gtccagccag atctagtcgc ttctttccaa agtgatcacg atcgtcc      1197
```

<210> SEQ ID NO 44
<211> LENGTH: 387
<212> TYPE: DNA
<213> ORGANISM: Curvularia spicifera

<400> SEQUENCE: 44

```
gttcacctcc agaccggtca atgcgtaagt ctcgcgccgc ctgaaaacac cacgggaacg     60

actgctaaca gccgctacag ggtaaccaaa ttggtgccgc cttctggcag accatttccg    120

gcgagcatgg cctcgacggc tctggtgtct acaacggcac ctctgacctt cagctcgagc    180

gcatgaacgt ctacttcaac gaagtacgtc cctcggtgaa gctccaacag acaaaagacc    240

aatactgatg tgcagcaggc ttccaacaac aagttcgtgc cccgtgccgt cctcgtcgat    300

ctcgagcctg gtactatgga cgctgtccgc gctggtccct ttggtcagct cttccgcccc    360

gacaacttcg tcttcggcca gtcgggt                                       387
```

-continued

<210> SEQ ID NO 45
<211> LENGTH: 590
<212> TYPE: DNA
<213> ORGANISM: Curvularia spicifera

<400> SEQUENCE: 45
ctaccgcaag agcaactgtg caagtccagc ttcagtccct ttcgatcccc ctcgcccagg 60
aagagattca cccacgagcg caaccagtcc gaggcggtcc agcgtccacg tcctatgagc 120
gtttgcagca actcgccagc agttcagcac accaaaagag cctccatcta cgtctccgac 180
gcttccatca tcctagcgca acgctcaccc atggcttctc cggtttcccc accagactcc 240
atgtcctccc ccatccatga atcgtctgat gccgtcgacc actatgctat cctggagatc 300
acccctagag caactaccga tgaggtcaag gctgcctacc gccgactacg ggtcgtctac 360
ttctcaagtg acgcgaagaa gtaccgagca ctgcaggcgg ccttcgacgt cttgatggac 420
ccgcaatccc gcgaagctta cgacgcaacc tatcaaccaa ctgccgcagc accagtatcg 480
ctcgctagca ttggtgagat cctggactcg gggaagctat ggcgacagga cagcgcccac 540
ggagacgacc cagtaatccc agaagaggaa gaggaggagg aggaggaagt 590

<210> SEQ ID NO 46
<211> LENGTH: 1458
<212> TYPE: DNA
<213> ORGANISM: Acremonium alternatum

<400> SEQUENCE: 46
tcttggtcat ttagaggaag taaaagtcgt aacaaggtct ccgttggtga accagcggag 60
ggatcattac cgagtgtaaa aactcccaaa ccattgtgaa cttaccactg ttgcttcggc 120
ggcctcgccc cgggcgcgtt cgcgcggccc ggacccaggc gtccgccgga ggctccaaac 180
tcttgtcttt tagtgtattt ctgagtggca taagcaaata aatcaaaact ttcagcaacg 240
gatctcttgg ttctggcatc gatgaagaac gcagcaaaat gcgataagta atgtgaattg 300
cagaattcag tgaatcatcg aatctttgaa cgcacattgc gcccgccagt attctggcgg 360
gcatgcctgt ctgagcgtca tttcaaccct caggacccgt tcgcgggacc tggcgttggg 420
gatcagcctg cccctggcgg cggctggccc tgaaatccag tggcggttcc ctcgcgaact 480
cctccgtgca gtaattaaac ctctcgcggc aggatagcgg ttgaaccacg ccgttaaacc 540
ccccacttct caaggttgac ctcagatcag gtaggaatac ccgctgaact taagcatatc 600
aataagcgga ggaaaagaaa ccaacaggga ttgccctagt aacggcgagt gaagcggcaa 660
cagctcaaat ttgaaatctg gcctcacggt ccgaattgta atttgtagag gatgtttctg 720
gcgacgtgtc ttccgagttc cctggaacgg gacgccatag agggtgagag ccccgtccgg 780
tcgtacacct agcctctgtg aaactccttc gacgagtcga gtagtttggg aatgctgctc 840
taaatgggag gtatacgtct tctaaagcta aataccggcc agagaccgat agcgcacaag 900
tagagtgatc gaaagatgaa aagcactttg aaaagagggt taaatagtac gtgaaattgc 960
tgaaagggaa gcgcttatga ccagacttgg gctcggtgaa tcatccggcg ttctcgccgg 1020
tgcactttgc cgtcccaggc cagcatcagt tcgcgccggg ggataaaggt ttcgggaatg 1080
tagctccttc gggagtgtta tagcccgttg cgtaataccc tggcgtggac tgaggtccgc 1140
gctctgcaag gatgctggcg taatggtcat cagtgacccg tcttgaaaca cggaccaagg 1200
agtcgtcttc gtatgcgagt gttcgggtgt caaaccccta cgcgtaatga aagtgaacgt 1260
aggagagagc ttcggcgcat ctccgaccga tcctgatgtt ctcggatgga tttgagtaag 1320
agcatacggg gccggacccg aaagaaggtg aactatgcct gtatagggtg aagccagagg 1380
aaactctggt ggaggctcgc agcggttctg acgtgcaaat cgatcgtcaa atatgggcat 1440
gggggcgaaa gactaatc 1458

<210> SEQ ID NO 47
<211> LENGTH: 290
<212> TYPE: DNA
<213> ORGANISM: Acremonium alternatum

<400> SEQUENCE: 47
atgtgcaagg ccggtttcgc cggtgacgat gctccccgag ctgttttccg taagtcaacc 60
ccactttcgc ttcccaagct cctaatcgcc cacacctggc gatatgggct ttgggggcct 120
gtaagcagcc gacacaagac taacgcgatg cgccagcttc cattgtcggt cgcccccgtc 180
accatgggta agtacgcgcg caaatgacac ctgtcagccc cctcgacgag cggcacaggc 240
tctgaccatt cgatagtatc atgattggta tgggacagaa ggactcgtac 290

<210> SEQ ID NO 48
<211> LENGTH: 380
<212> TYPE: DNA
<213> ORGANISM: Acremonium alternatum

<400> SEQUENCE: 48
ccggactggc cgaagacgaa gttgtcggga cggaagagct gaccgaaagg accggcgcgg 60
acggcatcca tggtaccggg ctcgagatcg acgaggacag cgcgaggaac gtacttgttg 120
ccagaggcct acagagggtc agcttggcca cagactgcgg gatactccaa attgctcacc 180
tcgttgaagt agacgctcat gcgctcgagc tggagctcag aggtgccgtt gtagacaccg 240
ttgctgtcga ggccatgctc gccagagatg gtctgccaga aggcagcacc aatctggtta 300
ccctgctcgg aggttagaca tggtaggcga tatcacatat ggcggaagta cttacgcact 360
gaccggtctg gaggtgaacc 380

<210> SEQ ID NO 49
<211> LENGTH: 1231
<212> TYPE: DNA
<213> ORGANISM: Acremonium alternatum

<400> SEQUENCE: 49
gatgatcgtg atcacttcgg gaaaaagcgc cttgacctgg ctgggcccct cttagctaaa 60
ttgttccgca acattattcg caggatcaac aacgagctgt cgacctacct caggcgatgt 120
gtcgagggcg gcaggaactt caacctcgct gtcggcatca agcctggcac actgtcgaac 180
gggttgaagt actctttggc aacaggcaac tggggagacc aaaagaaggc aatgagctcg 240
gttgctggag tgtcccaggt tctcaaccgc tacacatttg cgtcaacctt gtctcatttg 300
aggcgcacca acaccccccat tggccgtgat ggaaagctgg cgaagcctcg gcagctacac 360
aacacgcatt ggggtcttgt gtgtcccgcc gagacccccg agggtcaggc ttgtggtttg 420
gtgaagaacc tgtcactgat gtgtcacgtt tccgttggca cacctagcga acctctctac 480
ggatacttca tcaaccgtgg catggaagtg ctcgaagagt acgagcccca gcggttcccc 540
aacgccacca aggtgttcat caacggtgcc tgggtcggtg tgcacacaag cccgaaagat 600
ctcgtggata gcatcatgca tctgcggcgc tatggtgacc tgaaccatga agcttccgtc 660
atccgcgaca ttcgggatcg agagttcagg gtcgtcacgg atgctggtcg tgttatgcgc 720
ccagtattca ccgtgcagca agaagacaag ctagacgggc ccgagaaggg ctcgttgtgc 780

```
atgaccaagg agcatcttgc cggtttggat gactggcatc tggtcaacga ggagagggaa    840

gagatggcca cgggctggga gtacctcgtg aagagtgggt gtattgagta cttggacgcc    900

gaagaagaag agacggcaat gatttgcatg acaccagaag acttggagtc ttaccgcaag    960

gagaagtacc tcgatcagaa accccaggag cacaacgtgg aagccgagcc caacaagcga   1020

ctcaagacga agaccaaccc gacgacacac atgtacaccc actgcgagat tcatcccagt   1080

atgatcctcg gtatctgcgc cagcatcatc cccttcccgg atcataacca ggcatgtctc   1140

tacgccacca gacctcgaga ttacttacta atattgcatc tagtcgcccc gtaatactta   1200

ccaatctgcc atgggcaagc aggccatggg c                                 1231
```

<210> SEQ ID NO 50
<211> LENGTH: 790
<212> TYPE: DNA
<213> ORGANISM: Acremonium alternatum

<400> SEQUENCE: 50

```
gaatgccccg gtcattttgg tcacatcgag ctggcaaagc ccgtttacca ccccggcttc     60

atcaagaaag tcaagaagat tttggagatt gtctgccaca actgcagcaa ggtcttggcc    120

gatgaagttg gtctcacctg atccatgtct tgttccttag atgctaacat ggacctctca    180

gagcgacccc gagtttgtca ctgcgatccg tacgcgcgac ccgaaagtcc gcttccagcg    240

agtctgggct gtgtgcaaga agaagcggaa gtgtgagaac gaggatcgcc aagacaagaa    300

ggaagaggag ttcgcgcccg gcatgaagcc gcagacgcac aaccacggcg gctgtggaaa    360

cgagatgccc gcggttcgtc aagctggttt gcgtctcaac gcgcagttcg agatcaagga    420

agagggcgga gctaagcgca aggatactca agttatcctg cccgaccaag ctcacacaat    480

cctgcggcgg atatcggaac aggacctccg acacatgggc ctcaactcag agtatgcccg    540

cccagagtgg atggttctta ccgtccttcc ggtccccccg cctcccgttc gtccaagtat    600

ttccatggac ggcactggca cgggaatgcg gaacgaggat gatttgactt acaagcttgg    660

tgatatcatc cgagccaacg gaaacgtcaa gcaggctatc cgcgaaggct cgccggccca    720

cattgctcgc gatttcgaag agctgctcca gtaccatgta gccacctaca tggataatga    780

tattgctgga                                                           790
```

<210> SEQ ID NO 51
<211> LENGTH: 593
<212> TYPE: DNA
<213> ORGANISM: Acremonium alternatum

<400> SEQUENCE: 51

```
gtcctcgcct aatcaggagt cactagacga catacccgag gacgacatga tgggcgacct     60

tgcgcttggc ctttcgagca gcttcaagca acacgccctc cggaactcaa agggcaagac    120

cttctgggat accttctccg agacgagcag tgtcgcagga ccgagaacca cgccacctcc    180

gccgggagtg atggctcgac gtccatcgtc cggcaggagt gaggatgtga ccatggattc    240

gccgctccag caaagcagca tgccttggct acaaacacgg cacctttccg actcccagcg    300

ctcggactcg gcacctgcgg ccaaggagaa ggactccccg gcccagccac ccaccgctgc    360

agagataacg cgccgaatca acaacaaacg ccgccgtgac gatgacttcg acccggtgag    420

cttcaaacgc cgcgcagtga gtcccgggct cagcgtccac aactcgccgc tcccgcagag    480

cccaatgcag cagagcggtg cgccatgggg ttccaggccg ggaagcaatg gggcgacaa    540
```

-continued ggcgggaagc agtgcaccta gcgaatctgg tggtagcacg tcagggaata gga 593

<210> SEQ ID NO 52
<211> LENGTH: 1453
<212> TYPE: DNA
<213> ORGANISM: Chaetomium globosum

<400> SEQUENCE: 52
tcttggtcat ttagaggaag taaaagtcgt aacaaggtct ccgttggtga accagcggag 60
ggatcattac agagttgcaa aactccctaa accattgtga acgttaccta taccgttgct 120
tcggcgggcg gccccggggt ttaccccccg ggcgcccctg ggccccaccg cgggcgcccg 180
ccggaggtca ccaaactctt gataatttat ggcctctctg agtcttctgt actgaataag 240
tcaaaacttt caacaacgga tctcttggtt ctggcatcga tgaagaacgc agcgaaatgc 300
gataagtaat gtgaattgca gaattcagtg aatcatcgaa tctttgaacg cacattgcgc 360
ccgccagcat tctggcgggc atgcctgttc gagcgtcatt tcaaccatca agcccccggg 420
cttgtgttgg ggacctgcgg ctgccgcagg ccctgaaaag cagtggcggg ctcgctgtcg 480
caccgagcgt agtagcatac atctcgctct ggtcgcgccg cgggttccgg ccgttaaacc 540
accttttaac ccaaggttga cctcggatca ggtaggaaga cccgctgaac ttaagcatat 600
caataagcgg aggaaaagaa accaacaggg attgccctag taacggcgag tgaagcggca 660
acagctcaaa tttgaaatct ggcttcggcc cgagttgtaa tttgcagagg aagctttagg 720
cgcggcacct tctgagtccc ctggaacggg gcgccataga gggtgagagc cccgtatagt 780
tggatgccta gcctgtgtaa agctccttcg acgagtcgag tagtttggga atgctgctca 840
aaatgggagg taaatttctt ctaaagctaa ataccggcca gagaccgata gcgcacaagt 900
agagtgatcg aaagatgaaa agcactttga aaagagggtt aaatagcacg tgaaattgtt 960
gaaagggaag cgcttgtgac cagacttgcg ccgggcggat catccggtgt tctcaccggt 1020
gcactccgcc cggctcaggc cagcatcggt tctcgcgggg ggataaaggt cctgggaacg 1080
tagctcctcc gggagtgtta tagcccgggg cgtaatgccc tcgcggggac cgaggttcgc 1140
gcatctgcaa ggatgctggc gtaatggtca tcagcgaccc gtcttgaaac acggaccaag 1200
gagtcaaggt tttgcgcgag tgtttgggtg taaaacccgc acgcgtaatg aaagtgaacg 1260
taggtgagag cttcggcgca tcatcgaccg atcctgatgt tttcggatgg atttgagtag 1320
gagcgttaag ccttggaccc gaaagatggt gaactatgct tggatagggt gaagccagag 1380
gaaactctgg tggaggctcg cagcggttct gacgtgcaaa tcgatcgtca aatctgagca 1440
tgggggcgaa aga 1453

<210> SEQ ID NO 53
<211> LENGTH: 266
<212> TYPE: DNA
<213> ORGANISM: Chaetomium globosum

<400> SEQUENCE: 53
atgtgcaagg ccggtttcgc cggtgatgat gcaccccgcg ctgttttccg taagtctccc 60
agccccggcc ccggcccggt cggcgataag ccgagctccg gacgctcgtt ggcacaaaca 120
gacaagctaa cagcgccgtt tagcgtcgat tgtcggtcgt ccccgtcacc atgggtaggc 180
tttcagttcc ggtatctctg cgatatgggg tcgctggcta acgcgccgct agtattatga 240
tcggtatggg gcagaaggac tcgtac 266

<210> SEQ ID NO 54
<211> LENGTH: 923
<212> TYPE: DNA
<213> ORGANISM: Chaetomium globosum

<400> SEQUENCE: 54

```
tcctgaggga aacttcggcg gtaaccagct actagatggt tcgattagtc tttcgccccc     60

atgctcagat ttgacgatcg atttgcacgt cagaaccgct gcgagcctcc accagagttt    120

cctctggctt caccctatcc aagcatagtt caccatcttt cgggtccaag gcttaacgct    180

cctactcaaa tccatccgaa aacatcagga tcggtcgatg atgcgccgaa gctctcacct    240

acgttcactt tcattacgcg tgcgggtttt acacccaaac actcgcgcaa aaccttgact    300

ccttggtccg tgtttcaaga cgggtcgctg atgaccatta cgccagcatc cttgcagatg    360

cgcgaacctc ggtccccgcg agggcattac gccccgggct ataacactcc cggaggagct    420

acgttcccag gacctttatc cccccgcgag aaccgatgct ggcctgagcc gggcggagtg    480

caccggtgag aacaccggat gatccgcccg gcgcaagtct ggtcacaagc gcttcccttt    540

caacaatttc acgtgctatt taaccctctt ttcaaagtgc ttttcatctt tcgatcactc    600

tacttgtgcg ctatcggtct ctggccggta tttagcttta gaagaaattt acctcccatt    660

ttgagcagca ttcccaaact actcgactcg tcgaaggagc tttacacagg ctaggcatcc    720

aactatacgg ggctctcacc ctctatggcg ccccgttcca ggggactcag aaggtgccgc    780

gcctaaagct tcctctgcaa attacaactc gggccgaagc cagatttcaa atttgagctg    840

ttgccgcttc actcgccgtt actagggcaa tccctgttgg tttcttttcc tccgcttatt    900

gatatgctta agttcagcgg gtc                                            923
```

<210> SEQ ID NO 55
<211> LENGTH: 797
<212> TYPE: DNA
<213> ORGANISM: Chaetomium globosum

<400> SEQUENCE: 55

```
gagtgtccag gtcactttgg ccacattgag ctatccagac ccgttttcca ccccgggttc     60

atcaggcgtg tcaaaaagtt gctcgagatg gtctgccaca actgcagcaa ggtgttggct    120

gatcgtgtta gtgcaccttg cctgaccgag tgatgatttg ttttggcatg ctaactcttc    180

accaggagga cgagcaatat gctgctgcca tgcggattcg ggaccccaaa gtacgcttca    240

agcgagtttg ggatatttgc aagagtaaga agcgctgcga aaacgaagtg cgcaagggga    300

aagatggcga gttcaaaccc gacagcgaaa accaagccgc agagggtggc catggaggat    360

gtggcaacac gcagccagtc attcgccagc aggctctcac cctgtggggc agcgtcgaga    420

ccaaggacga ggatggtgtg aagaccaagg agaagaaggt catcacccca gaaatggccc    480

tgaacatctt ccgtcgcatg tcggacgacg agatgattga cattggcctc aatatttccc    540

aagctcgtcc ggaatggatg atcatcacgg ttcttcctgt cccgcctcct ccggtgcgcc    600

ccagtatttc catggacgga actggaacag gcttgcggaa tgaggacgat ctgacgtata    660

aactcggcga tatcatccgc gccaatggca acgtccgcca ggctattgcc gagggctctc    720

ctcagcatat catcaccgac tttgagaacc tactccagta ccacgtcgct acgtacatgg    780

ataatgacat cgccggt                                                   797
```

<210> SEQ ID NO 56
<211> LENGTH: 1132
<212> TYPE: DNA

<213> ORGANISM: Chaetomium globosum

<400> SEQUENCE: 56

```
cttccgtcaa tttctttaag tttcagcctt gcgaccatac tcccccagga gcccaaacat      60
tttgatttat cgtaaggtgc cgaacgggtc aaaaaataac gccgtccgat ccctaatcgg     120
catagtttag gttaagacta cgacggtatc tgatcgtatt cgatccccta actttcgttc     180
ctgattaatg aaaacatcct tggcaaatgc tttcgcagta gttagtcttc aataaatcca     240
agaatttcac ctctgacaat tgaatactga tgcccccgac tgtccctatt aatcattacg     300
gcggtcctag aaaccaacaa aatagaacca cacgtcctat tctattattc catgctaatg     360
tattcgagca taggccttct ttaagcgatc taatttgttc agagtaaaag tcctggttcc     420
ccggcacacc cagtgaaggg catgcggttc tccagaagga aagacccagc cgagccagtg     480
cacgcggtga ggcggaccgg ccggctaggc ccaaggttca actacgagct ttttaacctc     540
aacaacttta atatacgcta ttggagctgg aattaccgcg gctgctggca ccagacttgc     600
cctccaattg ttcctcgtta agggatttaa attgtactca ttccaattac aagacccgaa     660
agagccctgt atcagtattt attgtcacta cctccccgtg tcgggattgg gtaatttgcg     720
cgcctgctgc cttcctttgg atgtagtagc cgtttctcag gctccttctc cggggtcgag     780
ccctaaccct ccgttacccg ttgtcaccac ggctggccaa gacccagccg tcgaaagttg     840
atagggcaga aatttgaatg aaccatcgcc ggcgcaaggc cgtgcgattc gagaagttat     900
tatgaatcac cagagagccc cgaagggcat tggtttttaa tctaataaat acatcccttc     960
cgaagtcggg atttttagca tgtattagct ctagaattac cacggttatc catgtagtaa    1020
ggtactatca aataaacgat aactgattta atgagccatt cgcagtttcg cggtataatt    1080
gcttatactt agacatgcat ggcttaatct ttgagacaag catatgacta ct            1132
```

<210> SEQ ID NO 57
<211> LENGTH: 925
<212> TYPE: DNA
<213> ORGANISM: Chaetomium globosum

<400> SEQUENCE: 57

```
cttccgtcaa tttctttaag tttcagcctt gcgaccatac tcccccagga gcccaaacat      60
tttgatttat cgtaaggtgc cgaacgggtc aaaaaataac gccgtccgat ccctaatcgg     120
catagtttag gttaagacta cgacggtatc tgatcgtatt cgatccccta actttcgttc     180
ctgattaatg aaaacatcct tggcaaatgc tttcgcagta gttagtcttc aataaatcca     240
agaatttcac ctctgacaat tgaatactga tgcccccgac tgtccctatt aatcattacg     300
gcggtcctag aaaccaacaa aatagaacca cacgtcctat tctattattc catgctaatg     360
tattcgagca taggccttct ttaagcgatc taatttgttc agagtaaaag tcctggttcc     420
ccggcacacc cagtgaaggg catgcggttc tccagaagga aagacccagc cgagccagtg     480
cacgcggtga ggcggaccgg ccggctaggc ccaaggttca actacgagct ttttaacctc     540
aacaacttta atatacgcta ttggagctgg aattaccgcg gctgctggca ccagacttgc     600
cctccaattg ttcctcgtta agggatttaa attgtactca ttccaattac aagacccgaa     660
agagccctgt atcagtattt attgtcacta cctccccgtg tcgggattgg gtaatttgcg     720
cgcctgctgc cttcctttgg atgtagtagc cgtttctcag gctccttctc cggggtcgag     780
ccctaaccct ccgttacccg ttgtcaccac ggctggccaa gacccagccg tcgaaagttg     840
atagggcaga aatttgaatg aaccatcgcc ggcgcaaggc cgtgcgattc gagaagttat     900
```

tatgaatcac cagagagccc cgaag 925

<210> SEQ ID NO 58
<211> LENGTH: 518
<212> TYPE: DNA
<213> ORGANISM: Chaetomium globosum

<400> SEQUENCE: 58
gttcacctcc agaccggcca gtgcgtaagt tggaccgaat cgaacattac gaccgaccgg 60
ccgcgcagga taactgacat ggagctctct agggtaacca aatcggtgcc gctttctggt 120
acgtccaagc aaagcaaaca ctcttggctg atgacaatcg agactgactt cttttcaggc 180
agaccatctc tggcgagcac ggcctcgaca gcaatggcgt gtatgtgggc atgacagttc 240
ccaaccgata aatccccgct caccgcttcg ataggtacaa cggcacctcc gagctccagc 300
tcgagcgtat gaacgtgtac ttcaacgagg tcagtcgggt caaataattt tacacgaccg 360
agtgatggcg tgctcatagt attatacagg cttccggcaa caagtatgtt cctcgcgctg 420
tcctcgtcga cttggagccc ggcaccatgg atgccgtccg tgccggcccc ttcggccagc 480
tcttccgccc ggacaacttc gtcttcggcc agtcgggt 518

<210> SEQ ID NO 59
<211> LENGTH: 568
<212> TYPE: DNA
<213> ORGANISM: Chaetomium globosum

<400> SEQUENCE: 59
gaggaggagg aggagaggtt ggagagggag gcgttgcgtg ccgaggcgct ttgtgaggtc 60
aggcgggtta tggcgctgct ggaggatacg ctgcttgcgg acgggcggga gtgggttttg 120
ggcggtggtg gtggcggtga tggtggtggc agtgagggtg cgagaaaagg gccgacgttg 180
gcggatatcg aggccgtgtg ggtgcttcac tggatgattg gcattcctgg tgcgctgttc 240
aacgccgggt atgtgagcgc cgagcggttt ccgcgggtgt atgcgtgggt ggcgcggttt 300
caggcggcgg ttggggcggc gaaggccggg gtggtggtga agggcatgag cggggaggag 360
gcggcggtag tgttgaaggg gcagagagaa ggggtaggat attttgagaa ggagggggag 420
gtggacgccg cggacccgat cgtcaaggtg tacggattgg agaaagggag cagggtcgag 480
gtgtggccga cggactccgg ggctgggcat cgggatcagg gctgcctggt gagcctcgac 540
gccgaggaaa tagtctggga gacggacg 568

<210> SEQ ID NO 60
<211> LENGTH: 1503
<212> TYPE: DNA
<213> ORGANISM: Exserohilum rostrata

<400> SEQUENCE: 60
tcttggtcat ttagaggaag taaaagtcgt aacaaggtct ccgtaggtga acctgcggag 60
ggatcattac acaacaaaaa tatgagggtg tggtttgctg gcaacagcgt ccgccccaag 120
tatttttcac ccatgtcttt tgcgcacttt ttgtttcctg ggcgagttcg ctcgccacca 180
ggacccaacc ataaaccttt ttttatgcag ttgcaatcag cgtcagtata ataattcaat 240
ttattaaaac tttcaacaac ggatctcttg gttctggcat cgatgaagaa cgcagcgaaa 300
tgcgatacgt agtgtgaatt gcagaattca gtgaatcatc gaatctttga acgcacattg 360 cgcccctttgg tattccaaag ggcatgcctg ttcgagcgtc atttgtaccc tcaagctttg 420

-continued

```
cttggtgttg ggcgtctttt tgtctctccc cttgttgggg gagactcgcc ttaaaacgat    480

tggcagccga cctactggtt ttcggagcgc agcacaaatt tgcgccttcc aatccacggg    540

gcggcatcca gcaagccttt gttttctata acaaatccac attttgacct cggatcaggt    600

agggataccc gctgaactta agcatatcaa taagcggagg aaaagaaacc aacagggatt    660

gccctagtaa cggcgagtga agcggcaaca gctcaaattt gaaatctggc tctttcagag    720

tccgagttgt aatttgcaga gggcgctttg gctttggcag cggtccaagt tccttggaac    780

aggacgtcac agagggtgag aatcccgtac gtggtcgcta gctattgccg tgtaaagccc    840

cttcgacgag tcgagttgtt tgggaatgca gctctaaatg ggaggtaaat ttcttctaaa    900

gctaaatatt ggccagagac cgatagcgca caagtagagt gatcgaaaga tgaaaagcac    960

tttggaaaga gagtcaaaca gcacgtgaaa ttgttgaaag ggaagcgctt gcagccagac   1020

ttgcttgcag ttgctcatcc gggcttttgc ccggtgcact cttctgcagg caggccagca   1080

tcagtttggg cggtgggata aaggtctctg tcatgtacct ctcttcgggg aggccttata   1140

ggggaggcga cataccacca gcctagactg aggtccgcgc atctgctagg atgctggcgt   1200

aatggctgta agcggcccgt cttgaaacac ggaccaagga gtctaacatc tatgcgagtg   1260

tttgggtgtc aagcccgagc gcgtaatgaa agtgaacgga ggtgggaacc cgcaagggtg   1320

caccatcgac cgatcctgaa gtttacggaa ggatttgagt aagagcatgg ctgttgggac   1380

ccgaaagatg gtgaactatg cttgaatagg gtgaagccag aggaaactct ggtggaggct   1440

cgcagcggtt ctgacgtgca aatcgatcgt caaatttggg cataggggcg aaagactaat   1500

cga                                                                 1503
```

```
<210> SEQ ID NO 61
<211> LENGTH: 1197
<212> TYPE: DNA
<213> ORGANISM: Exserohilum rostrata

<400> SEQUENCE: 61

cccatggctt gcttgcccat agcagattgg taggtgttac gaggcgactg gttgtgatct     60

gggaaaggaa tgatactggc gcaaataccc agaatcatgg ccggatggat ttcacagtga    120

gtgtaggcat ggatacgagg atctggtagg ggcttgagac ggcgaagacg gtccttaccc    180

tctgtggagc gctccgctgc aggtaggccc atcttcatct ctcgccattc ttctaagtcc    240

tcgggagaga atgtaatcat ggcagtctct tcctcctcag catcgaggta ttcgacaaca    300

ccatcttgga taagacctct ccagccataa gtagcctgct caacctcctc ctgactccat    360

ccttgccttg tgctagtctc ttgttgttca gccttgagct tgttactaat ctccttggtg    420

aagatgaggt ggtttcggtt tggctttcga atatcgttct ctacaacaaa tagaggtctc    480

atgacacgac cagcatctgt gaagatcttg aactctcggt cacgaatgtc acgaatcaaa    540

ctcatctcgt aagatagagt tccgtttcgt cgaagctcct gcacgaccgt aacaagttgt    600

tgagcattgg aatgaacccc aacccaaaca ccattaacga aaaccttggt cgcatcgggg    660

ttttggttct ggtcgtattc ctcgagcagc tgcatgttac gttgcgtcat gaagtcgata    720

atgggcgacg catcgctacc gacactgacg taacacatga gagacaagtt cttgaccaga    780

ccgcaagcct gtccttcagg cgtctcagca gggcagacaa gaccccagtg ggagttgtgc    840

agttgacggg gcttggccaa tttaccatca cgtccaacag gagtatttgt tcgacgaaga    900

tgggacaatg tggaggcgta agtgtatcgg ttcaacacct gcgagacacc agccttggca    960

gatgctgcct tcttctggtc accccagttg cctgtagcca gagagtactt caatccgttc   1020
```

gtgatgatgc tggcttttac agccatctga acgttaaagt cctggttgtt ctcaacgcac 1080
cgctggaggt acttgtagac gtccttggta agcttcaaga agaggatacg gaacaagttg 1140
gcgattaaag gtccagcaag atccaggcgc ttctttccga aatgatcacg gtcatcc 1197

<210> SEQ ID NO 62
<211> LENGTH: 307
<212> TYPE: DNA
<213> ORGANISM: Exserohilum rostrata

<400> SEQUENCE: 62
cttccaggca tagtaatgtg gatattaggt gagagcgaaa tataagtgtc cctagaagtg 60
atagtgagaa ggctatggtg aggttgaaga aggtagatgg catattggta attatgaaca 120
tcatcataat ctaatgagtc gaaatcatta attttttttt aaactaatta ccatttactc 180
tgttcattct aatccttttt gtgttcattc atatgctagg cctagagata gaattgtgac 240
tagaataaag gctataatta ttatagtaga ggttttaatt gtttgaattg ctcatggtag 300
tggaagt 307

<210> SEQ ID NO 63
<211> LENGTH: 1439
<212> TYPE: DNA
<213> ORGANISM: Epicoccum nigrum

<400> SEQUENCE: 63
tcttggtcat ttagaggaag taaaagtcgt aacaaggttt ccgtaggtga acctgcggaa 60
ggatcattac ctagagtttg tggacttcgg tctgctacct cttacccatg tcttttgagt 120
accttcgttt cctcggcggg tccgcccgcc ggttggacaa cattcaaacc ctttgcagtt 180
gcaatcagcg tctgaaaaaa cttaatagtt acaactttca acaacggatc tcttggttct 240
ggcatcgatg aagaacgcag cgaaatgcga taagtagtgt gaattgcaga attcagtgaa 300
tcatcgaatc tttgaacgca cattgcgccc cttggtattc catggggcat gcctgttcga 360
gcgtcatttg taccttcaag ctctgcttgg tgttgggtgt tttgtctcgc ctccgcgcgc 420
agactcgcct taaaacaatt ggcagccggc gtattgattt cggagcgcag tacatctcgc 480
gctttgcact cataacgacg acgtccaaaa gtacattttt acactcttga cctcggatca 540
ggtagggata cccgctgaac ttaagcatat caataagcgg aggaaaagaa accaacaggg 600
attgccctag taacggcgag tgaagcggca acagctcaaa tttgaaatct ggcgtctttg 660
gcgtccgagt tgtaatttgc agagggcgct ttggcattgg cagcggtcca agttccttgg 720
aacaggacgt cacagagggt gagaatcccg tacgtggtcg ctagccttta ccgtgtaaag 780
ccccttcgac gagtcgagtt gtttgggaat gcagctctaa atgggaggta aatttcttct 840
aaagctaaat actggccaga gaccgatagc gcacaagtag agtgatcgaa agatgaaaag 900
cactttggaa agagagttaa aaagcacgtg aaattgttga aagggaagcg cttgcagcca 960
gacttgcctg tagttgctca tccgggtttc tacccggtgc actcttctac gggcaggcca 1020
gcatcagttt gggcggttgg ataaaggtct ctgtcatgta cctcccttcg gggagatctt 1080
ataggggaga cgacatgcaa ccagcctgga ctgaggtccg cgcatctgct aggatgctgg 1140
cgtaatggct gtaagcggcc cgtcttgaaa cacggaccaa ggagtctaac atctatgcga 1200
gtgtttgggt gtcaagcccg agcgcgtaat gaaagtgaac ggaggtggga acctttcggg 1260
gtgcaccatc gaccgatcct gatgtcttcg gatggatttg agtaagagca tagctgttgg 1320
gacccgaaag atggtgaact atgcttgaat agggtgaagc cagaggaaac tctggtggag 1380
gctcgcagcg gttctgacgt gcaaatcgat cgtcaaattt gggcataggg gcgaaagac 1439

<210> SEQ ID NO 64
<211> LENGTH: 383
<212> TYPE: DNA
<213> ORGANISM: Epicoccum nigrum

<400> SEQUENCE: 64
ccagactggc cgaagacgaa gttatcggga cggaagagct ggccgaaggg gccggcgcgg 60
acagcgtcca ttgtaccggg ctccaagtcg acgaggacgg cacggggaac gaacttgttg 120
ccagaggcct gcgggaggtc agcactcgca gtccgtctca ggaaagcgtg tcgtttctag 180
tacctcgttg aagtagacgt tcatgcgctc gagctggagg tccgaggtgc cgttgtagac 240
accggagccg tcgaggccat gctcgccgga gatggtctgc cagaaggcag caccgatttg 300
gttaccctgt cccttgtgag ctgccgtcca tgagagaaca tgcaagtggt gtacttacgc 360
actgaccggt ctggaggtga acc 383

<210> SEQ ID NO 65
<211> LENGTH: 1496
<212> TYPE: DNA
<213> ORGANISM: Curvularia protuberata

<400> SEQUENCE: 65
tcttggtcat ttagaggaag taaaagtcgt aacaaggtct ccgtaggtga acctgcggag 60
ggatcattac acaataacat atgaaggctg tacgccgctg cgcccccggg ccagttggct 120
gaggctggat tatttattac ccttgtcttt tgcgcacttg ttgtttcctg ggcgggttcg 180
cccgcctcca ggaccacacc ataaaccttt tttatgcagt tgcaatcagc gtcagtacaa 240
caaatgtaaa tcatttacaa ctttcaacaa cggatctctt ggttctggca tcgatgaaga 300
acgcagcgaa atgcgatacg tagtgtgaat tgcagaattc agtgaatcat cgaatctttg 360
aacgcacatt gcgccctttg gtattccaaa gggcatgcct gttcgagcgt catttgtacc 420
ctcaagcttt gcttggtgtt gggcgttttt gtctttggtt tgccaaagac tcgccttaaa 480
acgattggca gccggcctcc tggttacgca gcgcagcaca tttttgcgct tgcaatcagc 540
aagagggcgg cactccatca agactccttc tcacgtttga cctcggatca ggtagggata 600
cccgctgaac ttaagcatat caataagcgg aggaaaagaa accaacaggg attgccctag 660
taacggcgag tgaagcggca acagctcaaa tttgaaatct ggctctttta gggtccgagt 720
tgtaatttgc agagggcgct ttggctttgg cagcggtcca agttccttgg aacaggacgt 780
cacagagggt gagaatcccg tacgtggtcg ctagctattg ccgtgtaaag ccccttcgac 840
gagtcgagtt gtttgggaat gcagctctaa atgggaggta aatttcttct aaagctaaat 900
attggccaga gaccgatagc gcacaagtag agtgatcgaa agatgaaaag cactttggaa 960
agagagtcaa acagcacgtg aaattgttga aagggaagcg cttgcagcca gacttgcttg 1020
cagttgctca tccgggcttt tgcccggtgc actcttctgt aggcaggcca gcatcagttt 1080
gggcggtggg ataaaggtct ctgacacgtt ccttccttcg ggttggccat ataggggaga 1140
cgtcatacca ccagcctgga ctgaggtccg cgcatctgct aggatgctgg cgtaatggct 1200
gtaagcggcc cgtcttgaaa cacggaccaa ggagtctaac atctatgcga gtgtttgggt 1260
gtcaagcccg agcgcgtaat gaaagtgaac ggaggtggga acccgcaagg gcgcaccatc 1320
gaccgatcct gaagtttacg gaaggatttg agtaagagca tggctgttgg gacccgaaag 1380
atggtgaact atgcttgaat agggtgaagc cagaggaaac tctggtggag gctcgcagcg 1440
gttctgacgt gcaaatcgat cgtcaaattt gggcataggg gcgaaagact aatcga 1496

<210> SEQ ID NO 66
<211> LENGTH: 1010
<212> TYPE: DNA
<213> ORGANISM: Curvularia protuberata

<400> SEQUENCE: 66
acaccggcag ggccgttcca gaggatggtc tgcgcctcat cgatggcctc cttgtaaagc 60
ttgatcgact tctctccaca gtcgagaccc atccagccat ctgggatacc atccttgtcc 120
tcggcataac cgacgttggc gtccttgtcg aacttgtcgg cggtgatgta gtcaacaggc 180
agcacaatct tgacattgtt cttcttcgcc ttctccacga ggtccttgac ggtcttgcta 240
ccagcctcat cgaacaagct ttcaccaatc ttgacgccct cgagagtctt cttgaaggtg 300
aaggacatgc ctccgcaaat gatcaggctg ttgaccttgc caagcaggtt gtcgatcaat 360
tgaatcttgt cagagacctt ggcaccacca aggatggcga ggaaaggtcg cttggggttc 420
tcaagcgctt gtgcaaagta atcaagctcc ttcttgacaa ggaagccaga ggccttttgt 480
gggaggtcga caccgaccat ggagctgtgc gcgcggtgag cagtaccaaa agcgtcgtct 540
gtaaaccgtc agcctcgtgc tttcgcccat gaattcatag ttacttacta atgtagacgt 600
cgcccagagc agtcagtccc ttcctaaact catcgacctt gctcttgtcg accttctgct 660
tcttgcccgc atcatccttg tagctaccct cctcctcagc gtggaagcgc aggttctcga 720
ggaggatgac ctgaccaccg ctagcgttgt tgacggtatc ctctaccgac ttgccgacgc 780
agtcgtcggt gaaggtaacg ctcttgccga ggagcttctc gagttcggga acaaccggct 840
tgaggctgta cttcgcattg ggcttaccgt ctggccggcc aaggtgggac atgagaatga 900
cggccttggc gccattgtcg acggcgtact tgattgtggg aagtgcgcca acaatgcgct 960
ggttgttggt gatcttcttg tcggcgtcga gagggacgtt gaagtcgacc 1010

<210> SEQ ID NO 67
<211> LENGTH: 1443
<212> TYPE: DNA
<213> ORGANISM: Cladosporium cladosporioides

<400> SEQUENCE: 67
tcttggtcat ttagaggaag taaaagtcgt aacaaggtct ccgtaggtga acctgcggag 60
ggatcattac aagtgacccc ggtctaacca ccgggatgtt cataaccctt tgttgtccga 120
ctctgttgcc tccggggcga ccctgccttc gggcgggggc tccgggtgga cacttcaaac 180
tcttgcgtaa ctttgcagtc tgagtaaact taattaataa attaaaactt ttaacaacgg 240
atctcttggt tctggcatcg atgaagaacg cagcgaaatg cgataagtaa tgtgaattgc 300
agaattcagt gaatcatcga atctttgaac gcacattgcg ccccctggta ttccgggggg 360
catgcctgtt cgagcgtcat ttcaccactc aagcctcgct tggtattggg catcgcggtc 420
cgccgcgtgc ctcaaatcga ccggctgggt cttctgtccc ctaagcgttg tggaaactat 480
tcgctaaagg gtgttcggga ggctacgccg taaaacaacc ccatttctaa ggttgacctc 540
ggatcaggta gggatacccg ctgaacttaa gcatatcaat aagcggagga aaagaaacca 600
acagggattg ctctagtaac ggcgagtgaa gcagcaatag ctcaaatttg aaatctggcg 660
tcttcgacgt ccgagttgta atttgtagag gatgcttctg agtaaccacc gacctaagtt 720

-continued

```
ccttggaaca ggacgtcata gagggtgaga atcccgtatg cggtcggaaa ggtgctctat    780
acgtagctcc ttcgacgagt cgagttgttt gggaatgcag ctctaaatgg gaggtaaatt    840
tcttctaaag ctaaatattg gccagagacc gatagcgcac aagtagagtg atcgaaagat    900
gaaaagcact ttggaaagag agttaaaaag cacgtgaaat tgttaaaagg gaagggattg    960
caaccagact tgctcgcggt gttccgccgg tcttctgacc ggtctactcg ccgcgttgca   1020
ggccagcatc gtctggtgcc gctggataag acttgaggaa tgtagctcct tcgggagtgt   1080
tatagcctct tgtgatgcag cgagcgccgg gcgaggtccg cgcttcggct aggatgctgg   1140
cgtaatggtc gtaatccgcc cgtcttgaaa cacggaccaa ggagtctaac atctatgcga   1200
gtgttcgggt gtcaaacccc tacgcgtaat gaaagtgaac ggaggtgaga accgcaaggt   1260
gcatcatcga ccgatcctga tgtcttcgga tggatttgag taagagcata gctgttggga   1320
cccgaaagat ggtgaactat gcctgaatag ggtgaagcca gaggaaactc tggtggaggc   1380
tcgcagcggt tctgacgtgc aaatcgatcg tcaaatttgg gtataggggc gaaagactaa   1440
tcg                                                                 1443
```

<210> SEQ ID NO 68
<211> LENGTH: 1435
<212> TYPE: DNA
<213> ORGANISM: Cladosporium oxysporum

<400> SEQUENCE: 68

```
tcttggtcat ttagaggaag taaaagtcgt aacaaggtct ccgtaggtga acctgcggag     60
ggatcattac aagtgacccc ggtctaacca ccgggatgtt cataaccctt tgttgtccga    120
ctctgttgcc tccggggcga ccctgccttc gggcgggggc tccgggtgga cacttcaaac    180
tcttgcgtaa ctttgcagtc tgagtaaact taattaataa attaaaactt ttaacaacgg    240
atctcttggt tctggcatcg atgaagaacg cagcgaaatg cgataagtaa tgtgaattgc    300
agaattcagt gaatcatcga atctttgaac gcacattgcg ccccctggta ttccgggggg    360
catgcctgtt cgagcgtcat ttcaccactc aagcctcgct tggtattggg caacgcggtc    420
cgccgcgtgc ctcaaatcga ccggctgggt cttctgtccc ctaagcgttg tggaaactat    480
tcgctaaagg gtgctcggga ggctacgccg taaaacaaac ccatttctaa ggttgacctc    540
ggatcaggta gggatacccg ctgaacttaa gcatatcaat aagcggagga aaagaaacca    600
acagggattg ctctagtaac ggcgagtgaa gcagcaatag ctcaaatttg aaatctggcg    660
tcttcgacgt ccgagttgta atttgtagag gatgcttctg agtaaccacc gacctaagtt    720
ccttggaaca ggacgtcata gagggtgaga atcccgtatg cggtcggaaa ggtgctctat    780
acgtagctcc ttcgacgagt cgagttgttt gggaatgcag ctctaaatgg gaggtaaatt    840
tcttctaaag ctaaatattg gccagagacc gatagcgcac aagtagagtg atcgaaagat    900
gaaaagcact ttggaaagag agttaaaaag cacgtgaaat tgttaaaagg gaagggattg    960
caaccagact tgctcgcggt gttccgccgg tcttctgacc ggtctactcg ccgcgttgca   1020
ggccagcatc gtctggtgcc gctggataag acttgaggaa tgtagctccc tcgggagtgt   1080
tatagcctct tgtgatgcag cgagcgccgg gcgaggtccg cgcttcggct aggatgctgg   1140
cgtaatggtc gtaatccgcc cgtcttgaaa cacggaccaa ggagtctaac atctatgcga   1200
gtgttcgggt gtcaaacccc tacgcgtaat gaaagtgaac ggaggtgaga accgcaaggt   1260
gcatcatcga ccgatcctga tgtcttcgga tggatttgag taagagcata gctgttggga   1320
cccgaaagat ggtgaactat gcctgaatag ggtgaagcca gaggaaactc tggtggaggc   1380
```

-continued tcgcagcggt tctgacgtgc aaatcgatcg tcaaatttgg gtataggggc gaaag 1435

<210> SEQ ID NO 69
<211> LENGTH: 1439
<212> TYPE: DNA
<213> ORGANISM: Paecilomyces inflatus

<400> SEQUENCE: 69
tcttggtcat ttagaggaag taaaagtcgt aacaaggtct ccgttggtga accagcggag 60
ggatcattac agagtttaac gactcccaaa ccactgtgaa catacccgta ccgttgcctc 120
ggcgggcggc cccagggcgg ggccgcagcc tccccagcgg aggcgcccgc cgcaggtcgc 180
aaaactataa ctatatttag tggcatctct gagtaacttc caaacaatca aaactttcaa 240
caacggatct cttggttctg gcatcgatga agaacgcagc gaaatgcgat aagtaatgtg 300
aattgcagaa ttcagtgaat catcgaatct ttgaacgcac attgcgcccg ccagcattct 360
ggcgggcatg cctgtccgag cgtcatttca accctcaagc cctgcttggt gttggggcac 420
tacgcgcgag cgtaggccct caaaatcagt ggcggacccg ctggaggtcc gggcgtagta 480
acacatctcg cccgaggtcc ccagcgtgcc cctgccgtta aacccccaaa tttacagaag 540
gttgacctcg gatcaggtag gaatacccgc tgaacttaag catatcaata agcggaggaa 600
aagaaaccaa cagggattgc cctagtaacg gcgagtgaag cggcaacagc tcgaatttga 660
aatctggcct cggcccgagt tgtaatctgt agaggatgct tttggcgcgg tgccttccga 720
gtgccctgga acgggacgcc acagagggtg agagccccgt atggtcggac accaagcctg 780
tgtaaagctc cttcgacgag tcgggtagct tgggaatgct gctctaagtg ggaggtaaac 840
ttcttctaaa gctaaatact ggccagagac cgatagcgca caagtagagt gatcgaaaga 900
tgaaaagcac tttgaaaaga gggtcaaata gtacgtgaaa ttgttgaaag ggaagcgctc 960
atgaccagac ttgcgccggg ctgatcatcc agtggtctcc actggtgcac tctgcccggc 1020
tcaggccagc gtcggctgtc acggggggac aaaagcactg ggaaagtagc tctctccggg 1080
gagtgttata gccctatgca gaataccccc gcggcggccg aggtccgcgc tctgcaagga 1140
cgctggcgta atggtcatca gcgacccgtc ttgaaacacg gaccaaggag tcgaggtttt 1200
gcgcgagtgt tcgggtgcaa agccccagcg cgtaattaaa gtgaacgtag gtgagagctt 1260
cggcgcatca tcgaccgatc ctgatgtatt cggatggatt tgagtaggag cgtaaagcct 1320
cggacccgaa agatggtgaa ctatgcctgt atagggtgaa gccagaggaa actctggtgg 1380
aggctcgcag cggttctgac gtgcaaatcg atcgtcaaat atgggcatgg gggcgaaag 1439

<210> SEQ ID NO 70
<211> LENGTH: 1443
<212> TYPE: DNA
<213> ORGANISM: Epicoccum nigrum

<400> SEQUENCE: 70
tcttggtcat ttagaggaag taaaagtcgt aacaaggttt ccgtaggtga acctgcggaa 60
ggatcattac ctagagtttg tggacttcgg tctgctacct cttacccatg tcttttgagt 120
accttcgttt cctcggcggg tccgcccgcc ggttggacaa cattcaaacc ctttgcagtt 180
gcaatcagcg tctgaaaaaa cttaatagtt acaactttca acaacggatc tcttggttct 240
ggcatcgatg aagaacgcag cgaaatgcga taagtagtgt gaattgcaga attcagtgaa 300
tcatcgaatc tttgaacgca cattgcgccc cttggtattc catggggcat gcctgttcga 360

-continued

```
gcgtcatttg taccttcaag ctctgcttgg tgttgggtgt tttgtctcgc ctccgcgcgc    420

agactcgcct taaaacaatt ggcagccggc gtattgattt cggagcgcag tacatctcgc    480

gctttgcact cataacgacg acgtccaaaa gtacattttt acactcttga cctcggatca    540

ggtagggata cccgctgaac ttaagcatat caataagcgg aggaaaagaa accaacaggg    600

attgccctag taacggcgag tgaagcggca acagctcaaa tttgaaatct ggcgtctttg    660

gcgtccgagt tgtaatttgc agagggcgct ttggcattgg cagcggtcca agttccttgg    720

aacaggacgt cacagagggt gagaatcccg tacgtggtcg ctagccttta ccgtgtaaag    780

ccccttcgac gagtcgagtt gtttgggaat gcagctctaa atgggaggta aatttcttct    840

aaagctaaat actggccaga gaccgatagc gcacaagtag agtgatcgaa agatgaaaag    900

cactttggaa agagagttaa aaagcacgtg aaattgttga aagggaagcg cttgcagcca    960

gacttgcctg tagttgctca tccgggtttc tacccggtgc actcttctac gggcaggcca   1020

gcatcagttt gggcggttgg ataaaggtct ctgtcatgta cctcccttcg gggagatctt   1080

ataggggaga cgacatgcaa ccagcctgga ctgaggtccg cgcatctgct aggatgctgg   1140

cgtaatggct gtaagcggcc cgtcttgaaa cacggaccaa ggagtctaac atctatgcga   1200

gtgtttgggt gtcaagcccg agcgcgtaat gaaagtgaac ggaggtggga acctttcggg   1260

gtgcaccatc gaccgatcct gatgtcttcg gatggatttg agtaagagca tagctgttgg   1320

gacccgaaag atggtgaact atgcttgaat agggtgaagc cagaggaaac tctggtggag   1380

gctcgcagcg gttctgacgt gcaaatcgat cgtcaaattt gggcataggg gcgaaagact   1440

aat                                                                 1443


<210> SEQ ID NO 71
<211> LENGTH: 608
<212> TYPE: DNA
<213> ORGANISM: Epicoccum nigrum
<220> FEATURE:
<221> NAME/KEY: misc_feature
<222> LOCATION: (113)..(126)
<223> OTHER INFORMATION: n is a, c, g, or t

<400> SEQUENCE: 71

ctcctcctcc tcctcctgat cgaactcgcc ccccaccaac tccaccagcc cacccagccg     60

cccaaaaacc tccccatccc cgctagccgc ccccatggcc cggacaagca gcnnnnnnnn    120

nnnnnngtcc gggatggcct taggttcgct ctcgagctgc tccagccgcg acaggacatg    180

cagcagctcc ctgcgcagcg agtccggcgc cggcatgcgg ccccgcagcg gctggtcggc    240

gatgtatgtc ttgagcggga gcgcggcgcg caggatgagg tagggcgccg ctgcctgggc    300

gagtttgatg tgcgagtgcg agggcgaggg cgaggtactg gcggggcgtg cggccacgag    360

ggcgaagagg gaggccgtgc aggtgtagct catctttgtg cgcaaggtgg cggggaggac    420

ggccgtctgg ccggtgcgga cggagaggag gttggcgagg ggcgaggtgg tgatgggagg    480

gagttctcct tgtacgggag tgtggatgag ggaggtggtg aagaggttgc gggcgtatgt    540

cctgcggagg gtgtcgggga gggaggggga gtttagaggg ccgctgatca agtcgcgtag    600

ctctgtga                                                            608
```